US009751945B2

(12) United States Patent
Ploegh et al.

(10) Patent No.: US 9,751,945 B2
(45) Date of Patent: Sep. 5, 2017

(54) SORTASE-MODIFIED VHH DOMAINS AND USES THEREOF

(71) Applicant: Whitehead Institute for Biomedical Research, Cambridge, MA (US)

(72) Inventors: Hidde Ploegh, Brookline, MA (US); Maximilian Popp, Pittsford, NY (US); Juanjo Cragnolini, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 87 days.

(21) Appl. No.: 14/394,046

(22) PCT Filed: Apr. 15, 2013

(86) PCT No.: PCT/US2013/036630
§ 371 (c)(1),
(2) Date: Oct. 10, 2014

(87) PCT Pub. No.: WO2013/155526
PCT Pub. Date: Oct. 17, 2013

(65) Prior Publication Data
US 2015/0086576 A1     Mar. 26, 2015

Related U.S. Application Data

(60) Provisional application No. 61/624,114, filed on Apr. 13, 2012.

(51) Int. Cl.
| | |
|---|---|
| *A61K 47/48* | (2006.01) |
| *C07K 16/46* | (2006.01) |
| *C07K 16/28* | (2006.01) |
| *C07K 16/10* | (2006.01) |
| *C07K 16/44* | (2006.01) |
| *C07K 1/13* | (2006.01) |
| *C12N 9/50* | (2006.01) |
| *G01N 33/58* | (2006.01) |
| *A61K 39/00* | (2006.01) |

(52) U.S. Cl.
CPC .... *C07K 16/2833* (2013.01); *A61K 47/48561* (2013.01); *C07K 1/13* (2013.01); *C07K 16/1018* (2013.01); *C07K 16/44* (2013.01); *C07K 16/468* (2013.01); *C12N 9/50* (2013.01); *G01N 33/582* (2013.01); *A61K 2039/505* (2013.01); *C07K 2317/22* (2013.01); *C07K 2317/569* (2013.01); *C07K 2319/90* (2013.01)

(58) Field of Classification Search
CPC ........ A61K 2039/505; A61K 47/48561; C07K 16/243; C07K 2317/21; C07K 2317/24; C07K 2317/33; C07K 2317/34; C07K 2317/56; C07K 2317/565; C07K 2317/622; C07K 2317/73; C07K 2317/76; C07K 2317/92; C07K 16/468
See application file for complete search history.

(56) References Cited

U.S. PATENT DOCUMENTS

2014/0249296 A1    9/2014 Ploegh et al.

FOREIGN PATENT DOCUMENTS

| WO | WO2013/003555 A1 | 1/2013 |
| WO | WO 2013/155526 | 10/2013 |

OTHER PUBLICATIONS

Muyldermans 2001 (Reviews in Molecular Biotechnology 74:277-302).*
Zola et al 2008 (Curr Opin Mol Ther.10:68-74).*
Antos, et al., "Site-Specific N-and C-Terminal Labeling of a Single Polypeptide Using Sortases of Different Specificty", *J.Am.Chem. Soc.*, 131(31); 10800-10801(2009).
Levary, et al., "Protein-Protein Fusion Catalyzed by Sortase A", *PloS ONE*, 6(4); 1-6 (2011).
Tsukiji, et al., "Sortase-Mediated Litigation: A Gift from Gram-Positive Bacteria to Protein Engineering", *ChemBioChem*, 10; 787-798 (2009).
Sakamoto, et al., "Enzyme-Mediated Site-Specific Antibody-Protein Modification using a ZZ Domain as a Linker", *Bioconjugate Chem.*, 21; 2227-2233 (2010).
Sletten, et al., "Bioorthologonal Chemistry: Fishing for Selectivity in a Sea of functionality", *Angew.Chem.Int.Ed.*, 48; 6974-6998(2009).
Xiao, et al., "Synthesis of N-Terminally Linked Protein Dimers and Trimers by a Combined Native Chemical Litigation-CuAAC Click Chemistry Strategy", *Organic Letters*, 11(18); 4144-4147(2009).
International Search Report for International Application PCT/US2013/036630, dated Nov. 28, 2013.
Goyvaerts, Cleo, et al. "Development of the Nanobody display technology to target lentiviral vectors to antigen-presenting cells." *Gene therapy* 19.12 (2012): 1133-1140.
De Groeve, Kurt, et al. "Nanobodies as tools for in vivo imaging of specific immune cell types." *Journal of Nuclear Medicine* 51.5 (2010): 782-789.
Deschacht, Nick, et al. "A novel promiscuous class of camelid single-domain antibody contributes to the antigen-binding repertoire." *The Journal of Immunology* 184.10 (2010): 5696-5704.
Zhu, Xuekai, et al. "COMBODY: one-domain antibody multimer with improved avidity." *Immunology and cell biology* 88.6 (2010): 667-675.
Partial Supplementary European Search Report for Application No. EP 13 77 6100.3, dated Mar. 22, 2016.
Extended European Search Report for Application No. EP 13 77 6100.3 dated Jul. 22, 2016.
Carayanniotis, George, and Brian H. Barber. "Adjuvant-free IgG responses induced with antigen coupled to antibodies against class II MHC." (1987): 59-61. Nature 327.

(Continued)

*Primary Examiner* — Padma V Baskar
(74) *Attorney, Agent, or Firm* — Lisa M. Warren, Esq.; Morse, Barnes-Brown & Pendleton, P.C.

(57) ABSTRACT

In some aspects, polypeptides comprising single domain antibodies and methods of identifying single domain antibodies are provided. In some embodiments polypeptides comprising a single domain antibody and a sortase recognition sequence, are provided. In some aspects, products and methods of use in modulating the immune system, e.g., modulating an immune response, are provided.

15 Claims, 33 Drawing Sheets

(56) References Cited

OTHER PUBLICATIONS

Hawiger, Daniel, et al. "Dendritic cells induce peripheral T cell unresponsiveness under steady state conditions in vivo." *Journal of Experimental Medicine* 194.6 (2001): 769-780.

Kawamura, H. A. J. I. M. E., and J. A. Berzofsky. "Enhancement of antigenic potency in vitro and immunogenicity in vivo by coupling the antigen to anti-immunoglobulin." *The Journal of Immunology* 136.1 (1986): 58-65.

Bonifaz, Laura C., et al. "In vivo targeting of antigens to maturing dendritic cells via the DEC-205 receptor improves T cell vaccination." *Journal of Experimental Medicine* 199.6 (2004): 815-824.

White, Ann L., et al. "Ligation of CD11c during vaccination promotes germinal centre induction and robust humoral responses without adjuvant." *Immunology* 131.1 (2010): 141-151.

Lahoud, Mireille H., et al. "Targeting antigen to mouse dendritic cells via Clec9A induces potent CD4 T cell responses biased toward a follicular helper phenotype." *The Journal of Immunology* 187.2 (2011): 842-850.

Cohn, Lillian, and Lélia Delamarre. "Dendritic cell-targeted vaccines." *Frontiers in Immunology* 5 (2014): 255.

Chaplin, Jay W., Craig P. Chappell, and Edward A. Clark. "Targeting antigens to CD180 rapidly induces antigen-specific IgG, affinity maturation, and immunological memory." *Journal of Experimental Medicine* 210.10 (2013) 2135-2146.

Duarte, Joao N., et al. "Generation of Immunity against Pathogens via Single-Domain Antibody-Antigen Constructs." *The Journal of Immunology* 197.12 (2016): 4838-4847.

\* cited by examiner

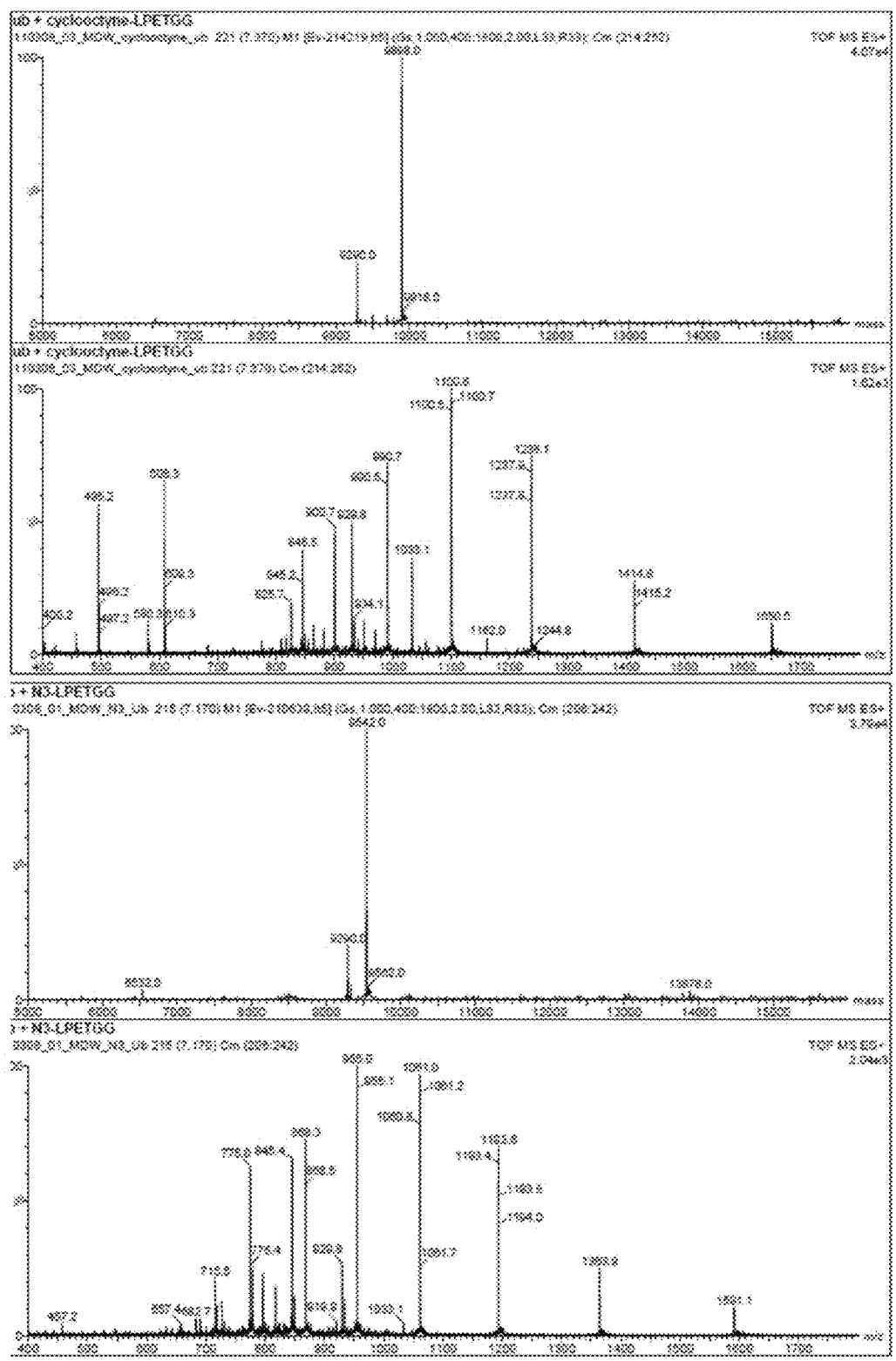
FIGURE 5 - CONTINUED

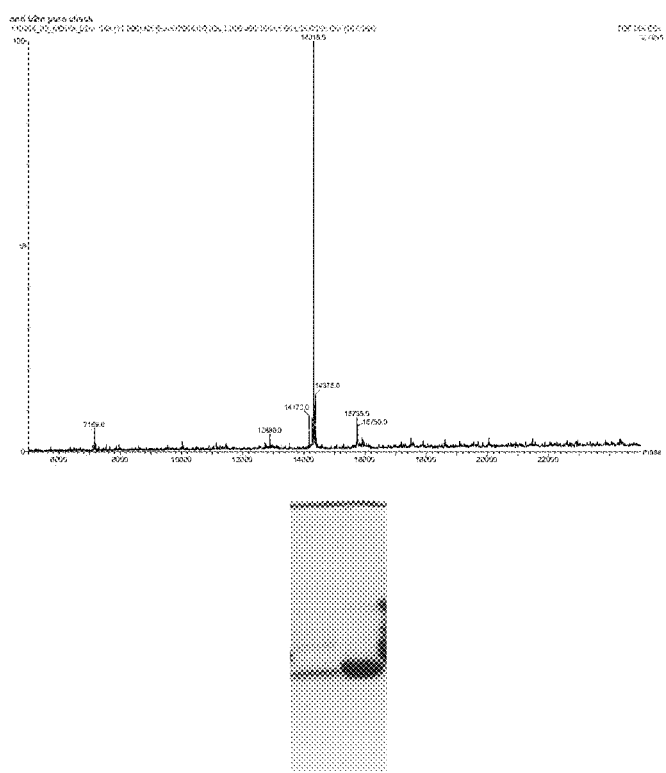
FIGURE 8 - CONTINUED

Fig. 13 Structure of VHHs cloned into pIII phage display vector

Fig. 15 Twelve VHH's identified by panning on hybridoma cells are labeled by sortase with a G3K(biotin)C(ATTO647N) multifunctional probe

Figure 22

A. Nucleotide sequence encoding VHH7 fusion protein

GGNATNNNNNNNNTNACNTTCCCCTCTAGAATAATTTTGTTTAACTTTAAGAAGGAGATATACATATGACCGGCCCGG
GAGCGGCCGCTCAGGTGCAGCTCGTGGAGTCAGGGGGAGGATTGGTGCAGGCTGGGGACTCTCTGAGACTCTCCTGC
GCAGCCTCTGGACGCACCTTCAGTCGCGGTGTAATGGGCTGGTTCCGCCGGGCTCCAGGGAAGGAGCGTGAGTTTGT
AGCAATCTTTAGCGGGAGTAGCTGGAGTGGTCGTAGTACATACTATTCAGACTCCGTAAAGGGCCGATTCACCATCT
CCAGAGACAACGCCAAGAACACGGTGTATCTGCAAATGAACGGCCTGAAACCTGAGGACACGGCCGTTTATTACTGT
GCAGCGGGATATCCGGAGGCGTATAGCGCCTATGGTCGGGAGAGTACATATGACTACTGGGGCCAGGGGACCCAGGT
CACCGTCTCCTCAGAACCCAAGACACCAAAACCACAACCGGCGCGCCAGGCCTGCACTAGTGGTTTACCAGAGACAG
GAGGAGGCAGCCATCACCATCATCACCATTAAGCTCGAGCACCACCACCACCACCACTGAGATCCGGCTGCTAACAA
AGCCCGAAAGGAAGCTGAGTTGGCTGCTGCCACCGCTGAGCAATAACTAGCATAACCCCTTGGGGCCTCTAAACGGG
TCTTGAGGGGTTTTTTGCTGAAAGGAGGAACTATATCCGGATTGGCGAATGGGACGCGCCCTGTAGCGGCGCATTAA
GCGCGGCGGGTGTGGTGGTTACGCGCAGCGTGACCGCTACACTTGCCAGCGCCCTAGCGCCCGCTCCTTTCGCTTCT
TCCCTTCCTTTCTCGCCACGTTCGCCGGCTTTCCCCGTCAAGCTCTAAATCGGGGGCTCCCTTTAAGGGTTCCGATT
TAGTGCTTTACGGCACCTCGACCCCAAAACTTGATAGGGTGATGGNCCACGTAGTGGGCCATCGCCCTGATAGACGG
TTTTCGCCCTTTGACGTGGAGTCCACGTNTTTAATANNGGACTNCTGTNNACTGGANNCAACNCTCANCCNATCTCG
NCTATCTTTGATTANANNNCAATTGCGATNCGCTNTNNNAAATGNCCTGATNACAANNTAACNCGNNNNNCAANTAN
NCTTNNNNNNTGNNNNNNCGNNNNNNGACNNNNNATTCCANNC (SEQ ID NO: 47)

B. VHH7 fusion protein sequence

<u>M</u>TGPGAAAQVQLVESGGGLVQAGDSLRLSCAASGRTFSRGVMGWFRRAPGKEREFVAIFSGSSWSGRSTYYSDSVKG
RFTISRDNAKNTVYLQMNGLKPEDTAVYYCAAGYPEAYSAYGRESTYDYWGQTQVTVSSEPKTPKPQPARQACTSG
<u>LPETGGGSHHHHHH</u> (SEQ ID NO: 48)

C. Nucleotide sequence encoding VHH7

GCTCAGGTGCAGCTCGTGGAGTCAGGGGGAGGATTGGTGCAGGCTGGGGACTCTCTGAGACTCTCCTGCGCAGCCTC
TGGACGCACCTTCAGTCGCGGTGTAATGGGCTGGTTCCGCCGGGCTCCAGGGAAGGAGCGTGAGTTTGTAGCAATCT
TTAGCGGGAGTAGCTGGAGTGGTCGTAGTACATACTATTCAGACTCCGTAAAGGGCCGATTCACCATCTCCAGAGAC
AACGCCAAGAACACGGTGTATCTGCAAATGAACGGCCTGAAACCTGAGGACACGGCCGTTTATTACTGTGCAGCGGG
ATATCCGGAGGCGTATAGCGCCTATGGTCGGGAGAGTACATATGACTACTGGGGCCAGGGGACCCAGGTCACCGTCT
CCTCAGAACCCAAGACACCAAAACCACAACCGGCGCGCCAGGCCTGCACTAGT (SEQ ID NO: 49)

D. VHH7 protein sequence

AQVQLVESGGGLVQAGDSLRLSCAASGRTFSRGVMGWFRRAPGKEREFVAIFSGSSWSGRSTYYSDSVKGRFTISRD
NAKNTVYLQMNGLKPEDTAVYYCAAGYPEAYSAYGRESTYDYWGQGTQVTVSSEPKTPKPQPARQACTS (SEQ ID
NO: 50)

E. VHH7 CDR sequences

CDR1: GRTFSRGV (SEQ ID NO: 51)

CDR2: FSGSSWSGRST (SEQ ID NO: 52)

CDR3: AAGYPEAYSAYGRESTYDY (SEQ ID NO: 53)

VHH52, VHH54, VHH62
Anti Influenza A Nucleoprotein

VHH7

CAGGTGCAGCTGCAGGAGTCAGGGGGAGGATTGGTGCAGGCTGGGGACTCTCTGAGA
CTCTCCTGCGCAGCCTCTGGACGCACCTTCAGTCGCGGTGTAATGGGCTGGTTCCGCC
GGGCTCCAGGGAAGGAGCGTGAGTTTGTAGCAATCTTTAGCGGGAGTAGCTGGAGTG
GTCGTAGTACATACTATTCAGACTCCGTAAAGGGCCGATTCACCATCTCCAGAGACA
ACGCCAAGAACACGGTGTATCTGCAAATGAACGGCCTGAAACCTGAGGACACGGCCG
TTTATTACTGTGCAGCGGGATATCCGGAGGCGTATAGCGCCTATGGTCGGGAGAGTA
CATATGACTACTGGGGCCAGGGGACCCAGGTCACCGTCTCCTCAGGAGGACTGCCGGA
AACCGGCGGCCACCACCATCACCATCAC (SEQ ID NO: 74)

VHH4

CAGGTGCAGCTGCAGGAGTCAGGGGGAGGATTGGTGCAGGCTGGGGGGTCTCTGAGA
CTCTCCTGTGCAGCCTCTGGAAGCACCCTCAGTAGCTATGGCATGGGCTGGTACCGCC
AGGCTCCAGGGAAGCAACGTGAAGTGGTCGCAACTATTAGTGCTACTGGTAGCATAA
GCTATGCAGACTCCGTGAAGGGCCGATTCACCATCTCCAGAGACAGTGCCAAGAACAC
GATGTATCTGCAACTGAACAGCCTGACACCTGAGGACACGGCCGTCTATTACTGTAAC
ACAATTTATAGGTCTACTCTCTACTGGGGCCAGGGGACCCAGGTCACCGTCTCCTCAG
GAGGACTGCCGGAAACCGGCGGCCACCACCATCACCATCAC (SEQ ID NO: 75)

FIG. 32

VHH52

CAGGTGCAGCTGCAGGAGTCAGGGGGAGGATTGGTGCAGGCTGGGGGCTCTCTGAGA
CTCACCTGTGCACTCTCTGAACGCACCAGTACCAGTTATGCACAGGGCTGGTTCCGCC
AGCCTCCAGGGAAAGAGCGTGAGTTTGTGGCGAGTCTTAGAACGCATGACGGCAACA
CACACTATACAGACTCCGTGAAGGGCCGATTCACCATCTCCAGAGACAACGCCGAGAA
CACGCTGTATCTGCAAATGAACAGCCTGAAAACTGAGGACACGGCCGTATATTATTG
TGCGGCATCCCTCGGTTACAGCGGTGCTTATGCGTCTGGGTATGACTACTGGGGCCAG
GGGACCCAGGTCACCGTCTCCTCAGGAGGACTGCCGGAAACCGGCGGCCACCACCATC
ACCATCAC (SEQ ID NO: 76)

VHH54

CAGGTGCAGCTGCAGGAGTCAGGGGGAGGATTGGTGCAGGCTGGGGGCTCTCTGAGA
CTCTCCTGTGCAGCCTCTGGACGCACCCTCAGTAGCTATGCCATGGGCTGGTTCCGCC
AGGCCCCAGGGAAGGAGCGTGAGTTAGTCTCAGCTATTAGCTGGAGTGGTCTTAGCA
CATACTATGAAGACTCCGTGAAGGGCCGATTCACCATCTCCAGAGACAACGCCAAGA
ACACGATGTATCTGCAAATGAACAGCCTGAAACCTGAGGACACGGCCATTTATTACT
GTGCAGCGGATATTGGGTGGCCCCTGCGGGCTGACTCTGGTTCCTGGGGCCAGGGGAC
CCAGGTCACCGTCTCCTCAGGAGGACTGCCGGAAACCGGCGGCCACCACCATCACCAT
CAC (SEQ ID NO: 77)

VHH62

CAGGTGCAGCTGCAGGAGTCAGGGGGAGGATTGGTGCAGCCTGGGGGGTCTCTGAGA
CTCTCCTGTGCAGCCTCTGGATTCACTTTGGATGGTTATGCCATAGGCTGGTTCCGCC
AGGCCCCAGGGAAGGAGCGTGAGGGGGTCTCATGTATTAGTAGTAGTGGTAAAAGCA
CAAACTATGCAGACTCCGTGAAGGGCCGATTCACCATCTCCAGAGACAACCAGCAGA
ACACGGTGTATCTGCAAATGAACAGCCTGAAACCTGAGGACACAGCCGTTTATTACT
GTGCAGCGACAGTTGGTTTATTTTGTGTTGGGGGGACCTACGGCATGGACTACTGGG
GCAAGGGGACCCAGGTCACCGTCTCCTCAGGAGGACTGCCGGAAACCGGCGGCCACCA
CCATCACCATCAC (SEQ ID NO: 78)

VHH68

CAGGTGCAGCTGCAGGAGTCAGGGGGAGGATTGGTGCAGGCTGGGGGCTCTCTGAGA
CTCTCCTGTGCAGTTCCTGGACGCACCTCCAATATCTTTGCCATGGGCTGGTTCCGCC
AGGCTCTAGGAAAGGAACGTGAGTTTGTAGCAGCAGTTACCTGGAGTTTAGGTAATA
CATACTACGCAGACTCCGTGAAGGGCCGATTCACCATCTCCAGAGACAACGCCAAGAA
CACAGTGTATCTGCAAATGAACAGCCTGAAACCTGAGGACACGGCCGTTTATTACTG
TGCAGCCGGGGAGGTAGGGCCTCTCCGGCAGCCGGATACGTATTTACACTGGGGCCAG
GGGACCCAGGTCACCGTCTCCTCAGGAGGACTGCCGGAAACCGGCGGCCACCACCATC
ACCATCAC (SEQ ID NO: 79)

SEQUENCE LISTING

```
<160> NUMBER OF SEQ ID NOS: 87

<210> SEQ ID NO 1
<211> LENGTH: 206
<212> TYPE: PRT
<213> ORGANISM: S. aureus

<400> SEQUENCE: 1

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Asn Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
            85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
            165                 170                 175

Lys Gln Leu Thr Leu Ile Thr Cys Asp Asp Tyr Asn Glu Lys Thr Gly
        180                 185                 190

Val Trp Glu Lys Arg Lys Ile Phe Val Ala Thr Glu Val Lys
    195                 200                 205

<210> SEQ ID NO 2
<211> LENGTH: 38
```

```
<212> TYPE: DNA
<213> ORGANISM: Artificial
<220> FEATURE:
<223> OTHER INFORMATION: forward primer
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t

<400> SEQUENCE: 2
cttgcggccg ctcagktgca gctcgtggag wcnggngg                              38

<210> SEQ ID NO 3
<211> LENGTH: 34
<212> TYPE: DNA
<213> ORGANISM: Artificial
<220> FEATURE:
<223> OTHER INFORMATION: reverse primer

<400> SEQUENCE: 3
gatcggcgcg ccgagggtc ttcgctgtgg tgcg                                   34

<210> SEQ ID NO 4
<211> LENGTH: 35
<212> TYPE: DNA
<213> ORGANISM: Artificial
<220> FEATURE:
<223> OTHER INFORMATION: reverse primer

<400> SEQUENCE: 4
gatcggcgcg ccggttgtgg ttttggtgtc ttggg                                 35

<210> SEQ ID NO 5
<211> LENGTH: 9
<212> TYPE: PRT
<213> ORGANISM: Unknown
<220> FEATURE:
<223> OTHER INFORMATION: tissue plasminogen activator chain A

<400> SEQUENCE: 5

Thr Thr Cys Cys Gly Leu Arg Gln Tyr
1               5

<210> SEQ ID NO 6
<211> LENGTH: 255
<212> TYPE: PRT
<213> ORGANISM: Unknown
<220> FEATURE:
<223> OTHER INFORMATION: Factor 1X chain A

<400> SEQUENCE: 6

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Glu Thr Thr Gly
        35                  40                  45

Val Lys Ile Thr Val Val Ala Gly Glu His Asn Ile Glu Glu Thr Glu
    50                  55                  60

His Thr Glu Gln Lys Arg Asn Val Ile Arg Ile Ile Pro His His Asn
65                  70                  75                  80
```

```
Tyr Asn Asn Asn Ala Ala Ala Ala Ala Ile Asn Lys Tyr Asn His
                85                  90                  95

Asp Ile Ala Leu Leu Glu Leu Asp Glu Pro Leu Val Leu Asn Ser Tyr
            100                 105                 110

Val Thr Pro Ile Cys Ile Ala Asp Lys Glu Tyr Thr Thr Thr Asn Asn
            115                 120                 125

Asn Ile Ile Ile Phe Leu Lys Phe Gly Ser Gly Tyr Val Ser Gly Trp
            130                 135                 140

Gly Arg Val Phe His Lys Gly Arg Ser Ala Leu Val Leu Gln Tyr Leu
145                 150                 155                 160

Arg Val Pro Leu Val Asp Arg Ala Thr Cys Leu Arg Ser Thr Lys Phe
                165                 170                 175

Thr Ile Tyr Asn Asn Met Phe Cys Ala Gly Gly Phe His Glu Gly
            180                 185                 190

Gly Gly Arg Arg Asp Ser Cys Gln Gly Asp Ser Gly Gly Pro His Val
            195                 200                 205

Thr Glu Val Glu Gly Thr Ser Phe Leu Thr Gly Ile Ile Ser Trp Gly
            210                 215                 220

Glu Glu Cys Ala Ala Met Met Lys Gly Lys Tyr Gly Ile Tyr Thr Lys
225                 230                 235                 240

Val Ser Arg Tyr Val Asn Trp Ile Lys Glu Lys Thr Lys Leu Thr
                245                 250                 255

<210> SEQ ID NO 7
<211> LENGTH: 57
<212> TYPE: PRT
<213> ORGANISM: Unknown
<220> FEATURE:
<223> OTHER INFORMATION: Factor 1X chain B

<400> SEQUENCE: 7

Met Thr Cys Asn Ile Lys Asn Gly Arg Cys Glu Gln Phe Cys Lys Asn
1               5                   10                  15

Ser Ala Asp Asn Lys Val Val Cys Ser Cys Thr Glu Gly Tyr Arg Leu
            20                  25                  30

Ala Glu Asn Gln Lys Ser Cys Glu Pro Ala Val Pro Phe Pro Cys Gly
            35                  40                  45

Arg Val Ser Val Ser Gln Thr Ser Lys
        50                  55

<210> SEQ ID NO 8
<211> LENGTH: 496
<212> TYPE: PRT
<213> ORGANISM: Unknown
<220> FEATURE:
<223> OTHER INFORMATION: Glucocerebrosidase

<400> SEQUENCE: 8

Glu Phe Ala Arg Pro Cys Ile Pro Lys Ser Phe Gly Tyr Ser Ser Val
1               5                   10                  15

Val Cys Val Cys Asn Ala Thr Tyr Cys Asp Ser Phe Asp Pro Pro Ala
            20                  25                  30

Leu Gly Thr Phe Ser Arg Tyr Glu Ser Thr Arg Ser Gly Arg Arg Met
            35                  40                  45

Glu Leu Ser Met Gly Pro Ile Gln Ala Asn His Thr Gly Thr Gly Leu
            50                  55                  60

Leu Leu Thr Leu Gln Pro Glu Gln Lys Phe Gln Lys Val Lys Gly Phe
65                  70                  75                  80
```

```
Gly Gly Ala Met Thr Asp Ala Ala Leu Asn Ile Leu Ala Leu Ser
                85                  90                  95

Pro Pro Ala Gln Asn Leu Leu Leu Lys Ser Tyr Phe Ser Glu Gly
            100                 105                 110

Ile Gly Tyr Asn Ile Ile Arg Val Pro Met Ala Ser Cys Asp Phe Ser
        115                 120                 125

Ile Arg Thr Tyr Thr Tyr Ala Asp Thr Pro Asp Asp Phe Gln Leu His
130                 135                 140

Asn Phe Ser Leu Pro Glu Glu Asp Thr Lys Leu Lys Ile Pro Leu Ile
145                 150                 155                 160

His Arg Ala Leu Gln Leu Ala Gln Arg Pro Val Ser Leu Leu Ala Ser
                165                 170                 175

Pro Trp Thr Ser Pro Thr Trp Leu Lys Thr Asn Gly Ala Val Asn Gly
            180                 185                 190

Lys Gly Ser Leu Lys Gly Gln Pro Gly Asp Ile Tyr His Gln Thr Trp
        195                 200                 205

Ala Arg Tyr Phe Val Lys Phe Leu Asp Ala Tyr Ala Glu His Lys Leu
        210                 215                 220

Gln Phe Trp Ala Val Thr Ala Glu Asn Glu Pro Ser Ala Gly Leu Leu
225                 230                 235                 240

Ser Gly Tyr Pro Phe Gln Cys Leu Gly Phe Thr Pro Glu His Gln Arg
                245                 250                 255

Asp Phe Ile Ala Arg Asp Leu Gly Pro Thr Leu Ala Asn Ser Thr His
            260                 265                 270

His Asn Val Arg Leu Leu Met Leu Asp Asp Gln Arg Leu Leu Leu Pro
        275                 280                 285

His Trp Ala Lys Val Val Leu Thr Asp Pro Glu Ala Ala Lys Tyr Val
        290                 295                 300

His Gly Ile Ala Val His Trp Tyr Leu Asp Phe Leu Ala Pro Ala Lys
305                 310                 315                 320

Ala Thr Leu Gly Glu Thr His Arg Leu Phe Pro Asn Thr Met Leu Phe
                325                 330                 335

Ala Ser Glu Ala Cys Val Gly Ser Lys Phe Trp Glu Gln Ser Val Arg
            340                 345                 350

Leu Gly Ser Trp Asp Arg Gly Met Gln Tyr Ser His Ser Ile Ile Thr
        355                 360                 365

Asn Leu Leu Tyr His Val Val Gly Trp Thr Asp Trp Asn Leu Ala Leu
370                 375                 380

Asn Pro Glu Gly Gly Pro Asn Trp Val Arg Asn Phe Val Asp Ser Pro
385                 390                 395                 400

Ile Ile Val Asp Ile Thr Lys Asp Thr Phe Tyr Lys Gln Pro Met Phe
                405                 410                 415

Tyr His Leu Gly His Phe Ser Lys Phe Ile Pro Glu Gly Ser Gln Arg
            420                 425                 430

Val Gly Leu Val Ala Ser Gln Lys Asn Asp Leu Asp Ala Val Ala Leu
        435                 440                 445

Met His Pro Asp Gly Ser Ala Val Val Val Leu Asn Arg Ser Ser
        450                 455                 460

Lys Asp Val Pro Leu Thr Ile Lys Asp Pro Ala Val Gly Phe Leu Glu
465                 470                 475                 480

Thr Ile Ser Pro Gly Tyr Ser Ile His Thr Tyr Leu Trp His Arg Gln
                485                 490                 495
```

```
<210> SEQ ID NO 9
<211> LENGTH: 390
<212> TYPE: PRT
<213> ORGANISM: Unknown
<220> FEATURE:
<223> OTHER INFORMATION: alpha galactosidase A

<400> SEQUENCE: 9

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Pro Asp Ser Cys
            20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365
```

```
Thr Ser Arg Leu Arg Ser His Ile Asn Pro Thr Gly Thr Val Leu Leu
    370                 375                 380

Gln Leu Glu Asn Thr Met
385                 390

<210> SEQ ID NO 10
<211> LENGTH: 479
<212> TYPE: PRT
<213> ORGANISM: Unknown
<220> FEATURE:
<223> OTHER INFORMATION: arylsulfatase-A (iduronidase, alpha-L-)

<400> SEQUENCE: 10

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
        35                  40                  45

Ser Leu Pro Ser Arg Ala Ala Leu Leu Thr Gly Arg Leu Pro Val Arg
    50                  55                  60

Met Gly Met Tyr Pro Gly Val Leu Val Pro Ser Ser Arg Gly Gly Leu
65                  70                  75                  80

Pro Leu Glu Glu Val Thr Val Ala Glu Val Leu Ala Ala Arg Gly Tyr
                85                  90                  95

Leu Thr Gly Met Ala Gly Lys Trp His Leu Gly Val Gly Pro Glu Gly
            100                 105                 110

Ala Phe Leu Pro Pro His Gln Gly Phe His Arg Phe Leu Gly Ile Pro
        115                 120                 125

Tyr Ser His Asp Gln Gly Pro Cys Gln Asn Leu Thr Cys Phe Pro Pro
130                 135                 140

Ala Thr Pro Cys Asp Gly Gly Cys Asp Gln Gly Leu Val Pro Ile Pro
145                 150                 155                 160

Leu Leu Ala Asn Leu Ser Val Glu Ala Gln Pro Pro Trp Leu Pro Gly
                165                 170                 175

Leu Glu Ala Arg Tyr Met Ala Phe Ala His Asp Leu Met Ala Asp Ala
            180                 185                 190

Gln Arg Gln Asp Arg Pro Phe Phe Leu Tyr Tyr Ala Ser His His Thr
        195                 200                 205

His Tyr Pro Gln Phe Ser Gly Gln Ser Phe Ala Glu Arg Ser Gly Arg
210                 215                 220

Gly Pro Phe Gly Asp Ser Leu Met Glu Leu Asp Ala Ala Val Gly Thr
225                 230                 235                 240

Leu Met Thr Ala Ile Gly Asp Leu Gly Leu Leu Glu Glu Thr Leu Val
                245                 250                 255

Ile Phe Thr Ala Asp Asn Gly Pro Glu Thr Met Arg Met Ser Arg Gly
            260                 265                 270

Gly Cys Ser Gly Leu Leu Arg Cys Gly Lys Gly Thr Thr Tyr Glu Gly
        275                 280                 285

Gly Val Arg Glu Pro Ala Leu Ala Phe Trp Pro Gly His Ile Ala Pro
290                 295                 300

Gly Val Thr His Glu Leu Ala Ser Ser Leu Asp Leu Leu Pro Thr Leu
305                 310                 315                 320

Ala Ala Leu Ala Gly Ala Pro Leu Pro Asn Val Thr Leu Asp Gly Phe
                325                 330                 335
```

```
Asp Leu Ser Pro Leu Leu Gly Thr Gly Lys Ser Pro Arg Gln Ser
            340                 345                 350

Leu Phe Phe Tyr Pro Ser Tyr Pro Asp Glu Val Arg Gly Val Phe Ala
            355                 360                 365

Val Arg Thr Gly Lys Tyr Lys Ala His Phe Phe Thr Gln Gly Ser Ala
    370                 375                 380

His Ser Asp Thr Thr Ala Asp Pro Ala Cys His Ala Ser Ser Ser Leu
385                 390                 395                 400

Thr Ala His Glu Pro Pro Leu Leu Tyr Asp Leu Ser Lys Asp Pro Gly
            405                 410                 415

Glu Asn Tyr Asn Leu Leu Gly Ala Thr Pro Glu Val Leu Gln Ala Leu
            420                 425                 430

Lys Gln Leu Gln Leu Leu Lys Ala Gln Leu Asp Ala Ala Val Thr Phe
            435                 440                 445

Gly Pro Ser Gln Val Ala Arg Gly Glu Asp Pro Ala Leu Gln Ile Cys
            450                 455                 460

Cys His Pro Gly Cys Thr Pro Arg Pro Ala Cys Cys His Cys Pro
465                 470                 475

<210> SEQ ID NO 11
<211> LENGTH: 474
<212> TYPE: PRT
<213> ORGANISM: Unknown
<220> FEATURE:
<223> OTHER INFORMATION: arylsulfatase B (N-acetylgalactos-amine-4-
      sulfatase) (1fsu)

<400> SEQUENCE: 11

Ser Arg Pro Pro His Leu Val Phe Leu Leu Ala Asp Asp Leu Gly Trp
1               5                   10                  15

Asn Asp Val Gly Phe His Gly Ser Arg Ile Arg Thr Pro His Leu Asp
            20                  25                  30

Ala Leu Ala Ala Gly Gly Val Leu Leu Asp Asn Tyr Tyr Thr Gln Pro
        35                  40                  45

Leu Thr Pro Ser Arg Ser Gln Leu Leu Thr Gly Arg Tyr Gln Ile Arg
    50                  55                  60

Thr Gly Leu Gln His Gln Ile Ile Trp Pro Cys Gln Pro Ser Cys Val
65                  70                  75                  80

Pro Leu Asp Glu Lys Leu Leu Pro Gln Leu Leu Lys Glu Ala Gly Tyr
                85                  90                  95

Thr Thr His Met Val Gly Lys Trp His Leu Gly Met Tyr Arg Lys Glu
            100                 105                 110

Cys Leu Pro Thr Arg Arg Gly Phe Asp Thr Tyr Phe Gly Tyr Leu Leu
        115                 120                 125

Gly Ser Glu Asp Tyr Tyr Ser His Glu Arg Cys Thr Leu Ile Asp Ala
    130                 135                 140

Leu Asn Val Thr Arg Cys Ala Leu Asp Phe Arg Asp Gly Glu Glu Val
145                 150                 155                 160

Ala Thr Gly Tyr Lys Asn Met Tyr Ser Thr Asn Ile Phe Thr Lys Arg
                165                 170                 175

Ala Ile Ala Leu Ile Thr Asn His Pro Pro Glu Lys Pro Leu Phe Leu
            180                 185                 190

Tyr Leu Ala Leu Gln Ser Val His Glu Pro Leu Gln Val Pro Glu Glu
        195                 200                 205

Tyr Leu Lys Pro Tyr Asp Phe Ile Gln Asp Lys Asn Arg His His Tyr
    210                 215                 220
```

```
Ala Gly Met Val Ser Leu Met Asp Glu Ala Val Gly Asn Val Thr Ala
225                 230                 235                 240

Ala Leu Lys Ser Ser Gly Leu Trp Asn Asn Thr Val Phe Ile Phe Ser
            245                 250                 255

Thr Asp Asn Gly Gly Gln Thr Leu Ala Gly Gly Asn Asn Trp Pro Leu
        260                 265                 270

Arg Gly Arg Lys Trp Ser Leu Trp Glu Gly Val Arg Gly Val Gly
    275                 280                 285

Phe Val Ala Ser Pro Leu Leu Lys Gln Lys Gly Val Lys Asn Arg Glu
290                 295                 300

Leu Ile His Ile Ser Asp Trp Leu Pro Thr Leu Val Lys Leu Ala Arg
305                 310                 315                 320

Gly His Thr Asn Gly Thr Lys Pro Leu Asp Gly Phe Asp Val Trp Lys
                325                 330                 335

Thr Ile Ser Glu Gly Ser Pro Ser Pro Arg Ile Glu Leu Leu His Asn
                340                 345                 350

Ile Asp Pro Asn Phe Val Asp Ser Ser Pro Cys Ser Ala Phe Asn Thr
            355                 360                 365

Ser Val His Ala Ala Ile Arg His Gly Asn Trp Lys Leu Leu Thr Gly
        370                 375                 380

Tyr Pro Gly Cys Gly Tyr Trp Phe Pro Pro Ser Gln Tyr Asn Val
385                 390                 395                 400

Ser Glu Ile Pro Ser Ser Asp Pro Pro Thr Lys Thr Leu Trp Leu Phe
                405                 410                 415

Asp Ile Asp Arg Asp Pro Glu Glu Arg His Asp Leu Ser Arg Glu Tyr
            420                 425                 430

Pro His Ile Val Thr Lys Leu Leu Ser Arg Leu Gln Phe Tyr His Lys
        435                 440                 445

His Ser Val Pro Val Tyr Phe Pro Ala Gln Asp Pro Arg Cys Asp Pro
    450                 455                 460

Lys Ala Thr Gly Val Trp Gly Pro Trp Met
465                 470

<210> SEQ ID NO 12
<211> LENGTH: 492
<212> TYPE: PRT
<213> ORGANISM: Unknown
<220> FEATURE:
<223> OTHER INFORMATION: beta-hexosaminidase A (2gjx)

<400> SEQUENCE: 12

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
                20                  25                  30

Gln Pro Gly Cys Ser Val Leu Asp Glu Ala Phe Gln Arg Tyr Arg Asp
            35                  40                  45

Leu Leu Phe Gly Thr Leu Glu Lys Asn Val Leu Val Ser Val Val
        50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
                100                 105                 110
```

-continued

Ser Ala Glu Gly Thr Phe Phe Ile Asn Lys Thr Glu Ile Glu Asp Phe
        115                 120                 125

Pro Arg Phe Pro His Arg Gly Leu Leu Asp Thr Ser Arg His Tyr
130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190

Pro Val Thr His Ile Tyr Thr Ala Gln Asp Val Lys Glu Val Ile Glu
        195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
        275                 280                 285

Asp Phe Thr Cys Trp Lys Ser Asn Pro Glu Ile Gln Asp Phe Met Arg
290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335

Trp Gln Glu Val Phe Asp Asn Lys Val Lys Ile Gln Pro Asp Thr Ile
            340                 345                 350

Ile Gln Val Trp Arg Glu Asp Ile Pro Val Asn Tyr Met Lys Glu Leu
        355                 360                 365

Glu Leu Val Thr Lys Ala Gly Phe Arg Ala Leu Leu Ser Ala Pro Trp
370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
            420                 425                 430

Leu Val Pro Arg Leu Trp Pro Arg Ala Gly Ala Val Ala Glu Arg Leu
        435                 440                 445

Trp Ser Asn Lys Leu Thr Ser Asp Leu Thr Phe Ala Tyr Glu Arg Leu
450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 13
<211> LENGTH: 492
<212> TYPE: PRT
<213> ORGANISM: Unknown
<220> FEATURE:

<223> OTHER INFORMATION: Hexosaminidase A and B chain A

<400> SEQUENCE: 13

```
Leu Trp Pro Trp Pro Gln Asn Phe Gln Thr Ser Asp Gln Arg Tyr Val
1               5                   10                  15
Leu Tyr Pro Asn Asn Phe Gln Phe Gln Tyr Asp Val Ser Ser Ala Ala
            20                  25                  30
Gln Pro Gly Cys Ser Val Leu Asp Glu Ala Phe Gln Arg Tyr Arg Asp
        35                  40                  45
Leu Leu Phe Gly Thr Leu Glu Lys Asn Val Leu Val Val Ser Val Val
50                  55                  60
Thr Pro Gly Cys Asn Gln Leu Pro Thr Leu Glu Ser Val Glu Asn Tyr
65                  70                  75                  80
Thr Leu Thr Ile Asn Asp Asp Gln Cys Leu Leu Leu Ser Glu Thr Val
                85                  90                  95
Trp Gly Ala Leu Arg Gly Leu Glu Thr Phe Ser Gln Leu Val Trp Lys
            100                 105                 110
Ser Ala Glu Gly Thr Phe Phe Ile Asn Lys Thr Glu Ile Glu Asp Phe
        115                 120                 125
Pro Arg Phe Pro His Arg Gly Leu Leu Leu Asp Thr Ser Arg His Tyr
130                 135                 140
Leu Pro Leu Ser Ser Ile Leu Asp Thr Leu Asp Val Met Ala Tyr Asn
145                 150                 155                 160
Lys Leu Asn Val Phe His Trp His Leu Val Asp Asp Pro Ser Phe Pro
                165                 170                 175
Tyr Glu Ser Phe Thr Phe Pro Glu Leu Met Arg Lys Gly Ser Tyr Asn
            180                 185                 190
Pro Val Thr His Ile Tyr Thr Ala Gln Asp Val Lys Glu Val Ile Glu
        195                 200                 205
Tyr Ala Arg Leu Arg Gly Ile Arg Val Leu Ala Glu Phe Asp Thr Pro
210                 215                 220
Gly His Thr Leu Ser Trp Gly Pro Gly Ile Pro Gly Leu Leu Thr Pro
225                 230                 235                 240
Cys Tyr Ser Gly Ser Glu Pro Ser Gly Thr Phe Gly Pro Val Asn Pro
                245                 250                 255
Ser Leu Asn Asn Thr Tyr Glu Phe Met Ser Thr Phe Phe Leu Glu Val
            260                 265                 270
Ser Ser Val Phe Pro Asp Phe Tyr Leu His Leu Gly Gly Asp Glu Val
        275                 280                 285
Asp Phe Thr Cys Trp Lys Ser Asn Pro Glu Ile Gln Asp Phe Met Arg
290                 295                 300
Lys Lys Gly Phe Gly Glu Asp Phe Lys Gln Leu Glu Ser Phe Tyr Ile
305                 310                 315                 320
Gln Thr Leu Leu Asp Ile Val Ser Ser Tyr Gly Lys Gly Tyr Val Val
                325                 330                 335
Trp Gln Glu Val Phe Asp Asn Lys Val Lys Ile Gln Pro Asp Thr Ile
            340                 345                 350
Ile Gln Val Trp Arg Glu Asp Ile Pro Val Asn Tyr Met Lys Glu Leu
        355                 360                 365
Glu Leu Val Thr Lys Ala Gly Phe Arg Ala Leu Leu Ser Ala Pro Trp
370                 375                 380
Tyr Leu Asn Arg Ile Ser Tyr Gly Pro Asp Trp Lys Asp Phe Tyr Val
385                 390                 395                 400
```

-continued

```
Val Glu Pro Leu Ala Phe Glu Gly Thr Pro Glu Gln Lys Ala Leu Val
                405                 410                 415
Ile Gly Glu Ala Cys Met Trp Gly Glu Tyr Val Asp Asn Thr Asn
            420                 425                 430
Leu Val Pro Arg Leu Trp Pro Arg Ala Gly Val Ala Glu Arg Leu
                435                 440                 445
Trp Ser Asn Lys Leu Thr Ser Asp Leu Thr Phe Ala Tyr Glu Arg Leu
450                 455                 460
Ser His Phe Arg Cys Glu Leu Leu Arg Arg Gly Val Gln Ala Gln Pro
465                 470                 475                 480
Leu Asn Val Gly Phe Cys Glu Gln Glu Phe Glu Gln
                485                 490

<210> SEQ ID NO 14
<211> LENGTH: 480
<212> TYPE: PRT
<213> ORGANISM: Unknown
<220> FEATURE:
<223> OTHER INFORMATION: Hexosaminidase A and B chain B

<400> SEQUENCE: 14

Pro Ala Leu Trp Pro Leu Pro Leu Ser Val Lys Met Thr Pro Asn Leu
1               5                   10                  15
Leu His Leu Ala Pro Glu Asn Phe Tyr Ile Ser His Ser Pro Asn Ser
                20                  25                  30
Thr Ala Gly Pro Ser Cys Thr Leu Leu Glu Glu Ala Phe Arg Arg Tyr
            35                  40                  45
His Gly Tyr Ile Phe Gly Thr Gln Val Gln Gln Leu Leu Val Ser Ile
    50                  55                  60
Thr Leu Gln Ser Glu Cys Asp Ala Phe Pro Asn Ile Ser Ser Asp Glu
65                  70                  75                  80
Ser Tyr Thr Leu Leu Val Lys Glu Pro Val Ala Val Leu Lys Ala Asn
                85                  90                  95
Arg Val Trp Gly Ala Leu Arg Gly Leu Glu Thr Phe Ser Gln Leu Val
                100                 105                 110
Tyr Gln Asp Ser Tyr Gly Thr Phe Thr Ile Asn Glu Ser Thr Ile Ile
            115                 120                 125
Asp Ser Pro Arg Phe Ser His Arg Gly Ile Leu Ile Asp Thr Ser Arg
130                 135                 140
His Tyr Leu Pro Val Lys Ile Ile Leu Lys Thr Leu Asp Ala Met Ala
145                 150                 155                 160
Phe Asn Lys Phe Asn Val Leu His Trp His Ile Val Asp Asp Gln Ser
                165                 170                 175
Phe Pro Tyr Gln Ser Ile Thr Phe Pro Glu Leu Ser Asn Lys Gly Ser
            180                 185                 190
Tyr Ser Leu Ser His Val Tyr Thr Pro Asn Asp Val Arg Met Val Ile
        195                 200                 205
Glu Tyr Ala Arg Leu Arg Gly Ile Arg Val Leu Pro Glu Phe Asp Thr
    210                 215                 220
Pro Gly His Thr Leu Ser Trp Gly Lys Gly Gln Lys Asp Leu Leu Thr
225                 230                 235                 240
Pro Cys Tyr Ser Asp Ser Phe Gly Pro Ile Asn Pro Thr Leu Asn Thr
                245                 250                 255
Thr Tyr Ser Phe Leu Thr Thr Phe Phe Lys Glu Ile Ser Glu Val Phe
            260                 265                 270
```

```
Pro Asp Gln Phe Ile His Leu Gly Gly Asp Glu Val Glu Phe Lys Cys
            275                 280                 285

Trp Glu Ser Asn Pro Lys Ile Gln Asp Phe Met Arg Gln Lys Gly Phe
290                 295                 300

Gly Thr Asp Phe Lys Lys Leu Glu Ser Phe Tyr Ile Gln Lys Val Leu
305                 310                 315                 320

Asp Ile Ile Ala Thr Ile Asn Lys Gly Ser Ile Val Trp Gln Glu Val
            325                 330                 335

Phe Asp Asp Lys Ala Lys Leu Ala Pro Gly Thr Ile Val Glu Val Trp
            340                 345                 350

Lys Asp Ser Ala Tyr Pro Glu Glu Leu Ser Arg Val Thr Ala Ser Gly
            355                 360                 365

Phe Pro Val Ile Leu Ser Ala Pro Trp Tyr Leu Asp Leu Ile Ser Tyr
370                 375                 380

Gly Gln Asp Trp Arg Lys Tyr Tyr Lys Val Glu Pro Leu Asp Phe Gly
385                 390                 395                 400

Gly Thr Gln Lys Gln Lys Gln Leu Phe Ile Gly Gly Glu Ala Cys Leu
            405                 410                 415

Trp Gly Glu Tyr Val Asp Ala Thr Asn Leu Thr Pro Arg Leu Trp Pro
            420                 425                 430

Arg Ala Ser Ala Val Gly Glu Arg Leu Trp Ser Ser Lys Asp Val Arg
435                 440                 445

Asp Met Asp Asp Ala Tyr Asp Arg Leu Thr Arg His Arg Cys Arg Met
            450                 455                 460

Val Glu Arg Gly Ile Ala Ala Gln Pro Leu Tyr Ala Gly Tyr Cys Asn
465                 470                 475                 480

<210> SEQ ID NO 15
<211> LENGTH: 481
<212> TYPE: PRT
<213> ORGANISM: Unknown
<220> FEATURE:
<223> OTHER INFORMATION: Hexosaminidase A and B chain C

<400> SEQUENCE: 15

Pro Ala Leu Trp Pro Leu Pro Leu Ser Val Lys Met Thr Pro Asn Leu
1               5                   10                  15

Leu His Leu Ala Pro Glu Asn Phe Tyr Ile Ser His Ser Pro Asn Ser
            20                  25                  30

Thr Ala Gly Pro Ser Cys Thr Leu Leu Glu Glu Ala Phe Arg Arg Tyr
            35                  40                  45

His Gly Tyr Ile Phe Gly Thr Gln Val Gln Gln Leu Leu Val Ser Ile
50                  55                  60

Thr Leu Gln Ser Glu Cys Asp Ala Phe Pro Asn Ile Ser Ser Asp Glu
65                  70                  75                  80

Ser Tyr Thr Leu Leu Val Lys Glu Pro Val Ala Val Leu Lys Ala Asn
            85                  90                  95

Arg Val Trp Gly Ala Leu Arg Gly Leu Glu Thr Phe Ser Gln Leu Val
            100                 105                 110

Tyr Gln Asp Ser Tyr Gly Thr Phe Thr Ile Asn Glu Ser Thr Ile Ile
            115                 120                 125

Asp Ser Pro Arg Phe Ser His Arg Gly Ile Leu Ile Asp Thr Ser Arg
            130                 135                 140

His Tyr Leu Pro Val Lys Ile Ile Leu Lys Thr Leu Asp Ala Met Ala
145                 150                 155                 160
```

```
Phe Asn Lys Phe Asn Val Leu His Trp His Ile Val Asp Asp Gln Ser
            165                 170                 175
Phe Pro Tyr Gln Ser Ile Thr Phe Pro Glu Leu Ser Asn Lys Gly Ser
        180                 185                 190
Tyr Ser Leu Ser His Val Tyr Thr Pro Asn Asp Val Arg Met Val Ile
            195                 200                 205
Glu Tyr Ala Arg Leu Arg Gly Ile Arg Val Leu Pro Glu Phe Asp Thr
        210                 215                 220
Pro Gly His Thr Leu Ser Trp Gly Lys Gly Gln Lys Asp Leu Leu Thr
225                 230                 235                 240
Pro Cys Tyr Ser Leu Asp Ser Phe Gly Pro Ile Asn Pro Thr Leu Asn
            245                 250                 255
Thr Thr Tyr Ser Phe Leu Thr Thr Phe Phe Lys Glu Ile Ser Glu Val
            260                 265                 270
Phe Pro Asp Gln Phe Ile His Leu Gly Gly Asp Glu Val Glu Phe Lys
        275                 280                 285
Cys Trp Glu Ser Asn Pro Lys Ile Gln Asp Phe Met Arg Gln Lys Gly
        290                 295                 300
Phe Gly Thr Asp Phe Lys Lys Leu Glu Ser Phe Tyr Ile Gln Lys Val
305                 310                 315                 320
Leu Asp Ile Ile Ala Thr Ile Asn Lys Gly Ser Ile Val Trp Gln Glu
            325                 330                 335
Val Phe Asp Asp Lys Ala Lys Leu Ala Pro Gly Thr Ile Val Glu Val
            340                 345                 350
Trp Lys Asp Ser Ala Tyr Pro Glu Glu Leu Ser Arg Val Thr Ala Ser
            355                 360                 365
Gly Phe Pro Val Ile Leu Ser Ala Pro Trp Tyr Leu Asp Leu Ile Ser
        370                 375                 380
Tyr Gly Gln Asp Trp Arg Lys Tyr Tyr Lys Val Glu Pro Leu Asp Phe
385                 390                 395                 400
Gly Gly Thr Gln Lys Gln Lys Gln Leu Phe Ile Gly Gly Glu Ala Cys
            405                 410                 415
Leu Trp Gly Glu Tyr Val Asp Ala Thr Asn Leu Thr Pro Arg Leu Trp
        420                 425                 430
Pro Arg Ala Ser Ala Val Gly Glu Arg Leu Trp Ser Ser Lys Asp Val
            435                 440                 445
Arg Asp Met Asp Asp Ala Tyr Asp Arg Leu Thr Arg His Arg Cys Arg
        450                 455                 460
Met Val Glu Arg Gly Ile Ala Ala Gln Pro Leu Tyr Ala Gly Tyr Cys
465                 470                 475                 480
Asn

<210> SEQ ID NO 16
<211> LENGTH: 492
<212> TYPE: PRT
<213> ORGANISM: Unknown
<220> FEATURE:
<223> OTHER INFORMATION: Hexosaminidase A and B chain D

<400> SEQUENCE: 16

Leu Trp Pro Trp Pro Gln Asn Phe Gln Thr Ser Asp Gln Arg Tyr Val
1               5                   10                  15
Leu Tyr Pro Asn Asn Phe Gln Phe Gln Tyr Asp Val Ser Ser Ala Ala
            20                  25                  30
Gln Pro Gly Cys Ser Val Leu Asp Glu Ala Phe Gln Arg Tyr Arg Asp
```

```
              35                  40                  45
Leu Leu Phe Gly Thr Leu Glu Lys Asn Val Leu Val Ser Val Val
 50                  55                  60

Thr Pro Gly Cys Asn Gln Leu Pro Thr Leu Glu Ser Val Glu Asn Tyr
 65                  70                  75                  80

Thr Leu Thr Ile Asn Asp Asp Gln Cys Leu Leu Ser Glu Thr Val
                 85                  90                  95

Trp Gly Ala Leu Arg Gly Leu Glu Thr Phe Ser Gln Leu Val Trp Lys
                100                 105                 110

Ser Ala Glu Gly Thr Phe Phe Ile Asn Lys Thr Glu Ile Glu Asp Phe
                115                 120                 125

Pro Arg Phe Pro His Arg Gly Leu Leu Leu Asp Thr Ser Arg His Tyr
            130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                    165                 170                 175

Tyr Glu Ser Phe Thr Phe Pro Glu Leu Met Arg Lys Gly Ser Tyr Asn
                180                 185                 190

Pro Val Thr His Ile Tyr Thr Ala Gln Asp Val Lys Glu Val Ile Glu
                195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                    245                 250                 255

Ser Leu Asn Asn Thr Tyr Glu Phe Met Ser Thr Phe Phe Leu Glu Val
                260                 265                 270

Ser Ser Val Phe Pro Asp Phe Tyr Leu His Leu Gly Gly Asp Glu Val
            275                 280                 285

Asp Phe Thr Cys Trp Lys Ser Asn Pro Glu Ile Gln Asp Phe Met Arg
            290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                    325                 330                 335

Trp Gln Glu Val Phe Asp Asn Lys Val Lys Ile Gln Pro Asp Thr Ile
                340                 345                 350

Ile Gln Val Trp Arg Glu Asp Ile Pro Val Asn Tyr Met Lys Glu Leu
            355                 360                 365

Glu Leu Val Thr Lys Ala Gly Phe Arg Ala Leu Leu Ser Ala Pro Trp
            370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                    405                 410                 415

Ile Gly Gly Glu Ala Cys Met Trp Gly Glu Tyr Val Asp Asn Thr Asn
                420                 425                 430

Leu Val Pro Arg Leu Trp Pro Arg Ala Gly Ala Val Ala Glu Arg Leu
            435                 440                 445

Trp Ser Asn Lys Leu Thr Ser Asp Leu Thr Phe Ala Tyr Glu Arg Leu
            450                 455                 460
```

```
Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 17
<211> LENGTH: 307
<212> TYPE: PRT
<213> ORGANISM: Unknown
<220> FEATURE:
<223> OTHER INFORMATION: phenylalanine hydroxylase (PAH) (1j8u)

<400> SEQUENCE: 17

Val Pro Trp Phe Pro Arg Thr Ile Gln Glu Leu Asp Arg Phe Ala Asn
1               5                   10                  15

Gln Ile Leu Ser Tyr Gly Ala Glu Leu Asp Ala Asp His Pro Gly Phe
            20                  25                  30

Lys Asp Pro Val Tyr Arg Ala Arg Arg Lys Gln Phe Ala Asp Ile Ala
        35                  40                  45

Tyr Asn Tyr Arg His Gly Gln Pro Ile Pro Arg Val Glu Tyr Met Glu
    50                  55                  60

Glu Glu Lys Lys Thr Trp Gly Thr Val Phe Lys Thr Leu Lys Ser Leu
65                  70                  75                  80

Tyr Lys Thr His Ala Cys Tyr Glu Tyr Asn His Ile Phe Pro Leu Leu
                85                  90                  95

Glu Lys Tyr Cys Gly Phe His Glu Asp Asn Ile Pro Gln Leu Glu Asp
            100                 105                 110

Val Ser Gln Phe Leu Gln Thr Cys Thr Gly Phe Arg Leu Arg Pro Val
        115                 120                 125

Ala Gly Leu Leu Ser Ser Arg Asp Phe Leu Gly Gly Leu Ala Phe Arg
    130                 135                 140

Val Phe His Cys Thr Gln Tyr Ile Arg His Gly Ser Lys Pro Met Tyr
145                 150                 155                 160

Thr Pro Glu Pro Asp Ile Cys His Glu Leu Leu Gly His Val Pro Leu
                165                 170                 175

Phe Ser Asp Arg Ser Phe Ala Gln Phe Ser Gln Glu Ile Gly Leu Ala
            180                 185                 190

Ser Leu Gly Ala Pro Asp Glu Tyr Ile Glu Lys Leu Ala Thr Ile Tyr
        195                 200                 205

Trp Phe Thr Val Glu Phe Gly Leu Cys Lys Gln Gly Asp Ser Ile Lys
    210                 215                 220

Ala Tyr Gly Ala Gly Leu Leu Ser Ser Phe Gly Glu Leu Gln Tyr Cys
225                 230                 235                 240

Leu Ser Glu Lys Pro Lys Leu Leu Pro Leu Glu Leu Glu Lys Thr Ala
                245                 250                 255

Ile Gln Asn Tyr Thr Val Thr Glu Phe Gln Pro Leu Tyr Tyr Val Ala
            260                 265                 270

Glu Ser Phe Asn Asp Ala Lys Glu Lys Val Arg Asn Phe Ala Ala Thr
        275                 280                 285

Ile Pro Arg Pro Phe Ser Val Arg Tyr Asp Pro Tyr Thr Gln Arg Ile
    290                 295                 300

Glu Val Leu
305

<210> SEQ ID NO 18
```

```
<211> LENGTH: 452
<212> TYPE: PRT
<213> ORGANISM: Unknown
<220> FEATURE:
<223> OTHER INFORMATION: Cathepsin A

<400> SEQUENCE: 18

Ala Pro Asp Gln Asp Glu Ile Gln Arg Leu Pro Gly Leu Ala Lys Gln
1               5                   10                  15

Pro Ser Phe Arg Gln Tyr Ser Gly Tyr Leu Lys Ser Ser Gly Ser Lys
            20                  25                  30

His Leu His Tyr Trp Phe Val Glu Ser Gln Lys Asp Pro Glu Asn Ser
        35                  40                  45

Pro Val Val Leu Trp Leu Asn Gly Gly Pro Gly Cys Ser Ser Leu Asp
    50                  55                  60

Gly Leu Leu Thr Glu His Gly Pro Phe Leu Val Gln Pro Asp Gly Val
65                  70                  75                  80

Thr Leu Glu Tyr Asn Pro Tyr Ser Trp Asn Leu Ile Ala Asn Val Leu
                85                  90                  95

Tyr Leu Glu Ser Pro Ala Gly Val Gly Phe Ser Tyr Ser Asp Asp Lys
            100                 105                 110

Phe Tyr Ala Thr Asn Asp Thr Glu Val Ala Gln Ser Asn Phe Glu Ala
        115                 120                 125

Leu Gln Asp Phe Phe Arg Leu Phe Pro Glu Tyr Lys Asn Asn Lys Leu
    130                 135                 140

Phe Leu Thr Gly Glu Ser Tyr Ala Gly Ile Tyr Ile Pro Thr Leu Ala
145                 150                 155                 160

Val Leu Val Met Gln Asp Pro Ser Met Asn Leu Gln Gly Leu Ala Val
                165                 170                 175

Gly Asn Gly Leu Ser Ser Tyr Glu Gln Asn Asp Asn Ser Leu Val Tyr
            180                 185                 190

Phe Ala Tyr Tyr His Gly Leu Leu Gly Asn Arg Leu Trp Ser Ser Leu
        195                 200                 205

Gln Thr His Cys Cys Ser Gln Asn Lys Cys Asn Phe Tyr Asp Asn Lys
    210                 215                 220

Asp Leu Glu Cys Val Thr Asn Leu Gln Glu Val Ala Arg Ile Val Gly
225                 230                 235                 240

Asn Ser Gly Leu Asn Ile Tyr Asn Leu Tyr Ala Pro Cys Ala Gly Gly
                245                 250                 255

Val Pro Ser His Phe Arg Tyr Glu Lys Asp Thr Val Val Gln Asp
            260                 265                 270

Leu Gly Asn Ile Phe Thr Arg Leu Pro Leu Lys Arg Met Trp His Gln
    275                 280                 285

Ala Leu Leu Arg Ser Gly Asp Lys Val Arg Met Asp Pro Pro Cys Thr
    290                 295                 300

Asn Thr Thr Ala Ala Ser Thr Tyr Leu Asn Asn Pro Tyr Val Arg Lys
305                 310                 315                 320

Ala Leu Asn Ile Pro Glu Gln Leu Pro Gln Trp Asp Met Cys Asn Phe
                325                 330                 335

Leu Val Asn Leu Gln Tyr Arg Arg Leu Tyr Arg Ser Met Asn Ser Gln
            340                 345                 350

Tyr Leu Lys Leu Leu Ser Ser Gln Lys Tyr Gln Ile Leu Leu Tyr Asn
        355                 360                 365

Gly Asp Val Asp Met Ala Cys Asn Phe Met Gly Asp Glu Trp Phe Val
    370                 375                 380
```

```
Asp Ser Leu Asn Gln Lys Met Glu Val Gln Arg Arg Pro Trp Leu Val
385                 390                 395                 400

Lys Tyr Gly Asp Ser Gly Glu Gln Ile Ala Gly Phe Val Lys Glu Phe
            405                 410                 415

Ser His Ile Ala Phe Leu Thr Ile Lys Gly Ala Gly His Met Val Pro
            420                 425                 430

Thr Asp Lys Pro Leu Ala Ala Phe Thr Met Phe Ser Arg Phe Leu Asn
            435                 440                 445

Lys Gln Pro Tyr
    450

<210> SEQ ID NO 19
<211> LENGTH: 145
<212> TYPE: PRT
<213> ORGANISM: Unknown
<220> FEATURE:
<223> OTHER INFORMATION: G-CSF

<400> SEQUENCE: 19

Leu Pro Gln Ser Phe Leu Leu Lys Cys Leu Glu Gln Val Arg Lys Ile
1               5                   10                  15

Gln Gly Asp Gly Ala Ala Leu Gln Glu Lys Leu Cys Ala Thr Tyr Lys
            20                  25                  30

Leu Cys His Pro Glu Glu Leu Val Leu Leu Gly His Ser Leu Gly Ile
        35                  40                  45

Pro Trp Ala Pro Leu Leu Ala Gly Cys Leu Ser Gln Leu His Ser Gly
    50                  55                  60

Leu Phe Leu Tyr Gln Gly Leu Leu Gln Ala Leu Glu Gly Ile Ser Pro
65                  70                  75                  80

Glu Leu Gly Pro Thr Leu Asp Thr Leu Gln Leu Asp Val Ala Asp Phe
                85                  90                  95

Ala Thr Thr Ile Trp Gln Gln Met Glu Glu Leu Gly Met Met Pro Ala
            100                 105                 110

Phe Ala Ser Ala Phe Gln Arg Arg Ala Gly Gly Val Leu Val Ala Ser
        115                 120                 125

His Leu Gln Ser Phe Leu Glu Val Ser Tyr Arg Val Leu Arg His Leu
    130                 135                 140

Ala
145

<210> SEQ ID NO 20
<211> LENGTH: 105
<212> TYPE: PRT
<213> ORGANISM: Unknown
<220> FEATURE:
<223> OTHER INFORMATION: GM-CSF

<400> SEQUENCE: 20

Glu His Val Asn Ala Ile Gln Glu Ala Arg Arg Leu Leu Asn Leu Ser
1               5                   10                  15

Arg Asp Thr Ala Ala Glu Met Asn Glu Thr Val Glu Val Ile Ser Glu
            20                  25                  30

Met Phe Asp Leu Gln Glu Pro Thr Cys Leu Gln Thr Arg Leu Glu Leu
        35                  40                  45

Tyr Lys Gln Gly Leu Arg Gly Ser Leu Thr Lys Leu Lys Gly Pro Leu
    50                  55                  60

Thr Met Met Ala Ser His Tyr Lys Gln His Cys Pro Pro Thr Pro Glu
```

-continued

```
                65                  70                  75                  80
Thr Ser Cys Ala Thr Gln Ile Ile Thr Phe Glu Ser Phe Lys Glu Asn
                    85                  90                  95
Leu Lys Asp Phe Leu Leu Val Ile Pro
                100                 105

<210> SEQ ID NO 21
<211> LENGTH: 165
<212> TYPE: PRT
<213> ORGANISM: Unknown
<220> FEATURE:
<223> OTHER INFORMATION: Interferon alfa-2

<400> SEQUENCE: 21

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 22
<211> LENGTH: 166
<212> TYPE: PRT
<213> ORGANISM: Unknown
<220> FEATURE:
<223> OTHER INFORMATION: Interferon beta-1

<400> SEQUENCE: 22

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95
```

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 23
<211> LENGTH: 242
<212> TYPE: PRT
<213> ORGANISM: Unknown
<220> FEATURE:
<223> OTHER INFORMATION: Interferon gamma-1b

<400> SEQUENCE: 23

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
            20                  25                  30

Ile Leu Lys Asn Trp Lys Glu Glu Ser Asp Arg Lys Ile Met Gln Ser
        35                  40                  45

Gln Ile Val Ser Phe Tyr Phe Lys Leu Phe Lys Asn Phe Lys Asp Asp
    50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Lys Arg Asp Asp Phe Glu Lys Leu
                85                  90                  95

Thr Asn Tyr Ser Val Thr Asp Leu Asn Val Gln Arg Lys Ala Ile Asp
            100                 105                 110

Glu Leu Ile Gln Val Met Ala Glu Leu Gly Ala Asn Val Ser Gly Glu
        115                 120                 125

Phe Val Lys Glu Ala Glu Asn Leu Lys Lys Tyr Phe Asn Asp Asn Gly
    130                 135                 140

Thr Leu Phe Leu Gly Ile Leu Lys Asn Trp Lys Glu Glu Ser Asp Arg
145                 150                 155                 160

Lys Ile Met Gln Ser Gln Ile Val Ser Phe Tyr Phe Lys Leu Phe Lys
                165                 170                 175

Asn Phe Lys Asp Asp Gln Ser Ile Gln Lys Ser Val Glu Thr Ile Lys
            180                 185                 190

Glu Asp Met Asn Val Lys Phe Phe Asn Ser Asn Lys Lys Lys Arg Asp
        195                 200                 205

Asp Phe Glu Lys Leu Thr Asn Tyr Ser Val Thr Asp Leu Asn Val Gln
    210                 215                 220

Arg Lys Ala Ile His Glu Leu Ile Gln Val Met Ala Glu Leu Ser Pro
225                 230                 235                 240

Ala Ala

<210> SEQ ID NO 24
<211> LENGTH: 122
<212> TYPE: PRT
<213> ORGANISM: Unknown
<220> FEATURE:
<223> OTHER INFORMATION: IL-2 (1M47)

<400> SEQUENCE: 24

Ser Thr Lys Lys Thr Gln Leu Gln Leu Glu His Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Phe Lys Phe Tyr Met Pro Lys Lys Ala Thr Glu Leu
            35                  40                  45

Lys His Leu Gln Cys Leu Glu Glu Leu Lys Pro Leu Glu Glu Val
50                  55                  60

Leu Asn Leu Ala Gln Asn Phe His Leu Arg Pro Arg Asp Leu Ile Ser
65                  70                  75                  80

Asn Ile Asn Val Ile Val Leu Glu Leu Lys Gly Phe Met Cys Glu Tyr
                85                  90                  95

Ala Asp Glu Thr Ala Thr Ile Val Glu Phe Leu Asn Arg Trp Ile Thr
            100                 105                 110

Phe Cys Gln Ser Ile Ile Ser Thr Leu Thr
            115                 120

<210> SEQ ID NO 25
<211> LENGTH: 152
<212> TYPE: PRT
<213> ORGANISM: Unknown
<220> FEATURE:
<223> OTHER INFORMATION: IL-1 (2nvh)

<400> SEQUENCE: 25

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
            35                  40                  45

Gly Glu Glu Ser Asn Asp Lys Ile Pro Val Ala Leu Gly Leu Lys Glu
50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
            85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
            130                 135                 140

Asp Phe Thr Met Gln Phe Val Ser
145                 150

<210> SEQ ID NO 26
<211> LENGTH: 148
<212> TYPE: PRT
<213> ORGANISM: Unknown
<220> FEATURE:
<223> OTHER INFORMATION: TNF-alpha (4tsv)

<400> SEQUENCE: 26

Asp Lys Pro Val Ala His Val Val Ala Asn Pro Gln Ala Glu Gly Gln
1               5                   10                  15

```
Leu Gln Trp Ser Asn Arg Arg Ala Asn Ala Leu Leu Ala Asn Gly Val
            20                  25                  30

Glu Leu Arg Asp Asn Gln Leu Val Val Pro Ile Glu Gly Leu Phe Leu
        35                  40                  45

Ile Tyr Ser Gln Val Leu Phe Lys Gly Gln Gly Cys Pro Ser Thr His
 50                  55                  60

Val Leu Leu Thr His Thr Ile Ser Arg Ile Ala Val Ser Tyr Gln Thr
 65                  70                  75                  80

Lys Val Asn Leu Leu Ser Ala Ile Lys Ser Pro Cys Gln Arg Glu Thr
                85                  90                  95

Pro Glu Gly Ala Glu Ala Lys Pro Trp Tyr Glu Pro Ile Tyr Leu Gly
            100                 105                 110

Gly Val Phe Gln Leu Glu Lys Gly Asp Arg Leu Ser Ala Glu Ile Asn
        115                 120                 125

Arg Pro Asp Tyr Leu Asp Phe Ala Glu Ser Gly Gln Val Tyr Phe Gly
    130                 135                 140

Ile Ile Ala Leu
145

<210> SEQ ID NO 27
<211> LENGTH: 144
<212> TYPE: PRT
<213> ORGANISM: Unknown
<220> FEATURE:
<223> OTHER INFORMATION: TNF-beta (lymphotoxin) (1tnr)

<400> SEQUENCE: 27

Lys Pro Ala Ala His Leu Ile Gly Asp Pro Ser Lys Gln Asn Ser Leu
 1               5                  10                  15

Leu Trp Arg Ala Asn Thr Asp Arg Ala Phe Leu Gln Asp Gly Phe Ser
            20                  25                  30

Leu Ser Asn Asn Ser Leu Leu Val Pro Thr Ser Gly Ile Tyr Phe Val
        35                  40                  45

Tyr Ser Gln Val Val Phe Ser Gly Lys Ala Tyr Ser Pro Lys Ala Thr
 50                  55                  60

Ser Ser Pro Leu Tyr Leu Ala His Glu Val Gln Leu Phe Ser Ser Gln
 65                  70                  75                  80

Tyr Pro Phe His Val Pro Leu Leu Ser Ser Gln Lys Met Val Tyr Pro
                85                  90                  95

Gly Leu Gln Glu Pro Trp Leu His Ser Met Tyr His Gly Ala Ala Phe
            100                 105                 110

Gln Leu Thr Gln Gly Asp Gln Leu Ser Thr His Thr Asp Gly Ile Pro
        115                 120                 125

His Leu Val Leu Ser Pro Ser Thr Val Phe Phe Gly Ala Phe Ala Leu
    130                 135                 140

<210> SEQ ID NO 28
<211> LENGTH: 166
<212> TYPE: PRT
<213> ORGANISM: Unknown
<220> FEATURE:
<223> OTHER INFORMATION: Erythropoietin

<400> SEQUENCE: 28

Ala Pro Pro Arg Leu Ile Cys Asp Ser Arg Val Leu Glu Arg Tyr Leu
 1               5                  10                  15

Leu Glu Ala Lys Glu Ala Glu Lys Ile Thr Thr Gly Cys Ala Glu His
```

```
                    20                  25                  30
Cys Ser Leu Asn Glu Lys Ile Thr Val Pro Asp Thr Lys Val Asn Phe
            35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Lys Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Asn Ser Asp Ala Ala Ser Ala Ala
                115                 120                 125

Pro Leu Arg Thr Ile Thr Ala Asp Thr Phe Arg Lys Leu Phe Arg Val
            130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 29
<211> LENGTH: 21
<212> TYPE: PRT
<213> ORGANISM: Unknown
<220> FEATURE:
<223> OTHER INFORMATION: Insulin Chain A

<400> SEQUENCE: 29

Gly Ile Val Glu Gln Cys Cys Thr Ser Ile Cys Ser Leu Tyr Gln Leu
1               5                   10                  15

Glu Asn Tyr Cys Asn
                20

<210> SEQ ID NO 30
<211> LENGTH: 29
<212> TYPE: PRT
<213> ORGANISM: Unknown
<220> FEATURE:
<223> OTHER INFORMATION: Insulin Chain B

<400> SEQUENCE: 30

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
                20                  25

<210> SEQ ID NO 31
<211> LENGTH: 166
<212> TYPE: PRT
<213> ORGANISM: Unknown
<220> FEATURE:
<223> OTHER INFORMATION: Growth hormone (GH) (Somatotropin) (1huw)

<400> SEQUENCE: 31

Phe Pro Thr Ile Pro Leu Ser Arg Leu Ala Asp Asn Ala Trp Leu Arg
1               5                   10                  15

Ala Asp Arg Leu Asn Gln Leu Ala Phe Asp Thr Tyr Gln Glu Phe Glu
                20                  25                  30

Glu Ala Tyr Ile Pro Lys Glu Gln Ile His Ser Phe Trp Trp Asn Pro
            35                  40                  45
```

```
Gln Thr Ser Leu Cys Pro Ser Glu Ser Ile Pro Thr Pro Ser Asn Lys
 50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Ala Leu Leu Lys Asn Tyr Gly Leu Leu Tyr Cys Phe Asn Lys Asp
            130                 135                 140

Met Ser Lys Val Ser Thr Tyr Leu Arg Thr Val Gln Cys Arg Ser Val
145                 150                 155                 160

Glu Gly Ser Cys Gly Phe
                165

<210> SEQ ID NO 32
<211> LENGTH: 242
<212> TYPE: PRT
<213> ORGANISM: Unknown
<220> FEATURE:
<223> OTHER INFORMATION: Follicle-stimulating hormone (FSH)

<400> SEQUENCE: 32

Cys His His Arg Ile Cys His Cys Ser Asn Arg Val Phe Leu Cys Gln
  1               5                  10                  15

Glu Ser Lys Val Thr Glu Ile Pro Ser Asp Leu Pro Arg Asn Ala Ile
                 20                  25                  30

Glu Leu Arg Phe Val Leu Thr Lys Leu Arg Val Ile Gln Lys Gly Ala
             35                  40                  45

Phe Ser Gly Phe Gly Asp Leu Glu Lys Ile Glu Ile Ser Gln Asn Asp
 50                  55                  60

Val Leu Glu Val Ile Glu Ala Asp Val Phe Ser Asn Leu Pro Lys Leu
 65                  70                  75                  80

His Glu Ile Arg Ile Glu Lys Ala Asn Asn Leu Leu Tyr Ile Asn Pro
                 85                  90                  95

Glu Ala Phe Gln Asn Leu Pro Asn Leu Gln Tyr Leu Leu Ile Ser Asn
                100                 105                 110

Thr Gly Ile Lys His Leu Pro Asp Val His Lys Ile His Ser Leu Gln
            115                 120                 125

Lys Val Leu Leu Asp Ile Gln Asp Asn Ile Asn Ile His Thr Ile Glu
130                 135                 140

Arg Asn Ser Phe Val Gly Leu Ser Phe Glu Ser Val Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Leu Glu Glu Leu
            180                 185                 190

Pro Asn Asp Val Phe His Gly Ala Ser Gly Pro Val Ile Leu Asp Ile
            195                 200                 205

Ser Arg Thr Arg Ile His Ser Leu Pro Ser Tyr Gly Leu Glu Asn Leu
210                 215                 220

Lys Lys Leu Arg Ala Arg Ser Thr Tyr Asn Leu Lys Lys Leu Pro Thr
225                 230                 235                 240
```

Leu Glu

```
<210> SEQ ID NO 33
<211> LENGTH: 130
<212> TYPE: PRT
<213> ORGANISM: Unknown
<220> FEATURE:
<223> OTHER INFORMATION: Leptin (1ax8)

<400> SEQUENCE: 33

Ile Gln Lys Val Gln Asp Asp Thr Lys Thr Leu Ile Lys Thr Ile Val
1               5                   10                  15

Thr Arg Ile Asn Asp Ile Leu Asp Phe Ile Pro Gly Leu His Pro Ile
            20                  25                  30

Leu Thr Leu Ser Lys Met Asp Gln Thr Leu Ala Val Tyr Gln Gln Ile
        35                  40                  45

Leu Thr Ser Met Pro Ser Arg Asn Val Ile Gln Ile Ser Asn Asp Leu
    50                  55                  60

Glu Asn Leu Arg Asp Leu Leu His Val Leu Ala Phe Ser Lys Ser Cys
65                  70                  75                  80

His Leu Pro Glu Ala Ser Gly Leu Glu Thr Leu Asp Ser Leu Gly Gly
                85                  90                  95

Val Leu Glu Ala Ser Gly Tyr Ser Thr Glu Val Val Ala Leu Ser Arg
            100                 105                 110

Leu Gln Gly Ser Leu Gln Asp Met Leu Trp Gln Leu Asp Leu Ser Pro
        115                 120                 125

Gly Cys
    130

<210> SEQ ID NO 34
<211> LENGTH: 62
<212> TYPE: PRT
<213> ORGANISM: Unknown
<220> FEATURE:
<223> OTHER INFORMATION: Insulin-like growth factor (or somatomedin)
      (1wqj)

<400> SEQUENCE: 34

Pro Glu Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Arg Ala Pro Gln Thr Gly Ile Val Asp Glu Cys Cys Phe
        35                  40                  45

Arg Ser Cys Asp Leu Arg Arg Leu Glu Met Tyr Cys Ala Pro
    50                  55                  60

<210> SEQ ID NO 35
<211> LENGTH: 125
<212> TYPE: PRT
<213> ORGANISM: Unknown
<220> FEATURE:
<223> OTHER INFORMATION: Adiponectin chain A

<400> SEQUENCE: 35

Met Tyr Arg Ser Ala Phe Ser Val Gly Leu Glu Thr Arg Val Thr Val
1               5                   10                  15

Pro Asn Val Pro Ile Arg Phe Thr Lys Ile Phe Tyr Asn Gln Gln Asn
            20                  25                  30
```

```
His Tyr Asp Gly Ser Thr Gly Lys Phe Tyr Cys Asn Ile Pro Gly Leu
            35                  40                  45

Tyr Tyr Phe Ser Tyr His Ile Thr Val Tyr Met Lys Asp Val Lys Val
 50                  55                  60

Ser Leu Phe Lys Lys Asp Lys Ala Val Leu Phe Thr Tyr Asp Gln Tyr
 65                  70                  75                  80

Gln Glu Asn Val Asp Gln Ala Ser Gly Ser Val Leu Leu His Leu Glu
                 85                  90                  95

Val Gly Asp Gln Val Trp Leu Gln Val Tyr Tyr Ala Asp Asn Val Asn
                100                 105                 110

Asp Ser Thr Phe Thr Gly Phe Leu Leu Tyr His Asp Thr
                115                 120                 125
```

<210> SEQ ID NO 36
<211> LENGTH: 111
<212> TYPE: PRT
<213> ORGANISM: Unknown
<220> FEATURE:
<223> OTHER INFORMATION: Adiponectin chain B

<400> SEQUENCE: 36

```
Met Tyr Arg Ser Ala Phe Ser Val Gly Leu Pro Asn Val Pro Ile Arg
 1               5                  10                  15

Phe Thr Lys Ile Phe Tyr Asn Gln Gln Asn His Tyr Asp Gly Ser Thr
                20                  25                  30

Gly Lys Phe Tyr Cys Asn Ile Pro Gly Leu Tyr Tyr Phe Ser Tyr His
            35                  40                  45

Ile Thr Val Tyr Met Lys Asp Val Lys Val Ser Leu Phe Lys Lys Asp
 50                  55                  60

Lys Val Leu Phe Thr Tyr Asp Gln Tyr Gln Glu Lys Val Asp Gln Ala
 65                  70                  75                  80

Ser Gly Ser Val Leu Leu His Leu Glu Val Gly Asp Gln Val Trp Leu
                 85                  90                  95

Gln Val Tyr Asp Ser Thr Phe Thr Gly Phe Leu Leu Tyr His Asp
                100                 105                 110
```

<210> SEQ ID NO 37
<211> LENGTH: 102
<212> TYPE: PRT
<213> ORGANISM: Unknown
<220> FEATURE:
<223> OTHER INFORMATION: Adiponectin chain C

<400> SEQUENCE: 37

```
Met Tyr Arg Ser Ala Phe Ser Val Gly Leu Glu Thr Arg Val Thr Val
 1               5                  10                  15

Pro Ile Arg Phe Thr Lys Ile Phe Tyr Asn Gln Gln Asn His Tyr Asp
                20                  25                  30

Gly Ser Thr Gly Lys Phe Tyr Cys Asn Ile Pro Gly Leu Tyr Tyr Phe
            35                  40                  45

Ser Tyr His Ile Thr Val Asp Val Lys Val Ser Leu Phe Lys Lys Asp
 50                  55                  60

Lys Ala Val Leu Phe Thr Gln Ala Ser Gly Ser Val Leu Leu His Leu
 65                  70                  75                  80

Glu Val Gly Asp Gln Val Trp Leu Gln Asn Asp Ser Thr Phe Thr Gly
                 85                  90                  95

Phe Leu Leu Tyr His Asp
                100
```

<210> SEQ ID NO 38
<211> LENGTH: 693
<212> TYPE: PRT
<213> ORGANISM: Unknown
<220> FEATURE:
<223> OTHER INFORMATION: Factor VIII chain A

<400> SEQUENCE: 38

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ala Ala Ser Ala Arg Ala Trp Pro Lys Met
    210                 215                 220

His Thr Val Asn Gly Tyr Val Asn Arg Ser Leu Pro Gly Leu Ile Gly
225                 230                 235                 240

Cys His Arg Lys Ser Val Tyr Trp His Val Ile Gly Met Gly Thr Thr
                245                 250                 255

Pro Glu Val His Ser Ile Phe Leu Glu Gly His Thr Phe Leu Val Arg
            260                 265                 270

Asn His Arg Gln Ala Ser Leu Glu Ile Ser Pro Ile Thr Phe Leu Thr
        275                 280                 285

Ala Gln Thr Leu Leu Met Asp Leu Gly Gln Phe Leu Leu Phe Cys His
    290                 295                 300

Ile Ser Ser His Gln His Asp Gly Met Glu Ala Tyr Val Lys Val Asp
305                 310                 315                 320

Ser Cys Pro Glu Glu Pro Gln Phe Asp Asp Asn Ser Pro Ser Phe
                325                 330                 335

Ile Gln Ile Arg Ser Val Ala Lys Lys His Pro Lys Thr Trp Val His
            340                 345                 350

Tyr Ile Ala Ala Glu Glu Glu Asp Trp Asp Tyr Ala Pro Leu Val Leu
        355                 360                 365
```

-continued

```
Ala Pro Asp Asp Arg Ser Tyr Lys Ser Gln Tyr Leu Asn Asn Gly Pro
    370                 375                 380

Gln Arg Ile Gly Arg Lys Tyr Lys Lys Val Arg Phe Met Ala Tyr Thr
385                 390                 395                 400

Asp Glu Thr Phe Lys Thr Arg Glu Ala Ile Gln His Glu Ser Gly Ile
                405                 410                 415

Leu Gly Pro Leu Leu Tyr Gly Glu Val Gly Asp Thr Leu Leu Ile Ile
            420                 425                 430

Phe Lys Asn Gln Ala Ser Arg Pro Tyr Asn Ile Tyr Pro His Gly Ile
        435                 440                 445

Thr Asp Val Arg Pro Leu Tyr Ser Arg Arg Leu Pro Lys Gly Val Lys
    450                 455                 460

His Leu Lys Asp Phe Pro Ile Leu Pro Gly Glu Ile Phe Lys Tyr Lys
465                 470                 475                 480

Trp Thr Val Thr Val Glu Asp Gly Pro Thr Lys Ser Asp Pro Arg Cys
                485                 490                 495

Leu Thr Arg Tyr Tyr Ser Ser Phe Val Asn Met Glu Arg Asp Leu Ala
            500                 505                 510

Ser Gly Leu Ile Gly Pro Leu Leu Ile Cys Tyr Lys Glu Ser Val Asp
        515                 520                 525

Gln Arg Gly Asn Gln Ile Met Ser Asp Lys Arg Asn Val Ile Leu Phe
    530                 535                 540

Ser Val Phe Asp Glu Asn Arg Ser Trp Tyr Leu Thr Glu Asn Ile Gln
545                 550                 555                 560

Arg Phe Leu Pro Asn Pro Ala Gly Val Gln Leu Glu Asp Pro Glu Phe
                565                 570                 575

Gln Ala Ser Asn Ile Met His Ser Ile Asn Gly Tyr Val Phe Asp Ser
            580                 585                 590

Leu Gln Leu Ser Val Cys Leu His Glu Val Ala Tyr Trp Tyr Ile Leu
        595                 600                 605

Ser Ile Gly Ala Gln Thr Asp Phe Leu Ser Val Phe Phe Ser Gly Tyr
    610                 615                 620

Thr Phe Lys His Lys Met Val Tyr Glu Asp Thr Leu Thr Leu Phe Pro
625                 630                 635                 640

Phe Ser Gly Glu Thr Val Phe Met Ser Met Glu Asn Pro Gly Leu Trp
                645                 650                 655

Ile Leu Gly Cys His Asn Ser Asp Phe Arg Asn Arg Gly Met Thr Ala
            660                 665                 670

Leu Leu Lys Val Ser Ser Cys Asp Lys Asn Thr Gly Asp Tyr Tyr Glu
        675                 680                 685

Asp Ser Tyr Glu Asp
    690

<210> SEQ ID NO 39
<211> LENGTH: 644
<212> TYPE: PRT
<213> ORGANISM: Unknown
<220> FEATURE:
<223> OTHER INFORMATION: Factor VIII chain B

<400> SEQUENCE: 39

Arg Ser Phe Gln Lys Lys Thr Arg His Tyr Phe Ile Ala Ala Val Glu
1               5                   10                  15

Arg Leu Trp Asp Tyr Gly Met Ser Ser Ser Pro His Val Leu Arg Asn
                20                  25                  30
```

```
Arg Ala Gln Ser Gly Ser Val Pro Gln Phe Lys Lys Val Val Phe Gln
            35                  40                  45
Glu Phe Thr Asp Gly Ser Phe Thr Gln Pro Leu Tyr Arg Gly Glu Leu
 50                  55                  60
Asn Glu His Leu Gly Leu Leu Gly Pro Tyr Ile Arg Ala Glu Val Glu
 65                  70                  75                  80
Asp Asn Ile Met Val Thr Phe Arg Asn Gln Ala Ser Arg Pro Tyr Ser
                 85                  90                  95
Phe Tyr Ser Ser Leu Ile Ser Tyr Glu Glu Asp Gln Arg Gln Gly Ala
                100                 105                 110
Glu Pro Arg Lys Asn Phe Val Lys Pro Asn Glu Thr Lys Thr Tyr Phe
            115                 120                 125
Trp Lys Val Gln His His Met Ala Pro Thr Lys Asp Glu Phe Asp Cys
        130                 135                 140
Lys Ala Trp Ala Tyr Ser Ser Asp Val Asp Leu Glu Lys Asp Val His
145                 150                 155                 160
Ser Gly Leu Ile Gly Pro Leu Leu Val Cys His Thr Asn Thr Leu Asn
                165                 170                 175
Pro Ala His Gly Arg Gln Val Thr Val Gln Glu Phe Ala Leu Phe Phe
            180                 185                 190
Thr Ile Phe Asp Glu Thr Lys Ser Trp Tyr Phe Thr Glu Asn Met Glu
        195                 200                 205
Arg Asn Cys Arg Ala Pro Cys Asn Ile Gln Met Glu Asp Pro Thr Phe
210                 215                 220
Lys Glu Asn Tyr Arg Phe His Ala Ile Asn Gly Tyr Ile Met Asp Thr
225                 230                 235                 240
Leu Pro Gly Leu Val Met Ala Gln Asp Gln Arg Ile Arg Trp Tyr Leu
                245                 250                 255
Leu Ser Met Gly Ser Asn Glu Asn Ile His Ser Ile His Phe Ser Gly
            260                 265                 270
His Val Phe Thr Val Arg Lys Lys Glu Glu Tyr Lys Met Ala Leu Tyr
        275                 280                 285
Asn Leu Tyr Pro Gly Val Phe Glu Thr Val Glu Met Leu Pro Ser Lys
290                 295                 300
Ala Gly Ile Trp Arg Val Glu Cys Leu Ile Gly Glu His Leu His Ala
305                 310                 315                 320
Gly Met Ser Thr Leu Phe Leu Val Tyr Ser Asn Lys Cys Gln Thr Pro
                325                 330                 335
Leu Gly Met Ala Ser Gly His Ile Arg Asp Phe Gln Ile Thr Ala Ser
            340                 345                 350
Gly Gln Tyr Gly Gln Trp Ala Pro Lys Leu Ala Arg Leu His Tyr Ser
        355                 360                 365
Gly Ser Ile Asn Ala Trp Ser Thr Lys Glu Pro Phe Ser Trp Ile Lys
370                 375                 380
Val Asp Leu Leu Ala Pro Met Ile Ile His Gly Ile Lys Thr Gln Gly
385                 390                 395                 400
Ala Arg Gln Lys Phe Ser Ser Leu Tyr Ile Ser Gln Phe Ile Ile Met
                405                 410                 415
Tyr Ser Leu Asp Gly Lys Lys Trp Gln Thr Tyr Arg Gly Asn Ser Thr
            420                 425                 430
Gly Thr Leu Met Val Phe Phe Gly Asn Val Asp Ser Ser Gly Ile Lys
        435                 440                 445
```

```
His Asn Ile Phe Asn Pro Pro Ile Ile Ala Arg Tyr Ile Arg Leu His
    450                 455                 460
Pro Thr His Tyr Ser Ile Arg Ser Thr Leu Arg Met Glu Leu Met Gly
465                 470                 475                 480
Cys Asp Leu Asn Ser Cys Ser Met Pro Leu Gly Met Glu Ser Lys Ala
                485                 490                 495
Ile Ser Asp Ala Gln Ile Thr Ala Ser Ser Tyr Phe Thr Asn Met Phe
                500                 505                 510
Ala Thr Trp Ser Pro Ser Lys Ala Arg Leu His Leu Gln Gly Arg Ser
            515                 520                 525
Asn Ala Trp Arg Pro Gln Val Asn Asn Pro Lys Glu Trp Leu Gln Val
530                 535                 540
Asp Phe Gln Lys Thr Met Lys Val Thr Gly Val Thr Thr Gln Gly Val
545                 550                 555                 560
Lys Ser Leu Leu Thr Ser Met Tyr Val Lys Glu Phe Leu Ile Ser Ser
                565                 570                 575
Ser Gln Asp Gly His Gln Trp Thr Leu Phe Phe Gln Asn Gly Lys Val
            580                 585                 590
Lys Val Phe Gln Gly Asn Gln Asp Ser Phe Thr Pro Val Val Asn Ser
            595                 600                 605
Leu Asp Pro Pro Leu Leu Thr Arg Tyr Leu Arg Ile His Pro Gln Ser
610                 615                 620
Trp Val His Gln Ile Ala Leu Arg Met Glu Val Leu Gly Cys Glu Ala
625                 630                 635                 640
Gln Asp Leu Tyr

<210> SEQ ID NO 40
<211> LENGTH: 578
<212> TYPE: PRT
<213> ORGANISM: Unknown
<220> FEATURE:
<223> OTHER INFORMATION: Human serum albumin chain A

<400> SEQUENCE: 40

Ser Glu Val Ala His Arg Phe Lys Asp Leu Gly Glu Glu Asn Phe Lys
1               5                   10                  15
Ala Leu Val Leu Ile Ala Phe Ala Gln Tyr Leu Gln Gln Cys Pro Phe
            20                  25                  30
Glu Asp His Val Lys Leu Val Asn Glu Val Thr Glu Phe Ala Lys Thr
        35                  40                  45
Cys Val Ala Asp Glu Ser Ala Glu Asn Cys Asp Lys Ser Leu His Thr
    50                  55                  60
Leu Phe Gly Asp Lys Leu Cys Thr Val Ala Thr Leu Arg Glu Thr Tyr
65                  70                  75                  80
Gly Glu Met Ala Asp Cys Cys Ala Lys Gln Glu Pro Glu Arg Asn Glu
                85                  90                  95
Cys Phe Leu Gln His Lys Asp Asp Asn Pro Asn Leu Pro Arg Leu Val
            100                 105                 110
Arg Pro Glu Val Asp Val Met Cys Thr Ala Phe His Asp Asn Glu Glu
        115                 120                 125
Thr Phe Leu Lys Lys Tyr Leu Tyr Glu Ile Ala Arg Arg His Pro Tyr
    130                 135                 140
Phe Tyr Ala Pro Glu Leu Leu Phe Phe Ala Lys Arg Tyr Lys Ala Ala
145                 150                 155                 160
Phe Thr Glu Cys Cys Gln Ala Ala Asp Lys Ala Ala Cys Leu Leu Pro
```

-continued

```
                165                 170                 175
Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
    210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
    370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr
        435                 440                 445

Leu Ser Val Val Leu Asn Gln Leu Cys Val Leu His Glu Lys Thr Pro
    450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
            500                 505                 510

Ser Glu Lys Glu Arg Gln Ile Lys Lys Gln Thr Ala Leu Val Glu Leu
        515                 520                 525

Val Lys His Lys Pro Lys Ala Thr Lys Glu Gln Leu Lys Ala Val Met
    530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala
```

-continued

```
<210> SEQ ID NO 41
<211> LENGTH: 303
<212> TYPE: PRT
<213> ORGANISM: Unknown
<220> FEATURE:
<223> OTHER INFORMATION: Human serum albumin chain B

<400> SEQUENCE: 41

Ile Lys Gly Gly Leu Phe Ala Asp Ile Ala Ser His Pro Trp Gln Ala
1               5                   10                  15

Ala Ile Phe Ala Lys His His Arg Arg Gly Gly Glu Arg Phe Leu Cys
            20                  25                  30

Gly Gly Ile Leu Ile Ser Ser Cys Trp Ile Leu Ser Ala Ala His Cys
        35                  40                  45

Phe Gln Gln Gln Gln Gln Glu Glu Glu Glu Arg Arg Arg Arg
    50                  55                  60

Phe Phe Phe Phe Phe Pro Pro Pro Pro Pro His His Leu Thr Val
65                  70                  75                  80

Ile Leu Gly Arg Thr Tyr Arg Val Val Pro Gly Glu Glu Glu Gln Lys
                85                  90                  95

Phe Glu Val Glu Lys Tyr Ile Val His Lys Glu Phe Asp Asp Asp Thr
            100                 105                 110

Tyr Asp Asn Asp Ile Ala Leu Leu Gln Leu Lys Ser Ser Ser Ser Ser
        115                 120                 125

Asp Asp Asp Asp Asp Ser Ser Ser Ser Ser Ser Ser Ser Arg
    130                 135                 140

Arg Arg Arg Arg Cys Ala Gln Glu Ser Ser Val Val Arg Thr Val Cys
145                 150                 155                 160

Leu Pro Pro Ala Asp Leu Gln Leu Pro Asp Trp Thr Glu Cys Glu Leu
                165                 170                 175

Ser Gly Tyr Gly Lys His Glu Ala Leu Ser Pro Phe Tyr Ser Glu Arg
            180                 185                 190

Leu Lys Glu Ala His Val Arg Leu Tyr Pro Ser Ser Arg Cys Thr Thr
        195                 200                 205

Thr Ser Ser Ser Gln Gln Gln His Leu Leu Asn Arg Thr Val Thr Asp
    210                 215                 220

Asn Met Leu Cys Ala Gly Asp Thr Thr Thr Arg Arg Arg Ser Ser Ser
225                 230                 235                 240

Asn Asn Asn Leu His Asp Ala Cys Gln Gly Asp Ser Gly Gly Pro Leu
                245                 250                 255

Val Cys Leu Asn Asp Gly Arg Met Thr Leu Val Gly Ile Ile Ser Trp
            260                 265                 270

Gly Leu Gly Cys Gly Gly Gln Gln Lys Asp Val Pro Gly Val Tyr Thr
        275                 280                 285

Lys Val Thr Asn Tyr Leu Asp Trp Ile Arg Asp Asn Met Arg Pro
    290                 295                 300

<210> SEQ ID NO 42
<211> LENGTH: 578
<212> TYPE: PRT
<213> ORGANISM: Unknown
<220> FEATURE:
<223> OTHER INFORMATION: Human serum albumin (1ao6)

<400> SEQUENCE: 42

Ser Glu Val Ala His Arg Phe Lys Asp Leu Gly Glu Glu Asn Phe Lys
1               5                   10                  15
```

```
Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
            35                  40                  45

Cys Val Ala Asp Glu Ser Ala Glu Asn Cys Asp Lys Ser Leu His Thr
 50                  55                  60

Leu Phe Gly Asp Lys Leu Cys Thr Val Ala Thr Leu Arg Glu Thr Tyr
 65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
            115                 120                 125

Thr Phe Leu Lys Lys Tyr Leu Tyr Glu Ile Ala Arg Arg His Pro Tyr
            130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175

Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
            195                 200                 205

Ala Trp Ala Val Ala Arg Leu Ser Gln Arg Phe Pro Lys Ala Glu Phe
            210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
            275                 280                 285

Val Glu Asn Asp Glu Met Pro Ala Asp Leu Pro Ser Leu Ala Ala Asp
            290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
            325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
            355                 360                 365

Val Phe Asp Glu Phe Lys Pro Leu Val Glu Glu Pro Gln Asn Leu Ile
            370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
            420                 425                 430
```

```
Cys Cys Lys His Pro Glu Ala Lys Arg Met Pro Cys Ala Glu Asp Tyr
            435                 440                 445

Leu Ser Val Val Leu Asn Gln Leu Cys Val Leu His Glu Lys Thr Pro
    450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
            485                 490                 495

Glu Phe Asn Ala Glu Thr Phe Thr Phe His Ala Asp Ile Cys Thr Leu
                500                 505                 510

Ser Glu Lys Glu Arg Gln Ile Lys Lys Gln Thr Ala Leu Val Glu Leu
    515                 520                 525

Val Lys His Lys Pro Lys Ala Thr Lys Glu Gln Leu Lys Ala Val Met
    530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
            565                 570                 575

Ala Ala

<210> SEQ ID NO 43
<211> LENGTH: 141
<212> TYPE: PRT
<213> ORGANISM: Unknown
<220> FEATURE:
<223> OTHER INFORMATION: Hemoglobin chain A

<400> SEQUENCE: 43

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 44
<211> LENGTH: 146
<212> TYPE: PRT
<213> ORGANISM: Unknown
<220> FEATURE:
<223> OTHER INFORMATION: Hemoglobin chain B

<400> SEQUENCE: 44

Val His Leu Thr Pro Glu Glu Lys Ser Ala Val Thr Ala Leu Trp Gly
1               5                   10                  15
```

```
Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 45
<211> LENGTH: 22
<212> TYPE: PRT
<213> ORGANISM: Unknown
<220> FEATURE:
<223> OTHER INFORMATION: VHH hinge region

<400> SEQUENCE: 45

Glu Pro Lys Thr Pro Lys Pro Gln Pro Gln Pro Gln Pro Gln Pro Gln
1               5                   10                  15

Pro Asn Pro Thr Thr Glu
            20

<210> SEQ ID NO 46
<211> LENGTH: 8
<212> TYPE: PRT
<213> ORGANISM: Unknown
<220> FEATURE:
<223> OTHER INFORMATION: VHH hinge region

<400> SEQUENCE: 46

Ala His His Ser Glu Asp Pro Ser
1               5

<210> SEQ ID NO 47
<211> LENGTH: 1197
<212> TYPE: DNA
<213> ORGANISM: Unknown
<220> FEATURE:
<223> OTHER INFORMATION: Nucleotide sequence encoding VHH7 fusion
      protein
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (17)..(17)
```

```
<223> OTHER INFORMATION: n is a, c, g, or t
<220> FEATURE:
<221> NAME/KEY: misc_feature
<222> LOCATION: (970)..(970)
<223> OTHER INFORMATION: n is a, c, g, or t
<220> FEATURE:
<221> NAME/KEY: misc_feature
<222> LOCATION: (1030)..(1030)
<223> OTHER INFORMATION: n is a, c, g, or t
<220> FEATURE:
<221> NAME/KEY: misc_feature
<222> LOCATION: (1038)..(1039)
<223> OTHER INFORMATION: n is a, c, g, or t
<220> FEATURE:
<221> NAME/KEY: misc_feature
<222> LOCATION: (1045)..(1045)
<223> OTHER INFORMATION: n is a, c, g, or t
<220> FEATURE:
<221> NAME/KEY: misc_feature
<222> LOCATION: (1050)..(1051)
<223> OTHER INFORMATION: n is a, c, g, or t
<220> FEATURE:
<221> NAME/KEY: misc_feature
<222> LOCATION: (1058)..(1059)
<223> OTHER INFORMATION: n is a, c, g, or t
<220> FEATURE:
<221> NAME/KEY: misc_feature
<222> LOCATION: (1064)..(1064)
<223> OTHER INFORMATION: n is a, c, g, or t
<220> FEATURE:
<221> NAME/KEY: misc_feature
<222> LOCATION: (1069)..(1069)
<223> OTHER INFORMATION: n is a, c, g, or t
<220> FEATURE:
<221> NAME/KEY: misc_feature
<222> LOCATION: (1072)..(1072)
<223> OTHER INFORMATION: n is a, c, g, or t
<220> FEATURE:
<221> NAME/KEY: misc_feature
<222> LOCATION: (1079)..(1079)
<223> OTHER INFORMATION: n is a, c, g, or t
<220> FEATURE:
<221> NAME/KEY: misc_feature
<222> LOCATION: (1093)..(1093)
<223> OTHER INFORMATION: n is a, c, g, or t
<220> FEATURE:
<221> NAME/KEY: misc_feature
<222> LOCATION: (1095)..(1097)
<223> OTHER INFORMATION: n is a, c, g, or t
<220> FEATURE:
<221> NAME/KEY: misc_feature
<222> LOCATION: (1108)..(1108)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1115)..(1117)
<223> OTHER INFORMATION: n is a, c, g, or t
<220> FEATURE:
<221> NAME/KEY: misc_feature
<222> LOCATION: (1123)..(1123)
<223> OTHER INFORMATION: n is a, c, g, or t
<220> FEATURE:
<221> NAME/KEY: misc_feature
<222> LOCATION: (1130)..(1130)
<223> OTHER INFORMATION: n is a, c, g, or t
<220> FEATURE:
<221> NAME/KEY: misc_feature
<222> LOCATION: (1135)..(1136)
<223> OTHER INFORMATION: n is a, c, g, or t
<220> FEATURE:
<221> NAME/KEY: misc_feature
<222> LOCATION: (1141)..(1141)
<223> OTHER INFORMATION: n is a, c, g, or t
<220> FEATURE:
<221> NAME/KEY: misc_feature
```

```
<222> LOCATION: (1144)..(1148)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1155)..(1156)
<223> OTHER INFORMATION: n is a, c, g, or t
<220> FEATURE:
<221> NAME/KEY: misc_feature
<222> LOCATION: (1160)..(1165)
<223> OTHER INFORMATION: n is a, c, g, or t
<220> FEATURE:
<221> NAME/KEY: misc_feature
<222> LOCATION: (1168)..(1172)
<223> OTHER INFORMATION: n is a, c, g, or t
<220> FEATURE:
<221> NAME/KEY: misc_feature
<222> LOCATION: (1175)..(1180)
<223> OTHER INFORMATION: n is a, c, g, or t
<220> FEATURE:
<221> NAME/KEY: misc_feature
<222> LOCATION: (1184)..(1188)
<223> OTHER INFORMATION: n is a, c, g, or t
<220> FEATURE:
<221> NAME/KEY: misc_feature
<222> LOCATION: (1195)..(1196)
<223> OTHER INFORMATION: n is a, c, g, or t

<400> SEQUENCE: 47
ggnatnnnnn nntnacnttc ccctctagaa taattttgtt taactttaag aaggagatat      60
acatatgacc ggcccgggag cggccgctca ggtgcagctc gtggagtcag ggggaggatt     120
ggtgcaggct ggggactctc tgagactctc ctgcgcagcc tctggacgca ccttcagtcg     180
cggtgtaatg ggctggttcc gccgggctcc agggaaggag cgtgagtttg tagcaatctt     240 tagcggggagt agctggagtg gtcgtagtac atactattca gactccgtaa agggccgatt     300
caccatctcc agagacaacg ccaagaacac ggtgtatctg caaatgaacg gcctgaaacc     360
tgaggacacg gccgttttat actgtgcagc gggatatccg gaggcgtata gcgcctatgg     420 tcggagagt acatatgact actggggcca ggggacccag gtcaccgtct cctcagaacc     480
caagacacca aaaccacaac cggcgcgcca ggcctgcact agtggtttac cagagacagg     540
aggaggcagc catcaccatc atcaccatta agctcgagca ccaccaccac caccactgag     600
atccggctgc taacaaagcc cgaaaggaag ctgagttggc tgctgccacc gctgagcaat     660
aactagcata accccttggg gcctctaaac gggtcttgag gggttttttg ctgaaaggag     720
gaactatatc cggattggcg aatgggacgc gccctgtagc ggcgcattaa gcgcggcggg     780
tgtggtggtt acgcgcagcg tgaccgctac acttgccagc gccctagcgc ccgctccttt     840 cgctttcttcc cttcctttct cgccacgttc gccggctttc ccgtcaagc tctaaatcgg     900 gggctccctt taagggttcc gatttagtgc tttacggcac ctcgacccca aaacttgata     960
gggtgatggn ccacgtagtg ggccatcgcc ctgatagacg gttttcgccc tttgacgttg    1020
agtccacgtn tttaatanng gactnctgtn nactggannc aacnctcanc cnatctcgnc    1080
tatctttgat tanannngaa ttgcgatncg ctntnnnaaa tgncctgatn acaanntaac    1140
ncgnnnnnca antanncttn nnnntgnnn nncgnnnnnn gacnnnnnat tccannc       1197

<210> SEQ ID NO 48
<211> LENGTH: 168
<212> TYPE: PRT
<213> ORGANISM: Unknown
<220> FEATURE:
```

<223> OTHER INFORMATION: VHH7 fusion protein sequence

<400> SEQUENCE: 48

Met Thr Gly Pro Gly Ala Ala Gln Val Gln Leu Val Glu Ser Gly
1               5                   10                  15

Gly Gly Leu Val Gln Ala Gly Asp Ser Leu Arg Leu Ser Cys Ala Ala
            20                  25                  30

Ser Gly Arg Thr Phe Ser Arg Gly Val Met Gly Trp Phe Arg Arg Ala
        35                  40                  45

Pro Gly Lys Glu Arg Glu Phe Val Ala Ile Phe Ser Gly Ser Ser Trp
    50                  55                  60

Ser Gly Arg Ser Thr Tyr Tyr Ser Asp Ser Val Lys Gly Arg Phe Thr
65                  70                  75                  80

Ile Ser Arg Asp Asn Ala Lys Asn Thr Val Tyr Leu Gln Met Asn Gly
                85                  90                  95

Leu Lys Pro Glu Asp Thr Ala Val Tyr Tyr Cys Ala Ala Gly Tyr Pro
            100                 105                 110

Glu Ala Tyr Ser Ala Tyr Gly Arg Glu Ser Thr Tyr Asp Tyr Trp Gly
        115                 120                 125

Gln Gly Thr Gln Val Thr Val Ser Ser Glu Pro Lys Thr Pro Lys Pro
    130                 135                 140

Gln Pro Ala Arg Gln Ala Cys Thr Ser Gly Leu Pro Glu Thr Gly Gly
145                 150                 155                 160

Gly Ser His His His His His His
                165

<210> SEQ ID NO 49
<211> LENGTH: 438
<212> TYPE: DNA
<213> ORGANISM: Unknown
<220> FEATURE:
<223> OTHER INFORMATION: Nucleotide sequence encoding VHH7

<400> SEQUENCE: 49
gctcaggtgc agctcgtgga gtcagggggga ggattggtgc aggctgggga ctctctgaga      60
ctctcctgcg cagcctctgg acgcaccttc agtcgcggtg taatgggctg gttccgccgg     120
gctccaggga aggagcgtga gtttgtagca atctttagcg ggagtagctg gagtggtcgt     180
agtacatact attcagactc cgtaaagggc cgattcacca tctccagaga caacgccaag     240
aacacggtgt atctgcaaat gaacggcctg aaacctgagg acacggccgt ttattactgt     300
gcagcgggat atccggaggc gtatagcgcc tatggtcggg agagtacata tgactactgg     360
ggccagggga cccaggtcac cgtctcctca gaacccaaga caccaaaacc acaaccggcg     420
cgccaggcct gcactagt                                                   438

<210> SEQ ID NO 50
<211> LENGTH: 146
<212> TYPE: PRT
<213> ORGANISM: Unknown
<220> FEATURE:
<223> OTHER INFORMATION: VHH7 protein sequence

<400> SEQUENCE: 50

Ala Gln Val Gln Leu Val Glu Ser Gly Gly Gly Leu Val Gln Ala Gly
1               5                   10                  15

Asp Ser Leu Arg Leu Ser Cys Ala Ala Ser Gly Arg Thr Phe Ser Arg
            20                  25                  30

```
Gly Val Met Gly Trp Phe Arg Arg Ala Pro Gly Lys Glu Arg Glu Phe
         35                  40                  45

Val Ala Ile Phe Ser Gly Ser Ser Trp Ser Gly Arg Ser Thr Tyr Tyr
 50                  55                  60

Ser Asp Ser Val Lys Gly Arg Phe Thr Ile Ser Arg Asp Asn Ala Lys
 65                  70                  75                  80

Asn Thr Val Tyr Leu Gln Met Asn Gly Leu Lys Pro Glu Asp Thr Ala
                 85                  90                  95

Val Tyr Tyr Cys Ala Ala Gly Tyr Pro Glu Ala Tyr Ser Ala Tyr Gly
                100                 105                 110

Arg Glu Ser Thr Tyr Asp Tyr Trp Gly Gln Gly Thr Gln Val Thr Val
            115                 120                 125

Ser Ser Glu Pro Lys Thr Pro Lys Pro Gln Pro Ala Arg Gln Ala Cys
        130                 135                 140

Thr Ser
145
```

<210> SEQ ID NO 51
<211> LENGTH: 8
<212> TYPE: PRT
<213> ORGANISM: Unknown
<220> FEATURE:
<223> OTHER INFORMATION: VHH7 CDR1

<400> SEQUENCE: 51

```
Gly Arg Thr Phe Ser Arg Gly Val
1               5
```

<210> SEQ ID NO 52
<211> LENGTH: 11
<212> TYPE: PRT
<213> ORGANISM: Unknown
<220> FEATURE:
<223> OTHER INFORMATION: VHH7 CDR2

<400> SEQUENCE: 52

```
Phe Ser Gly Ser Ser Trp Ser Gly Arg Ser Thr
1               5                   10
```

<210> SEQ ID NO 53
<211> LENGTH: 19
<212> TYPE: PRT
<213> ORGANISM: Unknown
<220> FEATURE:
<223> OTHER INFORMATION: VHH7 CDR3

<400> SEQUENCE: 53

```
Ala Ala Gly Tyr Pro Glu Ala Tyr Ser Ala Tyr Gly Arg Glu Ser Thr
1               5                   10                  15

Tyr Asp Tyr
```

<210> SEQ ID NO 54
<211> LENGTH: 115
<212> TYPE: PRT
<213> ORGANISM: Unknown
<220> FEATURE:
<223> OTHER INFORMATION: VHH7

<400> SEQUENCE: 54

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Leu Ser Ser Tyr
```

-continued

```
                    20                  25                  30
Gly Met Gly Trp Tyr Arg Gln Ala Pro Gly Lys Gln Arg Glu Val Val
                35                  40                  45

Ala Thr Ile Ser Ala Thr Gly Ser Ile Ser Tyr Ala Asp Ser Val Lys
        50                  55                  60

Gly Arg Phe Thr Ile Ser Arg Asp Ser Ala Lys Asn Thr Met Tyr Leu
65                  70                  75                  80

Gln Leu Asn Ser Leu Thr Pro Glu Asp Thr Ala Val Tyr Tyr Cys Asn
                85                  90                  95

Thr Ile Tyr Arg Ser Thr Leu Tyr Trp Gly Gln Gly Thr Gln Val Thr
                100                 105                 110

Val Ser Ser
        115

<210> SEQ ID NO 55
<211> LENGTH: 8
<212> TYPE: PRT
<213> ORGANISM: Unknown
<220> FEATURE:
<223> OTHER INFORMATION: VHH7 CDR1

<400> SEQUENCE: 55

Gly Arg Thr Phe Ser Arg Gly Val
1               5

<210> SEQ ID NO 56
<211> LENGTH: 11
<212> TYPE: PRT
<213> ORGANISM: Unknown
<220> FEATURE:
<223> OTHER INFORMATION: VHH7 CDR2

<400> SEQUENCE: 56

Ile Phe Ser Gly Ser Ser Trp Ser Gly Arg Ser
1               5                   10

<210> SEQ ID NO 57
<211> LENGTH: 17
<212> TYPE: PRT
<213> ORGANISM: Unknown
<220> FEATURE:
<223> OTHER INFORMATION: VHH7 CDR3

<400> SEQUENCE: 57

Gly Tyr Pro Glu Ala Tyr Ser Ala Tyr Gly Arg Glu Ser Thr Tyr Asp
1               5                   10                  15

Tyr

<210> SEQ ID NO 58
<211> LENGTH: 129
<212> TYPE: PRT
<213> ORGANISM: Unknown
<220> FEATURE:
<223> OTHER INFORMATION: VHH7

<400> SEQUENCE: 58

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Leu Ser Ser Tyr
                20                  25                  30

Gly Met Gly Trp Tyr Arg Gln Ala Pro Gly Lys Gln Arg Glu Val Val
                35                  40                  45
```

```
Ala Thr Ile Ser Ala Thr Gly Ser Ile Ser Tyr Ala Asp Ser Val Lys
        50                  55                  60

Gly Arg Phe Thr Ile Ser Arg Asp Ser Ala Lys Asn Thr Met Tyr Leu
 65              70                  75                  80

Gln Leu Asn Ser Leu Thr Pro Glu Asp Thr Ala Val Tyr Tyr Cys Asn
                85                  90                  95

Thr Ile Tyr Arg Ser Thr Leu Tyr Trp Gly Gln Gly Thr Gln Val Thr
            100                 105                 110

Val Ser Ser Gly Gly Leu Pro Glu Thr Gly Gly His His His His
            115                 120                 125

His
```

<210> SEQ ID NO 59
<211> LENGTH: 115
<212> TYPE: PRT
<213> ORGANISM: Unknown
<220> FEATURE:
<223> OTHER INFORMATION: VHH4

<400> SEQUENCE: 59

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Ser Thr Leu Ser Ser Tyr
            20                  25                  30

Gly Met Gly Trp Tyr Arg Gln Ala Pro Gly Lys Gln Arg Glu Val Val
            35                  40                  45

Ala Thr Ile Ser Ala Thr Gly Ser Ile Ser Tyr Ala Asp Ser Val Lys
        50                  55                  60

Gly Arg Phe Thr Ile Ser Arg Asp Ser Ala Lys Asn Thr Met Tyr Leu
 65              70                  75                  80

Gln Leu Asn Ser Leu Thr Pro Glu Asp Thr Ala Val Tyr Tyr Cys Asn
                85                  90                  95

Thr Ile Tyr Arg Ser Thr Leu Tyr Trp Gly Gln Gly Thr Gln Val Thr
            100                 105                 110

Val Ser Ser
        115
```

<210> SEQ ID NO 60
<211> LENGTH: 9
<212> TYPE: PRT
<213> ORGANISM: Unknown
<220> FEATURE:
<223> OTHER INFORMATION: VHH4 CDR1

<400> SEQUENCE: 60

```
Gly Ser Thr Leu Ser Ser Tyr Gly Met
 1               5
```

<210> SEQ ID NO 61
<211> LENGTH: 6
<212> TYPE: PRT
<213> ORGANISM: Unknown
<220> FEATURE:
<223> OTHER INFORMATION: VHH4 CDR2

<400> SEQUENCE: 61

```
Ile Ser Ala Thr Gly Ser
 1               5
```

<210> SEQ ID NO 62
<211> LENGTH: 9
<212> TYPE: PRT
<213> ORGANISM: Unknown
<220> FEATURE:
<223> OTHER INFORMATION: VHH4 CDR3

<400> SEQUENCE: 62

Asn Thr Ile Tyr Arg Ser Thr Leu Tyr
1               5

<210> SEQ ID NO 63
<211> LENGTH: 14
<212> TYPE: PRT
<213> ORGANISM: Unknown
<220> FEATURE:
<223> OTHER INFORMATION: hexahistidine (6X His)

<400> SEQUENCE: 63

Gly Gly Leu Pro Glu Thr Gly Gly His His His His His His
1               5                   10

<210> SEQ ID NO 64
<211> LENGTH: 129
<212> TYPE: PRT
<213> ORGANISM: Unknown
<220> FEATURE:
<223> OTHER INFORMATION: VHH4

<400> SEQUENCE: 64

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Leu Ser Ser Tyr
            20                  25                  30

Gly Met Gly Trp Tyr Arg Gln Ala Pro Gly Lys Gln Arg Glu Val Val
        35                  40                  45

Ala Thr Ile Ser Ala Thr Gly Ser Ile Ser Tyr Ala Asp Ser Val Lys
    50                  55                  60

Gly Arg Phe Thr Ile Ser Arg Asp Ser Ala Lys Asn Thr Met Tyr Leu
65                  70                  75                  80

Gln Leu Asn Ser Leu Thr Pro Glu Asp Thr Ala Val Tyr Tyr Cys Asn
                85                  90                  95

Thr Ile Tyr Arg Ser Thr Leu Tyr Trp Gly Gln Gly Thr Gln Val Thr
            100                 105                 110

Val Ser Ser Gly Gly Leu Pro Glu Thr Gly Gly His His His His His
        115                 120                 125

His

<210> SEQ ID NO 65
<211> LENGTH: 123
<212> TYPE: PRT
<213> ORGANISM: Unknown
<220> FEATURE:
<223> OTHER INFORMATION: VHH52

<400> SEQUENCE: 65

Gln Val Gln Leu Gln Glu Ser Gly Gly Gly Leu Val Gln Ala Gly Gly
1               5                   10                  15

Ser Leu Arg Leu Thr Cys Ala Leu Ser Glu Arg Thr Ser Thr Ser Tyr
            20                  25                  30

Ala Gln Gly Trp Phe Arg Gln Pro Pro Gly Lys Glu Arg Glu Phe Val
        35                  40                  45

```
Ala Ser Leu Arg Thr His Asp Gly Asn Thr His Tyr Thr Asp Ser Val
        50                  55                  60

Lys Gly Arg Phe Thr Ile Ser Arg Asp Asn Ala Glu Asn Thr Leu Tyr
 65                  70                  75                  80

Leu Gln Met Asn Ser Leu Lys Thr Glu Asp Thr Ala Val Tyr Tyr Cys
                85                  90                  95

Ala Ala Ser Leu Gly Tyr Ser Gly Ala Tyr Ala Ser Gly Tyr Asp Tyr
                100                 105                 110

Trp Gly Gln Gly Thr Gln Val Thr Val Ser Ser
            115                 120

<210> SEQ ID NO 66
<211> LENGTH: 121
<212> TYPE: PRT
<213> ORGANISM: Unknown
<220> FEATURE:
<223> OTHER INFORMATION: VHH54

<400> SEQUENCE: 66

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Leu Ser Ser Tyr
                20                  25                  30

Ala Met Gly Trp Phe Arg Gln Ala Pro Gly Lys Glu Arg Glu Leu Val
            35                  40                  45

Ser Ala Ile Ser Trp Ser Gly Leu Ser Thr Tyr Tyr Glu Asp Ser Val
        50                  55                  60

Lys Gly Arg Phe Thr Ile Ser Arg Asp Asn Ala Lys Asn Thr Met Tyr
 65                  70                  75                  80

Leu Gln Met Asn Ser Leu Lys Pro Glu Asp Thr Ala Ile Tyr Tyr Cys
                85                  90                  95

Ala Ala Asp Ile Gly Trp Pro Leu Arg Ala Asp Ser Gly Ser Trp Gly
                100                 105                 110

Gln Gly Thr Gln Val Thr Val Ser Ser
            115                 120

<210> SEQ ID NO 67
<211> LENGTH: 124
<212> TYPE: PRT
<213> ORGANISM: Unknown
<220> FEATURE:
<223> OTHER INFORMATION: VHH62

<400> SEQUENCE: 67

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Leu Asp Gly Tyr
                20                  25                  30

Ala Ile Gly Trp Phe Arg Gln Ala Pro Gly Lys Glu Arg Glu Gly Val
            35                  40                  45

Ser Cys Ile Ser Ser Ser Gly Lys Ser Thr Asn Tyr Ala Asp Ser Val
        50                  55                  60

Lys Gly Arg Phe Thr Ile Ser Arg Asp Asn Gln Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Thr Val Gly Leu Phe Cys Val Gly Gly Thr Tyr Gly Met Asp
```

```
                    100                 105                 110
Tyr Trp Gly Lys Gly Thr Gln Val Thr Val Ser Ser
            115                 120

<210> SEQ ID NO 68
<211> LENGTH: 123
<212> TYPE: PRT
<213> ORGANISM: Unknown
<220> FEATURE:
<223> OTHER INFORMATION: VHH68

<400> SEQUENCE: 68

Gln Val Gln Leu Gln Glu Ser Gly Gly Gly Leu Val Gln Ala Gly Gly
1               5                   10                  15

Ser Leu Arg Leu Ser Cys Ala Val Pro Gly Arg Thr Ser Asn Ile Phe
            20                  25                  30

Ala Met Gly Trp Phe Arg Gln Ala Leu Gly Lys Glu Arg Glu Phe Val
        35                  40                  45

Ala Ala Val Thr Trp Ser Leu Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Glu Val Gly Pro Leu Arg Gln Pro Asp Thr Tyr Leu His
            100                 105                 110

Trp Gly Gln Gly Thr Gln Val Thr Val Ser Ser
            115                 120

<210> SEQ ID NO 69
<211> LENGTH: 137
<212> TYPE: PRT
<213> ORGANISM: Unknown
<220> FEATURE:
<223> OTHER INFORMATION: VHH52

<400> SEQUENCE: 69

Gln Val Gln Leu Gln Glu Ser Gly Gly Gly Leu Val Gln Ala Gly Gly
1               5                   10                  15

Ser Leu Arg Leu Thr Cys Ala Leu Ser Glu Arg Thr Ser Thr Ser Tyr
            20                  25                  30

Ala Gln Gly Trp Phe Arg Gln Pro Pro Gly Lys Glu Arg Glu Phe Val
        35                  40                  45

Ala Ser Leu Arg Thr His Asp Gly Asn Thr His Tyr Thr Asp Ser Val
    50                  55                  60

Lys Gly Arg Phe Thr Ile Ser Arg Asp Asn Ala Glu Asn Thr Leu Tyr
65                  70                  75                  80

Leu Gln Met Asn Ser Leu Lys Thr Glu Asp Thr Ala Val Tyr Tyr Cys
                85                  90                  95

Ala Ala Ser Leu Gly Tyr Ser Gly Ala Tyr Ala Ser Gly Tyr Asp Tyr
            100                 105                 110

Trp Gly Gln Gly Thr Gln Val Thr Val Ser Ser Gly Gly Leu Pro Glu
            115                 120                 125

Thr Gly Gly His His His His His His
        130                 135

<210> SEQ ID NO 70
<211> LENGTH: 135
```

<212> TYPE: PRT
<213> ORGANISM: Unknown
<220> FEATURE:
<223> OTHER INFORMATION: VHH54

<400> SEQUENCE: 70

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Leu Ser Ser Tyr
            20                  25                  30

Ala Met Gly Trp Phe Arg Gln Ala Pro Gly Lys Glu Arg Glu Leu Val
        35                  40                  45

Ser Ala Ile Ser Trp Ser Gly Leu Ser Thr Tyr Tyr Glu Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Ile Tyr Tyr Cys
                85                  90                  95

Ala Ala Asp Ile Gly Trp Pro Leu Arg Ala Asp Ser Gly Ser Trp Gly
            100                 105                 110

Gln Gly Thr Gln Val Thr Val Ser Ser Gly Gly Leu Pro Glu Thr Gly
        115                 120                 125

Gly His His His His His His
    130                 135

<210> SEQ ID NO 71
<211> LENGTH: 138
<212> TYPE: PRT
<213> ORGANISM: Unknown
<220> FEATURE:
<223> OTHER INFORMATION: VHH62

<400> SEQUENCE: 71

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Gly Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Gly Lys Ser Thr Asn Tyr Ala Asp Ser Val
    50                  55                  60

Lys Gly Arg Phe Thr Ile Ser Arg Asp Asn Gln Gln Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Val Gly Leu Phe Cys Val Gly Gly Thr Tyr Gly Met Asp
            100                 105                 110

Tyr Trp Gly Lys Gly Thr Gln Val Thr Val Ser Ser Gly Gly Leu Pro
        115                 120                 125

Glu Thr Gly Gly His His His His His His
    130                 135

<210> SEQ ID NO 72
<211> LENGTH: 137
<212> TYPE: PRT
<213> ORGANISM: Unknown
<220> FEATURE:
<223> OTHER INFORMATION: VHH68

<400> SEQUENCE: 72

```
Gln Val Gln Leu Gln Glu Ser Gly Gly Gly Leu Val Gln Ala Gly Gly
1               5                   10                  15

Ser Leu Arg Leu Ser Cys Ala Val Pro Gly Arg Thr Ser Asn Ile Phe
            20                  25                  30

Ala Met Gly Trp Phe Arg Gln Ala Leu Gly Lys Glu Arg Glu Phe Val
        35                  40                  45

Ala Ala Val Thr Trp Ser Leu Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Glu Val Gly Pro Leu Arg Gln Pro Asp Thr Tyr Leu His
            100                 105                 110

Trp Gly Gln Gly Thr Gln Val Thr Val Ser Ser Gly Gly Leu Pro Glu
        115                 120                 125

Thr Gly Gly His His His His His His
    130                 135
```

<210> SEQ ID NO 73
<211> LENGTH: 185
<212> TYPE: PRT
<213> ORGANISM: Unknown
<220> FEATURE:
<223> OTHER INFORMATION: pIII phage display vector with VHH sequence
      inserts

<400> SEQUENCE: 73

```
Met Lys Tyr Leu Leu Pro Thr Ala Ala Ala Gly Leu Leu Leu Leu Ala
1               5                   10                  15

Ala Gln Pro Ala Met Ala Gly Pro Gly Ala Ala Gln Leu Gln Leu
            20                  25                  30

Val Glu Ser Gly Gly Gly Leu Val Gln Ala Gly Gly Ser Leu Arg Leu
        35                  40                  45

Ser Cys Ala Ala Ser Gly Arg Thr Phe Ser Ser Tyr Ala Met Ala Trp
    50                  55                  60

Phe Arg Gln Gly Pro Gly Lys Glu Arg Glu Phe Val Ala Thr Ile Ser
65                  70                  75                  80

Trp Ser Gly Gly Ser Thr His Tyr Ala Asp Ser Val Lys Gly Arg Phe
                85                  90                  95

Thr Ile Ser Arg Asp Asn Ala Lys Asn Thr Val Tyr Leu Gln Met Asn
            100                 105                 110

Ser Leu Lys Pro Glu Asp Thr Ala Val Tyr Tyr Cys Ala Thr Gly Glu
        115                 120                 125

Arg Tyr Tyr Gln Met Tyr Gly Leu Asn Pro Gly Asp Tyr Asp Tyr Trp
    130                 135                 140

Gly Gln Gly Thr Gln Val Thr Val Ser Ser Glu Pro Lys Thr Pro Lys
145                 150                 155                 160

Pro Gln Pro Ala Arg Gln Ala Cys Thr Ser Gly Leu Pro Glu Thr Gly
                165                 170                 175

Gly His His His His His His Ala Ala
            180                 185
```

<210> SEQ ID NO 74
<211> LENGTH: 429

<212> TYPE: DNA
<213> ORGANISM: Unknown
<220> FEATURE:
<223> OTHER INFORMATION: VHH7

<400> SEQUENCE: 74

```
caggtgcagc tgcaggagtc agggggagga ttggtgcagg ctggggactc tctgagactc      60
tcctgcgcag cctctggacg caccttcagt cgcggtgtaa tgggctggtt ccgccgggct     120
ccagggaagg agcgtgagtt tgtagcaatc tttagcggga gtagctggag tggtcgtagt     180
acatactatt cagactccgt aaagggccga ttcaccatct ccagagacaa cgccaagaac     240
acggtgtatc tgcaaatgaa cggcctgaaa cctgaggaca cggccgttta ttactgtgca     300
gcgggatatc ggaggcgta tagcgcctat ggtcgggaga gtacatatga ctactggggc     360
caggggaccc aggtcaccgt ctcctcagga ggactgccgg aaaccggcgg ccaccaccat     420
caccatcac                                                              429
```

<210> SEQ ID NO 75
<211> LENGTH: 387
<212> TYPE: DNA
<213> ORGANISM: Unknown
<220> FEATURE:
<223> OTHER INFORMATION: VHH4

<400> SEQUENCE: 75

```
caggtgcagc tgcaggagtc agggggagga ttggtgcagg ctgggggtc tctgagactc       60
tcctgtgcag cctctggaag caccctcagt agctatggca tgggctggta ccgccaggct     120
ccagggaagc aacgtgaagt ggtcgcaact attagtgcta ctggtagcat aagctatgca     180
gactccgtga agggccgatt caccatctcc agagacagtg ccaagaacac gatgtatctg     240
caactgaaca gcctgacacc tgaggacacg gccgtctatt actgtaacac aatttatagg     300
tctactctct actggggcca ggggacccag gtcaccgtct cctcaggagg actgccggaa     360
accggcggcc accaccatca ccatcac                                          387
```

<210> SEQ ID NO 76
<211> LENGTH: 411
<212> TYPE: DNA
<213> ORGANISM: Unknown
<220> FEATURE:
<223> OTHER INFORMATION: VHH52

<400> SEQUENCE: 76

```
caggtgcagc tgcaggagtc agggggagga ttggtgcagg ctgggggctc tctgagactc      60
acctgtgcac tctctgaacg caccagtacc agttatgcac agggctggtt ccgccagcct     120
ccagggaaag agcgtgagtt tgtggcgagt cttagaacgc atgacggcaa cacacactat     180
acagactccg tgaagggccg attcaccatc tccagagaca cgccgagaa cacgctgtat      240
ctgcaaatga cagcctgaa aactgaggac acggccgtat attattgtgc ggcatccctc      300
ggttacagcg gtgcttatgc gtctgggtat gactactggg gccaggggac ccaggtcacc     360
gtctcctcag gaggactgcc ggaaaccggc ggccaccacc atcaccatca c               411
```

<210> SEQ ID NO 77
<211> LENGTH: 405
<212> TYPE: DNA
<213> ORGANISM: Unknown
<220> FEATURE:
<223> OTHER INFORMATION: VHH54

<400> SEQUENCE: 77

```
caggtgcagc tgcaggagtc agggggagga ttggtgcagg ctgggggctc tctgagactc      60
tcctgtgcag cctctggacg caccctcagt agctatgcca tgggctggtt ccgccaggcc     120
ccagggaagg agcgtgagtt agtctcagct attagctgga gtggtcttag cacatactat     180
gaagactccg tgaagggccg attcaccatc tccagagaca acgccaagaa cacgatgtat     240
ctgcaaatga acagcctgaa acctgaggac acggccattt attactgtgc agcggatatt     300
gggtggcccc tgcgggctga ctctggttcc tggggccagg ggacccaggt caccgtctcc     360
tcaggaggac tgccggaaac cggcggccac caccatcacc atcac                    405
```

<210> SEQ ID NO 78
<211> LENGTH: 414
<212> TYPE: DNA
<213> ORGANISM: Unknown
<220> FEATURE:
<223> OTHER INFORMATION: VHH62

<400> SEQUENCE: 78

```
caggtgcagc tgcaggagtc agggggagga ttggtgcagc ctgggggtc tctgagactc       60
tcctgtgcag cctctggatt cactttggat ggttatgcca taggctggtt ccgccaggcc    120
ccagggaagg agcgtgaggg ggtctcatgt attagtagta gtggtaaaag cacaaactat    180
gcagactccg tgaagggccg attcaccatc tccagagaca accagcagaa cacggtgtat    240
ctgcaaatga acagcctgaa acctgaggac acagccgttt attactgtgc agcgacagtt    300
ggtttatttt gtgttggggg gacctacggc atggactact ggggcaaggg gacccaggtc    360
accgtctcct caggaggact gccggaaacc ggcggccacc accatcacca tcac          414
```

<210> SEQ ID NO 79
<211> LENGTH: 411
<212> TYPE: DNA
<213> ORGANISM: Unknown
<220> FEATURE:
<223> OTHER INFORMATION: VHH68

<400> SEQUENCE: 79

```
caggtgcagc tgcaggagtc agggggagga ttggtgcagg ctgggggctc tctgagactc      60
tcctgtgcag ttcctggacg cacctccaat atctttgcca tgggctggtt ccgccaggct    120
ctaggaaagg aacgtgagtt tgtagcagca gttacctgga gtttaggtaa tacatactac    180
gcagactccg tgaagggccg attcaccatc tccagagaca acgccaagaa cacagtgtat    240
ctgcaaatga acagcctgaa acctgaggac acggccgttt attactgtgc agccggggag    300
gtagggcctc tccggcagcc ggatacgtat ttacactggg gccaggggac ccaggtcacc    360
gtctcctcag gaggactgcc ggaaaccggc ggccaccacc atcaccatca c              411
```

<210> SEQ ID NO 80
<211> LENGTH: 184
<212> TYPE: PRT
<213> ORGANISM: Unknown
<220> FEATURE:
<223> OTHER INFORMATION: pIII phage display vector with VHH sequence
      inserts

<400> SEQUENCE: 80

```
Met Lys Tyr Leu Leu Pro Thr Ala Ala Ala Gly Leu Leu Leu Leu Ala
1               5                   10                  15

Ala Gln Pro Ala Met Ala Gly Pro Gly Ala Ala Ala Gln Leu Gln Leu
```

```
                 20                  25                  30
Val Glu Ser Gly Gly Gly Ser Val Gln Ala Gly Asp Ser Leu Arg Leu
             35                  40                  45

Ser Cys Ala Ala Ser Gly Arg Thr Phe Ser Arg Tyr Ala Met Ala Trp
         50                  55                  60

Phe Arg Arg Ala Pro Gly Lys Glu Arg Glu Phe Val Ala Ser Ile Ser
 65                  70                  75                  80

Arg Ser Ala Ser Asn Ile Asp Tyr Ala Asp Ser Val Lys Gly Arg Phe
                 85                  90                  95

Thr Ile Ser Arg Asp Asn Ala Lys Asn Thr Val Tyr Leu Gln Met Asp
            100                 105                 110

Ser Leu Lys Pro Glu Asp Thr Ala Val Tyr Tyr Cys Ala Ala Asp Leu
        115                 120                 125

Tyr Gly Ser Gly Thr Tyr Ser His Ala Thr Val Tyr Glu Tyr Trp Gly
            130                 135                 140

Gln Gly Thr Gln Val Thr Val Ser Ser Glu Pro Lys Thr Pro Lys Pro
145                 150                 155                 160

Gln Pro Ala Arg Gln Ala Cys Thr Ser Gly Leu Pro Glu Thr Gly Gly
                165                 170                 175

His His His His His His Ala Ala
            180
```

```
<210> SEQ ID NO 81
<211> LENGTH: 5
<212> TYPE: PRT
<213> ORGANISM: Unknown
<220> FEATURE:
<223> OTHER INFORMATION: recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 81

Leu Pro Xaa Thr Gly
1               5

<210> SEQ ID NO 82
<211> LENGTH: 6
<212> TYPE: PRT
<213> ORGANISM: Unknown
<220> FEATURE:
<223> OTHER INFORMATION: recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 82

Leu Pro Xaa Thr Gly Gly
1               5

<210> SEQ ID NO 83
<211> LENGTH: 6
<212> TYPE: PRT
<213> ORGANISM: Unknown
<220> FEATURE:
<223> OTHER INFORMATION: recognition motif

<400> SEQUENCE: 83

Leu Pro Glu Thr Gly Gly
1               5
```

```
<210> SEQ ID NO 84
<211> LENGTH: 38
<212> TYPE: DNA
<213> ORGANISM: Unknown
<220> FEATURE:
<223> OTHER INFORMATION: A1VHH-F1
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t

<400> SEQUENCE: 84
cttgcggccg ctcagktgca gctcgtggag wcnggngg                              38

<210> SEQ ID NO 85
<211> LENGTH: 34
<212> TYPE: DNA
<213> ORGANISM: Unknown
<220> FEATURE:
<223> OTHER INFORMATION: AlVHH-short hinge R1

<400> SEQUENCE: 85
gatcggcgcg ccgaggggtc ttcgctgtgg tgcg                                  34

<210> SEQ ID NO 86
<211> LENGTH: 35
<212> TYPE: DNA
<213> ORGANISM: Unknown
<220> FEATURE:
<223> OTHER INFORMATION: A1VHH-long hinge R1

<400> SEQUENCE: 86
gatcggcgcg ccggttgtgg ttttggtgtc ttggg                                 35

<210> SEQ ID NO 87
<211> LENGTH: 5
<212> TYPE: PRT
<213> ORGANISM: Unknown
<220> FEATURE:
<223> OTHER INFORMATION: recognition motif

<400> SEQUENCE: 87

Leu Pro Glu Thr Gly
1               5
```

SORTASE-MODIFIED VHH DOMAINS AND USES THEREOF

RELATED APPLICATION(S)

This application is a national stage filing under 35 U.S.C. 371 of International Application No. PCT/US2013/036630, filed Apr. 15, 3013, which claims the benefit of U.S. Provisional Application No. 61/624,114, filed on Apr. 13, 2012. The entire teachings of the above application(s) are incorporated herein by reference. International Application PCT/US2013/035145 was published under PCT Article 21(2) in English.

BACKGROUND OF THE INVENTION

Protein engineering is becoming a widely used tool in many areas of protein biochemistry. One engineering method is controlled protein ligation. Native chemical protein ligation relies on efficient preparation of synthetic peptide esters, which can be technically difficult to prepare for many proteins. Recombinant technologies can be used to generate protein-protein fusions, joining the C-terminus of one protein with the N-terminus of another protein. Intein-based protein ligation systems can also be used to join proteins. A prerequisite for this intein-mediated ligation method is that the target protein is expressed as a correctly folded fusion with the intein, which is often challenging. The difficulties of conventional native and recombinant ligation technologies significantly limit the application of protein ligation.

The transpeptidation reaction catalyzed by sortases has emerged as a general method for derivatizing proteins with various types of modifications. For conventional sortase modifications, target proteins are engineered to contain a sortase recognition motif (LPXT) near their C-termini. When incubated with synthetic peptides containing one or more N-terminal glycine residues and a recombinant sortase, these artificial sortase substrates undergo a transacylation reaction resulting in the exchange of residues C-terminal to the threonine residue with the synthetic oligoglycine peptide, resulting in the protein C-terminus being ligated to the N-terminus of the synthetic peptide.

SUMMARY OF THE INVENTION

Some aspects of this invention relate to sortase-mediated modification of proteins, in particular on the installation of reactive chemical groups, e.g., click chemistry handles, on protein sequences. Methods and reagents for the installation of reactive chemical groups on proteins are provided, as are modified proteins, e.g., proteins comprising a C-terminal or an N-terminal click chemistry handle. Further, methods to conjugate two proteins that are modified according to aspects of this invention are provided. Such methods are useful to dimerize monomeric proteins, and to generate chimeric proteins that combine the characteristics of heterologous single proteins, e.g., chimeric, bi-specific antibodies.

Some aspects of this invention provide methods, compositions, and reagents for the N-terminal or C-terminal addition of click chemistry handles to proteins using a sortase transacylation reaction. Some aspects of this invention provide methods for installing a click chemistry handle at or proximal to the C-terminus of a protein comprising a sortase recognition motif (e.g., LPXT) near the C-terminus. Some aspects of this invention provide methods for installing a click chemistry handle on the N-terminus of a protein comprising one or more N-terminal glycine residues.

For example, some embodiments provide a method of conjugating a target protein to a C-terminal click chemistry handle. In some embodiments, the method comprises providing the target protein with a C-terminal sortase recognition motif (e.g., LPXT); for example, as a C-terminal fusion. In some embodiments, the method further comprises contacting the target protein with an agent, for example, a peptide, a protein, or a compound, comprising 1-10 N-terminal glycine residues or an N-terminal alkylamine group, and the click chemistry handle. In some embodiments, the contacting is carried out in the presence of a sortase enzyme under conditions suitable for the sortase to transamidate the target protein and the peptide comprising the click chemistry handle, thus conjugating the target protein to the click-chemistry handle.

Some embodiments provide a method of conjugating a target protein to an N-terminal click chemistry handle is provided. In some embodiments, the method comprises providing the target protein with 1-10 N-terminal glycine residues or an N-terminal alkylamine group, for example, as an N-terminal fusion. In some embodiments, the method further comprises contacting the target protein with a peptide comprising a sortase recognition motif (e.g., LPXT), and the click chemistry handle. In some embodiments, the contacting is carried out in the presence of a sortase enzyme under conditions suitable for the sortase to transamidate the target protein and the peptide, thus conjugating the target protein to the click-chemistry handle.

Any chemical moiety can be installed on a protein using the methods described herein. Of particular use according to some aspects of this invention are click chemistry handles. Click chemistry handles are chemical moieties that provide a reactive group that can partake in a click chemistry reaction. Click chemistry reactions and suitable chemical groups for click chemistry reactions are well known to those of skill in the art, and include, but are not limited to terminal alkynes, azides, strained alkynes, dienes, dieneophiles, alkoxyamines, carbonyls, phosphines, hydrazides, thiols, and alkenes. For example, in some embodiments, an azide and an alkyne are used in a click chemistry reaction.

Some aspects of this invention provide modified proteins, for example, proteins comprising a C-terminal or an N-terminal click chemistry handle. Such proteins can be conjugated to other molecules, for example, proteins, nucleic acids, polymers, lipids, or small molecules, comprising a moiety that can react with the click chemistry handle of the protein. In some embodiments, the modified protein comprises an antigen-binding domain, for example, an antigen-binding domain of an antibody, e.g., a camelid antibody, a single-domain antibody, a VHH domain, a nanobody, or an ScFv, or an antigen-binding fragment thereof.

Some aspects of this invention provide methods for the conjugation, or ligation, of two protein molecules via click chemistry. In some embodiments, a first click chemistry handle is installed on the first protein, and a second click chemistry handle is installed on the second protein, wherein the first click chemistry handle can form a covalent bond with the second click chemistry handle. For example, some embodiments provide a method for post-translationally conjugating two proteins to form a chimeric protein. In some embodiments, the method comprises contacting a first protein conjugated to a first click-chemistry handle with a second protein conjugated to a second click chemistry handle under conditions suitable for the first click chemistry handle to react with the second click chemistry handle, thus generating a chimeric protein comprising the two proteins linked via a covalent bond.

The methods provided herein allow for the generation of N-terminus to N-terminus conjugation and of C-terminus to C-terminus conjugation of proteins, which cannot be achieved by recombinant means (e.g., expression of protein fusions). For example, in some embodiments, the first click chemistry handle is conjugated to the N-terminus of the first protein, and the second click chemistry handle is conjugated to the N-terminus of the second protein, and the chimeric protein is an N-terminus-to-N-terminus conjugation of the two proteins. In other embodiments, the first click chemistry handle is conjugated to the C-terminus of the first protein and the second click chemistry handle is conjugated to the C-terminus of the second protein, and the chimeric protein is a C-terminus-to-C-terminus conjugation of the two proteins. In some embodiments, click handles are used to join C- and N-termini of a first and a second polypeptides, e.g., as an alternative to producing a fusion protein recombinantly. This is particularly useful, e.g., if a fusion protein is very large, toxic, hard to purify, encoded by nucleic acid sequences that are hard to clone, or to avoid cloning.

Some embodiments of this invention provide chimeric proteins, for example, chimeric proteins that have been generated by post-translational conjugation of the two proteins according to aspects of this invention. Some embodiments provide chimeric, bi-specific antibodies, comprising two antigen-binding proteins, for example, single-domain antibodies, that are conjugated together via click chemistry. Some embodiments provide a bispecific, chimeric antibody comprises a first antibody or antigen-binding antibody fragment comprising a sortase recognition sequence, and a second antibody or antigen-binding antibody fragment comprising a sortase recognition sequence; and the first and the second antibody or antibody fragment are conjugated together via click chemistry.

It should be noted that the invention is not limited to the conjugation of antigen-binding proteins, but that any protein can be conjugated with any molecule which comprises a suitable click chemistry handle, or on which such a handle can be installed according to methods described herein or methods known to those of skill in the art. Accordingly, some embodiments provide chimeric proteins comprising a target protein with a sortase recognition motif (e.g., LPXT), and a second molecule conjugated to the protein via click chemistry. In some embodiments, the chimeric protein is generated by post-translationally installing a click chemistry handle on the target protein and contacting the target protein including the click chemistry handle with the second molecule, wherein the second molecule comprises a second click chemistry handle that can react with the click chemistry handle of the target protein to form a covalent bond.

Some embodiments provide modified proteins, for example, proteins comprising a sortase recognition motif (e.g., LPXT) and a click chemistry handle conjugated to the sortase recognition motif, for example, directly to one of the amino acids of the sortase recognition motif, or via a linker. In some embodiments, the modified protein comprises an antigen-binding domain, e.g., an antibody or an antigen-binding antibody fragment. Exemplary, modified proteins provided herein include, but are not limited to, a camelid antibody or antigen-binding fragment thereof, a VHH domain, a single-domain antibody, a nanobody, an scFv, or an adnectin. In some embodiments, the click chemistry handle is positioned at the C-terminus of the protein, while in other embodiments, the click chemistry handle is positioned at the N-terminus of the protein. In some embodiments, the click chemistry handle is selected from the group consisting of terminal alkyne, azide, strained alkyne, diene, dieneophile, alkoxyamine, carbonyl, phosphine, hydrazide, thiol, and alkene.

Some embodiments of this invention provide kits comprising one or more reagents useful in carrying out methods provided herein. For example, in some embodiments, the invention provides a kit comprising a first peptide comprising 1-10 glycine residues or a terminal alkylamine conjugated to a first click chemistry handle, and a second peptide comprising a sortase recognition motif conjugated to a second click chemistry handle, wherein the click chemistry handle of the first and the second peptide can react. In some embodiments, the kit comprises a first peptide comprising 1-10 glycine residues or a terminal alkylamine conjugated to a first click chemistry handle, and a second peptide comprising 1-10 glycine residues or a terminal alkylamine conjugated to a second click chemistry handle, wherein the click chemistry handle of the first and the second peptide can react. In some embodiments, the kit comprises a first peptide comprising a sortase recognition motif conjugated to a first click chemistry handle, and a second peptide comprising a sortase recognition motif conjugated to a second click chemistry handle, wherein the click chemistry handle of the first and the second peptide are capable of reacting with each other. In some embodiments, the kit further comprises a sortase enzyme. In some embodiments, the kit further comprises instructions for use, a catalyst, for example, a metal catalyst, and/or a reaction buffer.

The above summary is intended to give an overview over some aspects of this invention, and is not to be construed to limit the invention in any way. Additional aspects, advantages, and embodiments of this invention are described herein, and further embodiments will be apparent to those of skill in the art based on the instant disclosure. The entire contents of all references cited above and herein are hereby incorporated by reference.

BRIEF DESCRIPTION OF THE DRAWING

FIG. 29. Immunoprecipitation performed on MDCK cells radiolabelled with S35 and infected with influenza A virus. Lanes are labeled with name of the VHH used for immunoprecipitation. VHH52, VHH54, and VHH62 recognize the nucleoprotein of influenza A virus (band slightly above the 50 kD size marker). FluB is a positive control antiserum.

FIG. 31. Representative sequences encoding polypeptides comprising VHH that bind to MHC Class II proteins.

FIG. 32. Representative sequences encoding polypeptides comprising VHH that bind to influenza A virus proteins.

DEFINITIONS

Figure 1:
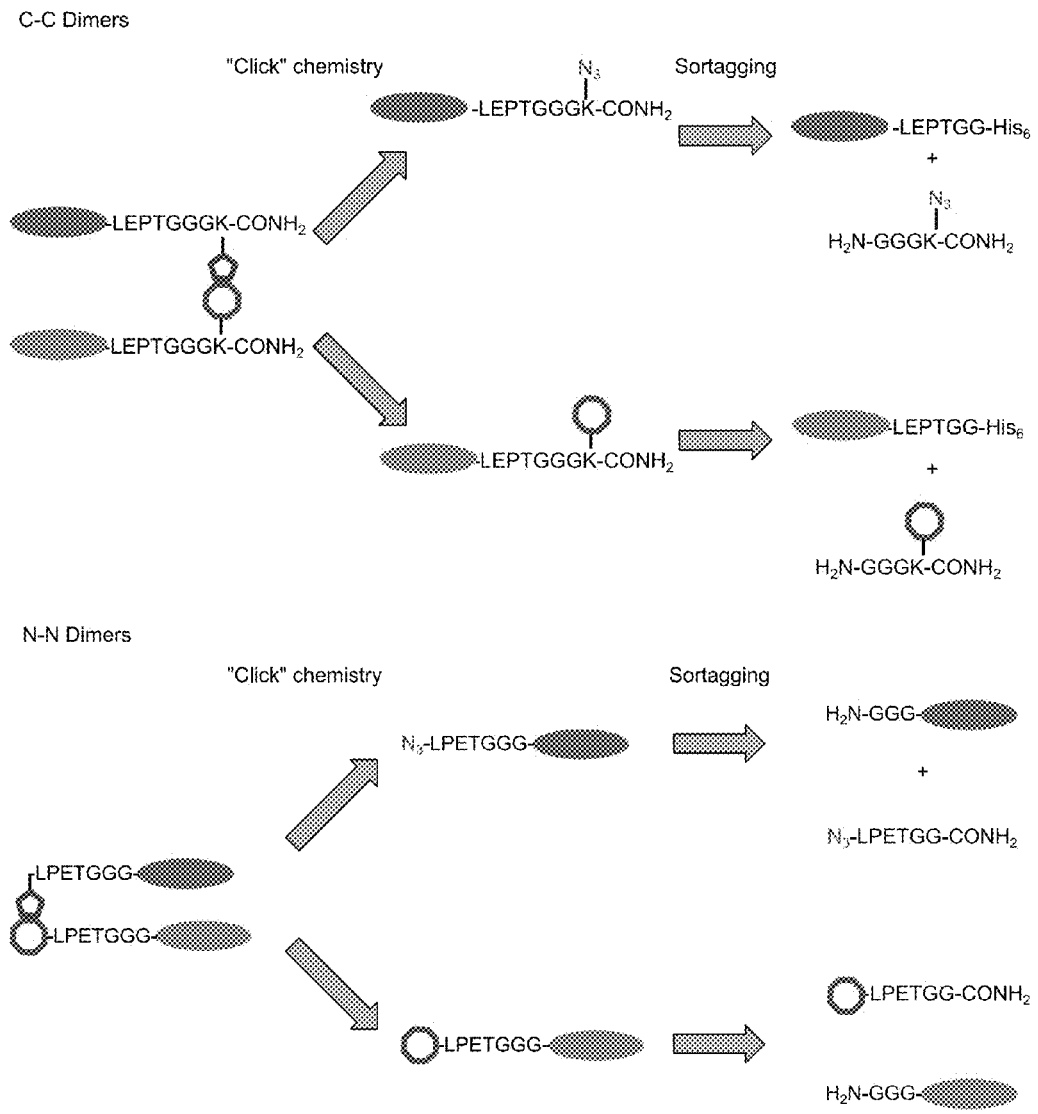
FIG. 1. Generation of C—C protein dimers and N—N protein dimers using sortases and click chemistry. In the upper panel, the term "LEPTGG" refers to a sortase recognition motif, for example, LPETGG.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1-4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms ($C_{1-20}$alkyl). In another embodiment, the alkyl group employed contains 1-15 carbon atoms ($C_{1-15}$alkyl). In another embodiment, the alkyl group employed contains 1-10 carbon atoms ($C_{1-10}$alkyl). In another embodiment, the alkyl group employed contains 1-8 carbon atoms ($C_{1-8}$alkyl). In another embodiment, the alkyl group employed contains 1-6 carbon atoms ($C_{1-6}$alkyl). In another embodiment, the alkyl group employed contains 1-5 carbon atoms ($C_{1-5}$alkyl). In another embodiment, the alkyl group employed contains 1-4 carbon atoms ($C_{1-4}$alkyl). In another embodiment, the alkyl group employed contains 1-3 carbon atoms ($C_{1-3}$alkyl). In another embodiment, the alkyl group employed contains 1-2 carbon atoms ($C_{1-2}$alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety. The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms ($C_{2-20}$alkenyl). In some embodiments, the alkenyl group employed in the invention contains 2-15 carbon atoms ($C_{2-15}$alkenyl). In another embodiment, the alkenyl group employed contains 2-10 carbon atoms ($C_{2-10}$alkenyl). In still other embodiments, the alkenyl group contains 2-8 carbon atoms ($C_{2-8}$alkenyl). In yet other embodiments, the alkenyl group contains 2-6 carbons ($C_{2-6}$alkenyl). In yet other embodiments, the alkenyl group contains 2-5 carbons ($C_{2-5}$alkenyl). In yet other embodiments, the alkenyl group contains 2-4 carbons ($C_{2-4}$alkenyl). In yet other embodiments, the alkenyl group contains 2-3 carbons ($C_{2-3}$alkenyl). In yet other embodiments, the alkenyl group contains 2 carbons ($C_2$alkenyl). Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety. The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms ($C_{2-20}$alkynyl). In some embodiments, the alkynyl group employed in the invention contains 2-15 carbon atoms ($C_{2-15}$alkynyl). In another embodiment, the alkynyl group employed contains 2-10 carbon atoms ($C_{2-10}$alkynyl). In still other embodiments, the alkynyl group contains 2-8 carbon atoms ($C_{2-8}$alkynyl). In still other embodiments, the alkynyl group contains 2-6 carbon atoms ($C_{2-6}$alkynyl). In still other embodiments, the alkynyl group contains 2-5 carbon atoms ($C_{2-5}$alkynyl). In still other embodiments, the alkynyl group contains 2-4 carbon atoms ($C_{2-4}$alkynyl). In still other embodiments, the alkynyl group contains 2-3 carbon atoms ($C_{2-3}$alkynyl). In still other embodiments, the alkynyl group contains 2 carbon atoms ($C_2$alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "carbocyclic" or "carbocyclyl" as used herein, refers to an as used herein, refers to a cyclic aliphatic group containing 3-10 carbon ring atoms ($C_{3-10}$carbocyclic). Carbocyclic group substituents include, but are not limited to, any of the substituents described herein, that result in the formation of a stable moiety.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that further contains one or more heteroatoms (e.g., oxygen, sulfur, nitrogen, phosphorus, or silicon atoms) between carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms and 1-6 heteroatoms ($C_{1-20}$heteroaliphatic). In certain embodiments, the heteroaliphatic group contains 1-10 carbon atoms and 1-4 heteroatoms ($C_{1-10}$heteroaliphatic). In certain embodiments, the heteroaliphatic group contains 1-6 carbon atoms and 1-3 heteroatoms ($C_{1-6}$heteroaliphatic). In certain embodiments, the heteroaliphatic group contains 1-5 carbon atoms and 1-3 heteroatoms ($C_{1-5}$heteroaliphatic). In certain embodiments, the heteroaliphatic group contains 1-4 carbon atoms and 1-2 heteroatoms ($C_{1-4}$heteroaliphatic). In certain embodiments, the heteroaliphatic group contains 1-3 carbon atoms and 1 heteroatom 3heteroaliphatic). In certain embodiments, the heteroaliphatic group contains 1-2 carbon atoms and 1 heteroatom ($C_{1-2}$heteroaliphatic). Heteroaliphatic group substituents include, but are not limited to, any of the substituents described herein, that result in the formation of a stable moiety.

The term "heteroalkyl," as used herein, refers to an alkyl moiety, as defined herein, which contain one or more heteroatoms (e.g., oxygen, sulfur, nitrogen, phosphorus, or silicon atoms) in between carbon atoms. In certain embodiments, the heteroalkyl group contains 1-20 carbon atoms and 1-6 heteroatoms ($C_{1-20}$ heteroalkyl). In certain embodiments, the heteroalkyl group contains 1-10 carbon atoms and 1-4 heteroatoms ($C_{1-10}$ heteroalkyl). In certain embodiments, the heteroalkyl group contains 1-6 carbon atoms and 1-3 heteroatoms ($C_{1-6}$ heteroalkyl). In certain embodiments, the heteroalkyl group contains 1-5 carbon atoms and 1-3 heteroatoms ($C_{1-5}$ heteroalkyl). In certain embodiments, the heteroalkyl group contains 1-4 carbon atoms and 1-2 heteroatoms ($C_{1-4}$ heteroalkyl). In certain embodiments, the heteroalkyl group contains 1-3 carbon atoms and 1 heteroatom ($C_{1-3}$ heteroalkyl). In certain embodiments, the heteroalkyl group contains 1-2 carbon atoms and 1 heteroatom ($C_{1-2}$ heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety.

The term "heteroalkenyl," as used herein, refers to an alkenyl moiety, as defined herein, which further contains one or more heteroatoms (e.g., oxygen, sulfur, nitrogen, phosphorus, or silicon atoms) in between carbon atoms. In certain embodiments, the heteroalkenyl group contains 2-20 carbon atoms and 1-6 heteroatoms ($C_{2-20}$ heteroalkenyl). In certain embodiments, the heteroalkenyl group contains 2-10 carbon atoms and 1-4 heteroatoms ($C_{2-10}$ heteroalkenyl). In certain embodiments, the heteroalkenyl group contains 2-6 carbon atoms and 1-3 heteroatoms ($C_{2-6}$ heteroalkenyl). In certain embodiments, the heteroalkenyl group contains 2-5 carbon atoms and 1-3 heteroatoms ($C_{2-5}$ heteroalkenyl). In certain embodiments, the heteroalkenyl group contains 2-4 carbon atoms and 1-2 heteroatoms ($C_{2-4}$ heteroalkenyl). In certain embodiments, the heteroalkenyl group contains 2-3 carbon atoms and 1 heteroatom ($C_{2-3}$ heteroalkenyl). The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which further contains one or more heteroatoms (e.g., oxygen, sulfur, nitrogen, phosphorus, or silicon atoms) in between carbon atoms. In certain embodiments, the heteroalkynyl group contains 2-20 carbon atoms and 1-6 heteroatoms ($C_{2-20}$ heteroalkynyl). In certain embodiments, the heteroalkynyl group contains 2-10 carbon atoms and 1-4 heteroatoms ($C_{2-10}$ heteroalkynyl). In certain embodiments, the heteroalkynyl group contains 2-6 carbon atoms and 1-3 heteroatoms ($C_{2-6}$ heteroalkynyl). In certain embodiments, the heteroalkynyl group contains 2-5 carbon atoms and 1-3 heteroatoms ($C_{2-5}$ heteroalkynyl). In certain embodiments, the heteroalkynyl group contains 2-4 carbon atoms and 1-2 heteroatoms ($C_{2-4}$ heteroalkynyl). In certain embodiments, the heteroalkynyl group contains 2-3 carbon atoms and 1 heteroatom ($C_{2-3}$ heteroalkynyl). The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety.

The term "aryl," as used herein, refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but are not limited to, phenyl, biphenyl, naphthyl, and the like, which may bear one or more substituents. Aryl substituents include, but are not limited to, any of the substituents described herein, that result in the formation of a stable moiety. The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

The term "heteroaryl," as used herein, refers to an aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety. The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety.

The term "acyl," as used herein, is a subset of a substituted alkyl group, and refers to a group having the general formula —C(=O)$R^A$, —C(=O)O$R^A$, —C(=O)—O—C(=O)$R^A$, —C(=O)S$R^A$, —C(=O)N($R^A$)$_2$, —C(=S)$R^A$, —C(=S)N($R^A$)$_2$, and —C(=S)S($R^A$), —C(=N$R^A$)$R^A$ C(=N$R^A$)O$R^A$, —C(=N$R^A$)S$R^A$, and —C(=N$R^A$)N($R^A$)$_2$, wherein $R^A$ is hydrogen; halogen; substituted or unsubstituted hydroxyl; substituted or unsubstituted thiol; substituted or unsubstituted amino; acyl; optionally substituted aliphatic; optionally substituted heteroaliphatic; optionally substituted alkyl; optionally substituted alkenyl; optionally substituted alkynyl; optionally substituted aryl, optionally substituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes (—CHO), carboxylic acids (—$CO_2$H), ketones, acyl halides, esters, amides, imines, carbonates, carbamates, and ureas. Acyl substituents include, but are not limited to, any of the substituents described herein, that result in the formation of a stable moiety.

The term "acylene," as used herein, is a subset of a substituted alkylene, substituted alkenylene, substituted alkynylene, substituted heteroalkylene, substituted heteroalkenylene, or substituted heteroalkynylene group, and refers to an acyl group having the general formulae: —$R^0$—(C=$X^1$)—$R^0$—, —$R^0$—$X^2$(C=$X^1$)—$R^0$—, or —$R^0$—$X^2$(C=$X^1$)$X^3$—$R^0$—, where $X^1$, $X^2$, and $X^3$ is, independently, oxygen, sulfur, or N$R^r$, wherein $R^r$ is hydrogen or optionally substituted aliphatic, and $R^0$ is an optionally substituted alkylene, alkenylene, alkynylene, heteroalkylene, heteroalkenylene, or heteroalkynylene group, as defined herein. Exemplary acylene groups wherein $R^0$ is alkylene includes —(CH$_2$)$_T$—O(C=O)—(CH$_2$)$_T$—; —(CH$_2$)$_T$—N$R^r$(C=O)—(CH$_2$)$_T$—; —(CH$_2$)$_T$—O(C=N$R^r$)—(CH$_2$)$_T$—; —(CH$_2$)$_T$—N$R^r$(C=N$R^r$)—(CH$_2$)$_T$—; —(CH$_2$)$_T$—(C=O)—(CH$_2$)$_T$—; —(CH$_2$)$_T$—(C=N$R^r$)—(CH$_2$)$_T$—; —(CH$_2$)$_T$—S(C=S)—(CH$_2$)$_T$—; —(CH$_2$)$_T$—N$R^r$(C=S)—(CH$_2$)$_T$—; —(CH$_2$)$_T$—S(C=N$R^r$)—(CH$_2$)$_T$—; —(CH$_2$)$_T$—O(C=S)—(CH$_2$)$_T$—; —(CH$_2$)$_T$—(C=S)—(CH$_2$)$_T$—; or —(CH$_2$)$_T$—S(C=O)—(CH$_2$)$_T$—, and the like, which may bear one or more substituents; and wherein each instance of T is, independently, an integer between 0 to 20. Acylene substituents include, but are not limited to, any of the substituents described herein, that result in the formation of a stable moiety.

The term "amino," as used herein, refers to a group of the formula (—NH$_2$). A "substituted amino" refers either to a mono-substituted amine (—NHR$^h$) of a disubstituted amine (—NR$^h_2$), wherein the R$^h$ substituent is any substituent as described herein that results in the formation of a stable moiety (e.g., an amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the disubstituted amino group (—NR$^h_2$) form a 5- to 6-membered heterocyclic ring.

The term "hydroxy" or "hydroxyl," as used herein, refers to a group of the formula (—OH). A "substituted hydroxyl" refers to a group of the formula (—OR$^i$), wherein R$^i$ can be any substituent which results in a stable moiety (e.g., a hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "thio" or "thiol," as used herein, refers to a group of the formula (—SH). A "substituted thiol" refers to a group of the formula (—SR$^r$), wherein R$^r$ can be any substituent that results in the formation of a stable moiety (e.g., a thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "imino," as used herein, refers to a group of the formula (=NR$^r$), wherein R$^r$ corresponds to hydrogen or any substituent as described herein, that results in the formation of a stable moiety (for example, an amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "azide" or "azido," as used herein, refers to a group of the formula (—N$_3$).

The terms "halo" and "halogen," as used herein, refer to an atom selected from fluorine (fluoro, —F), chlorine (chloro, —Cl), bromine (bromo, —Br), and iodine (iodo, —I).

A "leaving group" is an art-understood term referring to a molecular fragment that departs with a pair of electrons in heterolytic bond cleavage, wherein the molecular fragment is an anion or neutral molecule. See, for example, Smith, March's Advanced Organic Chemistry 6th ed. (501-502). Exemplary leaving groups include, but are not limited to, halo (e.g., chloro, bromo, iodo) and activated substituted hydroxyl groups, e.g., of the formula —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{aa}$)$_2$, —OP(=O)$_2$N(R$^{bb}$)$_2$, or —OP(=O)(NR$^{bb}$)$_2$ wherein R$^{aa}$ is optionally substituted aliphatic, optionally substituted heteroaliphatic, optionally substituted aryl, or optionally substituted heteroaryl; R$^{bb}$ is hydrogen, an amino protecting group, optionally substituted aliphatic, optionally substituted heteroaliphatic, optionally substituted aryl, or optionally substituted heteroaryl; and R$^{cc}$ is hydrogen, optionally substituted aliphatic, optionally substituted heteroaliphatic, optionally substituted aryl, or optionally substituted heteroaryl.

As used herein, the term Xaa refers to an amino acid for example, a standard amino acid of Table A, or a non-standard amino acid of table B. In some embodiments, the term Xaa refers to a compound e.g. of the formula:

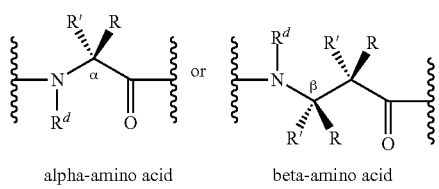

alpha-amino acid     beta-amino acid wherein each instance of R and R' independently are selected from the group consisting of hydrogen, optionally substituted aliphatic, optionally substituted heteroaliphatic, optionally substituted aryl, and optionally substituted heteroaryl; and R$^d$ is hydrogen or an amino protecting group. Amino acids encompassed by the above two formulae include, without limitation, natural alpha-amino acids such as D- and L-isomers of the 20 common naturally occurring alpha-amino acids found in polypeptides and proteins (e.g., A, R, N, C, D, Q, E, G, H, I, L, K, M, F, P, S, T, W, Y, V, as depicted in Table A below, also referred to herein as standard amino acids), non-standard alpha-amino acids (examples of which are depicted in Table B below), and beta-amino acids (standard or non-standard, e.g., beta-alanine).

TABLE A

Standard alpha-amino acids

| | R | R' |
|---|---|---|
| L-Alanine (A) | —CH$_3$ | —H |
| L-Arginine (R) | —CH$_2$CH$_2$CH$_2$—NHC(=NH)NH$_2$ | —H |
| L-Asparagine (N) | —CH$_2$C(=O)NH$_2$ | —H |
| L-Aspartic acid (D) | —CH$_2$CO$_2$H | —H |
| L-Cysteine (C) | —CH$_2$SH | —H |
| L-Glutamic acid (E) | —CH$_2$CH$_2$CO$_2$H | —H |
| L-Glutamine (Q) | —CH$_2$CH$_2$C(=O)NH$_2$ | —H |
| Glycine (G) | —H | —H |
| L-Histidine (H) | —CH$_2$-2-(1H-imidazole) | —H |
| L-Isoleucine (I) | -sec-butyl | —H |
| L-Leucine (L) | -iso-butyl | —H |
| L-Lysine (K) | —CH$_2$CH$_2$CH$_2$CH$_2$NH$_2$ | —H |
| L-Methionine (M) | —CH$_2$CH$_2$SCH$_3$ | —H |
| L-Phenylalanine (F) | —CH$_2$Ph | —H |
| L-Proline (P) | -2-(pyrrolidine) | —H |
| L-Serine (S) | —CH$_2$OH | —H |
| L-Threonine (T) | —CH$_2$CH(OH)(CH$_3$) | —H |
| L-Tryptophan (W) | —CH$_2$-3-(1H-indole) | —H |
| L-Tyrosine (Y) | —CH$_2$-(p-hydroxyphenyl) | —H |
| L-Valine (V) | -isopropyl | —H |

TABLE B

Non-standard alpha-amino acids

| | R | R' |
|---|---|---|
| D-Alanine | —H | —CH$_3$ |
| D-Arginine | —H | —CH$_2$CH$_2$CH$_2$—NHC(=NH)NH$_2$ |
| D-Asparagine | —H | —CH$_2$C(=O)NH$_2$ |
| D-Aspartic acid | —H | —CH$_2$CO$_2$H |
| D-Cysteine | —H | —CH$_2$SH |
| D-Glutamic acid | —H | —CH$_2$CH$_2$CO$_2$H |
| D-Glutamine | —H | —CH$_2$CH$_2$C(=O)NH$_2$ |
| D-Histidine | —H | —CH$_2$-2-(1H-imidazole) |
| D-Isoleucine | —H | -sec-butyl |
| D-Leucine | —H | -iso-butyl |
| D-Lysine | —H | —CH$_2$CH$_2$CH$_2$CH$_2$NH$_2$ |
| D-Methionine | —H | —CH$_2$CH$_2$SCH$_3$ |
| D-Phenylalanine | —H | —CH$_2$Ph |
| D-Proline | —H | -2-(pyrrolidine) |
| D-Serine | —H | —CH$_2$OH |
| D-Threonine | —H | —CH$_2$CH(OH)(CH$_3$) |
| D-Tryptophan | —H | —CH$_2$-3-(1H-indole) |
| D-Tyrosine | —H | —CH$_2$-(p-hydroxyphenyl) |
| D-Valine | —H | -isopropyl |
| R and R' are equal to: | | |
| α-methyl-Alanine (Aib) | —CH$_3$, —CH$_3$ | |
| α-methyl-Arginine | —CH$_3$, —CH$_2$CH$_2$CH$_2$—NHC(=NH)NH$_2$ | |
| α-methyl-Asparagine | —CH$_3$, —CH$_2$C(=O)NH$_2$ | |
| α-methyl-Aspartic acid | —CH$_3$, —CH$_2$CO$_2$H | |
| α-methyl-Cysteine | —CH$_3$, —CH$_2$SH | |
| α-methyl-Glutamic acid | —CH$_3$, —CH$_2$CH$_2$CO$_2$H | |
| α-methyl-Glutamine | —CH$_3$, —CH$_2$CH$_2$C(=O)NH$_2$ | |
| α-methyl-Histidine | —CH$_3$, —CH$_2$-2-(1H-imidazole) | |
| α-methyl-Isoleucine | —CH$_3$, -sec-butyl | |
| α-methyl-Leucine | —CH$_3$, -iso-butyl | |
| α-methyl-Lysine | —CH$_3$, —CH$_2$CH$_2$CH$_2$CH$_2$NH$_2$ | |
| α-methyl-Methionine | —CH$_3$, —CH$_2$CH$_2$SCH$_3$ | |
| α-methyl-Phenylalanine | —CH$_3$, —CH$_2$Ph | |
| α-methyl-Proline | —CH$_3$, -2-(pyrrolidine) | |
| α-methyl-Serine | —CH$_3$, —CH$_2$OH | |
| α-methyl-Threonine | —CH$_3$, —CH$_2$CH(OH)(CH$_3$) | |
| α-methyl-Tryptophan | —CH$_3$, —CH$_2$-3-(1H-indole) | |
| α-methyl-Tyrosine | —CH$_3$, —CH$_2$-(p-hydroxyphenyl) | |
| α-methyl-Valine | —CH$_3$, -isopropyl | |
| Norleucine | —H, —CH$_2$CH$_2$CH$_2$CH$_3$ | |

There are many known non-natural amino acids any of which may be included in the polypeptides of the present invention. See, for example, S. Hunt, The Non-Protein Amino Acids: In Chemistry and Biochemistry of the Amino Acids, edited by G. C. Barrett, Chapman and Hall, 1985. Some examples of non-natural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-aminocyclopropanecarboxylic acid, 1-amino-2-phenyl-cyclopropanecarboxylic acid, 1-aminocyclobutanecarboxylic acid, 4-aminocyclopentenecarboxylic acid, 3-aminocyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine.

The term "click chemistry" refers to a chemical philosophy introduced by K. Barry Sharpless of The Scripps Research Institute, describing chemistry tailored to generate covalent bonds quickly and reliably by joining small units comprising reactive groups together. Click chemistry does not refer to a specific reaction, but to a concept including reactions that mimick reactions found in nature. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. A distinct exothermic reaction makes a reactant "spring loaded". In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallisation or distillation).

The term "click chemistry handle," as used herein, refers to a reactant, or a reactive group, that can partake in a click chemistry reaction. For example, a strained alkyne, e.g., a cyclooctyne, is a click chemistry handle, since it can partake in a strain-promoted cycloaddition (see, e.g., Table 1). In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein, for example, in Tables 1 and 2, and in FIG. 2B. Other suitable click chemistry handles are known to those of skill in the art.

The terms "protein," "peptide" and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "conjugated" or "conjugation" refers to an association of two molecules, for example, two proteins, with one another in a way that they are linked by a direct or indirect covalent or non-covalent interaction. In the context of conjugation via click chemistry, the conjugation is via a covalent bond formed by the reaction of the click chemistry handles. In certain embodiments, the association is covalent, and the entities are said to be "conjugated" to one another. In some embodiments, a protein is post-translationally conjugated to another molecule, for example, a second protein, by forming a covalent bond between the protein and the other molecule after the protein has been translated, and, in some embodiments, after the protein has been isolated. In some embodiments, the post-translational conjugation of the protein and the second molecule, for example, the second protein, is effected via installing a click chemistry handle on the protein, and a second click chemistry handle, which can react to the first click chemistry handle, on the second molecule, and carrying out a click chemistry reaction in which the click chemistry handles react and form a covalent bond between the protein and the second molecule, thus generating a chimeric protein. In some embodiments, two proteins are conjugated at their respective C-termini, generating a C—C conjugated chimeric protein. In some embodiments, two proteins are conjugated at their respective N-termini, generating an N—N conjugated chimeric protein.

As used herein, a "detectable label" refers to a moiety that has at least one element, isotope, or functional group incorporated into the moiety which enables detection of the molecule, e.g., a protein or polypeptide, or other entity, to which the label is attached. Labels can be directly attached (i.e., via a bond) or can be attached by a tether (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; or an optionally substituted acylene, or any combination thereof, which can make up a tether). It will be appreciated that the label may be attached to or incorporated into a molecule, for example, a protein, polypeptide, or other entity, at any position.

In general, a label can fall into any one (or more) of five classes: a) a label which contains isotopic moieties, which may be radioactive or heavy isotopes, including, but not limited to, $^2$H, $^3$H, $^{13}$C, $^{14}$C, $^{15}$N, $^{18}$F, $^{31}$P, $^{32}$P, $^{35}$S, $^{67}$Ga, $^{76}$Br, $^{99m}$Tc (Tc-99m), $^{111}$In, $^{123}$I, $^{125}$I, $^{131}$I, $^{153}$Gd, $^{169}$Yb, and $^{186}$Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluoresceinisothiocyanate (FITC); d) a label which has one or more photo affinity moieties; and e) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluoresceinisothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, Renilla, or *Gaussia* luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising chromophores that emit light of different colors such as red, yellow, and cyan fluorescent proteins, etc. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, mTomato, T-Sapphire, mAmetrine, mKeima. See, e.g., Chalfie, M. and Kain, S R (eds.) Green fluorescent protein: properties, applications, and protocols (Methods of biochemical analysis, v. 47). Wiley-Interscience, Hoboken, N.J., 2006, and/or Chudakov, D M, et al., Physiol Rev. 90(3):1103-63, 2010 for discussion of GFP and numerous other fluorescent or luminescent proteins. In some embodiments, a label comprises a dark quencher, e.g., a substance that absorbs excitation energy from a fluorophore and dissipates the energy as heat.

The term "adjuvant" encompasses substances that accelerate, prolong, or enhance the immune response to an antigen. In some embodiments an adjuvant serves as a lymphoid system activator that enhances the immune response in a relatively non-specific manner, e.g., without having any specific antigenic effect itself. For example, in some embodiments an adjuvant stimulates one or more components of the innate immune system. In certain embodiments an adjuvant enhances antigen-specific immune responses when used in combination with a specific antigen or antigens, e.g., as a component of a vaccine. Adjuvants include, but are not limited to, aluminum salts (alum) such as aluminum hydroxide or aluminum phosphate, complete Freund's adjuvant, incomplete Freund's adjuvant, surface active substances such as lysolecithin, pluronic polyols, Amphigen, Avridine, bacterial lipopolysaccharides, 3-O-deacylated monophosphoryl lipid A, synthetic lipid A analogs or aminoalkyl glucosamine phosphate compounds (AGP), or derivatives or analogs thereof (see, e.g., U.S. Pat. No. 6,113,918), L121/squalene, muramyl dipeptide, polyanions, peptides, saponins, oil or hydrocarbon and water emulsions, particles such as ISCOMS (immunostimulating complexes), etc. In some embodiments an adjuvant stimulates dendritic cell maturation. In some embodiments an adjuvant stimulates expression of one or more costimulator(s), such as B7 or a B7 family member, by APCs, e.g., dendritic cells. In some embodiments an adjuvant comprises a CD40 agonist. In some embodiments a CD40 agonist comprises an anti-CD40 antibody. In some embodiments a CD40 agonist comprises a CD40 ligand, such as CD40L. In some embodiments an adjuvant comprises a ligand for a Toll-like receptor (TLR). In some embodiments an agent is a ligand for one or more of TLRs 1-13, e.g., at least for TLR3, TLR4, and/or TLR9. In some embodiments an adjuvant comprises a pathogen-derived molecular pattern (PAMP) or mimic thereof. In some embodiments an adjuvant comprises an immunostimulatory nucleic acid, e.g., a double-stranded nucleic acid, e.g., double-stranded RNA or an analog thereof. For example, in some embodiments an adjuvant comprises polyriboinosinic: polyribocytidylic acid (polyIC). In some embodiments an adjuvant comprises a nucleic acid comprising unmethylated nucleotides, e.g., a single-stranded CpG oligonucleotide. In some embodiments an adjuvant comprises a cationic polymer, e.g., a poly(amino acid) such as poly-L-lysine, poly-L-arginine, or poly-L-ornithine. In some embodiments an adjuvant comprises a nucleic acid (e.g., dsRNA, polyIC) and a cationic polymer. For example, in some embodiments an adjuvant comprises polyIC and poly-L-lysine. In some embodiments an adjuvant comprises a complex comprising polyIC, poly-L-lysine, and carboxymethylcellulose (referred to as polyICLC). In some embodiments an adjuvant comprises a CD40 agonist and a TLR ligand. For example, in some embodiments an adjuvant comprises (i) an anti-CD40 antibody and (ii) an immunostimulatory nucleic acid and/or a cationic polymer. In some embodiments an adjuvant comprises an anti-CD40 antibody, an immunostimulatory nucleic acid, and a cationic polymer. In some embodiments an adjuvant comprises (i) an anti-CD40 antibody and (ii) poly(IC) or poly(ICLC). Exemplary adjuvants of use in various embodiments are disclosed in, e.g., WO/2007/137427 and/or in WO/2009/086640 and/or in one or more references therein. In certain embodiments an adjuvant is pharmaceutically acceptable for administration to a human subject. In certain embodiments an adjuvant is pharmaceutically acceptable for administration to a non-human subject, e.g., for veterinary purposes.

The term "antibody", as used herein, refers to a glycoprotein belonging to the immunoglobulin superfamily. The terms antibody and immunoglobulin are used interchangeably. With some exceptions, mammalian antibodies are typically made of basic structural units each with two large heavy chains and two small light chains. There are several different types of antibody heavy chains, and several different kinds of antibodies, which are grouped into different isotypes based on which heavy chain they possess. Five different antibody isotypes are known in mammals, IgG, IgA, IgE, IgD, and IgM, which perform different roles, and help direct the appropriate immune response for each different type of foreign object they encounter. In some embodiments, an antibody is an IgG antibody, e.g., an antibody of the IgG1, 2, 3, or 4 human subclass. Antibodies from non-mammalian species (e.g., from birds, reptiles, *amphibia*) are also within the scope of the term, e.g., IgY antibodies.

Only part of an antibody is involved in the binding of the antigen, and antigen-binding antibody fragments, their preparation and use, are well known to those of skill in the art. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab') fragment (or F(ab')2 fragment), retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fe/pFc' regions to produce a functional antibody. See, e.g., U.S. Pat. Nos. 4,816,567, 5,225,539, 5,585,089, 5,693,762, and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab'), Fab, Fv, and Fd fragments; antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, the present invention provides so-called single chain antibodies (e.g., ScFv), (single) domain antibodies, and other antibodies, which, in some embodiments, find use as intracellular antibodies. Domain antibodies, camelid and camelized antibodies and fragments thereof, for example, VHH domains, or nanobodies, such as those described in patents and published patent applications of Ablynx NV and Domantis are also encompassed in the term antibody. The term "antigen-binding antibody fragment," as used herein, refers to a fragment of an antibody that comprises the paratope, or a fragment of the antibody that binds to the antigen the antibody binds to, with similar specificity and affinity as the intact antibody.

Antibodies, e.g., fully human monoclonal antibodies, may be identified using phage display (or other display methods such as yeast display, ribosome display, bacterial display). Display libraries, e.g., phage display libraries, are available (and/or can be generated by one of ordinary skill in the art) that can be screened to identify an antibody that binds to an antigen of interest, e.g., using panning. See, e.g., Sidhu, S. (ed.) *Phage Display in Biotechnology and Drug Discovery* (Drug Discovery Series; CRC Press; $1^{st}$ ed., 2005; Aitken, R. (ed.) *Antibody Phage Display: Methods and Protocols* (Methods in Molecular Biology) Humana Press; 2nd ed., 2009. In some embodiments, a monoclonal antibody is produced using recombinant methods in suitable host cells, e.g., prokaryotic or eukaryotic host cells. In some embodiments microbial host cells (e.g., bacteria, fungi) are used. Nucleic acids encoding antibodies or portions thereof may be isolated and their sequence determined. Such nucleic acid sequences may be inserted into suitable vectors (e.g., plasmids) and, e.g., introduced into host cells for expression. In some embodiments insect cells are used. In some embodiments mammalian cells, e.g., human cells, are used. In some embodiments, an antibody is secreted by host cells that produce it and may be isolated, e.g., from culture medium. Methods for production and purification of recombinant proteins are well known to those of ordinary skill in the art. It will be understood that such methods may be applied to produce and, optionally, purify, any protein of interest herein.

The term "chimeric antibody," as used herein, refers to an antibody, or an antigen-binding antibody fragment, conjugated to another molecule, for example, to a second antibody, or antigen-binding antibody fragment. Any antibody or antigen-binding antibody fragment, or antigen-binding protein domain can be used to generate a chimeric antibody according to aspects of this invention. In some embodiments, a chimeric antibody comprises two conjugated antibodies, or antibody fragments, or one antibody conjugated to an antibody fragment, wherein the antigen-binding domains of the conjugated molecules bind different antigens or different epitopes of the same antigen. Such chimeric antibodies are referred to herein as "bi-specific," since they bind two different antigens/epitopes.

The term "costimulator" refers to a molecule that provides a stimulus (or second signal) that promotes or is required, in addition to antigen, for stimulation of naïve T cells. Naturally occurring costimulators include various molecules expressed on the surface of or secreted by APCs, which molecules bind to receptors on the surfaces of, e.g., T cells. Examples of receptors to which costimulators bind include, e.g., CD28 family members (e.g., CD28 and inducible costimulator (ICOS)) and CD2 family members (e.g., CD2, SLAM). Examples of costimulators include various members of the B7 family of molecules such as B7-1 and B7-2 (which bind to CD28) and ICOS ligand (which binds to ICOS). In some embodiments a costimulator is provided by APCs such as DCs. In some embodiments expression of costimulator(s) by APCs is stimulated by an adjuvant, e.g., a CD40 ligand, PAMP or PAMP mimic, or TLR ligand. In some embodiments a costimulator is a soluble molecule. In some embodiments a soluble costimulator is a recombinantly produced polypeptide comprising at least a functional portion of the extracellular domain of a naturally occurring costimulator or a functional variant thereof.

The term "linker," as used herein, refers to a chemical group or molecule covalently linked to a molecule, for example, a protein, and a chemical group or moiety, for example, a click chemistry handle. In some embodiments, the linker is positioned between, or flanked by, two groups, molecules, or moieties and connected to each one via a covalent bond, thus connecting the two. In some embodiments, the linker is an amino acid or a plurality of amino acids. In some embodiments, the linker is an organic molecule, group, or chemical moiety.

The term "marker" or "cellular marker" refers to any molecular moiety (e.g., protein, peptide, carbohydrate, polysaccharide, nucleic acid (mRNA or other RNA species, DNA), lipid, or a combination thereof) that characterizes, indicates, or identifies one or more cell type(s), tissue type(s), cell lineages, or embryological tissue of origin and/or that characterizes, indicates, or identifies a particular physiological or pathological state, e.g., an activation state, cell cycle state, metabolic state, differentiation state, apoptotic state, diseased state, etc. In some embodiments, the presence, absence, or amount of certain marker(s) may indicate a particular physiological or diseased state of a subject, organ, tissue, or cell. In some embodiments a cell surface marker is a "cluster of differentiation" (CD) molecule. Numerous CD molecules are known in the art. See, e.g., H. Zola, et al., Leukocyte and Stromal Cell Molecules: the CD Markers, Wiley, N.J., 2007 and/or databases cited therein; Proceedings of the 9th International Workshop on Human Leukocyte Differentiation Antigens published in Immunology Letters, Volume 134, Issue 2, Pages 103-188 (30 Jan. 2011); Human Cell Differentiation Molecules database available at http://www.hcdm.org/MoleculeInformation/tabid/54/Default.aspx; and/or Human and Mouse CD Handbook, available at http://www.bdbiosciences.com/documents/cd_marker_handbook.pdf (BD Biosciences, San Jose, Calif., 2010). In some embodiments a cellular marker is cell type specific. For example, a cell type specific marker is typically present at a higher level on or in a particular cell type or cell types of interest than on or in many other cell types. In some instances a cell type specific marker is present at detectable levels only on or in a particular cell type of interest. However, it will be appreciated that useful cell type specific markers need not be absolutely specific for the cell type of interest. In some embodiments a cell type specific marker for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. In some embodiments a cell type specific marker is present at levels at least 4-5 fold, between 5-10 fold, or more than 10-fold greater than its average expression in a reference population. In some embodiments detection or measurement of a cell type specific marker can distinguish the cell type or types of interest from cells of many, most, or all other types. In general, the presence and/or abundance of most markers may be determined using standard techniques such as Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein microarray analysis, mass spectrometry, etc.

The term "purified" refers to agents that have been separated from some, many, or most of the components with which they are associated in nature or when originally generated. In general, such purification involves action of the hand of man. In some embodiments a purified agent is, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, 99.5%, 99.9%, 99.95%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, 99.5%, 99.9%, 99.95%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity. In some embodiments "partially purified" or "at least partially purified" with respect to a molecule produced by a cell means that a molecule produced by a cell is no longer present within the cell, e.g., the cell has been lysed and, optionally, at least some of the cellular material (e.g., cell wall, cell membrane(s), cell organelle(s)) has been removed and/or the molecule has been separated or segregated from at least some molecules of the same type (protein, RNA, DNA, etc.) that were present in the lysate or, in the case of a molecule that is secreted by a cell, the molecule has been separated from at least some components of the medium or environment into which it was secreted. In some embodiments, any agent disclosed herein is purified. In some embodiments a composition comprises one or more purified agents.

The term "sortagging," as used herein, refers to the process of adding a tag, for example, a click chemistry handle, onto a target molecule, for example, a target protein. It should be noted that the term is not limited to click chemistry handles, but also refers to processes in which other tags are added. Examples of suitable tags include, but are not limited to, amino acids, peptides, proteins, nucleic acids, polynucleotides, sugars, carbohydrates, polymers, lipids, fatty acids, and small molecules. Other suitable tags will be apparent to those of skill in the art and the invention is not limited in this aspect. In some embodiments, a tag comprises a sequence useful for purifying, expressing, solubilizing, and/or detecting a polypeptide. In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a tag comprises an HA, TAP, Myc, Flag, or GST tag, to name few examples. In some embodiments a tag comprises a solubility-enhancing tag (e.g., a SUMO tag, NUS A tag, SNUT tag, a Strep tag, or a monomeric mutant of the Ocr protein of bacteriophage T7). See, e.g., Esposito D and Chatterjee D K. Curr Opin Biotechnol.; 17(4):353-8 (2006). In some embodiments, a tag is cleavable, so that it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used. See, e.g., PCT/US05/05763.

A "variant" of a particular polypeptide or polynucleotide has one or more alterations (e.g., additions, substitutions, and/or deletions) with respect to a reference polypeptide or polynucleotide, which may be referred to as the "original polypeptide" or "original polynucleotide", respectively. An addition may be an insertion or may be at either terminus. A variant may be shorter or longer than the reference polypeptide or polynucleotide. The term "variant" encompasses "fragments". A "fragment" is a continuous portion of a polypeptide or polynucleotide that is shorter than the reference polypeptide or polynucleotide. In some embodiments a variant comprises or consists of a fragment. In some embodiments a fragment or variant is at least 20%, 30%, 40%, 50%, 60%, 70%, 80%, 90%, 92.5%, 95%, 96%, 97%, 98%, 99%, or more as long as the reference polypeptide or polynucleotide. In some embodiments a fragment may lack an N-terminal and/or C-terminal portion of a reference polypeptide. For example, a fragment may lack up to 5%, 10%, 15%, 20%, or 25% of the length of the polypeptide from either or both ends. A fragment may be an N-terminal, C-terminal, or internal fragment. In some embodiments a variant polypeptide comprises or consists of at least one domain of a reference polypeptide.

In some embodiments a variant polynucleotide hybridizes to a reference polynucleotide under art-recognized stringent conditions, e.g., high stringency conditions, for sequences of the length of the reference polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the reference polypeptide or polynucleotide over at least 20%, 30%, 40%, 50%, 60%, 70%, 80%, 90%, 95%, 96%, 97%, 98%, 99%, or 100% of the reference polypeptide or polynucleotide. In some embodiments a variant polypeptide comprises or consists of a polypeptide that is at least 50%, 60%, 70%, 80%, 90%, 95%, 96%, 97%, 98%, 99%, or more identical in sequence to the reference polypeptide over at least 20%, 30%, 40%, 50%, 60%, 70%, 80%, 90%, 95%, 96%, 97%, 98%, 99%, or 100% of the reference polypeptide, with the proviso that, for purposes of computing percent identity, a conservative amino acid substitution is considered identical to the amino acid it replaces. In some embodiments a variant polypeptide comprises or consists of a polypeptide that is at least 50%, 60%, 70%, 80%, 90%, 95%, 96%, 97%, 98%, 99%, or more identical to the reference polypeptide over at least 20%, 30%, 40%, 50%, 60%, 70%, 80%, 90%®, 95%, 96%, 97%, 98%, 99%, or 100% of the reference polypeptide, with the proviso that any one or more amino acid substitutions (up to the total number of such substitutions) may be restricted to conservative substitutions. In some embodiments a percent identity is measured over at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments the sequence of a variant polypeptide comprises or consists of a sequence that has N amino acid differences with respect to a reference sequence, wherein N is any integer between 1 and 10 or between 1 and 20 or any integer up to 1%, 2%, 5%, or 10% of the number of amino acids in the reference polypeptide, where an "amino acid difference" refers to a substitution, insertion, or deletion of an amino acid. In some embodiments a difference is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
| --- | --- | --- |
| | | I L V |
| | Polar - uncharged | C S T M |
| | | N Q |
| | Polar - charged | D E |
| | | K R |
| Aromatic | | H F W Y |

In some embodiments, proline (P) is considered to be in an individual group. In some embodiments, cysteine (C) is considered to be in an individual group. In some embodiments, proline (P) and cysteine (C) are each considered to be in an individual group. Within a particular group, certain substitutions may be of particular interest in certain embodiments, e.g., replacements of leucine by isoleucine (or vice versa), serine by threonine (or vice versa), or alanine by glycine (or vice versa).

In some embodiments a variant is a functional variant, i.e., the variant at least in part retains at least one activity of the reference polypeptide or polynucleotide. In some embodiments a variant at least in part retains more than one or substantially all known activities of the reference polypeptide or polynucleotide. An activity may be, e.g., a catalytic activity, binding activity, ability to perform or participate in a biological function or process, etc. In some embodiments an activity is one that has (or the lack of which has) a detectable effect on an observable phenotype of a cell or organism. In some embodiments an activity of a variant may be at least 10%, 20%, 30%, 40%, 50%, 60%, 70%, 80%, 90%, 95%, or more, of the activity of the reference polypeptide or polynucleotide, up to approximately 100%, approximately 125%, or approximately 150% of the activity of the reference polypeptide or polynucleotide, in various embodiments. In some embodiments a variant, e.g., a functional variant, comprises or consists of a polypeptide at least 80%, 90%, 92.5%, 95%, 96%, 97%, 98%, 99%. 99.5% or 100% identical to an reference polypeptide or polynucleotide over at least 70%, 75%, 80%, 85%, 90%, 95%, 96%, 97%, 98%, or 99% or 100% of the full length of the reference polypeptide or polynucleotide or over at least 70%, 75%, 80%, 85%, 90%, 92.5%, 95%, 96%, 97%, 98%, or 99% or 100% of a functional fragment of the reference polypeptide or polynucleotide. In some embodiments an alteration, e.g., a substitution or deletion, e.g., in a functional variant, does not alter or delete an amino acid or nucleotide that is known or predicted to be important for an activity, e.g., a known or predicted catalytic residue or residue involved in binding a substrate or cofactor. In some embodiments nucleotide(s), amino acid(s), or region(s) exhibiting lower degrees of conservation across species as compared with other amino acids or regions may be selected for alteration. Variants may be tested in one or more suitable assays to assess activity. In certain embodiments a polypeptide or polynucleotide sequence in the NCBI RefSeq database may be used as a reference sequence. In some embodiments a variant or fragment of a naturally occurring polypeptide or polynucleotide is a naturally occurring variant or fragment. In some embodiments a variant or fragment of a naturally occurring polypeptide or polynucleotide is not naturally occurring. Calculations of sequence identity can be performed as follows. Sequences are aligned for optimal comparison purposes and gaps can be introduced in one or both of a first and a second sequence for optimal alignment. When a position in the first sequence is occupied by the same residue as the corresponding position in the second sequence, the sequences are deemed to be identical at that position. The percent identity between the two sequences is a function of the number of identical positions shared by the sequences, taking into account the number of gaps, and the length of each gap, introduced for optimal alignment of the two sequences. Sequences can be aligned and/or percent identity determined with the use of a variety of algorithms and computer programs known in the art. For example, computer programs such as BLAST2, BLASTN, BLASTP, Gapped BLAST, etc., may be used to generate alignments and/or to obtain a percent identity. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877, 1993 is incorporated into the NBLAST and XBLAST programs of Altschul et al. (Altschul, et al., J. Mol. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See the Web site having URL www.ncbi.nlm.nih.gov and/or McGinnis, S. and Madden, T L, W20-W25 Nucleic Acids Research, 2004, Vol. 32, Web server issue. Other suitable programs include CLUSTALW (Thompson J D, Higgins D G, Gibson T J, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.) The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of TGA and TGB (here TGA and TGB are the sum of the number of residues and internal gap positions in sequences A and B in the alignment), and multiplying by 100. Percent identity may be evaluated over a window of evaluation. In some embodiments a window of evaluation may have a length of at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more, e.g., 100%, of the length of the shortest of the sequences being compared. In some embodiments a window of evaluation is at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments no more than 20%, 10%, 5%, or 1% of positions in either sequence or in both sequences over a window of evaluation are occupied by a gap. In some embodiments no more than 20%, 10%, 5%, or 1% of positions in either sequence or in both sequences are occupied by a gap.

DETAILED DESCRIPTION OF CERTAIN EMBODIMENTS

Some aspects of this invention relate to the recognition that the sortase transacylation reaction allows for the facile installation of all kinds of substituents at the C-terminus of a suitably modified protein. The sole requirement for a successful transacylation reaction is the presence of a suitably exposed sortase recognition motif, e.g., an LPXT or LPXTG motif, in the target protein. The design of nucleophiles that can be used in a sortase catalyzed reaction is likewise straight-forward: a short run (e.g., 1-10) of glycine residues, or even an alkylamine suffices to allow the reaction to proceed. The key advantages of using a sortase transacylation strategy to modify a target protein are the ease of synthesis, and execution of the reaction on native proteins under physiological conditions.

Some aspects of this invention relate to the recognition that the nucleophiles that are used in the sortase reaction can be modified to include any number of modifications: biotin, detectable labels (e.g., fluorophores), fatty acids, nucleic acids, lipids, radioisotopes, carbohydrates or even proteins with a suitably exposed N-terminal stretch of glycine residues. Further, some aspects of this invention provide that nucleophiles can be used in a sortase reaction that comprise reactive chemical moieties, for example, moieties, or "handles", suitable for a click chemistry reaction, e.g., a copper-free click chemistry reaction. Such nucleophiles, e.g., peptides comprising 1-10 glycine residues (e.g., GGG), or any compound (e.g. a peptide) comprising an alkylamine group, and a click chemistry handle, can be employed to install a C-terminal click chemistry handle on a target protein comprising a C-terminal sortase recognition motif. The sortase recognition motif does not have to be positioned at the very C-terminus, but it has to be sufficiently accessible by the enzyme to efficiently partake in the sortase reaction.

Similarly, click chemistry handles can be installed N-terminally on proteins comprising a short glycine run or a protein or any compound comprising an alkylamine group (e.g., at their N-terminus for proteins), by carrying out a sortase reaction using a peptide comprising a sortase recognition motif and the desired click chemistry handle. Any protein comprising either a sortase recognition motif, or 1-10 glycine residues, or a terminal alkylamine group, can, accordingly, be derivatized with a click chemistry handle according to aspects of this invention. The installation of a click chemistry handle on a target protein confers click chemistry reactivity to the protein. For example, a protein comprising a click chemistry handle, as described herein, can react with a second molecule, for example, a second molecule, comprising a second click chemistry handle, to form a covalent bond, thus conjugating the two molecules together.

In some embodiments, proteins carrying reactive click chemistry handles are conjugated together by carrying out the respective click chemistry reaction. This results in the proteins being conjugated to each other via a covalent bond. Since the inventive strategies allow installment of a click chemistry handle on either the C- or the N-terminus of a protein, two proteins so modified can be conjugated via a covalent bond from the C-terminus of the first protein to the N-terminus of the second protein, much like a conventional protein fusion. However, installing C-terminal, reactive click chemistry handles on both target proteins allows for the generation of proteins conjugated via a covalent click chemistry bond at their C-termini (C-to-C-termini, C—C), while installing N-terminal, reactive click chemistry handles on both target proteins allows for the generation of proteins conjugated at their N-termini (N-to-N-termini, N—N). Neither covalent C—C conjugation nor covalent N—N conjugation can be achieved by conventional protein engineering technologies, such as recombinant protein fusion technology.

Sortase-Mediated Installment of Click Chemistry Handles

Sortases, sortase-mediated transacylation reactions, and their use in transacylation (sometimes also referred to as transpeptidation) for protein engineering are well known to those of skill in the art (see, e.g., Ploegh et al., International Patent Application PCT/US2010/000274, and Ploegh et al., International Patent Application PCT/US2011/033303, the entire contents of each of which are incorporated herein by reference). In general, the transpeptidation reaction catalyzed by sortase results in the ligation of species containing a transamidase recognition motif with those bearing one or more N-terminal glycine residues. In some embodiments, the sortase recognition motif is a sortase recognition motif described herein. In certain embodiments, the sortase recognition motif is an LPXT motif or an LPXTG motif. As is known in the art, the substitution of the C-terminal residue of the recognition sequence with a moiety exhibiting poor nucleophilicity once released from the sortase provides for a more efficient ligation.

The sortase transacylation reaction provides means for efficiently linking an acyl donor with a nucleophilic acyl acceptor. This principle is widely applicable to many acyl donors and a multitude of different acyl acceptors. Previously, the sortase reaction was employed for ligating proteins and/or peptides to one another, ligating synthetic peptides to recombinant proteins, linking a reporting molecule to a protein or peptide, joining a nucleic acid to a protein or peptide, conjugating a protein or peptide to a solid support or polymer, and linking a protein or peptide to a label. Such products and processes save cost and time associated with ligation product synthesis and are useful for conveniently linking an acyl donor to an acyl acceptor.

Sortase-mediated transacylation reactions are catalyzed by the transamidase activity of sortase. A transamidase is an enzyme that can form a peptide linkage (i.e., amide linkage) between an acyl donor compound and a nucleophilic acyl acceptor containing a $NH_2$—$CH_2$-moiety. In some embodiments, the sortase is sortase A (SrtA). However, it should be noted that any sortase, or transamidase, catalyzing a transacylation reaction can be used in some embodiments of this invention, as the invention is not limited to the use of sortase A. Sortases are enzymes having transamidase activity and have been isolated from Gram-positive bacteria. They have, as part of their cell wall structure, peptidoglycan as well as polysaccharides and/or teichoic acids. Gram-positive bacteria include the following genera: *Actinomyces, Bacillus, Bifidobacterium, Cellulomonas, Clostridium, Corynebacterium, Micrococcus, Mycobacterium, Nocardia, Staphylococcus, Streptococcus*, and *Streptomyces*.

Sortase-Mediated Installation of C-Terminal Click Chemistry Handles

In certain embodiments, a sortase-mediated transacylation reaction for installing a C-terminal click chemistry handle on a protein comprises a step of contacting a protein comprising a transamidase recognition sequence of the structure:

wherein the transamidase recognition sequence is an amino acid sequence motif recognized by a transamidase enzyme; a transamidase recognition sequence is also referred to herein as a sortase recognition sequence or a sortase recognition motif;

X is —O—, —NR—, or —S—; wherein R is hydrogen, substituted or unsubstituted aliphatic, or substituted or unsubstituted heteroaliphatic;

$A^1$ is an amino acid sequence of at least 3 amino acids in length;

$R^1$ is acyl, substituted or unsubstituted aliphatic, substituted or unsubstituted heteroaliphatic, substituted or unsubstituted aryl, or substituted or unsubstituted heteroaryl;

with a nucleophilic compound of formula:

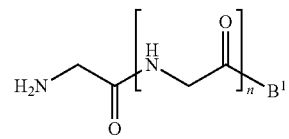

wherein $B^1$ is acyl, substituted or unsubstituted aliphatic, substituted or unsubstituted heteroaliphatic, substituted or unsubstituted aryl, substituted or unsubstituted heteroaryl, an amino acid, a peptide, a protein, a polynucleotide, a carbohydrate, a tag, a metal atom, a contrast agent, a catalyst, a non-polypeptide polymer, a recognition element, a small molecule, a lipid, a linker, or a label; wherein B1 comprises a click chemistry handle; and n is 0 or an integer from 1 to 100, inclusive;

in the presence of a transamidase enzyme, for example, a sortase, under suitable conditions to form a compound of formula:

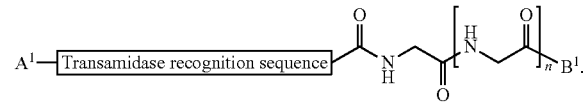

It will be understood by those of skill in the art that the click chemistry handle may be incorporated into $B^1$ in any manner and at any position that can be envisioned by those of skill in the art. For example, $B^1$ may comprise an amino acid, (e.g., lysine) and the click chemistry handle may be attached, for example, to the central carbon of the amino acid, the side chain of the amino acid, or to the carboxyl group of the amino acid, or any other position. Other ways of incorporating the click chemistry handle into $B^1$ will be apparent to those of skill in the art, and the invention is not limited in this respect.

It will further be understood that, depending on the nature of $B^1$, the click chemistry handle may be installed at the very C-terminus of the target protein, or, e.g. if B' comprises a first amino acid comprising the click chemistry handle, and a number of additional amino acids, the resulting, modified protein will comprise the click chemistry handle close to, but not directly at the C-terminus. As will be apparent to those of skill in the art, a similar situation exists for the N-terminal installation of the click chemistry handle described below.

One of ordinary skill will appreciate that, in certain embodiments, the C-terminal amino acid of the transamidase recognition sequence is omitted. That is, an acyl group

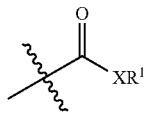

replaces the C-terminal amino acid of the transamidase recognition sequence. In some embodiments, the acyl group is

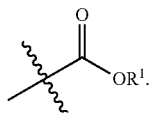

In some embodiments, the acyl group is

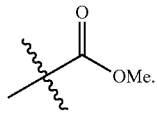 [SMILES: *C(=O)OC]

In some embodiments, the sortase, or transamidase, recognition sequence is LPXT, wherein X is a standard or non-standard amino acid. In some embodiments, X is selected from D, E, A, N, Q, K, or R. In some embodiments, the recognition sequence is selected from LPXT, LPXT, SPXT, LAXT, LSXT, NPXT, VPXT, IPXT, and YPXR. In some embodiments X is selected to match a naturally occurring transamidase recognition sequence. In some embodiments, the transamidase recognition sequence is selected from: LPKT, LPIT, LPDT, SPKT, LAET, LAAT, LAET, LAST, LAET, LPLT, LSRT, LPET, VPDT, IPQT, YPRR, LPMT, LPLT, LAFT, LPQT, NSKT, NPQT, NAKT, and NPQS. In some embodiments, e.g., in certain embodiments in which sortase A is used (see below), the transamidase recognition motif comprises the amino acid sequence $X_1PX_2X_3$, where $X_1$ is leucine, isoleucine, valine or methionine; $X_2$ is any amino acid; $X_3$ is threonine, serine or alanine; P is proline and G is glycine. In specific embodiments, as noted above $X_1$, is leucine and $X_3$ is threonine. In certain embodiments, $X_2$ is aspartate, glutamate, alanine, glutamine, lysine or methionine. In certain embodiments, e.g., where sortase is utilized, the recognition sequence often comprises the amino acid sequence $NPX_1TX_2$, where $X_1$ is glutamine or lysine; $X_2$ is asparagine or glycine; N is asparagine; P is proline and T is threonine. The invention encompasses the recognition that selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis.

In some embodiments, X is —O—. In some embodiments, X is —NR—. In some embodiments, X is —NH—. In some embodiments, X is —S—.

In certain embodiments, $R^1$ is substituted aliphatic. In certain embodiments, $R^1$ is unsubstituted aliphatic. In some embodiments, $R^1$ is substituted $C_{1-12}$ aliphatic. In some embodiments, $R^1$ is unsubstituted $C_{1-12}$ aliphatic. In some embodiments, $R^1$ is substituted $C_{1-6}$ aliphatic. In some embodiments, $R^1$ is unsubstituted $C_{1-6}$ aliphatic. In some embodiments, $R^1$ is $C_{1-3}$ aliphatic. In some embodiments, $R^1$ is butyl. In some embodiments, $R^1$ is n-butyl.

In some embodiments, $R^1$ is isobutyl. In some embodiments, $R^1$ is propyl. In some embodiments, $R^1$ is n-propyl. In some embodiments, $R^1$ is isopropyl. In some embodiments, $R^1$ is ethyl. In some embodiments, $R^1$ is methyl.

In certain embodiments, $R^1$ is substituted aryl. In certain embodiments, $R^1$ is unsubstituted aryl. In certain embodiments, $R^1$ is substituted phenyl. In certain embodiments, $R^1$ is unsubstituted phenyl.

In some embodiments, $A^1$ comprises a protein. In some embodiments, $A^1$ comprises a peptide. In some embodiments, $A^1$ comprises an antibody, an antibody chain, an antibody fragment, an antibody epitope, an antigen-binding antibody domain, a VHH domain, a single-domain antibody, a camelid antibody, a nanobody, or an adnectin. In some embodiments, $A^1$ comprises a recombinant protein, a protein comprising one or more D-amino acids, a branched peptide, a therapeutic protein, an enzyme, a polypeptide subunit of a multisubunit protein, a transmembrane protein, a cell surface protein, a methylated peptide or protein, an acylated peptide or protein, a lipidated peptide or protein, a phosphorylated peptide or protein, or a glycosylated peptide or protein. In some embodiments, $A^1$ is an amino acid sequence comprising at least 3 amino acids. In some embodiments, $A^1$ comprises a protein. In some embodiments, $A^1$ comprises a peptide. In some embodiments, $A^1$ comprises an antibody. In some embodiments, $A^1$ comprises an antibody fragment. In some embodiments, $A^1$ comprises an antibody epitope. In some embodiments, $A^1$ comprises green fluorescent protein. In some embodiments, $A^1$ comprises ubiquitin.

In some embodiments, B1 comprises a click chemistry handle. In some embodiments, B1 comprises a click chemistry handle described herein. In some embodiments, B1 comprises a click chemistry handle described in Table 1, in Table 2, or in FIG. 2B. In some embodiments, B1 comprises a click chemistry handle described in Kolb, Finn and Sharpless *Angewandte Chemie International Edition* (2001) 40: 2004-2021; Evans, *Australian Journal of Chemistry* (2007) 60: 384-395); Joerg Lahann, click *Chemistry for Biotechnology and Materials Science,* 2009, John Wiley & Sons Ltd, ISBN 978-0-470-69970-6; or Becer, Hoogenboom, and Schubert, click *Chemistry beyond Metal-Catalyzed Cycloaddition,* Angewandte Chemie International Edition (2009) 48: 4900-4908; the entire contents of each of which are incorporated herein by reference. For example, in certain embodiments, B1 comprises a terminal alkyne, azide, strained alkyne, diene, dienophile, alkoxyamine, carbonyl, phosphine, hydrazide, thiol, or alkene moiety. In some embodiments, B1 comprises a click chemistry handle described in Table 1 or Table 2, or in FIG. 2B.

In certain embodiments, n is an integer from 0 to 50, inclusive. In certain embodiments, n is an integer from 0 to 20, inclusive. In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6.

Sortase-Mediated Installation of N-Terminal Click Chemistry Handles

In certain embodiments, a sortase-mediated transacylation reaction for installing an N-terminal click chemistry handle on a protein comprises a step of contacting a protein of the structure:

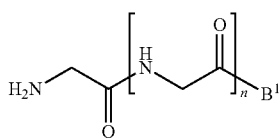

wherein
n is 0 or an integer between 1-100, inclusive; and
B1 is a protein comprising an amino acid sequence of at least three amino acid residues;
with a molecule of the structure

wherein
the transamidase recognition sequence is an amino acid sequence motif recognized by a transamidase enzyme; a transamidase recognition sequence is also referred to herein as a sortase recognition sequence or a sortase recognition motif;
X is —O—, —NR—, or —S—; wherein R is hydrogen, substituted or unsubstituted aliphatic, or substituted or unsubstituted heteroaliphatic;
A¹ is acyl, substituted or unsubstituted aliphatic, substituted or unsubstituted heteroaliphatic, substituted or unsubstituted aryl, substituted or unsubstituted heteroaryl, an amino acid, a peptide, a protein, a polynucleotide, a carbohydrate, a tag, a metal atom, a contrast agent, a catalyst, a non-polypeptide polymer, a recognition element, a small molecule, a lipid, a linker, or a label; wherein A¹ comprises a click chemistry handle; and
R¹ is hydrogen, acyl, substituted or unsubstituted aliphatic, substituted or unsubstituted heteroaliphatic, substituted or unsubstituted aryl, or substituted or unsubstituted heteroaryl;
in the presence of a transamidase enzyme, for example, a sortase, under suitable conditions to form a compound of formula:

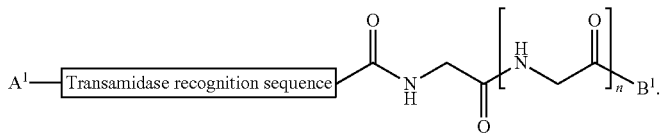

It will be understood by those of skill in the art that the click chemistry handle may be incorporated into A¹ in any manner and at any position that can be envisioned by those of skill in the art. For example, A¹ may comprise an amino acid, (e.g., lysine) and the click chemistry handle may be attached, for example, to the central carbon of the amino acid, the side chain of the amino acid, or to the amino group of the amino acid, or any other position. Other ways of incorporating the click chemistry handle into A¹ will be apparent to those of skill in the art, and the invention is not limited in this respect.

One of ordinary skill will appreciate that, in certain embodiments, the C-terminal amino acid of the transamidase recognition sequence is omitted. That is, an acyl group

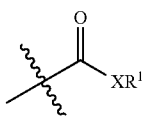

replaces the C-terminal amino acid of the transamidase recognition sequence. In some embodiments, the acyl group is

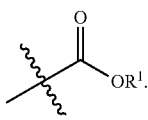

In some embodiments, the acyl group is

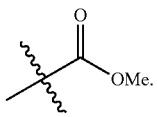 [SMILES: *C(=O)OC]

In some embodiments, the sortase, or transamidase, recognition sequence is LPXT, wherein X is a standard or non-standard amino acid. In some embodiments, X is selected from D, E, A, N, Q, K, or R. In some embodiments, the recognition sequence is selected from LPXT, LPXT, SPXT, LAXT, LSXT, NPXT, VPXT, IPXT, and YPXR. In some embodiments X is selected to match a naturally occurring transamidase recognition sequence. In some embodiments, the transamidase recognition sequence is selected from: LPKT, LPIT, LPDT, SPKT, LAET, LAAT, LAET, LAST, LAET, LPLT, LSRT, LPET, VPDT, IPQT, YPRR, LPMT, LPLT, LAFT, LPQT, NSKT, NPQT, NAKT, and NPQS. In some embodiments, e.g., in certain embodiments in which sortase A is used (see below), the transamidase recognition motif comprises the amino acid sequence $X_1PX_2X_3$, where $X_1$ is leucine, isoleucine, valine or methionine; $X_2$ is any amino acid; $X_3$ is threonine, serine or alanine; P is proline and G is glycine. In specific embodiments, as noted above $X_1$, is leucine and $X_3$ is threonine. In certain embodiments, $X_2$ is aspartate, glutamate, alanine, glutamine, lysine or methionine. In certain embodiments, e.g., where sortase B is utilized, the recognition sequence often comprises the amino acid sequence $NPX_1TX_2$, where $X_1$ is glutamine or lysine; $X_2$ is asparagine or glycine; N is asparagine; P is proline and T is threonine. The invention encompasses the recognition that selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis.

In some embodiments, X is —O—. In some embodiments, X is —NR—. In some embodiments, X is —NH—. In some embodiments, X is —S—.

In certain embodiments, $R^1$ is substituted aliphatic. In certain embodiments, $R^1$ is unsubstituted aliphatic. In some embodiments, $R^1$ is substituted $C_{1-12}$ aliphatic. In some embodiments, $R^1$ is unsubstituted $C_{1-12}$ aliphatic. In some embodiments, $R^1$ is substituted $C_1$-6 aliphatic. In some embodiments, $R^1$ is unsubstituted $C_{1-6}$ aliphatic. In some embodiments, $R^1$ is $C_{1-3}$ aliphatic. In some embodiments, $R^1$ is butyl. In some embodiments, $R^1$ is n-butyl. In some embodiments, $R^1$ is isobutyl. In some embodiments, $R^1$ is propyl. In some embodiments, $R^1$ is n-propyl. In some embodiments, $R^1$ is isopropyl. In some embodiments, $R^1$ is ethyl. In some embodiments, $R^1$ is methyl.

In certain embodiments, $R^1$ is substituted aryl. In certain embodiments, $R^1$ is unsubstituted aryl. In certain embodiments, $R^1$ is substituted phenyl. In certain embodiments, $R^1$ is unsubstituted phenyl.

In some embodiments, $B^1$ comprises a protein. In some embodiments, $B^1$ comprises a peptide. In some embodiments, $B^1$ comprises an antibody, an antibody chain, an antibody fragment, an antibody epitope, an antigen-binding antibody domain, a VHH domain, a single-domain antibody, a camelid antibody, a nanobody, or an adnectin. In some embodiments, $B^1$ comprises a recombinant protein, a protein comprising one or more D-amino acids, a branched peptide, a therapeutic protein, an enzyme, a polypeptide subunit of a multisubunit protein, a transmembrane protein, a cell surface protein, a methylated peptide or protein, an acylated peptide or protein, a lipidated peptide or protein, a phosphorylated peptide or protein, or a glycosylated peptide or protein. In some embodiments, $B^1$ is an amino acid sequence comprising at least 3 amino acids. In some embodiments, $B^1$ comprises a protein. In some embodiments, $B^1$ comprises a peptide. In some embodiments, $B^1$ comprises an antibody. In some embodiments, $B^1$ comprises an antibody fragment. In some embodiments, $B^1$ comprises an antibody epitope. In some embodiments, $B^1$ comprises green fluorescent protein. In some embodiments, $B^1$ comprises ubiquitin.

In some embodiments, $A^1$ comprises a click chemistry handle. In some embodiments, $A^1$ comprises a click chemistry handle described herein. In some embodiments, $A^1$ comprises a click chemistry handle described in Table 1, in Table 2, or in FIG. 2B. In some embodiments, $A^1$ comprises a click chemistry handle described in Kolb, Finn and Sharpless *Angewandte Chemie International Edition* (2001) 40: 2004-2021; Evans, *Australian Journal of Chemistry* (2007) 60: 384-395); Joerg Lahann, click *Chemistry for Biotechnology and Materials Science,* 2009, John Wiley & Sons Ltd, ISBN 978-0-470-69970-6; or Becer, Hoogenboom, and Schubert, click *Chemistry beyond Metal-Catalyzed Cycloaddition*, Angewandte Chemie International Edition (2009) 48: 4900-4908; the entire contents of each of which are incorporated herein by reference. For example, in certain embodiments, $A^1$ comprises a terminal alkyne, azide, strained alkyne, diene, dieneophile, alkoxyamine, carbonyl, phosphine, hydrazide, thiol, or alkene moiety. In some embodiments, $A^1$ comprises a click chemistry handle described in Table 1 or Table 2, or in FIG. 2B.

In certain embodiments, n is an integer from 0 to 50, inclusive. In certain embodiments, n is an integer from 0 to 20, inclusive. In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6.

Suitable Enzymes and Recognition Motifs

In certain embodiments, the transamidase is a sortase. Enzymes identified as "sortases" from Gram-positive bacteria cleave and translocate proteins to proteoglycan moieties in intact cell walls. Among the sortases that have been isolated from *Staphylococcus aureus*, are sortase A (Srt A) and sortase B (Srt B). Thus, in certain embodiments, a transamidase used in accordance with the present invention is a sortase A, e.g., from *S. aureus*. In certain embodiments, a transamidase is a sortase B, e.g., from *S. aureus*.

Sortases have been classified into 4 classes, designated A, B, C, and D, based on sequence alignment and phylogenetic analysis of 61 sortases from Gram positive bacterial genomes (Dramsi S, Trieu-Cuot P, Bierne H, Sorting sortases: a nomenclature proposal for the various sortases of Gram-positive bacteria. Res Microbiol. 156(3):289-97, 2005. These classes correspond to the following subfamilies, into which sortases have also been classified by Comfort and Clubb (Comfort D, Clubb R T. A comparative genome analysis identifies distinct sorting pathways in gram-positive bacteria. Infect Immun., 72(5):2710-22, 2004): Class A (Subfamily 1), Class B (Subfamily 2), Class C (Subfamily 3), Class D (Subfamilies 4 and 5). The aforementioned references disclose numerous sortases and recognition motifs. See also Pallen, M. J.; Lam, A. C.; Antonio, M.; Dunbar, K. *TRENDS in Microbiology,* 2001, 9(3), 97-101. Those skilled in the art will readily be able to assign a sortase to the correct class based on its sequence and/or other characteristics such as those described in Drami, et al., supra. The term "sortase A" is used herein to refer to a class A sortase, usually named SrtA in any particular bacterial species, e.g., SrtA from *S. aureus*. Likewise "sortase B" is used herein to refer to a class B sortase, usually named SrtB in any particular bacterial species, e.g., SrtB from *S. aureus*. The invention encompasses embodiments relating to a sortase A from any bacterial species or strain. The invention encompasses embodiments relating to a sortase B from any bacterial species or strain. The invention encompasses embodiments relating to a class C sortase from any bacterial species or strain. The invention encompasses embodiments relating to a class D sortase from any bacterial species or strain.

Amino acid sequences of Srt A and Srt B and the nucleotide sequences that encode them are known to those of skill in the art and are disclosed in a number of references cited herein, the entire contents of all of which are incorporated herein by reference. The amino acid sequences of *S. aureus* SrtA and SrtB are homologous, sharing, for example, 22% sequence identity and 37% sequence similarity. The amino acid sequence of a sortase-transamidase from *Staphylococcus aureus* also has substantial homology with sequences of enzymes from other Gram-positive bacteria, and such transamidases can be utilized in the ligation processes described herein. For example, for SrtA there is about a 31% sequence identity (and about 44% sequence similarity) with best alignment over the entire sequenced region of the S. pyogenes open reading frame. There is about a 28% sequence identity with best alignment over the entire sequenced region of the A. naeslundii open reading frame. It will be appreciated that different bacterial strains may exhibit differences in sequence of a particular polypeptide, and the sequences herein are exemplary.

In certain embodiments a transamidase bearing 18% or more sequence identity, 20% or more sequence identity, or 30% or more sequence identity with the S. pyogenes, A. naeslundii, S. mutans, E. faecalis or B. subtilis open reading frame encoding a sortase can be screened, and enzymes having transamidase activity comparable to Srt A or Srt B from S. aureas can be utilized (e.g., comparable activity sometimes is 10% of Srt A or Srt B activity or more).

Thus in some embodiments of the invention the sortase is a sortase A (SrtA). SrtA recognizes the motif LPXTG, with common recognition motifs being, e.g., LPKTG, LPATG, LPNTG. In some embodiments LPETG is used. However, motifs falling outside this consensus may also be recognized. For example, in some embodiments the motif comprises an 'A' rather than a 'T' at position 4, e.g., LPXAG, e.g., LPNAG. In some embodiments the motif comprises an 'A' rather than a 'G' at position 5, e.g., LPXTA, e.g., LPNTA. In some embodiments the motif comprises a 'G' rather than 'P' at position 2, e.g., LGXTG, e.g., LGATG. In some embodiments the motif comprises an 'I' rather than 'L' at position 1, e.g., IPXTG, e.g., IPNTG or IPETG.

It will be appreciated that the terms "recognition motif" and "recognition sequence", with respect to sequences recognized by a transamidase or sortase, are used interchangeably. The term "transamidase recognition sequence" is sometimes abbreviated "TRS" herein.

In some embodiments of the invention the sortase is a sortase B (SrtB), e.g., a sortase B of S. aureus, B. anthracis, or L. monocytogenes. Motifs recognized by sortases of the B class (SrtB) often fall within the consensus sequences NPXTX, e.g., NP[Q/K]-[T/s]-[N/G/s], such as NPQTN or NPKTG. For example, sortase B of S. aureus or B. anthracis cleaves the NPQTN or NPKTG motif of IsdC in the respective bacteria (see, e.g., Marraffini, L. and Schneewind, O., Journal of Bacteriology, 189(17), p. 6425-6436, 2007). Other recognition motifs found in putative substrates of class B sortases are NSKTA, NPQTG, NAKTN, and NPQSS. For example, SrtB from L. monocytogenes recognizes certain motifs lacking P at position 2 and/or lacking Q or K at position 3, such as NAKTN and NPQSS (Mariscotti J F, Garcia-Del Portillo F, Pucciarelli M G. The listeria monocytogenes sortase-B recognizes varied amino acids at position two of the sorting motif. J Biol Chem. 2009 Jan. 7. [Epub ahead of print])

In some embodiments, the sortase is a class C sortase. Class C sortases may utilize LPXTG as a recognition motif.

In some embodiments, the sortase is a class D sortase. Sortases in this class are predicted to recognize motifs with a consensus sequence NA-[E/A/S/H]-TG (Comfort D, supra). Class D sortases have been found, e.g., in Streptomyces spp., Corynebacterium spp., Tropheryma whipplei, Thermobifida fusca, and Bifidobacterium longhum. LPXTA or LAXTG may serve as a recognition sequence for class D sortases, e.g., of subfamilies 4 and 5, respectively subfamily-4 and subfamily-5 enzymes process the motifs LPXTA and LAXTG, respectively). For example, B. anthracis Sortase C, which is a class D sortase, has been shown to specifically cleave the LPNTA motif in B. anthracis BasI and BasH (Marrafini, supra).

See Barnett and Scott for description of a sortase from that recognizes QVPTGV motif (Barnett, T C and Scott, J R, Differential Recognition of Surface Proteins in Streptococcus pyogenes by Two Sortase Gene Homologs. Journal of Bacteriology, Vol. 184, No. 8, p. 2181-2191, 2002).

The invention contemplates use of sortases found in any gram positive organism, such as those mentioned herein and/or in the references (including databases) cited herein. The invention also contemplates use of sortases found in gram negative bacteria, e.g., Colwellia psychrerythraea, Microbulbifer degradans, Bradyrhizobium japonicum, Shewanella oneidensis, and Shewanella putrefaciens. They recognize sequence motifs LP[Q/K]T[A/S]T. In keeping with the variation tolerated at position 3 in sortases from gram positive organisms, a sequence motif LPXT[A/S], e.g., LPXTA or LPSTS may be used.

The invention contemplates use of sortase recognition motifs from any of the experimentally verified or putative sortase substrates listed at http://bamics3.cmbi.kun.nl/jos/sortase_substrates/help.html, the contents of which are incorporated herein by reference, and/or in any of the above-mentioned references. In some embodiments the sortase recognition motif is selected from: LPKTG, LPITG, LPDTA, SPKTG, LAETG, LAATG, LAHTG, LASTG, LAETG, LPLTG, LSRTG, LPETG, VPDTG, IPQTG, YPRRG, LPMTG, LPLTG, LAFTG, LPQTS, it being understood that in various embodiments of the invention the $5^{th}$ residue is replaced, as described elsewhere herein. For example, the sequence used may be LPXT, LAXT, LPXA, LGXT, IPXT, NPXT, NPQS, LPST, NSKT, NPQT, NAKT, LPIT, LAET, or NPQS. The invention comprises embodiments in which 'X' in any sortase recognition motif disclosed herein or known in the art is any standard or non-standard amino acid. Each variation is disclosed. In some embodiments, X is selected from the 20 standard amino acids found most commonly in proteins found in living organisms. In some embodiments, e.g., where the recognition motif is LPXTG or LPXT, X is D, E, A, N, Q, K, or R. In some embodiments, X in a particular recognition motif is selected from those amino acids that occur naturally at position 3 in a naturally occurring sortase substrate. For example, in some embodiments X is selected from K, E, N, Q, A in an LPXTG or LPXT motif where the sortase is a sortase A. In some embodiments X is selected from K, S, E, L, A, N in an LPXTG or LPXT motif and a class C sortase is used.

In some embodiments, a recognition sequence further comprises one or more additional amino acids, e.g., at the N or C terminus. For example, one or more amino acids (e.g., up to 5 amino acids) having the identity of amino acids found immediately N-terminal to, or C-terminal to, a 5 amino acid recognition sequence in a naturally occurring sortase substrate may be incorporated. Such additional amino acids may provide context that improves the recognition of the recognition motif.

The term "transamidase recognition sequence" may refer to a masked or unmasked transamidase recognition sequence. A unmasked transamidase recognition sequence can be recognized by a transamidase. An unmasked transamidase recognition sequence may have been previously masked, e.g., as described herein. In some embodiments, a "masked transamidase recognition sequence" is a sequence that is not recognized by a transamidase but that can be readily modified ("unmasked") such that the resulting sequence is recognized by a transamidase. For example, in some embodiments at least one amino acid of a masked transamidase recognition sequence has a side chain that comprises a moiety that inhibits, e.g., substantially prevents, recognition of the sequence by a transamidase of interest, wherein removal of the moiety allows the transamidase to recognize the sequence. Masking may, for example, reduce recognition by at least 80%, 90%, 95%, or more (e.g., to undetectable levels) in certain embodiments. By way of example, in certain embodiments a threonine residue in a transamidase recognition sequence such as LPXTG is phosphorylated, thereby rendering it refractory to recognition and cleavage by SrtA. The masked recognition sequence can be unmasked by treatment with a phosphatase, thus allowing it to be used in a SrtA-catalyzed transamidation reaction.

In some embodiments, a variant of a naturally occurring sortase may be used. Such variants may be produced through processes such as directed evolution, site-specific modification, etc. In some embodiments, a transamideasse having higher transamidase activity than a naturally occurring sortase may be used. For example, variants of S. aureus sortase A with up to a 140-fold increase in LPETG-coupling activity compared with the starting wild-type enzyme have been identified (Chen, I., et al., PNAS 108(28): 11399-11404, 2011). In some embodiments such a sortase variant is used in a composition or method of the invention. In some embodiments a sortase variant comprises any one or more of the following substitutions relative to a wild type S. aureus SrtA: P94S or P94R, D160N, D165A, K190E, and K196T mutations. An exemplary wild type S. aureus SrtA sequence (Gene ID: 1125243, NCBI RefSeq Acc. No. NP_375640) is shown below, with the afore-mentioned positions underlined:

```
MKKWTNRLMTIAGVVLILVAAYLFAKPHIDNYLHDKDKDEKIEQYD

KNVKEQASKDNKQQAKPQIPKDKSKVAGYIEIPDADIKEPVYPGPA

TPEQLNRGVSFAEENESLDDQNISIAGHTFIDRPNYQFTNLKAAKK

GSMVYFKVGNETRKYKMTSIRDVKPTDVEVLDEQKGKDKQLTLITC

DDYNEKTGVWEKRKIFVATEVK (SEQ ID NO: 1)
```

It will be appreciated that transamidase fragments having transamidation activity can be utilized in the methods described herein. As described in PCT/US2010/000274, such fragments can be identified by producing transamidase fragments by known recombinant techniques or proteolytic techniques, for example, and determining the rate of protein or peptide ligation. The fragment sometimes consists of about 80% of the full-length transamidase amino acid sequence, and sometimes about 70%, about 60%, about 50%, about 40% or about 30% of the full-length transamidase amino acid sequence such as that of S. aureus Sortase A (GenBank Accession number AAD48437). In some embodiments, the fragment lacks an N-terminal portion of the full-length sequence, e.g., the fragment lacks the N-terminal portion extending to the end of the membrane anchor sequence. In some embodiments the fragment comprises the C-terminus of a full-length transamidase amino acid sequence. In some embodiments, a catalytic core region from a sortase is utilized, e.g., a region is from about position 60 to about position 206 of SrtA, e.g., S. aureus SrtA, or about from position 82 to about position 249 of SrtAstrep.

Transamidases from other organisms also can be utilized in the processes described herein. Such transamidases often are encoded by nucleotide sequences substantially identical or similar to the nucleotide sequences that encode Srt A and Srt B. A similar or substantially identical nucleotide sequence may include modifications to the native sequence, such as substitutions, deletions, or insertions of one or more nucleotides. Included are nucleotide sequences that sometimes are 55%, 60%, 65%, 70%, 75%, 80%, or 85% or more identical to a native nucleotide sequence, and often are 90% or 95% or more identical to the native nucleotide sequence (each identity percentage can include a 1%, 2%, 3% or 4% variance). One test for determining whether two nucleic acids are substantially identical is to determine the percentage of identical nucleotide sequences shared between the nucleic acids.

Calculations of sequence identity can be performed as follows. Sequences are aligned for optimal comparison purposes and gaps can be introduced in one or both of a first and a second nucleic acid sequence for optimal alignment. Also, non-homologous sequences can be disregarded for comparison purposes. The length of a reference sequence aligned for comparison purposes sometimes is 30% or more, 40% or more, 50% or more, often 60% or more, and more often 70%, 80%, 90%, 100% of the length of the reference sequence. The nucleotides at corresponding nucleotide positions then are compared among the two sequences. When a position in the first sequence is occupied by the same nucleotide as the corresponding position in the second sequence, the nucleotides are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two nucleotide sequences can be determined using the algorithm of Meyers & Miller, CABIOS 4: 11 17 (1989), which has been incorporated into the ALIGN program (version 2.0), using a PAM 120 weight residue table, a gap length penalty of 12 and a gap penalty of 4. Percent identity between two nucleotide sequences can be determined using the GAP program in the GCG software package (available at www.gcg.com), using a NWSgapdna. CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frame shift gap penalty of 5.

It will also be understood that in methods described herein, ligation may be performed by contacting the transamidase, acyl donor, and nucleophilic acyl acceptor with one another under suitable conditions to effect ligation of the acyl donor to the acyl acceptor. Contacting these components with one another can be accomplished by adding them to one body of fluid and/or in one reaction vessel, for example, or otherwise placing the components in close proximity to one another and allowing them to collide. The components in the system may be mixed in a variety of manners, such as by oscillating a vessel, subjecting a vessel to a vortex generating apparatus, repeated mixing with a pipette or pipettes, or by passing fluid containing one assay component over a surface having another assay component immobilized thereon, for example. The components may be added in any order to the system. Ligation may be performed in any convenient vessel (e.g., tubes such as microfuge tubes, flask, dish), microtiter plates (e.g., 96-well or 384-well plates), glass slides, silicon chips, filters, or any solid or semisolid support having surface (optionally coated) having molecules immobilized thereon and optionally oriented in an array (see, e.g., U.S. Pat. No. 6,261,776 and Fodor, Nature 364: 555-556 (1993)), and microfluidic devices (see, e.g., U.S. Pat. Nos. 6,440,722; 6,429,025; 6,379,974; and 6,316, 781). The system can include attendant equipment such as signal detectors, robotic platforms, and pipette dispensers. The reaction mixture may be cell free and often does not include bacterial cell wall components or intact bacterial cell walls. The reaction mixture may be maintained at any convenient temperature at which the ligation reaction can be performed. In some embodiments, the ligation is performed at a temperature ranging from about 15 degrees C. to about 50 degrees C. In some embodiments, the ligation is performed at a temperature ranging from about 23 degrees C. to about 37 degrees C. In certain embodiments, the temperature is room temperature (e.g., about 25 degrees C. If desired the temperature can be optimized by repetitively performing the same ligation procedure at different temperatures and determining ligation rates. Any convenient assay volume and component ratio may be utilized. In certain embodiments, a component ratio of 1:1000 or greater transamidase enzyme to acyl donor is utilized, or a ratio of 1:1000 or greater transamidase enzyme to acyl acceptor is utilized. In specific embodiments, ratios of enzyme to acyl donor or enzyme to acyl acceptor is about 1:1, including 1:2 or greater, 1:3 or greater, 1:4 or greater, 1:5 or greater, 1:6 or greater, 1:7 or greater, 1:8 or greater, and 1:9 or greater. In some embodiments, the acyl donor is present at a concentration ranging from about 10 µM to about 10 mM. In some embodiments, the acyl donor is present at a concentration ranging from about 100 µM to about 1 mM. In some embodiments, the acyl donor is present at a concentration ranging from about 100 µM to about 5 mM. In some embodiments, the acyl donor is present at a concentration ranging from about 200 µM to about 1 mM. In some embodiments, the acyl donor is present at a concentration ranging from about 200 µM to about 800 µM. In some embodiments, the acyl donor is present at a concentration ranging from about 400 µM to about 600 µM. In certain embodiments, the nucleophilic acyl acceptor is present at a concentration ranging from about 1 µM to about 500 µM. In certain embodiments, the nucleophilic acyl acceptor is present at a concentration ranging from about 15 µM to about 150 µM. In certain embodiments, the nucleophilic acyl acceptor is present at a concentration ranging from about 25 µM to about 100 µM. In certain embodiments, the nucleophilic acyl acceptor is present at a concentration ranging from about 40 µM to about 60 µM. In certain embodiments, the transamidase is present at a concentration ranging from about 1 µM to about 500 µM. In certain embodiments, the transamidase is present at a concentration ranging from about 15 µM to about 150 µM. In certain embodiments, the transamidase is present at a concentration ranging from about 25 µM to about 100 µM. In certain embodiments, the transamidase is present at a concentration ranging from about 40 µM to about 60 In certain embodiments, the ligation method is performed in a reaction mixture comprising an aqueous environment. Water with an appropriate buffer and/or salt content often may be utilized. An alcohol or organic solvent may be included in certain embodiments. The amount of an organic solvent often does not appreciably esterify a protein or peptide in the ligation process (e.g., esterified protein or peptide often increase only by 5% or less upon addition of an alcohol or organic solvent). Alcohol and/or organic solvent contents if present sometimes are 20% or less, 15% or less, 10% or less or 5% or less, or 1% or less, and in embodiments where a greater amount of an alcohol or organic solvent is utilized, 30% or less, 40% or less, 50% or less, 60% or less, 70% or less, or 80% or less alcohol or organic solvent is present. In certain embodiments, the system includes only an alcohol or an organic solvent, with only limited amounts of water if it is present. In some embodiments, suitable ligation conditions comprise a buffer. One of ordinary skill in the art will be familiar with a variety of buffers that could be used in accordance with the present invention. In some embodiments, the buffer solution comprises calcium ions. In certain embodiments, the buffer solution does not contain substances that precipitate calcium ions. In some embodiments, the buffer solution does not include phosphate ions. In some embodiments, the buffer solution does not contain chelating agents. In some embodiments, suitable ligation conditions comprise pH in the range of 6 to 8.5. In some embodiments, suitable ligation conditions comprise pH in the range of 6 to 8. In some embodiments, suitable ligation conditions comprise pH in the range of 6 to 7.5. In some embodiments, suitable ligation conditions comprise pH in the range of 6.5 to 8.5. In some embodiments, suitable ligation conditions comprise pH in the range of 7 to 8.5. In some embodiments, suitable ligation conditions comprise pH in the range of 7.5 to 8.5. In some embodiments, suitable ligation conditions comprise pH in the range of 7.0 to 8.5. In some embodiments, suitable ligation conditions comprise pH in the range of 7.3 to 7.8. It will be understood that the afore-mentioned concentrations, ratios, and conditions are exemplary and non-limiting. Higher or lower concentrations and/or different conditions may be used in various embodiments.

One or more components for ligation or a ligation product may be immobilized to a solid support. The attachment between an assay component and the solid support may be covalent or non-covalent (e.g., U.S. Pat. No. 6,022,688 for non-covalent attachments). The solid support may be one or more surfaces of the system, such as one or more surfaces in each well of a microtiter plate, a surface of a glass slide or silicon wafer, Biacore chip, a surface of a particle, e.g., a bead (e.g., Lam, Nature 354: 82-84 (1991)) that is optionally linked to another solid support, or a channel in a microfluidic device, for example. Types of solid supports, linker molecules for covalent and non-covalent attachments to solid supports, and methods for immobilizing nucleic acids and other molecules to solid supports are known (e.g., U.S. Pat. Nos. 6,261,776; 5,900,481; 6,133,436; and 6,022,688; and WIPO publication WO 01/18234). Any material may be used, e.g., plastic (e.g., polystyrene), metal, glass, cellulose, gels (e.g., formed at least in part from organic polymers such as PDMS), etc. In some embodiments the solid support is semi-solid and/or gel-like, deformable, flexible, or the like.

Modified Proteins Comprising Click Chemistry Handles

Some embodiments provide a modified protein (PRT) comprising a C-terminal click chemistry handle (CCH), wherein the modified protein comprises a structure according to Formula (I):

PRT-LPXT-[Xaa]$_y$-CCH  (I).

Some embodiments provide a modified protein (PRT) comprising an N-terminal click chemistry handle (CCH), wherein the modified protein comprises a structure according to Formula (I) according to Formula (II):

CHH—[Xaa]$_y$-LPXT-PRT  (II).

wherein, in Formulas (I) and (II):
  PRT is an amino acid sequence of at least three amino acids;
  each instance of Xaa is independently an amino acid residue;
  y is 0 or an integer between 1-100
  LPXT is a sortase recognition motif; and
  CCH is a click chemistry handle.

In some embodiments, a modified protein is provided that consists of a structure according to formula (I) or formula (II).

Click Chemistry

Two proteins comprising a click chemistry handle each (e.g., a first protein comprising a click chemistry handle providing a nucleophilic (Nu) group and a second protein comprising an electrophilic (E) group that can react with the Nu group of the first click chemistry handle) can be covalently conjugated under click chemistry reaction conditions. Click chemistry is a chemical philosophy introduced by Sharpless in 2001 and describes chemistry tailored to generate substances quickly and reliably by joining small units together (see, e.g., Kolb, Finn and Sharpless *Angewandie Chemie International Edition* (2001) 40: 2004-2021; Evans, *Australian Journal of Chemistry* (2007) 60: 384-395). Additional exemplary click chemistry handles, reaction conditions, and associated methods useful according to aspects of this invention are described in Joerg Lahann, *Click Chemistry for Biotechnology and Materials Science,* 2009, John Wiley & Sons Ltd, ISBN 978-0-470-69970-6, the entire contents of which are incorporated herein by reference.

Click chemistry should be modular, wide in scope, give high chemical yields, generate inoffensive byproducts, be (1) The Huisgen 1,3-dipolar cycloaddition (e.g., the Cu(I)-catalyzed stepwise variant, often referred to simply as the "click reaction"; see, e.g., Tornoe et al., *Journal of Organic Chemistry* (2002) 67: 3057-3064). Copper and ruthenium are the commonly used catalysts in the reaction. The use of copper as a catalyst results in the formation of 1,4-regioisomer whereas ruthenium results in formation of the 1,5-regioisomer;
(2) Other cycloaddition reactions, such as the Diels-Alder reaction;
(3) Nucleophilic addition to small strained rings like epoxides and aziridines;
(4) Nucleophilic addition to activated carbonyl groups; and
(4) Addition reactions to carbon-carbon double or triple bonds.

Conjugation of Proteins Via Click Chemistry Handles

For two proteins to be conjugated via click chemistry, the click chemistry handles of the proteins have to be reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to those described in Table I:

TABLE I

Exemplary click chemistry handles and reactions, wherein each ocurrence of $R_1$, $R_2$, is independently PRT-LPXT-[Xaa]$_y$-, or -[Xaa]$_y$-LPXT-PRT, according to Formulas (I) and (II).

| Reactants | Product | Reaction |
|---|---|---|
| terminal alkyne + azide | triazole | 1,3-dipolar cycloaddition |
| strained alkyne + azide | fused triazole | Strain-promoted cycloaddition |
| diene + dienophile | cyclohexene | Diels-Alder reaction |
| thiol (R—SH) + alkene | thioether | Thiol-ene reaction | stereospecific, be physiologically stable, exhibit a large thermodynamic driving force (e.g., >84 kJ/mol to favor a reaction with a single reaction product), and/or have high atom economy. Several reactions have been identified which fit this concept:

In some preferred embodiments, click chemistry handles are used that can react to form covalent bonds in the absence of a metal catalyst. Such click chemistry handles are well known to those of skill in the art and include the click chemistry handles described in Becer, Hoogenboom, and Schubert, click *Chemistry beyond Metal-Catalyzed Cycloaddition,* Angewandte Chemie International Edition (2009) 48: 4900-4908.

Baskin, S. L. Amacher, C. R. Bertozzi, Science 2008, 320, 664-667; c) J. A. Johnson, J. M. Baskin, C. R. Bertozzi, J. F. Koberstein, N. J. Turro, Chem. Commun. 2008, 3064-

TABLE 2 exemplary click chemistry handles and reactions.
From Becer, Hoogenboom, and Schubert, *click Chemistry beyond Metal-Catalyzed Cycloaddition,* Angewandte Chemie International Edition (2009) 48: 4900-4908.

| | Reagent A | Reagent B | Mechanism | Notes on reaction[a] | Reference |
|---|---|---|---|---|---|
| 0 | azide | alkyne | Cu-catalyzed [3 + 2] azide-alkyne cycloaddition (CuAAC) | 2 h at 60° C. in $H_2O$ | [9] |
| 1 | azide | cyclooctyne | strain-promoted [3 + 2] azide-alkyne cycloaddition (SPAAC) | 1 h at RT | [6-8, 10, 11] |
| 2 | azide | activated alkyne | [3 + 2] Huisgen cycloaddition | 4 h at 50° C. | [12] |
| 3 | azide | electron-deficient alkyne | [3 + 2] cycloaddittion | 12 h at RT in $H_2O$ | [13] |
| 4 | azide | aryne | [3 + 2] cycloaddittion | 4 h at RT in THF with crown ether or 24 h at RT in $CH_3CN$ | [14, 15] |
| 5 | tetrazine | alkene | Diels-Alder retro-[4 + 2] cycloaddition | 40 min at 25° C. (100% yield) $N_2$ is the only by-product | [36-38] |
| 6 | tetrazole | alkene | 1,3-dipolar cycloaddition (photoclick) | few min UV irradiation and then overnight at 4° C. | [39, 40] |
| 7 | dithioester | diene | hetero-Diels-Alder cycloaddition | 10 min at RT | [43] |
| 8 | anthracene | maleimide | [4 + 2] Diels-Alder reaction | 2 days at reflux in toluene | [41] |
| 9 | thiol | alkene | radical addition (thio click) | 30 min UV (quantitative conv.) or 24 h UV irradiation (>96%) | [19-23] |
| 10 | thiol | enone | Michael addition | 24 h at RT in $CH_3CN$ | [27] |
| 11 | thiol | maleimide | Michael addition | 1 h at 40° C. in THF or 16 h at RT in dioxane | [24-26] |
| 12 | thiol | para-fluoro | nucleophilic substitution | overnight at RT in DMF or 60 min at 40° C. in DMF | [32] |
| 13 | amine | para-fluoro | nucleophilic substitution | 20 min MW at 95° C. in NMP as solvent | [30] |

[a]RT = room temperature, DMF = N,N-dimethylformamide, NMP = N-methylpyrolidone, THF = tetrahydrofuran, $CH_3CN$ = acetonitrile.

Additional click chemistry handles suitable for use in the methods of protein conjugation described herein are well known to those of skill in the art, and such click chemistry handles include, but are not limited to, the click chemistry reaction partners, groups, and handles described in [1] H. C. Kolb, M. G. Finn, K. B. Sharpless, Angew. Chem. 2001, 113, 2056-2075; Angew. Chem. Int. Ed. 2001, 40, 2004-2021. [2] a) C. J. Hawker, K. L. Wooley, Science 2005, 309, 1200-1205; b) D. Fournier, R. Hoogenboom, U. S. Schubert, Chem. Soc. Rev. 2007, 36, 1369-1380; c) W. H. Binder, R. Sachsenhofer, Macromol. Rapid Commun. 2007, 28, 15-54; d) H. C. Kolb. K. B. Sharpless, Drug Discovery Today 2003, 8, 1128-1137; e) V. D. Bock, H. Hiemstra, J. H. van Maarseveen, Eur. J. Org. Chem. 2006, 51-68. [3] a) V. O. Rodionov, V. V. Fokin, M. G. Finn, Angew. Chem. 2005, 117, 2250-2255; Angew. Chem. Int. Ed. 2005, 44, 2210-2215; b) P. L. Golas, N. V. Tsarevsky, B. S. Sumerlin, K. Matyjaszewski, Macromolecules 2006, 39, 6451-6457; c) C. N. Urbani, C. A. Bell, M. R. Whittaker, M. J. Monteiro, Macromolecules 2008, 41, 1057-1060; d) S. Chassaing, A. S. S. Sido, A. Alix, M. Kumarraja, P. Pale, J. Sommer, Chem. Eur. J. 2008, 14, 6713-6721; e) B. C. Boren, S. Narayan, L. K. Rasmussen, L. Zhang, H. Zhao, Z. Lin, G. Jia, V. V. Fokin, J. Am. Chem. Soc. 2008, 130, 8923-8930; f) B. Saba, S. Sharma, D. Sawant, B. Kundu, Synlett 2007, 1591-1594. [4] J. F. Lutz, Angew. Chem. 2008, 120, 2212-2214; Angew. Chem. Int. Ed. 2008, 47, 2182-2184. [5] a) Q. Wang, T. R. Chan, R. Hilgraf, V. V. Fokin, K. B. Sharpless, M. G. Finn, J. Am. Chem. Soc. 2003, 125, 3192-3193; b) J. Gierlich, G. A. Burley, P. M. E. Gramlich, D. M. Hammond, T. Carell, Org. Lett. 2006, 8, 3639-3642. [6] a) J. M. Baskin, J. A. Prescher, S. T. Laughlin, N. J. Agard, P. V. Chang, I. A. Miller, A. Lo, J. A. Codelli, C. R. Bertozzi, Proc. Natl. Acad. Sci. USA 2007, 104, 16793-16797; b) S. T. Laughlin, J. M. 3066; d) J. A. Codelli, J. M. Baskin, N. J. Agard, C. R. Bertozzi, J. Am. Chem. Soc. 2008, 130, 11486-11493; e) E. M. Sletten, C. R. Bertozzi, Org. Lett. 2008, 10, 3097-3099; f) J. M. Baskin, C. R. Bertozzi, QSAR Comb. Sci. 2007, 26, 1211-1219. [7] a) G. Wittig, A. Krebs, Chem. Ber. Reel. 1961, 94, 3260-3275; b) A. T. Blomquist, L. H. Liu, J. Am. Chem. Soc. 1953, 75, 2153-2154. [8] D. H. Ess, G. O. Jones, K. N. Houk, Org. Lett. 2008, 10, 1633-1636. [9] W. D. Sharpless, P. Wu, T. V. Hansen, J. G. Lindberg, J. Chem. Educ. 2005, 82, 1833-1836. [10] Y. Zou, J. Yin, Bioorg. Med. Chem. Lett. 2008, 18, 5664-5667. [11] X. Ning, J. Guo, M. A. Wolfert, G. J. Boons, Angew. Chem. 2008, 120, 2285-2287; Angew. Chem. Int. Ed. 2008, 47, 2253-2255. [12] S. Sawoo, P. Dutta, A. Chakraborty, R. Mukhopadhyay, O. Bouloussa, A. Sarkar, Chem. Commun. 2008, 5957-5959. [13] a) Z. Li, T. S. Seo, J. Ju, Tetrahedron Lett. 2004, 45, 3143-3146; b) S. S. van Berkel, A. J. Dirkes, M. F. Debets, F. L. van Delft, J. J. L. Cornelissen, R. J. M. Nolte, F. P. J. Rutjes, ChemBioChem 2007, 8, 1504-1508; c) S. S. van Berkel, A. J. Dirks, S. A. Meeuwissen, D. L. L. Pingen, O. C. Boerman, P. Laverman, F. L. van Delft, J. J. L. Cornelissen, F. P. J. Rutjes, ChemBio-Chem 2008, 9, 1805-1815. [14] F. Shi, J. P. Waldo, Y. Chen, R. C. Larock, Org. Lett. 2008, 10, 2409-2412. [15] L. Campbell-Verduyn, P. H. Elsinga, L. Mirfeizi, R. A. Dierckx, B. L. Feringa, Org. Biomol. Chem. 2008, 6, 3461-3463. [16] a) The Chemistry of the Thiol Group (Ed.: S. Patai), Wiley, New York, 1974; b) A. F. Jacobine, In Radiation Curing in Polymer Science and Technology III (Eds.: J. D. Fouassier, J. F. Rabek), Elsevier, London, 1993, Chap. 7, pp. 219-268. [17] C. E. Hoyle, T. Y. Lee, T. Roper, J. Polym. Sci. Part A 2008, 42, 5301-5338. [18] L. M. Campos, K. L. Killops, R. Sakai, J. M. J. Paulusse, D. Damiron, E. Drockenmuller, B. W. Messmore, C. J. Hawker, Macromolecules 2008, 41, 7063-

7070. [19] a) R. L. A. David, J. A. Kornfield, Macromolecules 2008, 41, 1151-1161; b) C. Nilsson, N. Simpson, M. Malkoch, M. Johansson, E. Malmstrom, J. Polym. Sci. Part A 2008, 46, 1339-1348; c) A. Dondoni, Angew. Chem. 2008, 120, 9133-9135; Angew. Chem. Int. Ed. 2008, 47, 8995-8997; d) J. F. Lutz, H. Schlaad, Polymer 2008, 49, 817-824. [20] A. Gress, A. Voelkel, H. Schlaad, Macromolecules 2007, 40, 7928-7933. [21] N. ten Brummelhuis, C. Diehl, H. Schlaad, Macromolecules 2008, 41, 9946-9947. [22] K. L. Killops, L. M. Campos, C. J. Hawker, J. Am. Chem. Soc. 2008, 130, 5062-5064. [23] J. W. Chan, B. Yu, C. E. Hoyle, A. B. Lowe, Chem. Commun. 2008, 4959-4961. [24] a) G. Moad, E. Rizzardo, S. H. Thang, Ace. Chem. Res. 2008, 41, 1133-1142; b) C. Barner-Kowollik, M. Buback, B. Charleux, M. L. Coote, M. Drache, T. Fukuda, A. Goto, B. Klumperman, A. B. Lowe, J. B. McLeary, G. Moad, M. J. Monterio, R. D. Sanderson, M. P. Tonge, P. Vana, J. Polym. Sci. Part A 2006, 44, 5809-5831. [25] a) R. J. Pounder, M. J. Stanford, P. Brooks, S. P. Richards, A. P. Dove, Chem. Commun. 2008, 5158-5160; b) M. J. Stanford, A. P. Dove, Macromolecules 2009, 42, 141-147. [26] M. Li, P. De, S. R. Gondi, B. S. Sumerlin, J. Polym. Sci. Part A 2008, 46, 5093-5100. [27] Z. J. Witczak, D. Lorchak, N. Nguyen, Carbohydr. Res. 2007, 342, 1929-1933. [28] a) D. Samaroo, M. Vinodu, X. Chen, C. M. Drain, J. Comb. Chem. 2007, 9, 998-1011; b) X. Chen, D. A. Foster, C. M. Drain, Biochemistry 2004, 43, 10918-10929; c) D. Samaroo, C. E. Soll, L. J. Todaro, C. M. Drain, Org. Lett. 2006, 8, 4985-4988. [29] P. Battioni, O. Brigaud, H. Desvaux, D. Mansuy, T. G. Traylor, Tetrahedron Lett. 1991, 32, 2893-2896. [30] C. Ott, R. Hoogenboom, U. S. Schubert, Chem. Commun. 2008, 3516-3518. [31] a) V. Ladmiral, G. Mantovani, G. J. Clarkson, S. Cauet, J. L. Irwin, D. M. Haddleton, J. Am. Chem. Soc. 2006, 128, 4823-4830; b) S. G. Spain, M. I. Gibson, N. R. Cameron, J. Polym. Sci. Part A 2007, 45, 2059-2072. [32] C. R. Becer, K. Babiuch, K. Pilz, S. Hornig, T. Heinze, M. Gottschaldt, U. S. Schubert, Macromolecules 2009, 42, 2387-2394. [33] Otto Paul Hermann Diets and Kurt Alder first documented the reaction in 1928. They received the Nobel Prize in Chemistry in 1950 for their work on the eponymous reaction. [34] a) H. L. Holmes, R. M. Husband, C. C. Lee, P. Kawulka, J. Am. Chem. Soc. 1948, 70, 141-142; b) M. Lautens, W. Klute, W. Tarn, Chem. Rev. 1996, 96, 49-92; c) K. C. Nicolaou, S. A. Snyder, T. Montagnon, G. Vassilikogiannakis, Angew. Chem. 2002, 114, 1742-1773; Angew. Chem. Int. Ed. 2002, 41, 1668-1698; d) E. J. Corey, Angew. Chem. 2002, 114, 1724-1741; Angew. Chem. Int. Ed. 2002, 41, 1650-1667. [35] a) H. Durmaz, A. Dag, O. Altintas, T. Erdogan, G. Hizal, U. Tunca, Macromolecules 2007, 40, 191-198; b) H. Durmaz, A. Dag, A. Hizal, G. Hizal, U. Tunca, J. Polym. Sci. Part A 2008, 46, 7091-7100; c) A. Dag, H. Durmaz, E. Demir, G. Hizal, U. Tunca, J. Polym. Sci. Part A 2008, 46, 6969-6977; d) B. Gacal, H. Akat, D. K. Balta, N. Arsu, Y. Yagci, Macromolecules 2008, 41, 2401-2405; e) A. Dag, H. Durmaz, U. Tunca, G. Hizal, J. Polym. Sci. Part A 2009, 47, 178-187. [36] M. L. Blackman, M. Royzen, J. M. Fox, J. Am. Chem. Soc. 2008, 130, 13518-13519. [37] It should be noted that trans-cyclooctene is the most reactive dienophile toward tetrazines and seven orders of magnitude more reactive than cis-cyclooctene. [38] N. K. Devaraj, R. Weissleder, S. A. Hilderbrand, Bioconjugate Chem. 2008, 19, 2297-2299. [39] W. Song, Y. Wang, J. Qu, Q. Lin, J. Am. Chem. Soc. 2008, 130, 9654-9655. [40] W. Song, Y. Wang, J. Qu, M. M. Madden, Q. Lin, Angew. Chem. 2008, 120, 2874-2877; Angew. Chem. Int. Ed. 2008, 47, 2832-2835. [41] A. Dag, H. Durmaz, G. Hizal, U. Tunca, J. Polym. Sci. Part A 2008, 46, 302-313. [42] a) A. J. Inglis, S. Sinnwell, T. P. Davis, C. Barner-Kowollik, M. H. Stenzel, Macromolecules 2008, 41, 4120-4126; b) S. Sinnwell, A. J. Inglis, T. P. Davis, M. H. Stenzel, C. Barner-Kowollik, Chem. Commun. 2008, 2052-2054. [43] A. J. Inglis, S. Sinwell, M. H. Stenzel, C. Barner-Kowollik, Angew. Chem. 2009, 121, 2447-2450; Angew. Chem. Int. Ed. 2009, 48, 2411-2414. All references cited above are incorporated herein by reference for disclosure of click chemistry handles suitable for installation on proteins according to inventive concepts and methods provided herein.

For example, in some embodiments, a first protein is provided comprising a C-terminal strained alkyne group, for example, a C-terminal cyclooctyne group as the click chemistry handle, and a second protein is provided comprising a C-terminal azide group as the click chemistry handle. The two click chemistry handles are reactive with each other, as they can carry out a strain-promoted cycloaddition, which results in the first and the second protein being conjugated via a covalent bond. In this example, the two C-termini of the proteins are conjugated together, which is also referred to as a C—C, or a C to C, conjugation.

In certain embodiments, a first molecule, for example, a first protein, comprising a nucleophilic click chemistry handle (Nu) selected from —SH, —OH, —NHR$^{b5}$, —NH—NHR$^{b5}$, or —N=NH, is conjugated to a second molecule, for example, a second protein, comprising the electrophilic partner click chemistry handle (E)

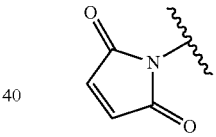

to form a chimeric protein with a conjugated group of the formula:

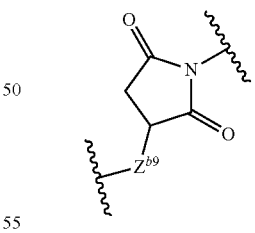

wherein $Z^{b9}$ is —S—, —O—, —N(R$^{b5}$)—, —NH—N(R$^{b5}$)—, or —N=N—. In some embodiments, the nucleophilic click chemistry handle Nu is —SH and $Z^{b9}$ is —S—. In certain embodiments, Nu is —OH and $Z^{b9}$ is —O—. In certain embodiments, Nu is —NHR$^{b5}$ and $Z^{b9}$ is —N(R$^{b5}$)—. In certain embodiments, Nu is —NH—NHR$^{b5}$ and $Z^{b9}$ is —NH—N(R$^{b5}$)—. In certain embodiments, Nu is —N=NH and $Z^{19}$ is —N=N—. In certain embodiments, R$^{b5}$ is hydrogen.

In certain embodiments, Nu is —SH, —OH, —NHR$^{b5}$, —NH—NHR$^{b5}$, or —N=NH, and E is

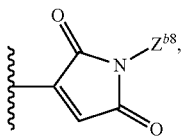

and the two molecules, for example, two proteins, are conjugated to form a chimeric molecule, for example, a chimeric protein wherein Nu and E are joined to form a conjugated group of the formula:

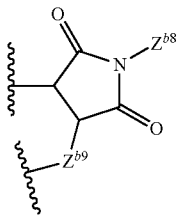

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —NH$R^{b5}$ and $Z^{b9}$ is —N($R^{b5}$)—. In certain embodiments, Nu is —NH—NH$R^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen.

In certain embodiments, Nu is —SH, —OH, —NH$R^{b5}$, —NH—NH$R^{b5}$, or —N=NH, and E is

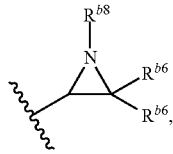

and the two molecules, for example, two proteins, are conjugated to form a chimeric molecule, for example, a chimeric protein wherein Nu and E are joined to form a conjugated group of the formula:

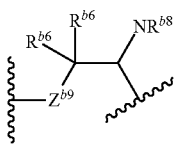

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —NH$R^{b5}$ and $Z^{b9}$ is —N($R^{b5}$)—. In certain embodiments, Nu is —NH—NH$R^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen. In certain embodiments, $R^{b6}$ is hydrogen, optionally substituted aliphatic, or optionally substituted heteroaliphatic. In certain embodiments, $R^{b6}$ is hydrogen or $C_{1-6}$alkyl. In certain embodiments, $R^{b6}$ is hydrogen or —CH$_3$. In certain embodiments, $R^{b8}$ is hydrogen. In certain embodiments, $R^{b8}$ is an amino protecting group.

In certain embodiments, Nu is —SH, —OH, —NH$R^{b5}$, —NH—NH$R^{b5}$, or —N=NH, and E is

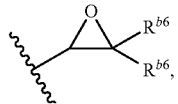

and the two molecules, for example, two proteins, are conjugated to form a chimeric molecule, for example, a chimeric protein wherein Nu and E are joined to form a conjugated group of the formula

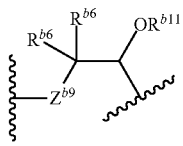

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —NH$R^{b5}$ and $Z^{b9}$ is —N($R^{b5}$)—. In certain embodiments, Nu is —NH—NH$R^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen. In certain embodiments, $R^{b6}$ is hydrogen, optionally substituted aliphatic, or optionally substituted heteroaliphatic. In certain embodiments, $R^{b6}$ is hydrogen or $C_{1-6}$alkyl. In certain embodiments, $R^{b6}$ is hydrogen or —CH$_3$. In certain embodiments, $R^{b11}$ is hydrogen. In certain embodiments, $R^{b11}$ is an oxygen protecting group.

In certain embodiments, Nu is —SH, —OH, —NH$R^{b5}$, —NH—NH$R^{b5}$, or —N=NH, and E is —CO$_2R^{b6}$, —COX$^{b7}$, and the two molecules, for example, two proteins, are conjugated to form a chimeric molecule, for example, a chimeric protein wherein Nu and E are joined to form a conjugated group of the formula:

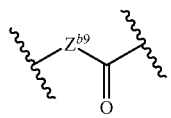

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —NH$R^{b5}$ and $Z^{b9}$ is —N($R^{b5}$)—. In certain embodiments, Nu is —NH—NH$R^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen.

In certain embodiments, Nu is —SH, —OH, —NH$R^{b5}$, —NH—NH$R^{b5}$, or —N=NH, and E is

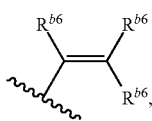

and the two molecules, for example, two proteins, are conjugated to form a chimeric molecule, for example, a chimeric protein wherein Nu and E are joined to form a conjugated group of the formula:

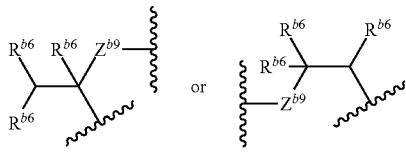

wherein $Z^{b9}$ is —S—, —O—, —N($R^{b5}$)—, —NH—N($R^{b5}$)—, or —N═N—. In certain embodiments, Nu is —SH and $Z^{b9}$ is —S—. In certain embodiments, Nu is —OH and $Z^{b9}$ is —O—. In certain embodiments, Nu is —NH$R^{b5}$ and $Z^{b9}$ is —N($R^{b5}$)—. In certain embodiments, Nu is —NH—NH$R^{b5}$ and $Z^{b9}$ is —NH—N($R^{b5}$)—. In certain embodiments, Nu is —N═NH and $Z^{b9}$ is —N═N—. In certain embodiments, $R^{b5}$ is hydrogen. In certain embodiments, $R^{b6}$ is hydrogen, optionally substituted aliphatic, or optionally substituted heteroaliphatic. In certain embodiments, $R^{b6}$ is hydrogen or $C_{1-6}$alkyl. In certain embodiments, $R^{b6}$ is hydrogen or —CH$_3$.

In certain embodiments, Nu is —SH, —OH, —NH$R^{b5}$, —NH—NH$R^{b5}$, or —N═NH, and E is

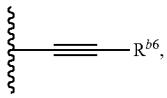

and the two molecules, for example, two proteins, are conjugated to form a chimeric molecule, for example, a chimeric protein wherein Nu and E are joined to form a conjugated group of the formula:

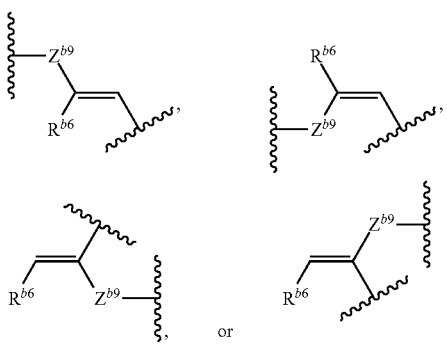

wherein $Z^{b9}$ is —S—, —O—, —N($R^{b5}$)—, —NH—N($R^{b5}$)—, or —N═N—. In certain embodiments, Nu is —SH and $Z^{b9}$ is —S— (a thiol-yne reaction). In certain embodiments, Nu is —OH and $Z^{b9}$ is —O—. In certain embodiments, Nu is —NH$R^{b5}$ and $Z^{b9}$ is —N($R^{b5}$)—. In certain embodiments, Nu is —NH—NH$R^{b5}$ and $Z^{b9}$ is —NH—N ($R^{b5}$)—. In certain embodiments, Nu is —N═NH and $Z^{b9}$ is —N═N—. In certain embodiments, $R^{b5}$ is hydrogen. In certain embodiments, $R^{b6}$ is hydrogen, optionally substituted aliphatic, or optionally substituted heteroaliphatic. In certain embodiments, $R^{b6}$ is hydrogen or $C_{1-6}$alkyl. In certain embodiments, $R^{b6}$ is hydrogen or —CH$_3$.

In certain embodiments, Nu is —SH, —OH, —NH$R^{b5}$, —NH—NH$R^{b5}$, or —N═NH, and E is

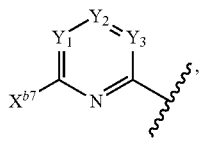

and the two molecules, for example, two proteins, are conjugated to form a chimeric molecule, for example, a chimeric protein wherein Nu and E are joined to form a conjugated group of the formula:

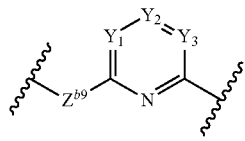

wherein $Z^{b9}$ is —S—, —O—, —N($R^{b5}$)—, —NH—N($R^{b5}$)—, or —N═N—. In certain embodiments, Nu is —SH and $Z^{b9}$ is —S— (a thiol-yne reaction). In certain embodiments, Nu is —OH and $Z^{b9}$ is —O—. In certain embodiments, Nu is —NH$R^{b5}$ and $Z^{b9}$ is —N($R^{b5}$)—. In certain embodiments, Nu is —NH—NH$R^{b5}$ and $Z^{b9}$ is —NH—N($R^{b5}$)—. In certain embodiments, Nu is —N═NH and $Z^{b9}$ is —N═N—.

In certain embodiments, Nu is —SH, —OH, —NH$R^{b5}$, —NH—NH$R^{b5}$, or —N═NH, and E is

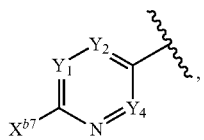

and the two molecules, for example, two proteins, are conjugated to form a chimeric molecule, for example, a chimeric protein wherein Nu and E are joined to form a conjugated group of the formula:

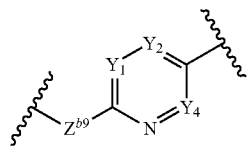

wherein $Z^{b9}$ is —S—, —O—, —N($R^{b5}$)—, —NH—N($R^{b5}$)—, or —N═N—. In certain embodiments, Nu is —SH and $Z^{b9}$ is —S— (a thiol-yne reaction). In certain embodiments, Nu is —OH and $Z^{b9}$ is —O—. In certain embodiments, Nu is —NH$R^{b5}$ and $Z^{b9}$ is —N($R^{b5}$)—. In certain embodiments, Nu is —NH—NHR$^{b5}$ and Z$^{b9}$ is —NH—N(R$^{b5}$)—. In certain embodiments, Nu is —N=NH and Z$^{b9}$ is —N=N—.

In certain embodiments, Nu is —SH, —OH, —NHR$^{b5}$, —NH—NHR$^{b5}$, or —N=NH, and E is

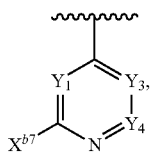

and the two molecules, for example, two proteins, are conjugated to form a chimeric molecule, for example, a chimeric protein wherein Nu and E are joined to form a conjugated group of the formula:

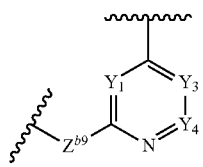

wherein Z$^{b9}$ is —S—, —O—, —N(R$^{b5}$)—, —NH—N(R$^{b5}$)—, or —N=N—. In certain embodiments, Nu is —SH and Z$^{b9}$ is —S— (a thiol-yne reaction). In certain embodiments, Nu is —OH and Z$^{b9}$ is —O—. In certain embodiments, Nu is —NHR$^{b5}$ and Z$^{b9}$ is —N(R$^{b5}$)—. In certain embodiments, Nu is —NH—NHR$^{b5}$ and Z$^{b9}$ is —NH—N(R$^{b5}$)—. In certain embodiments, Nu is —N=NH and Z$^{b9}$ is —N=N—.

In certain embodiments, Nu is —SH, —OH, —NHR$^{b5}$, —NH—NHR$^{b5}$, or —N=NH, and E is

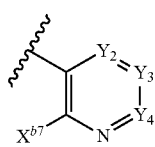

and the two molecules, for example, two proteins, are conjugated to form a chimeric molecule, for example, a chimeric protein wherein Nu and E are joined to form a conjugated group of the formula:

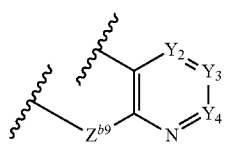

wherein Z$^{b9}$ is —S—, —O—, —N(R$^{b5}$)—, —NH—N(R$^{b5}$)—, or —N=N—. In certain embodiments, Nu is —SH and Z$^{b9}$ is —S— (a thiol-yne reaction). In certain embodiments, Nu is —OH and Z$^{b9}$ is —O—. In certain embodiments, Nu is —NHR$^{b5}$ and Z$^{b9}$ is —N(R$^{b5}$)—. In certain embodiments, Nu is —NH—NHR$^{b5}$ and Z$^{b9}$ is —NH—N(R$^{b5}$)—. In certain embodiments, Nu is —N=NH and Z$^{b9}$ is —N=N—.

In certain embodiments, Nu is —N=NH and E is —CHO, are conjugated to form a homodimer or a heterodimer polypeptide of Formula (III) wherein Nu and E are joined to form a conjugated group of the Formula:

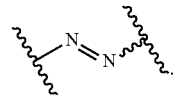

In certain embodiments, Nu is —NHR$^{b5}$, R$^{b5}$ is hydrogen, and E is —CHO, and the two molecules, for example, two proteins, are conjugated to form a chimeric molecule, for example, a chimeric protein wherein Nu and E are joined to form a conjugated group of the formula:

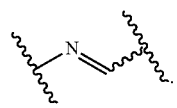

In certain embodiments, Nu is —NH—N(R$^{b5}$)—, R$^{b5}$ is hydrogen, and E is —CHO, and the two molecules, for example, two proteins, are conjugated to form a chimeric molecule, for example, a chimeric protein wherein Nu and E are joined to form a conjugated group of the formula:

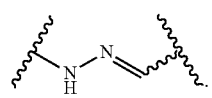

In certain embodiments, Nu is

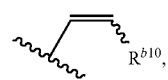

and E is

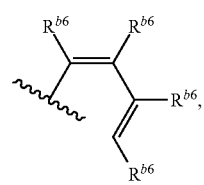

and the two molecules, for example, two proteins, are conjugated via a Diels-Alder reaction to form a chimeric molecule, for example, a chimeric protein wherein Nu and E are joined to form a conjugated group of the formula:

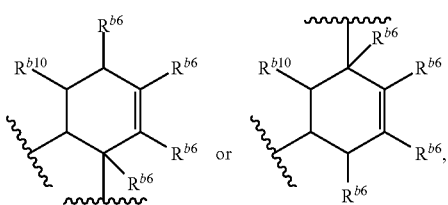

In certain embodiments, $R^{b10}$ is hydrogen. In certain embodiments, $R^{b6}$ is hydrogen or optionally substituted aliphatic, e.g., acyl.

In certain embodiments, Nu is —$N_3$, and E is

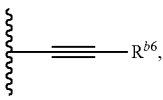

and the two molecules, for example, two proteins, are conjugated via a Huisgen 1,3-dipolar cycloaddition reaction to form a chimeric molecule, for example, a chimeric protein wherein Nu and E are joined to form a conjugated group of the formula:

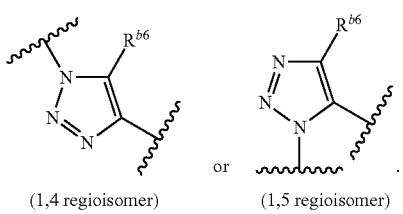

(1,4 regioisomer)     (1,5 regioisomer)

In certain embodiments, $R^{b6}$ is hydrogen, optionally substituted aliphatic, or optionally substituted heteroaliphatic. In certain embodiments, $R^{b6}$ is hydrogen or $C_{1-6}$alkyl. In certain embodiments, $R^{b6}$ is hydrogen or —$CH_3$. In certain embodiments, $R^{b6}$ is hydrogen.

In certain embodiments, two proteins, each comprising a click chemistry handle Nu, wherein each Nu is independently —SH, —OH, —$NHR^{b5}$, —NH—$NHR^{b5}$, or —N=NH, are conjugated by reacting the two polypeptides with a bis-electrophile of formula $$X^{b7}—W_3—X^{b7}$$

wherein $X^{b7}$ is a leaving group, and $W_3$ is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; or optionally substituted heteroarylene, to provide a conjugated group of formula:

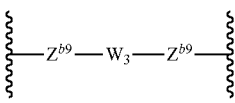

wherein $Z^{b9}$ is —O—, —S—, —$N(R^{b5})$—, —NH—N$(R^{b5})$—, or —N=N—. In certain embodiments, each Nu is —SH and each $Z^{b9}$ is —S—. In certain embodiments, each Nu is —OH and each $Z^{b9}$ is —O—. In certain embodiments, each Nu is —$NHR^{b5}$ and each $Z^{b9}$ is —$N(R^{b5})$—. In certain embodiments, each Nu is —NH—$NHR^{b5}$ and each $Z^{b9}$ is —NH—$N(R^{b5})$—. In certain embodiments, each Nu is —N=NH and each $Z^{b9}$ is —N=N—. In certain embodiments, $W_3$ is optionally substituted alkylene. In certain embodiments, $W_3$ is optionally substituted arylene. In certain embodiments, $W_3$ is optionally substituted heteroarylene. Various combinations of the two Nu groups and two $X^{b7}$ groups are contemplated. In certain embodiments, the two Nu groups, and thus the two $Z^{b9}$ groups, are the same. In certain embodiments, the two Nu groups, and thus the two $Z^{b9}$ groups, are different. In certain embodiments, the two $X^{b7}$ groups are the same. In certain embodiments, the two $X^{b7}$ groups are different.

In certain embodiments, wherein $W_3$ is optionally substituted alkylene, the bis-electrophile is of the Formula:

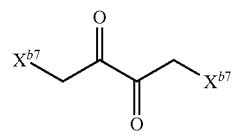

wherein $X^{b7}$ is —Br, —Cl, or —I.

For example, when the bis-electrophile is of the formula:

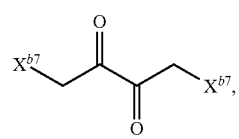

the resulting conjugated group is of the Formula

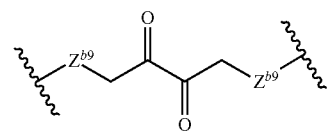

In certain embodiments, wherein $W_3$ is optionally substituted heteroarylene, the bis-electrophile is of the Formula:

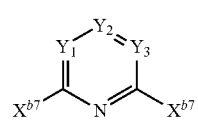

wherein $X^{b7}$ is —Br, —Cl, or —I.

For example, when the bis-electrophile is of the Formula:

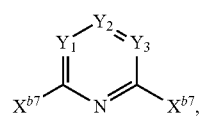

the resulting conjugated group is of the Formula

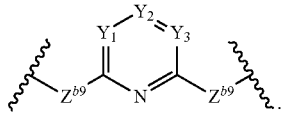

In certain embodiments, two proteins, each comprising a click chemistry handle E, wherein each E is independently selected from a leaving group, —CHO, —CO$_2$R$^{b6}$, —COX$^{b7}$,

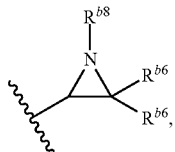 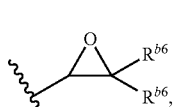 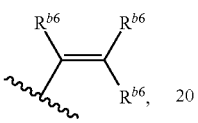

 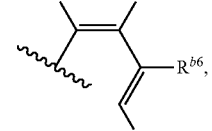

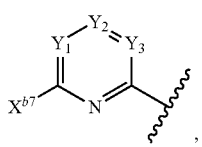, 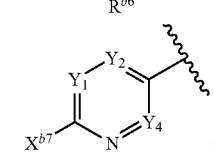

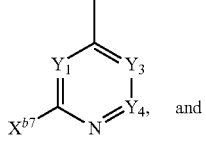, and 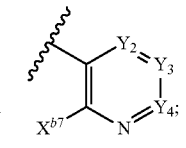;

are conjugated by reacting the two polypeptides with a bis-nucleophile Nu-W$_4$-Nu wherein each Nu is —SH, —OH, —NHR$^{b5}$, —NH—NHR$^{b5}$, —N═NH, —N═C, —N$_3$, or

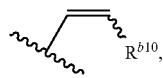, and W$_4$ is independently represents optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; or a combination thereof; to provide a conjugated polypeptide. The two E groups conjugated to W$_4$ independently correspond to any of the above described conjugated groups, also listed below:

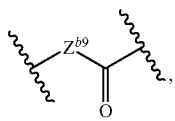 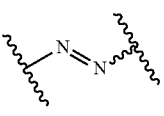 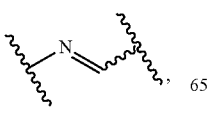

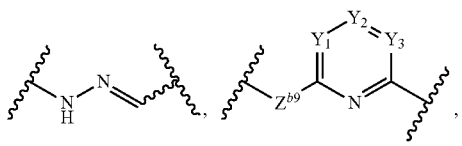

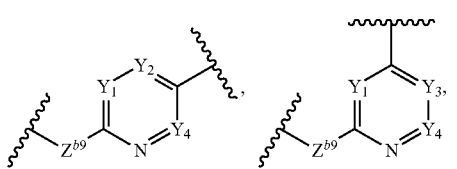

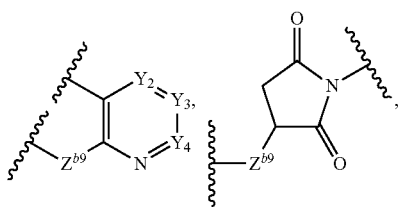

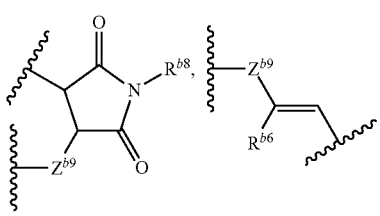

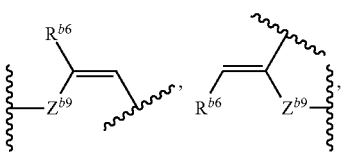

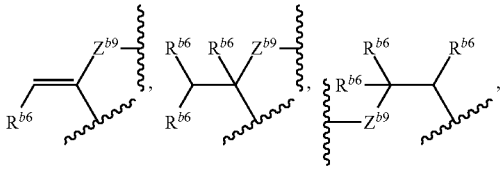

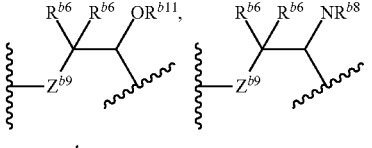

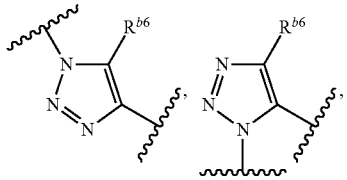

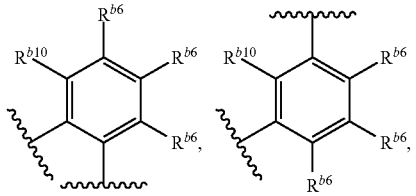

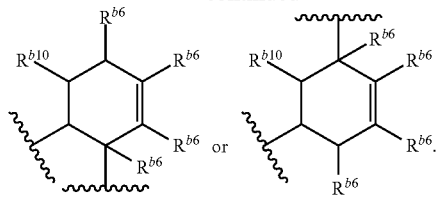

Various combinations of the two E groups are contemplated. In certain embodiments, the two E groups are the same. In certain embodiments, the two E groups are different. In certain embodiments, the two Nu groups, and thus the two $Z^{b9}$ groups, are different. In certain embodiments, the two $X^{b7}$ groups are the same. In certain embodiments, the two $X^{b7}$ groups are different.

Chimeric Proteins and Uses Thereof

Some embodiments of this invention provide chimeric proteins, for example, proteins comprising a sortase recognition motif and conjugated to a second molecule via click chemistry. In some embodiments, the chimeric protein comprises an antibody or antibody fragment, for example, a nanobody. In some embodiments, the antibody, or antibody fragment, is a therapeutic antibody or antibody fragment, for example, an antibody or antibody fragment that binds to a therapeutic target antigen. Some embodiments embrace any therapeutic antibody known to those of skill in the art, since the invention is not limited in this respect. Further, any antibody or antibody fragment binding to a therapeutic antigen, for example, to the same or a different epitope of the therapeutic antigen as a known therapeutic antibody, can be employed in some embodiments of this invention, for example, for the generation of chimeric antibodies as described herein. Some embodiments provide chimeric antibodies that are generated as the result of derivatizing such therapeutic antibodies, or antibodies binding therapeutic antigens, according to methods described herein In some embodiments, a chimeric protein targets a specific antigen, cell type, or site in a cell population, tissue, organism, or subject. For example, in some embodiments, a chimeric, bi-specific antibody is provided that comprises a first antigen binding domain that targets the antibody to a target site (e.g., an organ, a cell or cell type (e.g., a diseased cell, such as a tumor cell), a tissue, or a site of disease) and a second antigen binding domain that provides a function, e.g., a therapeutic function. Such therapeutic function may be provided by a toxin, or by a molecule attracting a specific cell or cell type to the target site. In some embodiments, a chimeric protein is provided that comprises an antibody targeting a specific cell, cell type, tissue, or site, for example, in a subject, wherein the antibody is conjugated via click chemistry to a therapeutic agent, for example, a small molecule, or a therapeutic polypeptide. In some embodiments, a therapeutic protein as provided herein binds to a tumor antigen as target antigens. In some embodiments, a therapeutic protein as provided herein binds to an antigens of a known or potential pathogen (e.g., a virus, a bacterium, a fungus, or a parasite).

Those of skill in the art will understand that chimeric polypeptides and proteins as provided herein may comprise any therapeutic agent that either comprises or can be linked to a click chemistry handle.

In some embodiments, the methods and reagents described herein are used to attach a target protein to a solid or semi-solid support or a surface, e.g., a particle (optionally magnetic), a microparticle, a nanoparticle, a bead, a slide, a filter, or a well (e.g., of multiwell/microtiter plate).

In some embodiments, the methods and reagents described herein, and the modified proteins, for example, the chimeric proteins, or the chimeric antibodies described herein, are used in vitro, in vivo, in research, for detection, for screening, in diagnostic assays, or in therapeutic applications. Exemplary, non-limiting therapeutic applications include treatment of infectious diseases, treatment of cancer, and treatment of metabolic disease. Other therapeutic uses will be evident to those of skill in the art, since the invention is not limited in this respect.

Selected Target Proteins

Without limiting the invention in any way, this section discusses certain target proteins. In general, any protein or polypeptide can be modified to carry a click chemistry handle and/or conjugated to another molecule via click chemistry according to methods provided herein. In some embodiments the target protein comprises or consists of a polypeptide that is at least 80%, or at least 90%, e.g., at least 95%, 86%, 97%, 98%, 99%, 99.5%, or 100% identical to a naturally occurring protein or polypeptide. In some embodiments, the target protein has no more than 1, 2, 3, 4, 5, 6, 7, 8, 9, or 10 amino acid differences relative to a naturally occurring sequence. In some embodiments the naturally occurring protein is a mammalian protein, e.g., of human origin. In some embodiments, the protein is an antibody, an antibody fragment, or protein comprising an antigen-binding domain. In some embodiments the naturally occurring protein is a cytokine, e.g., a type I cytokine. In some embodiments of particular interest, the target protein is a four-helix bundle protein, e.g., a four-helix bundle cytokine. Exemplary four-helix bundle cytokines include, e.g., certain interferons (e.g., a type I interferon, e.g., IFN-α), interleukins (e.g., IL-2, IL-3, IL-4, IL-5, IL-6, IL-7, IL-12), and colony stimulating factors (e.g., G-CSF, GM-CSF, M-CSF). The IFN can be, e.g., interferon alpha 2a or interferon alpha 2b. See, e.g., Mott H R and Campbell I D. *"Four-helix bundle growth factors and their receptors: protein protein interactions."* Curr Opin Struct Biol. 1995 February; 5(1):114-21; Chaiken I M, Williams W V. *"Identifying structure function relationships in four-helix bundle cytokines: towards de novo mimetics design."* Trends Biotechnol. 1996 October; 14(10):369-75; Klaus W, et al., *"The three-dimensional high resolution structure of human interferon alpha-2a determined by heteronuclear NMR spectroscopy in solution"*. J Mol Biol., 274(4):661-75, 1997, for further discussion of certain of these cytokines.

In some embodiments, the cytokine has a similar structure to one or more of the afore-mentioned cytokines. For example, the cytokine can be an IL-6 class cytokine such as leukemia inhibitory factor (LIF) or oncostatin M. In some embodiments, the cytokine is one that in nature binds to a receptor that comprises a GP 130 signal transducing subunit. Other four-helix bundle proteins of interest include growth hormone (GH), prolactin (PRL), and placental lactogen. In some embodiments, the target protein is an erythropoiesis stimulating agent, e.g., erythropoietin (EPO), which is also a four-helix bundle cytokine. In some embodiments, an erythropoiesis stimulating agent is an EPO variant, e.g., darbepoetin alfa, also termed novel erythropoiesis stimulating protein (NESP), which is engineered to contain five N-linked carbohydrate chains (two more than recombinant HuEPO). In some embodiments, the protein comprises five helices. For example, the protein can be an interferon beta, e.g., interferon beta-1a or interferon beta-1b, which (as will be appreciated) is often classified as a four-helix bundle cytokine. In some embodiments, a target protein is IL-9, IL-10, IL-11, IL-13, or IL-15. See, e.g., Hunter, C A, Nature Reviews Immunology 5, 521-531, 2005, for discussion of certain cytokines. See also Paul, W E (ed.), Fundamental Immunology, Lippincott Williams & Wilkins; 6th ed., 2008. Any protein described in the references cited herein, all of which are incorporated herein by reference, can be used as a target protein.

In some embodiments, a target protein is a protein that is approved by the US Food & Drug Administration (or an equivalent regulatory authority such as the European Medicines Evaluation Agency) for use in treating a disease or disorder in humans. Such proteins may or may not be one for which a PEGylated version has been tested in clinical trials and/or has been approved for marketing.

In some embodiments, a target protein is a neurotrophic factor, i.e., a factor that promotes survival, development and/or function of neural lineage cells (which term as used herein includes neural progenitor cells, neurons, and glial cells, e.g., astrocytes, oligodendrocytes, microglia). For example, in some embodiments, the target protein is a factor that promotes neurite outgrowth. In some embodiments, the protein is ciliary neurotrophic factor (CNTF; a four-helix bundle protein) or an analog thereof such as Axokine, which is a modified version of human Ciliary neurotrophic factor with a 15 amino acid truncation of the C terminus and two amino acid substitutions, which is three to five times more potent than CNTF in in vitro and in vivo assays and has improved stability properties.

In some embodiments, the target protein is one that forms homodimers or heterodimers, (or homo- or heterooligomers comprising more than two subunits, such as tetramers). In certain embodiments the homodimer, heterodimer, or oligomer structure is such that a terminus of a first subunit is in close proximity to a terminus of a second subunit. For example, an N-terminus of a first subunit is in close proximity to a C-terminus of a second subunit. In certain embodiments the homodimer, heterodimer, or oligomer structure is such that a terminus of a first subunit and a terminus of a second subunit are not involved in interaction with a receptor, so that the termini can be joined via a non-genetically encoded peptide element without significantly affecting biological activity. In some embodiments, termini of two subunits of a homodimer, heterodimer, or oligomer are conjugated via click chemistry using a method described herein, thereby producing a dimer (or oligomer) in which at least two subunits are covalently joined. For example, the neurotrophins nerve growth factor (NGF); brain-derived neurotrophic factor (BDNF); neurotrophin 3 (NT3); and neurotrophin 4 (NT4) are dimeric molecules which share approximately 50% sequence identity and exist in dimeric forms. See, e.g., Robinson R C, et al., "*Structure of the brain-derived neurotrophic factor/neurotrophin 3 heterodimer.*", Biochemistry. 34(13):4139-46, 1995; Robinson R C, et al., "*The structures of the neurotrophin 4 homodimer and the brain-derived neurotrophic factor/neurotrophin 4 heterodimer reveal a common Trk-binding site.*" Protein Sci. 8(12):2589-97, 1999, and references therein. In some embodiments, the dimeric protein is a cytokine, e.g., an interleukin.

In some embodiments, the target protein is an enzyme, e.g., an enzyme that is important in metabolism or other physiological processes. As is known in the art, deficiencies of enzymes or other proteins can lead to a variety of disease. Such diseases include diseases associated with defects in carbohydrate metabolism, amino acid metabolism, organic acid metabolism, porphyrin metabolism, purine or pyrimidine metabolism, lysosomal storage disorders, blood clotting, etc. Examples include Fabry disease, Gaucher disease, Pompe disease, adenosine deaminase deficiency, asparaginase deficiency, porphyria, hemophilia, and hereditary angioedema. In some embodiments, a protein is a clotting or coagulation factor, (e.g., factor VII, VIIa, VIII or IX). In other embodiments a protein is an enzyme that plays a role in carbohydrate metabolism, amino acid metabolism, organic acid metabolism, porphyrin metabolism, purine or pyrimidine metabolism, and/or lysosomal storage, wherein exogenous administration of the enzyme at least in part alleviates the disease.

In some embodiments, a target protein comprises a receptor or receptor fragment (e.g., extracellular domain). In some embodiments the receptor is a TNFα receptor. In certain embodiments, the target protein comprises urate oxidase.

One of skill in the art will be aware of the sequences of proteins described herein. Without limitation, sequences of certain target protein are found in, e.g., U.S. Ser. Nos. 10/773,530; 11/531,531; U.S. Ser. Nos. 11/707,014; 11/429, 276; 11/365,008. In some embodiments, a target protein is listed in Table T. The invention encompasses application of the inventive methods to any of the proteins described herein and any proteins known to those of skill in the art. Naturally occurring sequences, e.g., genomic, mRNA, and polypeptide sequences, from a wide variety of species, including human, are known in the art and are available in publicly accessible databases such as those available at the National Center for Biotechnology Information (www.ncbi.nih.gov) or Universal Protein Resource (www.uniprot.org). Databases include, e.g., GenBank, RefSeq, Gene, UniProtKB/SwissProt, UniProtKB/Trembl, and the like. Sequences, e.g., nucleic acid (e.g., mRNA) and polypeptide sequences, in the NCBI Reference Sequence database may be used as reference sequences. It will be appreciated that multiple alleles of a gene may exist among individuals of the same species. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations often do not alter the encoded amino acid sequence, although DNA polymorphisms that lead to changes in the sequence of the encoded proteins can exist. Examples of polymorphic variants can be found in, e.g., the Single Nucleotide Polymorphism Database (db-SNP), available at the NCBI website at www.ncbi.nlm.nih gov/projects/SNP/. (Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (Md.): National Center for Biotechnology Information (US); 2002 (www.ncbi.nlm.nih.gov/bookshelf/br.fcgi?book=handbook&part=ch5). Multiple isoforms of certain proteins may exist, e.g., as a result of alternative RNA splicing or editing. In general, where aspects of this disclosure pertain to a gene or gene product, embodiments pertaining to allelic variants or isoforms are encompassed unless indicated otherwise. Certain embodiments may be directed to particular sequence(s), e.g., particular allele(s) or isoform(s). It will be understood that a polypeptide may be encoded by any of numerous different nucleic acid sequences due to the degeneracy of the genetic code. If a polypeptide is produced recombinantly, a nucleic acid sequence encoding the polypeptide may be selected or codon optimized for expression in a particular species, if desired. It should be understood that wherever reference is made herein to a protein or polypeptide, e.g., a naturally occurring protein or polypeptide, the invention provides embodiments in which a variant or fragment, e.g., a functional variant or fragment, may be used. (See discussion of variants and fragments above).

In some embodiments, the invention provides modified versions of any target protein, wherein the modified version comprises (i) one or more nucleophilic residues such as glycine at the N-terminus (e.g., between 1 and 10 residues) and, optionally, a cleavage recognition sequence, e.g., a protease cleavage recognition sequence that masks the nucleophilic residue(s); or (ii) a sortase recognition motif at or near the C-terminus. In some embodiments, the target protein comprises both (i) and (ii). Such modified proteins can be used in the methods of protein conjugation as described herein.

One of skill in the art will be aware that certain proteins, e.g., secreted eukaryotic (e.g., mammalian) proteins, often undergo intracellular processing (e.g., cleavage of a secretion signal prior to secretion and/or removal of other portion(s) that are not required for biological activity), to generate a mature form. Such mature, biologically active versions of target proteins are used in certain embodiments of the invention.

TABLE T

| selected target protein sequences | |
|---|---|
| Tissue plasminogen activator (1rtf) | Chain A:TTCCGLRQY (SEQ ID NO: 5)<br><br>Chain B:<br>IKGGLFADIASHPWQAAIFAKHHRRGGERFLCGGILISSCWILSAA<br>HCFQQQQQEEEEERRRRRFFFFFPPPPPPHHLTVILGRTYRVVPGE<br>EEQKFEVEKYIVHKEFDDDTYDNDIALLQLKSSSSSDDDDDSSSSS<br>SSSSSRRRRRCAQESSVVRTVCLPPADLQLPDWTECELSGYGKHE<br>ALSPFYSERLKEAHVRLYPSSRCTTTSSSQQQHLLNRTVTDNMLC<br>AGDTTTRRRSSSNNNLFIDACQGDSGGPLVCLNDGRMTLVGIISW<br>GLGCGGQQKDVPGVYTKVTNYLDWIRDNMRP(SEQ ID NO: 41) |
| Factor IX | Chain A:<br>VVGGEDAKPGQFPWQVVINGKVDAFCGGSIVNEKWIVTAAHCV<br>EETTGVKITVVAGEHNIEETEHTEQKRNVIRIIPHEINYNNNAAAA<br>AAINKYNHDIALLELDEPLVLNSYVTPICIADKEYTTTNNNIIIFLK<br>FGSGYVSGWGRVEHKGRSALVLQYLRVPLVDRATCLRSTKFTIY<br>NNMFCAGGFFHEGGGRRDSCQGDSGGPHVTEVEGTSFLTGIISW<br>GEECAAMMKGKYGIYTKVSRYVNWIKEKTKLT(SEQ ID NO: 6)<br><br>Chain B:<br>MTCNIKNGRCEQFCKNSADNKVVCSCTEGYRLAENQKSCEPAVP<br>FPCGRVSVSQTSK(SEQ ID NO: 7) |
| Glucocerebrosidase | EFARPCIPKSFGYSSVVCVCNATYCDSFDPPALGTFSRYESTRSGR<br>RMELSMGPIQANHTGTGLLLTLQPEQKFQKVKGFGGAMTDAAA<br>LNILALSPPAQNLLLKSYFSEEGIGYNIIRVPMASCDFSIRTYTYAD<br>TPDDFQLHNFSLPEEDTKLKIPLIHRALQLAQRPVSLLASPWTSPT<br>WLKTNGAVNGKGSLKGQPGDIYHQTWARYFVKFLDAYAEHKL<br>QFWAVTAENEPSAGLLSGYPFQCLGFTPEHQRDFIARDLGPTLAN<br>STHHNVRLLMLDDQRLLLPHWAKVVLTDPEAAKYVHGIAVHW<br>YLDFLAPAKATLGETHRLFPNTMLFASEACVGSKFWEQSVRLGS<br>WDRGMQYSIISIITNLLYHVVGWTDWNLALNPEGGPNWVRNEV<br>DSPIIVDITKDTFYKQPMFYHLGHESKFIPEGSQRVGLVASQKNDL<br>DAVALMHPDGSAVVVVLNRSSKDVPLTIKDPAVGFLETISPGYSI<br>HTYLWHRQ(SEQ ID NO: 8) |
| alpha galactosidase A | LDNGLARTPTMGWLHWERFMCNLDCQEEPDSCISEKLFMEMAE<br>LMVSEGWKDAGYEYLCIDDCWMAPQRDSEGRLQADPQRFPHGI<br>RQLANYVHSKGLKLGIYADVGNKTCAGFPGSFGYYDIDAQTFAD<br>WGVDLLKFDGCYCDSLENLADGYKHMSLALNRTGRSIVYSCEW<br>PLYMWPFQKPNYTEIRQYCNHWRNFADIDDSWKSIKSILDWTSF<br>NQERIVDVAGPGGWNDPDMLVIGNFGLSWNQQVTQMALWAIM<br>AAPLFMSNDLRHISPQAKALLQDKDVIAINQDPLGKQGYQLRQG<br>DNFEVWERPLSGLAWAVAMINRQEIGGPRSYTIAVASLGKGVAC<br>NPACFITQLLPVKRKLGFYEWTSRLRSHINPTGTVLLQLENTM<br>(SEQ ID NO: 9) |
| arylsulfatase-A (iduronidase, α-L-) | RPPNIVLIFADDLGYGDLGCYGHPSSTTPNLDQLAAGGLRFTDFY<br>VPVSLPSRAALLTGRLPVRMGMYPGVLVPSSRGGLPLEEVTVAE<br>VLAARGYLTGMAGKWHLGVGPEGAFLPPHQGFHRFLGIPYSHD<br>QGPCQNLTCFPPATPCDGGCDQGLVPIPLLANLSVEAQPPWLPGL<br>EARYMAFAHDLMADAQRQDRPFFLYYASHHTHYPQFSGQSFAE<br>RSGRGPFGDSLMELDAAVGTLMTAIGDLGLLEETLVIFTADNGPE<br>TMRMSRGGCSGLLRCGKGTTYEGGVREPALAFWPGHIAPGVTHE<br>LASSLDLLPTLAALAGAPLPNVTLDGFDLSPLLLGTGKSPRQSLFF<br>YPSYPDEVRGVFAVRTGKYKAHFFTQGSAHSDTTADPACHASSS<br>LTAHEPPLLYDLSKDPGENYNLLGATPEVLQALKQLQLLKAQLD<br>AAVTFGPSQVARGEDPALQICCHPGCTPRPACCHCP<br>(SEQ ID NO: 10) |

TABLE T-continued selected target protein sequences

| | |
|---|---|
| arylsulfatase B (N-acetylgalactos- amine-4- sulfatase) (1fsu) | SRPPHLVELLADDLGWNDVGFHGSRIRTPHLDALAAGGVLLDNY YTQPLTPSRSQLLTGRYQIRTGLQHQIIWPCQPSCVPLDEKLLPQL LKEAGYTTHMVGKWHLGMYRKECLPTRRGFDTYFGYLLGSEDY YSHERCTLIDALNVTRCALDFRDGEEVATGYKNMYSTNIFTKRAI ALITNHPPEKPLFLYLALQSVHEPLQVPEEYLKPYDFIQDKNRHH YAGMVSLMDEAVGNVTAALKSSGLWNNTVFIFSTDNGGQTLAG GNNWPLRGRKWSLWEGGVRGVGFVASPLLKQKGVKNRELIHIS DWLPTLVKLARGHTNGTKPLDGFDVWKTISEGSPSPRIELLHNID PNFVDSSPCSAFNTSVHAAIRHGNWKLLTGYPGCGYWFPPPSQY NVSEIPSSDPPTKTLWLFDIDRDPEERHDLSREYPHIVTKLLSRLQF YHKHSVPVYFPAQDPRCDPKATGVWGPWM (SEQ ID NO: 11) |
| beta-hexosaminidase A (2gjx) | LWPWPQNFQTSDQRYVLYPNNFQFQYDVSSAAQPGCSVLDEAF QRYRDLLFGTLEKNVLVVSVVTPGCNQLPTLESVENYTLTNDDQ CLLLSETVWGALRGLETFSQLVWKSAEGTFFINKTEIEDFPRFPHR GLLLDTSRHYLPLSSILDTLDVMAYNKLNVFHWHLVDDPSFPYES FTFPPELMRKGSYNPVTHIYTAQDVKEVIEYARLRGIRVLAEFDTP GHTLSWGPGIPGLLTPCYSGSEPSGTFGPVNPSLNNTYEFMSTFFL EVSSVFPDFYLHLGGDEVDFTCWKSNPEIQDFMRKKGFGEDFKQ LESFYIQTLLDIVSSYGKGYVVWQEVFDNKVKIQPDTIIQVWREDI PVNYMKELELVTKAGFRALLSAPWYLNRISYGPDWKDFYVVEPL AFEGTPEQKALVIGGEACMWGEYVDNTNLVPRLWPRAGAVAER LWSNKLTSDLTFAYERLSHFRCELLRRGVQAQPLNVGFCEQEFEQ (SEQ ID NO: 12) |
| Hexosaminidase A and B (2gjx) | Chain A:<br>LWPWPQNFQTSDQRYVLYPNNFQFQYDVSSAAQPGCSVLDEAF QRYRDLLFGTLEKNVLVVSVVTPGCNQLPTLESVENYTLTINDDQ CLLLSETVWGALRGLETFSQLVWKSAEGTFFINKTEIEDEPRFPHR GLLLDTSRHYLPLSSILDTLDVMAYNKLNVFHWHLVDDPSFPYES FTFPPELMRKGSYNPVTHIYTAQDVKEVIEYARLRGIRVLAEFDTP GHTLSWGPGIPGLLTPCYSGSEPSGTFGPVNPSLNNTYEFMSTFFL EVSSVFPDFYLHLGGDEVDFTCWKSNPEIQDFMRKKGFGEDFKQ LESFYIQTLLDIVSSYGKGYVVWQEVFDNKVKIQPDTIIQVWREDI PVNYMKELELVTKAGFRALLSAPWYLNRISYGPDWKDFYVVEPL AFEGTPEQKALVIGGEACMWGEYVDNTNLVPRLWPRAGAVAER LWSNKLTSDLTFAYERLSHFRCELLRRGVQAQPLNVGFCEQEFEQ (SEQ ID NO: 13)<br><br>Chain B:<br>PALWPLPLSVKMTPNLLHLAPENFYISHSPNSTAGPSCTLLEEAFR RYHGYIFGTQVQQLLVSITLQSECDAFPNISSDESYTLLVKEPVAV LKANRVWGALRGLETESQLVYQDSYGTFTINESTIIDSPRFSHRGI LIDTSRHYLPVKIILKTLIDAMAFNKENVLHWHIVDDQSFPYQSITF PELSNKGSYSLSHVYTPNDVRMVIEYARLRGIRVLPEFDTPGHTLS WGKGQKDLLTPCYSDSFGPINPTLINITTYSFLTTFEKEISEVEPDQFI HLGGDEVEFKCWESNPKIQDFMRQKGFGTDFKKLESFYIQKVLDI IATINKGSIVWQEVEDDKAKLAPGTIVEVWKDSAYPEELSRVTAS GFPVILSAPWYLDLISYGQDWRKYYKVEPLDEGGTQKQKQLFIG GEACLWGEYVDATNLTPRLWPRASAVGERLWSSKDVRDMDDA YDRLTRHRCRMVERGIAAQPLYAGYCN (SEQ ID NO: 14)<br><br>Chain C:<br>PALWPLPLSVKMTPNLLHLAPENFYISHSPNSTAGPSCTLLEEAFR RYHGYIFGTQVQQLLVSITLQSECDAFPNISSDESYTLLVKEPVAV LKANRVWGALRGLETESQLVYQDSYGTFTINESTIIDSPRFSHRGI LIDTSRHYLPVKIILKTLDAMAFNKFNVLHWHIVDDQSFPYQSITF PELSNKGSYSLSHVYTPNDVRMVIEYARLRGIRVLPEFDTPGHTLS WGKGQKDLLTPCYSLDSFGPINPTLNTTYSFLTTFFKEISEVFPDQ FIHLGGDEVEFKCWESNPKIQDFMRQKGEGTDFKKLESFYIQKVL DIIATINKGSIVWQEVEDDKAKLAPGTIVEVWKDSAYPEELSRVT ASGFPVILSAPWYLDLISYGQDWRKYYKVEPLDFGGTQKQKQLFI GGEACLWGEYVDATNLTPRLWPRASAVGERLWSSKDVRDMDD AYDRLTRHRCRMVERGIAAQPLYAGYCN (SEQ ID NO: 15)<br><br>Chain D:<br>LWPWPQNFQTSDQRYVLYPNNFQFQYDVSSAAQPGCSVLDEAF QRYRDLLFGTLEKNVLVVSVVTPGCNQLPTLESVENYTLTINDDQ CLLLSETVWGALRGLETESQLVWKSAEGTFF1NKTEIEDEPRFPHR GLLLDTSRHYLPLSSILDTLDVMAYNKLNVFHWHLVDDPSFPYES FTFPPELMRKGSYNPVTHIYTAQDVKEVIEYARLRGIRVLAEFDTP GHTLSWGPGIPGLLTPCYSGSEPSGTFGPVNPSLNNTYEFMSTFFL EVSSVFPDFYLHLGGDEVDFTCWKSNPEIQDFMRKKGFGEDFKQ LESFYIQTLLDIVSSYGKGYVVWQEVFDNKVKIQPDTIIQVWREDI PVNYMKELELVTKAGFRALLSAPWYLNRISYGPDWKDFYVVEPL AFEGTPEQKALVIGGEACMWGEYVDNTNLVPRLWPRAGAVAER LWSNKLTSDLTFAYERLSHFRCELLRRGVQAQPLNVGFCEQEFEQ (SEQ ID NO: 16) |

TABLE T-continued selected target protein sequences

| | |
|---|---|
| phenylalanine hydroxylase (PAH)(1j8u) | VPWFPRTIQELDRFANQILSYGAELDADHPGFKDPVYRARRKQFA DIAYNYRHGQPIPRVEYMEEEKKTWGTVFKTLKSLYKTHACYEY NHIFPLLEKYCGFHEDNIPQLEDVSQFLQTCTGFRLRPVAGLLSSR DFLGGLAFRVFFICTQYIRHGSKPMYTPEPDICHELLGHVPLFSDRS FAQFSQEIGLASLGAPDEYIEKLATIYWFTVEFGLCKQGDSIKAYG AGLLSSFGELQYCLSEKPKLLPLELEKTAIQNYTVTEFQPLYYVAE SFNDAKEKVRNFAATIPRPFSVRYDPYTQRIEVL (SEQ ID NO: 17) |
| Cathepsin A | APDQDEIQRLPGLAKQPSFRQYSGYLKSSGSKHLHYWFVESQKD PENSPVVLWLNGGPGCSSLDGLLTEHGPFLVQPDGVTLEYNPYS WNLIANVLYLESPAGVGFSYSDDKFYATNDTEVAQSNFEALQDF FRLFPEYKNNKLFLTGESYAGIYIPTLAVLVMQDPSMNLQGLAVG NGLSSYEQNDNSLVYFAYYHGLLGNRLWSSLQTHCCSQNKCNF YDNKDLECVTNLQEVARIVGNSGLNIYNLYAPCAGGVPSHFRYE KDTVVVQDLGNIFTRLPLKRMWHQALLRSGDKVRMDPPCTNTT AASTYLNNPYVRKALNIPEQLPQWDMCNFLVNLQYRRLYRSMN SQYLKLLSSQKYQILLYNGDVDMACNFMGDEWFVDSLNQKMEV QRRPWLVKYGDSGEQIAGFVKEFSHIAFLTIKGAGHMVPTDKPLA AFTMFSRFLNKQPY (SEQ ID NO: 18) |
| G-CSF | LPQSFLLKCLEQVRKIQGDGAALQEKLCATYKLCHPEELVLLGHS LGIPWAPLLAGCLSQLHSGLFLYQGLLQALEGISPELGPTLDTLQL DVADFATTIWQQMEELGMMPAFASAFQRRAGGVLVASHLQSFL EVSYRVLRHLA (SEQ ID NO: 19) |
| GM-CSF | EHVNAIQEARRLLNLSRDTAAEMNETVEVISEMFDLQEPTCLQTR LELYKQGLRGSLTKLKGPLTMMASHYKQHCPPTPETSCATQIITF ESFKENLKDFLLVIP (SEQ ID NO: 20) |
| Interferon alfa-2 | CDLPQTHSLGSRRTLMLLAQMRKISLFSCLKDRHDFGFPQEEFGN QFQKAETIPVLHEMIQQIFNLFSTKDSSAAWDETLLDKFYTELYQ QLNDLEACVIQGVGVTETPLMKEDSILAVRKYFQRITLYLKEKKY SPCAWEVVRAEIMRSFSLSTNLQESLRSKE (SEQ ID NO: 21) |
| Interferon beta-1 | MSYNLLGFLQRSSNFQCQKLLWQLNGRLEYCLKDRMNFDIPEEI KQLQQFQKEDAALTIYEMLQNIFAIFRQDSSSTGWNETIVENLLA NVYHQINHLKTVLEEKLEKEDFTRGKLMSSLHLKRYYGRILHYL KAKEYSHCAWTIVRVEILRNFYFINRLTGYLRN (SEQ ID NO: 22) |
| Interferon gamma-1b | MQDPYVKEAENLKKYFNAGHSDVADNGTLFLGILKNWKEESDR KIMQSQIVSFYFKLFKNFKDDQSIQKSVETIKEDMNVKFFNSNKK KRDDFEKLTNYSVTDLNVQRKAIDELIQVMAELGANVSGEFVKE AENLKKYFNDNGTLFLGILKNWKEESDRKIMQSQIVSFYFKLFKN FKDDQSIQKSVETIKEDMNVKFFNSNKKKRDDFEKLTNYSVTDL NVQRKAIHELIQVMAELSPAA (SEQ ID NO: 23) |
| IL-2 (1M47) | STKKTQLQLEHLLLDLQMILNGINNYKNPKLTRMLTFKFYMPKK ATELKHLQCLEEELKPLEEVLNLAQNFHLRPRDLISNINIVLELK GFMCEYADETATIVEFLNRWITFCQSIISTLT (SEQ ID NO: 24) |
| IL-1 (2nvh) | APVRSLNCTLRDSQQKSLVMSGPYELKALHLQGQDMEQQVVFS MSFVQGEESNDKIPVALGLKEKNLYLSCVLKDDKPTLQLESVDP KNYPKKKMEKRFVFNKIEINNKLEFESAQFPNWYISTSQAENMPV FLGGTKGGQDITDFTMQFVS (SEQ ID NO: 25) |
| TNF-alpha (4tsv) | DKPVAHVVANPQAEGQLQWSNRRANALLANGVELRDNQLVVPI EGLFLIYSQVLFKGQGCPSTHVLLTHTISRIAVSYQTKVNLLSAIKS PCQRETPEGAEAKPWYEPIYLGGVFQLEKGDRLSAEINRPDYLDF AESGQVYFGIIAL (SEQ ID NO: 26) |
| TNF-beta (lymphotoxin) (1tnr) | KPAAHLIGDPSKQNSLLWRANTDRAFLQDGFSLSNNSLLVPTSGI YFVYSQVVFSGKAYSPKATSSPLYLAHEVQLFSSQYPFHVPLLSS QKMVYPGLQEPWLHSMYHGAAFQLTQGDQLSTHTDGIPHLVLSP STVFFGAFAL (SEQ ID NO: 27) |
| Erythropoietin | APPRLICDSRVLERYLLEAKEAEKITTGCAEHCSLNEKITVPDTKV NFYAWKRMEVGQQAVEVWQGLALLSEAVLRGQALLVKSSQPW EPLQLHVDKAVSGLRSLTTLLRALGAQKEAISNSDAASAAPLRTI TADTFRKLFRVYSNFLRGKLKLYTGEACRTGDR (SEQ ID NO: 28) |
| Insulin | Chain A: GIVEQCCTSICSLYQLENYCN (SEQ ID NO: 29)<br><br>Chain B: FVNQHLCGSHLVEALYLVCGERGFFYTPK (SEQ ID NO: 30) |

TABLE T-continued selected target protein sequences

| | |
|---|---|
| Growth hormone (GH) (Somatotropin) (1huw) | FPTIPLSRLADNAWLRADRLNQLAFDTYQEFEEAYIPKEQIHSFW WNPQTSLCPSESIPTPSNKEETQQKSNLELLRISLLLIQSWLEPVQ FLRSVFANSLVYGASDSNVYDLLKDLEEGIQTLMGRLEALLKNYG LLYCFNKDMSKVSTYLRTVQCRSVEGSCGF (SEQ ID NO: 31) |
| Follicle-stimulating hormone (FSH) | CHHRICHCSNRVELCQESKVTEIPSDLPRNAIELREYLTKLRVIQK GAFSGEGDLEKIEISQNDVLEVIEADVFSNLPKLHEIRIEKANNLLY INPEAFQNLPNLQYLLISNTGIKHLPDVHKIHSLQKVLLDIQDNINI HTIERN SPVGLSFESVILWLNKNGIQEIHNCAFNGTQLDELNLSDN NNLEELPNDVFHGASGPVILDISRTRIHSLPSYGLENLKKLRARST YNLKKLPTLE (SEQ ID NO: 32) |
| Leptin (1ax8) | IQKVQDDTKTLIKTIVTRINDILDFIPGLHPILTLSKMDQTLAVYQQ ILTSMPSRNVIQISNDLENLRDLLHVLAFSKSCHLPEASGLETLDSL GGVLEASGYSTEVVALSRLQGSLQDMLWQLDLSPGC (SEQ ID NO: 33) |
| Insulin-like growth factor (or somatomedin) (1wqj) | PETLCGAELVDALQFVCGDRGFYFNKPTGYGSSSRRAPQTGIVDE CCFRSCDLRRLEMYCAP (SEQ ID NO: 34) |
| Adiponectin (1c28) | Chain A:<br>MYRSAFSVGLETRVTVPNVPIRETKIFYNQQNHYDGSTGKEYCNI PGLYYFSYHITVYMKDVKVSLEKKDKAVLFTYDQYQENVDQAS GSVLLHLEVGDQVWLQVYYADNVNDSTFTGFLLYHDT (SEQ ID NO: 35)<br><br>Chain B:<br>MYRSAFSVGLPNVPIRFTKIFYNQQNHYDGSTGKFYCNIPGLYYF SYHITVYMKDVKVSLFKKDKVLFTYDQYQEKVDQASGSVLLHL EVGDQVWLQVYDSTFTGFLLYHD (SEQ ID NO: 36)<br><br>Chain C:<br>MYRSAFSVGLETRVTVPIRFTKIFYNQQNHYDGSTGKFYCNIPGL YYFSYHITVDVKVSLEKKDKAVLFTQASGSVLLHLEVGDQVWLQ NDSTFTGFLLYHD (SEQ ID NO: 37) |
| Factor VIII (aka anti-hemophilic factor) (2r7e) | Chain A:<br>ATRRYYLGAVELSWDYMQSDLGELPVDAREPPRVPKSFPENTSV VYKKTLFVEFTDHLFNIAKPRPPWMGLLGPTIQAEVYDTVVITLK NMASHPVSLHAVGVSYWKASEGAEYDDQTSQREKEDDKVFPGG SHTYVWQVLKENGPMASDPLCLTYSYLSHVDLVKDLNSGLIGAL LVCREGSLAKEKTQTLHKFILLFAVFDEGKSWHSETKNAASARA WPKMHTVNGYVNRSLPGLIGCHRKSVYWHVIGMGTTPEVHSIFL EGHTFLVRNHRQASLEISPITFLTAQTLLMDLGQFLLFCHISSHQH DGMEAYVKVDSCPEEPQFDDDNSPSFIQIRSVAKKHPKTWVHYIA AEEEDWDYAPLVLAPDDRSYKSQYLNNGPQRIGRKYKKVRFMA YTDETFKTREAIQHESGILGPLLYGEVGDTLLIIFKNQASRPYNIYP HGITDVRPLYSRRLPKGVKHLKDFPILPGEIFKYKWTVTVEDGPT KSDPRCLTRYYSSFVNMERDLASGLIGPLLICYKESVDQRGNQIM SDKRNVILFSVEDENRSWYLTENIQRFLPNPAGVQLEDPEFQASNI MHSINGYVFDSLQLSVCLHEVAYWYILSIGAQTDFLSVFFSGYTF KHKMVYEDTLTLFPPFSGETVFMSMENPGLWILGCHNSDFRNRGM TALLKVSSCDKNTGDYYEDSYED (SEQ ID NO: 38)<br><br>Chain B:<br>RSFQKKTRHYFIAAVERLWDYGMSSSPHVLRNRAQSGSVPQFKK VVEQEFTDGSFTQPLYRGELNEHLGLLGPYIRAEVEDNIMVTERN QASRPYSFYSSLISYEEDQRQGAEPRKNFVKPNETKTYFWKVQH HMAPTKDEFDCKAWAYSSDVDLEKDVHSGLIGPLLVCHTNTLNP AHGRQVTVQEFALEFTIFDETKSWYFTENMERNCRAPCNIQMED PTFKENYRFHAINGYIMDTLPGLVMAQDQRIRWYLLSMGSNENI HSIHFSGHVETVRKKEEYKMALYNLYPGVFETVEMLPSKAGIWR VECLIGEHLHAGMSTLFLVYSNKCQTPLGMASGHIRDFQITASGQ YGQWAPKLARLHYSGSINAWSTKEPFSWIKVDLLAPMIIHGIKTQ GARQKFSSLYISQFIIMYSLDGKKWQTYRGNSTGTLMVFFGNVDS SGIKHNIFNPPIIARYIRLHPTHYSIRSTLRMELMGCDLNSCSMPLG MESKAISDAQITASSYFTNMFATWSPSKARLHLQGRSNAWRPQV NNPKEWLQVDFQKTMKVTGVTTQGVKSLLTSMYVKEFLISSSQD GHQWTLFFQNGKVKVFQGNQDSFTPVVNSLDPPLLTRYLRIHPQS WVHQIALRMEVLGCEAQDLY (SEQ ID NO: 39) |
| Human serum albumin (1ao6) | Chain A:<br>SEVAHRFKDLGEENFKALVLIAFAQYLQQCPFEDHVKLVNEVTEF AKTCVADESAENCDKSLHTLFGDKLCTVATLRETYGEMADCCA KQEPERNECFLQHKDDNPNLPRLVRPEVDVMCTAFHDNEETFLK |

TABLE T-continued selected target protein sequences

```
                    KYLYEIARRHPYFYAPELLFFAKRYKAAFTECCQAADKAACLLP
                    KLDELRDEGKASSAKQRLKCASLQKFGERAFKAWAVARLSQRFP
                    KAEFAEVSKLVTDLTKVHTECCHGDLLECADDRADLAKYICENQ
                    DSISSKLKECCEKPLLEKSHCIAEVENDEMPADLPSLAADFVESKD
                    VCKNYAEAKDVFLGMFLYEYARRHPDYSVVLLLRLAKTYETTLE
                    KCCAAADPHECYAKVFDEFKPLVEEPQNLIKQNCELFEQLGEYKF
                    QNALLVRYTKKVPQVSTPTLVEVSRNLGKVGSKCCKHPEAKRMP
                    CAEDYLSVVLNQLCVLHEKTPVSDRVTKCCTESLVNRRPCFSALE
                    VDETYVPKEFNAETFTFHADICTLSEKERQIKKQTALVELVKHKP
                    KATKEQLKAVMDDFAAFVEKCCKADDKETCFAEEGKKLVAASQ
                    AA (SEQ ID NO: 40)

Chain B:
                    SEVAHRFKDLGEENFKALVLIAFAQYLQQCPFEDHVKLVNEVTEF
                    AKTCVADESAENCDKSLHTLFGDKLCTVATLRETYGEMADCCA
                    KQEPERNECFLQHKDDNPNLPRLVRPEVDVMCTAFHDNEETFLK
                    KYLYEIARRHPYFYAPELLFFAKRYKAAFTECCQAADKAACLLP
                    KLDELRDEGKASSAKQRLKCASLQKFGERAFKAWAVARLSQRFP
                    KAEFAEVSKLVTDLTKVHTECCHGDLLECADDRADLAKYICENQ
                    DSISSKLKECCEKPLLEKSHCIAEVENDEMPADLPSLAADFVESKD
                    VCKNYAEAKDVFLGMFLYEYARRHPDYSVVLLLRLAKTYETTLE
                    KCCAAADPHECYAKVFDEFKPLVEEPQNLIKQNCELFEQLGEYKF
                    QNALLVRYTKKVPQVSTPTLVEVSRNLGKVGSKCCKHPEAKRMP
                    CAEDYLSVVLNQLCVLHEKTPVSDRVTKCCTESLVNRRPCFSALE
                    VDETYVPKEFNAETFTFHADICTLSEKERQIKKQTALVELVKHKP
                    KATKEQLKAVMDDFAAFVEKCCKADDKETCFAEEGKKLVAASQ
                    AA (SEQ ID NO: 42)

Hemoglobin (1bz0)   Chain A:
                    VLSPADKTNVKAAWGKVGAHAGEYGAEALERMFLSFPTTKTYF
                    PHFDLSHGSAQVKGHGKKVADALTNAVAHVDDMPNALSALSDL
                    HAHKLRVDPVNFKLLSHCLLVTLAAHLPAEFTPAVHASLDKFLA
                    SVSTVLTSKYR (SEQ ID NO: 43)

Chain B:
                    VHLTPEEKSAVTALWGKVNVDEVGGEALGRLLVVYPWTQRFFE
                    SFGDLSTPDAVMGNPKVKAHGKKVLGAFSDGLAHLDNLKGTFA
                    TLSELHCDKLHVDPENFRLLGNVLVCVLAHHFGKEFTPPVQAAY
                    QKVVAGVANALAHKYH (SEQ ID NO: 44)
```

It will be appreciated that considerable structure/function information is available regarding many of the afore-mentioned proteins, as well as sequences from different mammalian species, that can be used to design variants of the naturally occurring sequence that retain significant biological activity (e.g., at least 25%, 75%, 90% or more of the activity of the naturally occurring protein). For example, crystal structures or NMR structures of a number of proteins, in some instances in a complex with the corresponding receptor, are available. In addition, it will be understood that, if the naturally occurring N- and C-termini are not located in close proximity to each other in the native structure, a naturally occurring sequence can be extended at the N- and/or C-termini, e.g., with a flexible peptide spacer so that the termini can come into close proximity.

In various embodiments, an antibody binds to an antigen of interest. An antigen of interest may be or may comprise, for example, a polypeptide, a polysaccharide, a carbohydrate, a lipid, a nucleic acid, or combination thereof. An antigen may be naturally occurring or synthetic in various embodiments. In some embodiments, an antigen is naturally produced by and/or comprises a polypeptide or peptide that is genetically encoded by a pathogen, an infected cell, or a neoplastic cell (e.g., a cancer cell). In some embodiments, an antigen is an autoantigen ("self antigen"), or an agent that has the capacity to initiate or enhance an autoimmune response. In some embodiments, an antigen is produced or genetically encoded by a virus, bacteria, fungus, or parasite which, in some embodiments, is a pathogenic agent. In some embodiments, an agent (e.g., virus, bacterium, fungus, parasite) infects and, in some embodiments, causes disease in, at least one mammalian or avian species, e.g., human, non-human primate, bovine, ovine, equine, caprine, and/or porcine species. In some embodiments, a pathogen is intracellular during at least part of its life cycle. In some embodiments, a pathogen is extracellular. It will be appreciated that an antigen that originates from a particular source may, in various embodiments, be isolated from such source, or produced using any appropriate means (e.g., recombinantly, synthetically, etc.), e.g., for purposes of using the antigen, e.g., to identify, generate, test, or use an antibody thereto). An antigen may be modified, e.g., by conjugation to another molecule or entity (e.g., an adjuvant), chemical or physical denaturation, etc. In some embodiments, an antigen is an envelope protein, capsid protein, secreted protein, structural protein, cell wall protein or polysaccharide, capsule protein or polysaccharide, or enzyme. In some embodiments an antigen is a toxin, e.g., a bacterial toxin.

Exemplary viruses include, e.g., Retroviridae (e.g., lentiviruses such as human immunodeficiency viruses, such as HIV-I); Caliciviridae (e.g. strains that cause gastroenteritis); Togaviridae (e.g. equine encephalitis viruses, rubella viruses); Flaviridae (e.g. dengue viruses, encephalitis viruses, yellow fever viruses, hepatitis C virus); Coronaviridae (e.g. coronaviruses); Rhabdoviridae (e.g. vesicular stomatitis viruses, rabies viruses); Filoviridae (e.g. Ebola viruses); Paramyxoviridae (e.g. parainfluenza viruses, mumps virus, measles virus, respiratory syncytial virus); Orthomyxoviridae (e.g. influenza viruses); Bunyaviridae (e.g. Hantaan viruses, bunga viruses, phleboviruses and Nairo viruses); Arenaviridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae; Herpesviridae (herpes simplex virus (HSV) 1 and 2, varicella zoster virus, cytomegalovirus (CMV), EBV, KSV); Poxviridae (variola viruses, vaccinia viruses, pox viruses); and Picornaviridae (e.g. polio viruses, hepatitis A virus; enteroviruses, human coxsackie viruses, rhinoviruses, echoviruses).

Exemplary bacteria include, e.g., *Helicobacter pylori, Borellia burgdorferi, Legionella pneumophilia, Mycobacteria* (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae, Campylobacter* sp., *Enterococcus* sp., *Chlamydia* sp., *Haemophilus influenzae, Bacillus anthracia, Corynebacterium diphtheriae, Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira, Actinomyces israelii* and *Francisella tularensis*.

Exemplary fungi include, e.g., *Aspergillus*, such as *Aspergillus flavus, Aspergillus fumigatus, Aspergillus niger, Blastomyces*, such as *Blastomyces dermatitidis, Candida*, such as *Candida albicans, Candida glabrata, Candida guilliermondii, Candida krusei, Candida parapsilosis, Candida tropicalis, Coccidioides*, such as *Coccidioides immitis, Cryptococcus*, such as *Cryptococcus neoformans, Epidermophyton, Fusarium, Histoplasma*, such as *Histoplasma capsulatum, Malassezia*, such as *Malassezia furfur, Microsporum, Mucor, Paracoccidioides*, such as *Paracoccidioides brasiliensis, Penicillium*, such as *Penicillium marneffei, Pichia*, such as *Pichia anomala, Pichia guilliermondii, Pneumocystis*, such as *Pneumocystis carinii, Pseudallescheria*, such as *Pseudallescheria boydii, Rhizopus*, such as *Rhizopus oryzae, Rhodotorula*, such as *Rhodotorula rubra, Scedosporium*, such as *Scedosporium apiospermum, Schizophyllum*, such as *Schizophyllum commune, Sporothrix*, such as *Sporothrix schenckii, Trichophyton*, such as *Trichophyton mentagrophytes, Trichophyton rubrum, Trichophyton verrucosum, Trichophyton violaceutn, Trichosporon*, such as *Trichosporon asahii, Trichosporon cutaneum, Trichosporon inkin*, and *Trichosporon mucoides*.

Exemplary parasites include, e.g., parasites of the genus *Plasmodium* (e.g. *Plasmodium falciparum, P. vivax, P. ovale* and *P. malariae*), *Trypanosoma, Toxoplasma* (e.g., *Toxoplasma gondii*), *Leishmania* (e.g., *Leishmania major*), *Schistosoma*, or *Cryptosporidium*. In some embodiments the parasite is a protozoan. In some embodiments the parasite belongs to the phylum Apicomplexa. In some embodiments the parasite resides extracellularly during at least part of its life cycle. Examples include nematodes, trematodes (flukes), and cestodes. In some embodiments antigens from *Ascaris* or *Trichuris* are contemplated. In various embodiments, the antigen can orignate from any component of the parasite. In various embodiments the antigen can be derived from parasites at any stage of their life cycle of the parasite, e.g., any stage that occurs within an infected organism such as a mammalian or avian organism. In some embodiments the antigen is derived from eggs of the parasite or substances secreted by the parasite.

In some embodiments, an antigen is a tumor antigen (TA). In general, a tumor antigen can be any antigenic substance produced by tumor cells (e.g., tumorigenic cells or in some embodiments tumor stromal cells, e.g., tumor-associated cells such as cancer-associated fibroblasts). In many embodiments, a tumor antigen is a molecule (or portion thereof) that is differentially expressed by tumor cells as compared with non-tumor cells. Tumor antigens may include, e.g., proteins that are normally produced in very small quantities and are expressed in larger quantities by tumor cells, proteins that are normally produced only in certain stages of development, proteins whose structure (e.g., sequence or post-translational modification(s)) is modified due to mutation in tumor cells, or normal proteins that are (under normal conditions) sequestered from the immune system. Tumor antigens may be useful in, e.g., identifying or detecting tumor cells (e.g., for purposes of diagnosis and/or for purposes of monitoring subjects who have received treatment for a tumor, e.g., to test for recurrence) and/or for purposes of targeting various agents (e.g., therapeutic agents) to tumor cells. For example, in some embodiments, a chimeric antibody is provided, comprising an antibody of antibody fragment that binds a tumor antigen, and conjugated via click chemistry to a therapeutic agent, for example, a cytotoxic agent. In some embodiments, a TA is an expression product of a mutated gene, e.g., an oncogene or mutated tumor suppressor gene, an overexpressed or aberrantly expressed cellular protein, an antigen encoded by an oncogenic virus (e.g., HBV; HCV; herpesvirus family members such as EBV, KSV; papilloma virus, etc.), or an oncofetal antigen. Oncofetal antigens are normally produced in the early stages of embryonic development and largely or completely disappear by the time the immune system is fully developed. Examples are alphafetoprotein (AFP, found, e.g., in germ cell tumors and hepatocellular carcinoma) and carcinoembryonic antigen (CEA, found, e.g., in bowel cancers and occasionally lung or breast cancer). Tyrosinase is an example of a protein normally produced in very low quantities but whose production is greatly increased in certain tumor cells (e.g., melanoma cells). Other exemplary TAs include, e.g., CA-125 (found, e.g., in ovarian cancer); MUC-1 (found, e.g., in breast cancer); epithelial tumor antigen (found, e.g., in breast cancer); melanoma-associated antigen (MAGE; found, e.g., in malignant melanoma); prostatic acid phosphatase (PAP, found in prostate cancer). In some embodiments, a TA is at least in part exposed at the cell surface of tumor cells. In some embodiments, a tumor antigen comprises an abnormally modified polypeptide or lipid, e.g., an aberrantly modified cell surface glycolipid or glycoprotein. It will be appreciated that a TA may be expressed by a subset of tumors of a particular type and/or by a subset of cells in a tumor.

Exemplary therapeutic antibodies that are useful in the production of chimeric antibodies or proteins according to methods provided herein include, but are not limited to, the following antibodies (target of the antibody is listed in parentheses together with exemplary non-limiting therapeutic indications):

Abciximab (glycoprotein IIb/IIIa; cardiovascular disease), Adalimumab (TNF-α, various auto-immune disorders, e.g., rheumatoid arthritis), Alemtuzumab (CD52; chronic lymphocytic leukemia), Basiliximab (IL-2Rα receptor (CD25); transplant rejection), Bevacizumab (vascular endothelial growth factor A; various cancers, e.g., colorectal cancer, non-small cell lung cancer, glioblastoma, kidney cancer; wet age-related macular degeneration), Catumaxomab, Cetuximab (EGF receptor, various cancers, e.g., colorectal cancer, head and neck cancer), Certolizumab (e.g., Certolizumab pegol) (TNF alpha; Crohn's disease, rheumatoid arthritis), Daclizumab (IL-2Rα receptor (CD25); transplant rejection), Eculizumab (complement protein C5; paroxysmal nocturnal hemoglobinuria), Efalizumab (CD11a; psoriasis), Gemtuzumab (CD33; acute myelogenous leukemia (e.g., with calicheamicin)), Ibritumomab tiuxetan (CD20; Non-Hodgkin lymphoma (e.g., with yttrium-90 or indium-111)), Infliximab (TNF alpha; various autoimmune disorders, e.g., rheumatoid arthritis) Muromonab-CD3 (T Cell CD3 receptor; transplant rejection), Natalizumab (alpha-4 (α4) integrin; multiple sclerosis, Crohn's disease), Omalizumab (IgE; allergy-related asthma), Palivizumab (epitope of RSV F protein; Respiratory Syncytial Virus infection), Panitumumab (EGF receptor; cancer, e.g., colorectal cancer), Ranibizumab (vascular endothelial growth factor A; wet age-related macular degeneration) Rituximab (CD20; Non-Hodgkin lymphoma), Tositumomab (CD20; Non-Hodgkin lymphoma), Trastuzumab (ErbB2; breast cancer), and any antigen-binding fragment thereof.

In some embodiments, a therapeutic monoclonal antibody and a second agent useful for treating the same disease are conjugated using an inventive approach described herein. In some embodiments, the second agent comprises a polypeptide, peptide, small molecule, or second antibody.

In some embodiments, a monoclonal antibody and a cytokine, e.g., an interferon, e.g., interferon alpha, are conjugated using an inventive approach described herein. Optionally, the monoclonal antibody and cytokine are both useful for treating the same disease.

In some embodiments, an inventive approach described herein is used to conjugate two (or more) subunits (e.g., separate polypeptide chains) of a multi-subunit protein. In some embodiments, a multi-subunit protein is a receptor (e.g., a cell surface receptor). In some embodiments, a multi-subunit protein is an enzyme. In some embodiments, a multi-subunit protein is a cytokine. In some embodiments, a multi-subunit protein is a channel or transporter. In some embodiments, such linkage facilitates proper folding of the multi-subunit protein (e.g., accelerates folding or increases proportion of correctly folded functional proteins).

In some embodiments, a target protein or a polypeptide comprises a protein transduction domain. For example, an inventive approach may be used to link a protein transduction domain to a polypeptide of interest.

In some embodiments, an inventive approach described herein is used to produce a vaccine, e.g., a monovalent or polyvalent vaccine. For example, two or more antigens (e.g., of one or more pathogenic agents such as those mentioned above or tumor antigen) may be joined using an inventive approach. In some embodiments, the resulting agent may be administered to a subject, e.g., in an appropriate composition, optionally comprising suitable carrier(s) or excipient(s). In some embodiments, the resulting agent is used ex vivo, e.g., stimulate or be taken up by immune system cells, e.g., T cells, antigen-presenting cells (e.g., dendritic cells), which may have been previously obtained from a donor. In some embodiments, a donor is a subject to whom the cells are subsequently to be administered. In some embodiments, a vaccine is of use to immunize a mammalian or avian subject against a pathogen or tumor, e.g., to induce or augment an immune response directed to the pathogen (or cells infected by the pathogen) or tumor.

In some embodiments, an antigen and a cytokine are conjugated using the inventive approach described herein, wherein the cytokine optionally modulates, e.g., stimulates, proliferation, differentiation, and/or at least one activity of immune system cells, e.g., T cells (e.g., T cells belonging to a subset such as cytotoxic, helper, regulatory, or natural killer cells), B cells, macrophages, etc.

It will be understood that in some aspects, the invention encompasses agents produced according to methods described herein, and compositions comprising such agents. It will be understood that, in some aspects, the invention encompasses methods of using such agents, e.g., for one or more purposes described herein, or other purposes.

Sortase-facilitated Modification of VHH Domains, and Aspects Relating Thereto

In some aspects, the invention relates to VHH domains, methods of obtaining VHH domains, and/or the use of sortase in connection with VHH domains. In some aspects, methods of obtaining a VHH domain are provided, wherein the VHH domain binds to a target entity of interest. In some aspects, methods of obtaining a polypeptide comprising a VHH domain are provided, wherein the VHH domain binds to a target entity. In some aspects, methods of obtaining a polypeptide comprising a VHH domain are provided, wherein the polypeptide binds to the target entity via the VHH domain. In some aspects methods comprising determining the identity of a target antigen to which a VHH domain binds are provided. In some aspects certain of the methods comprise producing a polypeptide comprising the VHH domain and a TRS. In some embodiments certain of the methods comprise modifying a polypeptide comprising a VHH domain and a TRS using sortase. In some embodiments, sortase-modified polypeptides comprising a VHH domain are provided. In some embodiments methods of making or using sortase-modified polypeptides comprising a VHH domain are provided. The terms "VHH" and "VHH domain" are interchangeably herein. Where the term VHH is used herein, the disclosure provides certain embodiments pertaining to an antigen-binding fragment of the VHH. In some embodiments an antigen-binding fragment of a VHH comprises at least 1, 2, or all 3 CDRs of a VHH domain that binds to a target entity. In some aspects, the invention provides a composition comprising (a) a polypeptide comprising a VHH domain that binds to a target entity; and (b) the target entity. In some embodiments the VHH domain is bound to the target entity.

In some aspects, the invention provides a polypeptide comprising a VHH domain that binds to an antigen. In some embodiments an antigen is any molecule or complex comprising at least one epitope recognized by a B cell, e.g., a mammalian or avian B cell. In some embodiments the antigen comprises a protein, e.g., a polypeptide encoded or expressed by an organism. A polypeptide antigen may comprise or consist of a full length polypeptide or a portion thereof, such as a peptide at least about 6, 7, 8, 9, 10, 11, 12, 13, 14, or 15 amino acids long, in various embodiments. In some embodiments an antigen is a synthetic antigen whose sequence or structure, in some embodiments, resembles that of a naturally occurring antigen. For example, in some embodiments the sequence of a naturally occurring antigen may be altered by addition, deletion, or substitution of one or more amino acids. In some embodiments an antigen comprises a portion at least 80%, 85%, 90%, 95%, 96%, 96%, 97%, 98%, 99%, or more identical in sequence to at least a portion of a naturally occurring polypeptide, wherein the portion of the naturally occurring polypeptide is at least 10; 20; 30; 40; 50; 100; 200; 500; 1,000; 2,000; 3,000, or more amino acids long. In some embodiments a synthetic antigen comprises portions derived from multiple distinct antigens. For example, in some embodiments an antigen comprises two or more peptides that are naturally found in different proteins of a pathogen of interest. In some embodiments an antigen comprises two or more peptides or polysaccharides that are naturally found in different variants, strains, subtypes, or serotypes of a pathogen of interest. In some embodiments an antigen comprises a sequence or structure that is highly conserved among multiple variants, strains, subtypes, or serotypes of a pathogen of interest. In some embodiments an antigen comprises one or more immunodominant epitopes, which may be derived from the same larger molecule or from different molecules in various embodiments. In some aspects, the invention provides a composition comprising (a) a polypeptide comprising a VHH domain that binds to an antigen; and (b) the antigen. In some embodiments the VHH domain is bound to the antigen.

In some embodiments the invention provides nucleic acid(s) that encode a polypeptide comprising a VHH domain that binds to an antigen. In some embodiments the nucleic acid comprises expression control elements, e.g., a promoter, operably linked to the nucleic acid sequence encoding the VHH. In some embodiments the promoter is selected to be functional in an organism that encodes or expresses the protein. In some embodiments the nucleic acid is codon optimized for expression in an organism that encodes or expresses the protein. In some embodiments the invention provides a vector comprising one or more of the nucleic acid(s). In some embodiments a protein encoded or expressed by an organism is an intracellular protein. In some embodiments a protein encoded or expressed by an organism is a cell surface protein. In some embodiments the polypeptide comprises a detectable label, which, in some embodiments comprises a fluorescent polypeptide. In some embodiments the polypeptide is a fusion protein comprising a VHH and a detectable, e.g., fluorescent, polypeptide. In some embodiments the polypeptide is a sortase-usable nucleophile. In some embodiments the polypeptide comprises at least one N-terminal glycine residue. In some embodiments the polypeptide comprises a TRS. In some embodiments the polypeptide is modified using sortase. In some embodiments a polypeptide, e.g., a polypeptide comprising a VHH or other antigen-binding polypeptide, is expressed intracellularly and remains inside a cell (i.e., is not secreted). In some embodiments a polypeptide comprises a sequence that directs the polypeptide to a subcellular organelle, e.g., the nucleus, mitochondria, or other organelle. In some embodiments a polypeptide comprises a secretion signal sequence. In some embodiments a nucleic acid sequence that encodes a polypeptide is at least in part codon optimized for expression by cell(s) of a particular organism or group of organisms (e.g., yeast, mammals, insects, bacteria, nematodes, or one or more genera or species thereof). In some embodiments a subcellular targeting sequence or secretion signal sequence is selected to be functional in a particular organism or group of organisms of interest.

In some aspects, the invention provides a collection or kit comprising at least one polypeptide comprising a VHH domain that binds to an antigen, e.g., a protein encoded or expressed by an organism or comprising at least one nucleic acid that encodes the polypeptide. In some embodiments the collection or kit comprises at least 5, 10, 15, 20, 25, polypeptides comprising collectively VHH domains that bind to at least 5, 10, 15, 20, 25, or more distinct antigens, e.g., proteins, of an organism. In some embodiments at least 2 of the proteins are labeled with different detectable labels.

In some embodiments an organism is a "model organism". In some aspects, a model organism is a non-human species that is studied to, e.g., understand particular biological phenomena, with the expectation that discoveries made in or using the organism model will provide insight into the workings of other organisms. In some aspects, a model organism is a non-human species that is relatively non-pathogenic (at least to humans having a normally functioning immune system) that is studied with the expectation that discoveries made in or using the model organism will provide insight into the workings of a related species that is a human pathogen. In some embodiments a model organism serves as a disease model that can be studied to gain insight into disease pathogenesis, host response, and/or to test candidate therapies. In some embodiments a model organism is a prokaryote. In some embodiments a model organism is a eukaryote. In some embodiments a model organism is an invertebrate animal. In some embodiments a model organism is a vertebrate animal. In some embodiments a model organism is, e.g., a frog (e.g., *Xenopus laevis*), fish, e.g., zebrafish (*Danio rerio*) or Medaka, worm (e.g., *C. elegans*), a planarian (e.g., *Schmidtea mediterranea*); *Daphnia* (water flea); insect, e.g., a fruit fly (e.g., *D. melanogaster*); a fungus (e.g., yeast such as *S. cerevesiae, S. pombe* or *C. albicans* or *U. maydis*) or *N. crassa*; an amoeba (e.g., *D. discoideum*), a plant (e.g., *A. thaliana*), a bird (e.g., a chicken (e.g., *Gallus gallus*), a non-human mammal (e.g., a rodent such as a mouse (e.g., *Mus musculus*) or rat (e.g., *Rattus norvegicus*)). In some embodiments an organism is a human, e.g., a human in need of treatment for a disease or condition.

According to certain embodiments, a camelid is immunized with an immunogen. In some embodiments a camelid is an Old World camelid, e.g., a dromedary (Arabian camel) or a Bactrian camel. In some embodiments a camelid is a New World camelid, e.g., a llama, vicuna, alpaca, or guanaco. In general, a camelid can be immunized using standard methods. For example, various protocols for camelid immunization are described in references cited herein. In some embodiments a camelid is immunized multiple times, e.g., 2-10 times spaced apart by 1-12 weeks, e.g., about 2-4 weeks apart. In some embodiments immunization is subcutaneous or intradermal, though other routes may be used. As used herein, the term "immunogen" refers to a composition comprising one or more antigen(s) that can elicit an immune response, e.g., an adaptive immune response, when introduced into a subject. In some embodiments, an immunogen comprises multiple antigens. In some embodiments, an adjuvant is also administered to the camelid. For example, in some embodiments a composition comprising an immunogen and an adjuvant is administered. In some embodiments an immunogen comprises a heterogeneous mixture of antigens. "Heterogeneous mixture" in this context means that at least 10 different antigens are present and at least partly intermingled in a composition and does not imply that the immunogen was prepared by mixing, although mixing may be used in some embodiments. In some embodiments a heterogeneous mixture comprises or is at least in part derived from a target entity that comprises multiple distinct antigens. In some embodiments a heterogeneous mixture of antigens is prepared by a process that does not comprise mixing together multiple isolated or purified antigens, e.g., multiple isolated or purified antigens the identity of which is known. In some embodiments an immunogen comprises, for example, at least 10; 100; 1,000; 10,000 antigens, or more. In some embodiments an immunogen comprises a heterogeneous mixture of antigens of diverse structure and/or including antigens of different biomolecule class (e.g., polypeptides, lipids, carbohydrates, and/or nucleic acids). In some embodiments an immunogen comprises a heterogeneous mixture comprising at least 10, 100; 1,000; 5,000, or more proteins. In some embodiments, no particular protein in the heterogeneous mixture constitutes more than about 5%, more than about 1%, more than about 0.5%, or more than about 0.1%, of the polypeptide material present in the heterogeneous mixture by dry weight or by moles. In some embodiments one or more of the proteins are glycoproteins. In some embodiments the immunogen further comprises at least one nucleic acid, lipid, and/or carbohydrate. For purposes hereof, an immune response that occurs in response to a heterogenous mixture of antigens may be referred to as a "heterogenous immune response". In some embodiments an immunogen, e.g., an immunogen comprising a heterogeneous mixture of antigens, is administered to a camelid in order to cause the camelid to generate an antibody comprising a VHH domain, wherein the antibody or a nucleic acid sequence encoding at least a portion of a VHH domain is to be obtained from the camelid and subsequently used and/or modified as described herein. In some embodiments an immunogen, e.g., an immunogen comprising a heterogeneous mixture of antigens, is administered to a camelid in order to elicit production of antibodies capable of binding to one or more antigens in the immunogen, but not specifically to a particular predetermined target antigen. In other words, the identity of the target antigen is not predetermined. Thus in some embodiments, certain methods described herein are distinct from methods in which a camelid is immunized with an isolated or purified antigen of known identity in order to generate antibodies to that particular antigen.

In some embodiments an immunogen comprises or is at least in part derived from a target entity or from multiple distinct target entities. In general, a target entity can be any entity that comprises one or more antigens, e.g., one or more antigens or antigen sources mentioned herein. In some embodiments a target entity is a parasite, cell, cell organelle, or virus, or a part of any of the foregoing such as a capsid, envelope, coat, cell wall, cellular membrane (e.g., plasma membrane, endoplasmic reticulum membrane, organelle membrane), subcellular complex (e.g., a protein or RNA/protein assembly such as a spliceosome, ribosome, or proteasome), flagellum, fimbria, or pilus. In some embodiments an immunogen comprises a tissue sample, tissue lysate, tissue fraction, cell lysate, or cell lysate fraction. In some embodiments an immunogen comprises or is at least in part derived from a cellular organelle, e.g., nucleus, nucleolus, mitochondria, endosome, lysosome, peroxisome, or a lysate or fraction thereof. In some embodiments an immunogen comprises or is at least in part derived from one or more cellular membranes, e.g., plasma membrane, endoplasmic reticulum membrane, organelle membrane, etc. "Derived from" in this context encompasses situations in which a target entity is subjected to one or more processing steps that may at least partially disrupt or otherwise alter the structure of the target entity and/or remove or isolate some of its original components. For example, in some embodiments an immunogen that is at least in part derived from a target entity comprises some but not all of the components that are present in the target entity and/or comprises one or more components whose structure or organization is altered in the immunogen as compared to the target entity. In some embodiments at least some antigens are present in an immunogen in substantially the same form as present in the unprocessed target entity. In some embodiments an immunogen comprises or is at least in part from a population of target entities of the same type (e.g., cells of the same type, viruses of the same type). The members of the population may be obtained from the same source or from different sources in various embodiments. For example, in some embodiments an immunogen comprises or is at least in part derived from cells. Cells can be of any cell type in various embodiments. Cells can be obtained or isolated using any suitable method and/or from any suitable source. In some embodiments cells are primary cells. In some embodiments cells of a cell line, e.g., an immortalized cell line, are used. In some embodiments cells are in a tissue sample. In some embodiments cells exhibit and/or are selected based on any one or more criteria or combination thereof. For example, in some embodiments cells express one or more markers, e.g., one or more cell surface markers. In some embodiments cell(s) exhibit one or more morphological characteristics, functional properties, or have a particular gene expression profile. In some embodiments at least 5%, 10%, 20%, 30%, 40%, 50%, 60%, 70%, 80%, 90%, 95%, 96%, 97%, 98%, 99%, or more of the cells in a sample or population of cells are of a particular cell type or exhibit one or more phenotypic characteristics of interest, e.g., expression of one or more cell surface markers and/or one or more morphological characteristics. It will be understood that different preparations of an immunogen may be used if a camelid is immunized multiple times. Such preparations may be prepared in substantially the same or equivalent ways and/or from substantially the same or equivalent source(s). In some embodiments an immunogen comprises or is at least in part from 2, 3, 4, 5, or more different target entities, each of which comprises a heterogeneous mixture of antigens. In some embodiments a camelid is immunized with multiple immunogens comprising or at least in part derived from different target entities. In some embodiments an immunogen is produced at least in part by physical and/or chemical disruption of a tissue sample or cells. In some embodiments cells are at least partly permeabilized. In some embodiments an immunogen comprises a cell lysate or a fraction thereof. A lysate may be obtained, for example, using any standard method of lysate preparation in various embodiments. In some embodiments a lysate is prepared using a detergent, which may be an ionic or non-ionic detergent in various embodiments, e.g., Tween, NP-40, CHAPS, Brij, etc. In some embodiments a lysate or fraction is prepared under conditions that would not be expected to substantially denature or degrade proteins or, in some embodiments, protein-protein interactions. In some embodiments a lysate is prepared at least in part using physical means such as sonication, bead beating, douncing, scraping, or the like. In some embodiments a fraction is obtained by any of various separation methods such as size exclusion, ion exchange, immunopurification, immunodepletion, centrifugation (e.g., sucrose gradient centrifugation), filtering, function-based selection procedures (e.g., a fraction that exhibits a particular biological or biochemical activity of interest), or combinations thereof.

In some embodiments, a VHH domain is obtained from a camelid that produces a heterogeneous immune response, e.g., following immunization with an immunogen comprising a heterogeneous mixture of antigens. For example, in some embodiments the camelid produces multiple distinct antibodies that bind to diverse different antigens present in the immunogen and/or that have a range of affinities. In some embodiments the camelid may also produce antibodies to pathogens or other immunogenic substances to which it has been exposed, in addition to antibodies to components of the immunogen. In some embodiments the camelid may produce tens, hundreds, thousands, or more antibodies capable of binding to distinct epitopes or antigens. In some embodiments, certain methods disclosed herein provide means for efficiently deconvoluting a heterogeneous immune response and generating useful monoclonal binding agents comprising a VHH domain. In some embodiments a method comprises (a) identifying one or more VHH domains having a property of interest from among multiple VHH domains; and (b) characterizing a target antigen to which the VHH domain binds. In some embodiments a property of interest is the ability to bind to a target entity of interest. In some embodiments the multiple VHH domains arise as part of a heterogenous immune response. In some embodiments the method comprises determining the identity of a target antigen to which a VHH domain binds. Thus in some embodiments methods disclosed herein comprise (a) identifying one or more VHH domains having a property of interest; and (b) characterizing or determining the identity of a target antigen to which the VHH domain binds. In some embodiments, "deconvoluting" a heterogeneous immune response comprises mapping a VHH domain produced by a camelid back to the antigen to which it binds by determining the identity of the target antigen. In some embodiments, deconvoluting a heterogeneous immune response comprises mapping each of multiple distinct VHH domains (e.g., at least 2, 5, 10, or more distinct VHH domains) produced by a camelid back to the antigens to which they bind by determining the identities of the target antigens. In some embodiments, sortase is used in identifying a VHH domain and/or in characterizing or determining the identity of a target antigen to which a VHH domain binds.

According to certain of the methods, one or more samples that serves as a source of lymphocytes is obtained from an immunized camelid at one or more time points after immunization. In general, a sample can be obtained from any of a variety of fluids or tissues that comprise B-lineage cells that express mRNA encoding a VHH domain. For example, in various embodiments lymphocytes are obtained from blood, lymph, or lymphoid tissue, e.g., spleen, lymph node tissue, bone marrow, or other tissue in which B cells are formed, develop, and/or are found in appreciable quantities. In some embodiments lymphocytes comprise mature B cells that produce and, in at least some embodiments secrete, an antibody comprising a VHH domain. In some embodiments lymphocytes are obtained from peripheral blood. In some embodiments lymphocytes are obtained from a lymph node draining an immunization site. In some embodiments B cells are isolated from a mixed population of cells comprising multiple different types of lymphocytes (e.g., B cells and T cells). For example, lymphocytes that express a B cell surface marker may be selected using, e.g., flow cytometry.

Nucleic acid sequences encoding VHH domains are obtained from the lymphocytes, e.g., using any of a variety of methods. In some embodiments lymphocytes are obtained from a single animal that has been immunized with an immunogen of interest. In some embodiments lymphocytes obtained from multiple animals that have been immunized with an immunogen of interest are pooled prior to isolation of nucleic acids encoding VHH domains. In some embodiments RNA transcripts (e.g., total RNA or mRNA) are isolated from the lymphocytes, reverse transcribed into cDNA, and used as a template for the specific amplification of VHH sequences present in the pool of transcripts. Any of a variety of amplification procedures may be used. For example, the polymerase chain reaction (PCR) may be used. In some embodiments genomic sequences encoding VHH domains are isolated and amplified. In some embodiments primers designed to universally prime reverse transcription of mammalian immunoglobulin mRNA templates at conserved sequence motifs can be used. In some embodiments primers designed based, e.g., on a representative sampling of random cDNAs encoding VHH domains (e.g., of a particular camelid species) are used to amplify other VHH domains from camelids of that species or in some embodiments of a different camelid species. In some embodiments RNA transcripts obtained from lymphocytes obtained from multiple camelids that have been immunized with an immunogen of interest are pooled prior to reverse transcription. In some embodiments cDNAs obtained by reverse transcription of RNA transcripts from lymphocytes obtained from multiple animals that have been immunized with an immunogen of interest are pooled prior to amplification. In some embodiments nucleic acids encoding VHH domains originating from multiple camelids that have been immunized with an immunogen of interest are pooled after isolation or amplification. In some embodiments, multiple camelids are of the same camelid species. In some aspects a VHH domain comprises a polypeptide having the following structure:

FR1-CDR1-FR2-CDR2-FR3-CDR3-FR4 in which FR1 to FR4 refer to VHH domain framework regions 1 to 4, respectively, and in which CDR1 to CDR3 refer to VHH domain complementarity determining regions 1 to 3, respectively. (See, e.g., WO 2008/142164 and references cited therein, all of which are incorporated herein by reference, for discussion of exemplary VHH domain features and sequences.) In general, as known in the art, the sequence of the framework regions can vary somewhat among different VHH domains arising in a particular individual camelid or among different camelids of a particular camelid species and/or in different camelid species. One of ordinary skill in the art will also appreciate that the sequence of framework regions can vary among different VHH subfamil(ies). In various embodiments a VHH domain can be a member of any of the various subfamilies of VHH domains known in the art. In some embodiments primers that amplify at least a sequence encoding FR1-CDR1-FR2-CDR2-FR3-CDR3-FR4 are used. In some embodiments PCR amplification of camelid VHH domains, e.g., alpaca VHH domains, is performed using primers described in the Examples. In some embodiments PCR amplification of camelid VHHs, e.g., llama or alpaca VHHs, is performed using primers described in Maass, D., supra. In some embodiments PCR amplification of camelid VHHs, e.g., llama VHHs, is performed using primers described in Harmsen, M, et al, Molecular Immunology 37 (2000) 579-590. In certain embodiments at least a portion of a framework region, e.g., at least an N-terminal portion of FR1 and/or at least a C-terminal portion of FR4, may be absent. In certain embodiments, for example, up to about 10%, 20%, 30%, 40%, 50%, 60%, 70%, 80%, 90%, or 100% of an N-terminal portion of FR1 and/or a C-terminal portion of FR4 may be absent. As known in the art, naturally occurring camelid antibodies comprising VHH domains (sometimes referred to as "HCAbs") also possess a hinge region, which joins the VHH domain to the CH2 domain (see, e.g., van der Linden, Journal of Immunological Methods 240 (2000) 185-195; Maass, D., et al., Journal of Immunological Methods 324 (2007) 13-25). Two distinct hinge sequence types have been found in camelids, commonly referred to as the short hinge (IgG2) and the long hinge (IgG3).

In some embodiments a polypeptide comprising a VHH domain comprises at least a portion of a hinge region, e.g., the polypeptide has the structure:

FR1-CDR1-FR2-CDR2-FR3-CDR3-FR4-HINGE wherein HINGE represents at least a portion of a hinge region. In various embodiments the length of HINGE ranges from 1 amino acid (aa) up to the full length of a hinge region. In some embodiments the length of HINGE is between 1 and 25 aa, e.g., between 5 and 20 aa. In some embodiments primers that amplify a nucleic acid comprising a sequence that encodes CDR1 FR2-CDR2-FR3-CDR3 are used. In some embodiments primers that amplify a nucleic acid comprising a sequence that encodes L-CDR1-FR2-CDR2-FR3-CDR3 are used, where L represents at least a portion of a VHH leader sequence located N-terminal to CDR1. In some embodiments primers that prime within a sequence encoding a VHH leader located upstream of CDR1 are used. In some embodiments primers that amplify a nucleic acid comprising a sequence that encodes FR1-CDR1-FR2-CDR2-FR3-CDR3 are used. In some embodiments primers that amplify a nucleic acid comprising a sequence that encodes CDR1-FR2-CDR2-FR3-CDR3-FR4 are used. In some embodiments primers that amplify a nucleic acid comprising a sequence that encodes FR1-CDR1-FR2-CDR2-FR3-CDR3-FR4 are used. In some embodiments one or more reverse primers that prime within a hinge region coding sequence are used. In some embodiments primers that amplify a nucleic acid comprising a sequence that encodes FR1-CDR1-FR2-CDR2-FR3-CDR3-FR4-HINGE are used. In some embodiments HINGE represents at least a portion of a short hinge region. In some embodiments HINGE represents at least a portion of a long hinge region. In some embodiments primers that prime within a sequence encoding a VHH leader and within a sequence encoding a hinge region are used. In some embodiments one or more reverse primers that prime within a CH2 coding sequence are used, so that the hinge region and at least a portion of CH2 are amplified. In some embodiments primers that amplify a nucleic acid comprising a sequence that encodes one or more CDRs are used, e.g., CDR1, CDR2, and/or CDR3. In some embodiments primers are designed to selectively amplify VHH domains as compared with VH domains found in conventional antibodies. The term "conventional antibody" as used herein refers to an antibody having the structure of a typical naturally occurring mammalian antibody containing two heavy chains and two light chains. In some embodiments primers are selected based on sequence regions that are highly conserved among randomly selected VHHs originating from one or more camelid species. In some embodiments a primer is designed based on a region that is at least 80% or at least 90% identical in at least 80% or at least 90% of a set of at least 50 randomly selected sequences encoding VHH leaders or VHH hinge regions in a camelid species of interest. In some embodiments a primer that is degenerate at one or more positions is used, wherein the degenerate position corresponds to a position of variability within a region that is overall highly conserved. In some embodiments a hinge region comprises a sequence that is identical to or at least 80%, 90%, 95%, 96%, 97%, 98%, 99%, or more identical to an HCAb hinge region obtained from an immunized or non-immunized camelid, e.g., any such hinge region known in the art. In some embodiments a hinge region comprises a sequence that is identical to or at least 80%, 90%, 95%, 96%, 97%, 98%, 99%, or more identical to an HCAb hinge region hinge region depicted in FIG. 13 or in Maass, supra or van der Linden, supra. In some embodiments a sequence encoding at least the N-terminal 1, 2, 3, 4, 5, 6, 7, or 8 amino acids of a hinge region, e.g., at least 1, 2, 3, 4, 5, 6, 7, or 8 amino acids of a hinge region comprising EPKTPKPQPQPQPQPQPQPNPTTE (SEQ ID NO: 45) or AHHSEDPS (SEQ ID NO: 46) is amplified. In some embodiments amplification is performed using a first primer pair appropriate for amplifying sequences that encode at least a portion of short hinge region and a second primer pair appropriate for amplifying sequences that encode at least a portion of a long hinge region. In some embodiments the same forward primer (e.g., a primer that primes within a leader sequence upstream of a sequence that encodes FR1) is used for both reactions. In some embodiments amplifications are performed together in the same vessel. In some embodiments amplifications are performed separately and the amplification products are pooled. In some embodiments a forward and/or reverse primer comprises a restriction site that facilitates cloning or amplification products into a vector. In some embodiments a primer may encode at least a portion of a TRS.

In some embodiments of any aspect herein, a nucleic acid that encodes a VHH comprises a portion that encodes at least a portion of a VHH leader region. In some embodiments the nucleic acid encodes a polypeptide comprising at least a portion of a VHH leader region located immediately N-terminal to FR1. In some embodiments of any aspect herein, a nucleic acid that encodes a VHH comprises a portion that encodes at least a portion of a hinge region, e.g., the nucleic acid encodes a polypeptide comprising at least a portion of a hinge region located immediately C-terminal to FR4. Where the term VHH is used herein with regard to any aspect of the disclosure, the disclosure provides embodiments pertaining to (L)VHH(H), where L represents at least a portion of a VHH leader region and H represents at least a portion of a hinge region, and wherein parentheses indicate that L and/or H can be present or absent in various embodiments. Such aspects include, but are not limited to, polypeptides comprising or consisting of (L)VHH(H), nucleic acids that encode such polypeptides, vectors comprising such nucleic acids, compositions comprising any of the foregoing, and methods relating to any of the foregoing. In certain embodiments of any aspect, L and/or H is replaced with at least a portion of a heterologous leader or hinge sequence.

In some aspects, one or more VHHs that bind to a target entity are identified. VHHs that bind to a target entity can be identified using any of a variety of methods. In some embodiments one or more VHHs that bind to a target entity is identified using a display technology. In some embodiments nucleic acids, e.g., amplification products, comprising VHH coding sequences are cloned into a display vector. A "display vector" is a vector suitable for inserting a nucleic acid that encodes a polypeptide of interest, so that the nucleic acid can be translated and the resulting polypeptide displayed. In general, the amplification products comprise a library of sequences encoding multiple distinct VHH domains. For example, in some embodiments the amplification products comprise at least $10^6$, $10^7$, $10^8$, or $10^9$ distinct VHH coding sequences. In some embodiments the resulting display vectors form a library having a complexity of at least $10^6$, $10^7$, $10^8$, or $10^9$ (i.e., the library comprises vectors that encode collectively at least $10^6$, $10^7$, $10^8$, or $10^9$ distinct VHH domains). Display technologies encompass a variety of techniques in which polypeptides are presented in a format in which they are physically associated with a nucleic acid that encodes them and in which they can be selected based on a property of interest, such as ability to bind to a target or catalyze a reaction. Display technologies include, e.g., phage display, yeast display, plasmid display, ribosome display, and bacterial display. For example, polypeptides can be displayed on the surface of phage (e.g., fused to at least a portion of a phage coat protein), yeast, or bacteria that have the encoding nucleic acid incorporated within or on ribosomes that have the encoding nucleic acid physically attached thereto. The link of phenotype (polypeptide) to genotype (nucleic acid that encodes the polypeptide) provided by a display technology enables selection of and, if desired, enrichment for, molecules having a desired property of interest, e.g., molecules with high specific affinities for a given antigen, followed by identification of the co-selected encoding nucleic acid. See, e.g., Speight R E, et al., Chem Biol. (2001) 8(10):951-65; Dufner P, et al., (2006) Trends Biotechnol. 24:523-529; Colby, D. W. et al. (2004) Methods Enzymol. 388, 348-358; Feldhaus, M. J. and Siegel, R. W. (2004) J. Immunol. Methods 290, 69-80; B. R. Harvey, et al. Proc Natl Acad Sci USA, 101 (2004), pp. 9193-9198; B. R. Harvey, et al. Proc Natl Acad Sci USA, 101 (2004), pp. 9193-9198B. R. Harvey, et al., J Immunol Meth, 308 (2006), pp. 43-52; Zahnd C, et al., (2007) Nat Methods. 4(3):269-79 for exemplary discussion of various display technologies.

In some embodiments a phage display vector comprises a phage genome or a phagemid. It will be understood that when a phagemid is used, bacteria can be co-infected with helper phage. Phage display often involves use of filamentous phage (e.g., M13). Other phage display platforms include those based on 2, phage or T7 phage. In certain embodiments yeast display uses the α-agglutinin yeast adhesion receptor to display recombinant proteins on the surface of *S. cerevisiae*. Ribosome display technology is based on the formation of a messenger RNA (mRNA)-ribosome-nascent polypeptide ternary complex in a cell-free protein synthesis system. The complex provides a physical linkage between phenotype (polypeptide) and genotype (mRNA). Sequence information for a polypeptide of interest can be selected by affinity purification of the complex. In some embodiments a bacterial display system may utilize a nucleic acid that encodes a fusion protein comprising a bacterial signal sequence (e.g., Lpp), a bacterial transmembrane domain (e.g., from a bacterial outer membrane protein such as OmpA), and a polypeptide to be displayed. The fusion protein can be expressed using any of a variety or promoters. In some embodiments an inducible promoter such as a tet, araBAD, or lac promoter or a hybrid promoter such as a lac-ara promoter is used. For purposes of description certain aspects of the invention are described herein with respect to embodiments in which the display vector is a phage display vector. However, any of a variety of other display vectors may be used in various embodiments.

In some aspects, the invention provides a display vector, e.g., a phage display vector, that encodes a transamidase recognition sequence (TRS). In some aspects, the invention provides a display vector that comprises a nucleic acid sequence that encodes a polypeptide comprising: (a) a VHH domain; and (b) a TRS. In some embodiments the transamidase recognition sequence is located C-terminal with respect to the VHH domain. As noted above, in some embodiments a polypeptide comprising a VHH comprises at least a portion of a hinge region, e.g., at least a portion of a hinge region is located between the VIM domain and the TRS. In some embodiments a nucleic acid comprising a sequence that encodes a VHH domain is inserted into a display vector that encodes a TRS. In some embodiments a sequence that encodes a TRS is inserted into a display vector following insertion of a sequence that encodes a VHH domain. In some embodiments a sequence that encodes a VHH domain and a sequence that encodes a TRS may be inserted into a display vector using a single ligation reaction.

In some embodiments a display vector comprises one or more sequences that encode one or more additional elements, wherein the sequence(s) are positioned in frame with a sequence that encodes a TRS or in frame with a sequence that encodes a VHH and a TRS. An additional element may be represented as $(Xaa)_n$, where the Xaa may be independently selected. In various embodiments a sequence that encodes an additional element may be positioned 5' or 3' with respect to a sequence that encodes a TRS and/or may be positioned 5' or 3' with respect to a sequence that encodes a VHH. In some embodiments a display vector comprises a sequence encoding a polypeptide represented as: $(Xaa)_i$-TRS-$(Xaa)_j$, wherein i and j can each independently range from 0 up to 10, 25, 50, 100, 250, 500, or more in various embodiments. In some embodiments a display vector comprises a sequence encoding a polypeptide represented as: $(Xaa)_i$-VHH-$(Xaa)_j$-TRS-$(Xaa)_k$, where i, j, and k can each independently range from 0 up to 10, 25, 50, 100, 250, 500, or more in various embodiments. In some embodiments an additional element comprises a peptide tag. In some embodiments an additional element comprises a peptide linker. In some embodiments a polypeptide comprises multiple tags (of the same or different sequence) and/or multiple linkers (of the same or different sequence). In some embodiments a peptide linker is between 1 and 30 amino acids long, e.g., 1-5, 1-10, 1-20, or 1-25 amino acids. In some embodiments a peptide linker comprises or consists of one or more Gly, Ser, or Ala residues. In some embodiments the amino acids are independently selected from Gly, Ser, and Ala, or from Gly and Ser. In some embodiments a peptide linker comprises or consists of $(G)_n$ or $(A)_n$, where n is any integer between 1 and 10, e.g., $(G)_1$, $(G)_2$, $(G)_3$, $(G)_4$, $(G)_5$. In some embodiments an additional element comprises a cleavage site for a protease.

In some embodiments the polypeptide is encoded as part of a fusion protein comprising one or more segment(s) that facilitates display of the polypeptide. For example, in some embodiments a polypeptide segment comprises a leader sequence that directs secretion or localization of the polypeptide by a host cell that expresses it. In some embodiments a polypeptide segment causes the polypeptide to be displayed at the surface of a phage particle or cell. In some embodiments a polypeptide segment comprises at least a portion of a naturally occurring polypeptide that is normally present at the surface of a phage particle or cell. For example, in some embodiments the polypeptide is a fusion protein comprising at least a portion of a phage coat protein. Thus in some embodiments nucleic acids comprising VHH coding sequences are inserted between and in frame with a nucleic acid sequence that encodes a leader sequence that directs secretion and a nucleic acid sequence that encodes at least a portion of a phage coat protein. The abbreviation "CP" will be used to refer to at least a portion of a coat protein. In some embodiments CP comprises a sufficient portion of the coat protein so that a fusion protein comprising it is displayed at the surface of the phage. In some embodiments the leader L directs secretion to the bacterial periplasm where phage particles are assembled. In some embodiments the leader sequence is from the phage coat protein. In some embodiments the vector comprises the M13 gene III leader sequence and M13 gene III, which encodes a truncated version of M13 phage coat protein pIII. For example, in some embodiments the phage display vector comprises the following nucleic acid elements, where "cs" stands for "coding sequence": Leader cs-insertion site sequence—TRS cs—CP cs, wherein "insertion site sequence" (ISS) represents a sequence into which a nucleic acid encoding a polypeptide of interest, e.g., a polypeptide comprising a VHH, can be inserted to result in a nucleic acid that comprises a continuous reading frame comprising the leader cs, the nucleic acid comprising a VHH cs, the TRS cs, and the CP cs In other words, the vector encodes a fusion protein comprising the leader, VHH, TRS, and CP. In some embodiments an ISS comprises one or more sites for cleavage by a restriction enzyme so that a nucleic acid digested with the restriction enzyme can be conveniently ligated into similarly digested vector DNA. In some embodiments the one or more restriction sites are selected so to preserve the reading frame. In some embodiments sequences encoding one or more additional elements (Xaa)$_n$, as described above, are present so that an encoded fusion protein will include such one or more additional element(s).

In some embodiments a phage display vector comprises a promoter appropriate to express the nucleic acid in a suitable host cell (e.g., a bacterial host cell such as *E. coli*), wherein the open reading frame is operably linked to the promoter, so that the open reading frame can be expressed in the cell. Suitable promoters are known in the art. In some embodiments the promoter is inducible. The library of display vectors is transferred into suitable host cells as known in the art. In some embodiments, e.g., if the phage display vector is a phagemid, the host cells are infected with helper phage in addition to the phage display vector. A host cell infected with a phage display vector produces phage particles that have one or more copies of the VHH encoded by the display vector incorporated into their coat ("displayed") as part of a fusion protein, e.g., as a polypeptide comprising VHH-TRS-CP. Thus, infection of a population of host cells with a library of phage display vectors encoding different VHH domains results in production of multiple phage particles in which individual VHHs comprising distinct sequences are displayed on the surface of phage particles. The phage particles contain the nucleic acid encoding the VHH displayed at their surface, allowing straightforward recovery of the sequence encoding the VHH.

In some embodiments phage that display VHHs having a desired specificity are selected, e.g., by panning. In some embodiments panning comprises incubating phage of a phage display library (or part of such library) with a target under conditions in which interaction between the phage and target can occur. In some embodiments a target is a target antigen, target entity, or surrogate of a target entity. A surrogate of a target entity can be any entity that is sufficiently similar to a target entity so that the surrogate has at least some, many or most of the same antigens accessible to the phage as would the target entity itself. One of ordinary skill in the art would be able to select a suitable surrogate target entity. For example, if a target entity is a primary cell, in some embodiments a surrogate is a cell of an immortalized cell line of the same cell type. In some embodiments the target is immobilized to a support prior to incubation with phage. In some embodiments the target is not immobilized, and interaction occurs in solution. Complexes comprising phage and target are recovered from the solution. Phage that bind to the target are recovered and can be used to infect additional host cells to allow replication and one or more repeated rounds of selection. In some embodiments one or more selection steps can include use of a competitor (e.g., a non-target entity) or particular incubation conditions to enrich for phage that express VHH domains specific for the target entity and/or that exhibit a desired property such as stability under selected conditions.

In some embodiments a phage display vector nucleic acid sequence comprises a stop codon, e.g., an amber codon, upstream of and in frame with the sequence that encodes at least a portion of a phage coat protein. For example, in some embodiments the phage display vector comprises the following nucleic acid elements:

Leader cs-ISS-TRS cs-Stop Codon-CP cs

A nucleic acid sequence comprising a portion that encodes a VHH domain, optionally further comprising at least a portion of a hinge region, is inserted downstream of and in frame with the leader coding sequence and upstream of and in frame with the TRS coding sequence, and stop codon. When produced in suitable host cells that comprise a suppressor of the stop codon, e.g., cells having an amber suppressor mutation such as *E. coli* strains TG-1 or XL1-Blue, the sequence is translated to produce a fusion protein comprising the leader, VHH, TRS, and CP, as described above. When produced in host cells that do not comprise a suppressor of the stop codon, translation of the sequence results in production of a polypeptide comprising the leader, VHH, and TRS but lacking the CP. In some embodiments the leader is cleaved off by the host cells, resulting in a polypeptide comprising VHH-TRS (without a leader or CP). In some aspects, the present disclosure encompasses the recognition that, in at least some embodiments, a display vector used to identify a VHH domain that binds to a target entity can be used to produce sufficient quantities of a sortaggable polypeptide comprising the VHH domain to permit production of useful amounts of sortagged polypeptide, e.g., amounst sufficient for testing the sortagged polypeptide for one or more properties of interest.

For example, in some embodiments a polypeptide comprising a VHH and a TRS is sortagged with any of a variety of molecules, e.g., an amino acid, a peptide, a protein, a polynucleotide, a carbohydrate, a tag, a metal atom, a chelating agent, a contrast agent, a catalyst, a non-polypeptide polymer, a recognition element, a small molecule, a lipid, a label, an epitope, a small molecule, a therapeutic agent, a cross-linker, a toxin, a radioisotope, an antigen, or a click chemistry handle. In some embodiments the sortagged polypeptide is tested in one or more assays. In some embodiments one or more such assays is used determine whether the polypeptide and/or the VHH domain thereof is suitable for use in one or more applications, methods, or assays, of interest. For example, in some embodiments the polypeptide is sortagged with a detectable label, and ability of the sortagged polypeptide to detectably stain a target entity is assessed. In some embodiments specificity of a VHH for a target entity is tested by evaluating the ability of a polypeptide comprising a VHH sortagged with a detectable agent to stain one or more non-target entities. Other properties that may be assessed include, e.g., solubility, stability, expression level, internalization by cells, pharmacokinetic parameters (e.g., plasma half-life) following administration to a non-human animal, localization in vivo after administration to a non-human animal or any desired functional properties. In some embodiments multiple sortagged polypeptides comprising the same VHH domain are produced, wherein the polypeptides are sortagged with different molecules. In some embodiments the different molecules facilitate testing or use of the sortagged polypeptides in different assays, methods, or applications.

After isolation of phage that bind to a target (e.g., a target entity such as those described herein), the display vector and/or a nucleic acid encoding a polypeptide comprising the VHH domain are isolated from the selected phage. A nucleic acid encoding a polypeptide comprising a VHH domain can be manipulated or used in any of a variety of ways. For example, in some embodiments the nucleic acid is inserted into a different vector, amplified, translated in vitro, sequenced, and/or altered (e.g., by random or site-directed mutagenesis). In some embodiments the nucleic acid or vector is used to generate VHH variants that have, for example, higher affinity for a target, altered kinetics (e.g., altered $k_{on}$ and/or $k_{off}$), increased neutralizing ability, increased stability, increased specificity, increased catalytic activity, or other propert(ies) of interest. Standard techniques for generating variants or nucleic acids encoding variants, such as error-prone PCR or site-directed mutagenesis or chemical synthesis, may be used. In some embodiments a variant is designed based on the sequence of the VHH. In some embodiments one or more nucleic acids encoding a CDR is isolated. In some embodiments one or more of such nucleic acids encoding a CDR is used to construct an additional phage display library, which library may be used, e.g., to identify additional VHH that bind to the target entity. In some embodiments one or more such nucleic acids encoding a CDR is joined to a nucleic acid that encodes a heterologous framework region, e.g., a framework region from a different VHH or a framework region from an antibody other than a VHH. In some embodiments nucleic acids encoding CDR1, CDR2, and CDR3 of a VHH are assembled with nucleic acids encoding framework regions, at least some of which may be heterologous framework regions, to create a nucleic acid encoding a polypeptide comprising such CDRs and FRs. For example, in some embodiments nucleic acids encoding CDR1, CDR2, and CDR3 from a VHH identified as described herein are inserted between FR regions in a nucleic acid encoding a scaffold comprising FR1-FR2-FR3-FR4, where FR1, FR2, FR3, FR4 represent framework regions, to form a nucleic acid that encodes a polypeptide comprising FR1-CDR1-FR2 CDR2-FR3-CDR3-FR4. In some embodiments the sequences of the FR regions may be found in or derived from any VHH. In various embodiments the FR regions may be found in or derived from a VHH of any VHH class. In some embodiments the antibody comprises FR regions found in or derived from two or more different VHH domains and/or different VHH domain classes. In some embodiments a VHH is at least partly humanized, e.g., by altering one or more framework amino acids in the VHH to more closely resemble the sequence of a human VH framework region. In some embodiments at least 2,3, or 4 of the FR regions are at least partly humanized. In some embodiments a hinge region, if present, is at least partly humanized. See, e.g., Vincke, C., et al. J. Biol Chem. (2009) 284(5): 3273-84 for exemplary humanization strategies that may be used in certain embodiments. See also Presta L G (2006) Adv Drug Deliv Rev 58:640-656, for discussion of certain aspects of antibody humanization. In some embodiments a VHH is altered to more closely resemble a VH domain of a mouse or other non-human animal.

In some embodiments, the characteristics and/or identity of the antigen to which a selected phage comprising a VHH domain binds may not be known at the time the phage is isolated. For example, in some embodiments the target entity and the immunogen comprising or derived from the target entity comprise multiple potential target antigens, e.g., a heterogenous mixture of antigens, and the phage is isolated based at least in part on ability of the VHH encoded thereby to bind to the immunogen or a surrogate thereof. In such embodiments, the identity of the target antigen would generally not be apparent, since the VHH may bind to any of a variety of different antigens present in the immunogen. In some embodiments, a method comprises characterizing a target antigen to which a VHH (e.g., a VHH that binds to a target entity) binds. In some embodiments, a method comprises determining the identity of a target antigen to which a VHH (e.g., a VHH that binds to a target entity) binds. In some embodiments, a polypeptide comprising the VHH is sortagged and tested in one or more assays prior to characterizing or determining the identity of the target antigen. In some aspects, the ability to sortag the polypeptide facilitates testing the polypeptide to identify a VHH domain that exhibits one or more desired properties. In some embodiments, a decision whether to proceed with characterizing or determining the identity of the target antigen may be made based at least in part on results of such testing.

In some aspects, the disclosure provides methods of characterizing a target antigen to which a sortaggable polypeptide comprising a VHH binds. In some aspects, the disclosure provides methods of determining the identity of a target antigen to which a sortaggable polypeptide comprising a VHH binds. In some embodiments the methods make use of the sortaggable nature of the polypeptide. In some embodiments the ability to sortag a polypeptide comprising a VHH facilitates testing the polypeptide to identify a VHH domain that exhibits desired properties. In some embodiments the ability to sortag a polypeptide comprising a VHH facilitates characterizing or determining the identity of the target antigen. In some embodiments, the ability to sortag a polypeptide comprising a VHH both (a) facilitates testing the polypeptide to identify a VHH domain that exhibits desired properties prior to characterizing or determining the identity of the target antigen; and (b) facilitates characterizing or determining the identity of the target antigen.

In some embodiments a method of characterizing a target antigen to which a VHH binds comprises: (a) exposing a polypeptide comprising a VHH and a TRS (e.g., comprising VHH-TRS) to the immunogen or a surrogate thereof under conditions in which the target antigen can bind to the VHH; (b) separating material that binds to the VHH from material that does not bind to the VHH; and (c) subjecting material that binds to the VHH to at least one characterization procedure. In some embodiments, the polypeptide is immobilized to a support prior to exposure to the immunogen or surrogate thereof. In some embodiments immobilization facilitates separating material that binds to the VHH from material that does not bind to the VHH. For example, the support can be removed from a vessel containing the immunogen after allowing binding to occur (or unbound components of the immunogen can be removed from the vessel after allowing binding to occur) or the support can be washed while retaining the VHH and material bound thereto. Thus, in some embodiments a method of characterizing a target antigen to which a VHH binds comprises: (a) immobilizing a polypeptide comprising a VHH and a TRS (e.g., comprising VHH-TRS) to a support using a sortase-catalyzed reaction; (b) exposing the support to the immunogen or a surrogate thereof under conditions in which the target antigen can bind to the VHH; (c) separating material that binds to the VHH from material that does not bind to the VHH; and (d) subjecting material that binds to the VHH to at least one characterization procedure.

In some embodiments a sortaggable polypeptide comprising a VHH-TRS is expressed in cells (e.g., *E. coli*). In some embodiments a crude lysate of such cells is incubated in vitro with sortase and a nuclease usable by sortase ("sortase-usable nucleophile") comprising a first member of a binding pair, so that the polypeptide becomes sortagged with the first member of the binding pair. In some embodiments the crude lysate comprising the sortagged polypeptide is incubated with a moiety comprising the second member of the binding pair, under conditions suitable for the first and second members of the binding pair to bind to each other. In some embodiments the polypeptide comprising the sortagged VHH is then isolated from the crude lysate via binding of the first and second members of the binding pair. For example, in some embodiments the second member of the binding pair is attached to a support, and the polypeptide comprising the sortagged VHH is immobilized to a support via binding of the first and second members of the binding pair. In some embodiments the second member of the binding pair is linked to a moiety that can be purified using an affinity-based approach.

In some embodiments immobilizing a polypeptide to a support comprises (a) incubating a crude lysate of cells (e.g., $E.\ coli$) that express a sortaggable polypeptide comprising a VHH (e.g., comprising VHH-TRS) with sortase and a sortase-usable nucleophile comprising a first member of a binding pair, so that the VHH becomes sortagged with the first member of the binding pair; and (b) exposing (incubating) a support that has the second member of the binding pair (attached thereto under conditions suitable for at least some of the polypeptides to become immobilized to the support via binding of the first and second members of the binding pair to each other. In some embodiments the polypeptide may be at least partially purified from the crude lysate prior to sortagging. For example, the lysate may be subjected to fractionation, or if the polypeptide comprises a tag, the tag may be used to at least partly purify the polypeptide. In certain embodiments the sortase-usable nucleophile can be represented as follows, where $B^1$ comprises a first member of a binding pair and n is 0 to 100.

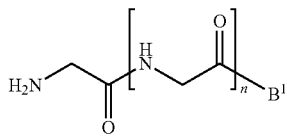

Polypeptides comprising a sortagged VHH are exposed to (incubated with) a support that has the second member of the binding pair ($B^2$) attached thereto under conditions suitable for at least some of the polypeptides to become immobilized to the support via binding of the first and second members of the binding pair to each other. Any of a variety of different binding pairs can be used in various embodiments. Binding pairs can comprise, e.g., antigen-antibody, biotin-avidin, complementary oligonucleotides, aptamer-polypeptide, or any of various other pairs of molecules that exhibit strong and relatively specific binding to each other. In some embodiments the sortase-usable nucleophile comprises a small molecule as a first binding pair member. For example, in some embodiments the sortase-usable nucleophile comprises a fluorescent dye or non-fluorescent hapten, e.g., fluorescein, tetramethylrhodamine, Texas Red, dansyl, an Alexa Fluor, dinitrophenyl (DNP), biotin or nitrotyrosine. In some embodiments the sortase-usable nucleophile comprises a tag such as an HA tag, 6×His tag, or Myc tag. In some embodiments the second binding pair member comprises a protein, e.g., an antibody, that binds to the small molecule or tag. In some embodiments the tag comprises 6×His, and the support comprises a metal ion (e.g., nickel or cobalt), e.g., Ni Sepharose, NTA-agarose, His60 Ni, HisPur resin, or TALON resin. Where the term "avidin" is used herein, embodiments pertaining to avidin, streptavidin, or derivatives and structurally related molecules (analogs) that have the ability to specifically bind to biotin, such as Neutravidin and nitroavidin (also known as CaptAvidin™), are provided. In some embodiments a biotin binding protein (BPP) that does not comprise avidin is used, e.g., instead of avidin. Where the term "biotin" is used herein, embodiments pertaining to biotin or a biotin analog such as desthiobiotin, 2-iminobiotin, diaminobiotin, etc., are provided. One of ordinary skill in the art can select an appropriate biotin and/or avidin or combination depending, e.g., on factors such as the desired strength and/or durability/reversibility of the interaction. For example, desthiobiotin is a biotin analogue that binds less tightly to biotin-binding proteins and is easily displaced by biotin, which may be desirable for certain applications.

For purposes of description it will be assumed that biotin and avidin are used as the binding pair. In some embodiments the nucleophile comprises $(G)_n$X-biotin, where X represents any moiety to which biotin can be attached, e.g., an amino acid sequence comprising at least one amino acid having an amine-containing side chain (e.g., lysine). For example, in some embodiments the molecule comprises $(G)_3$K-biotin. In some embodiments polypeptides comprising VHHs sortagged with a biotin-containing nucleophile are retrieved by adsorption onto a support comprising avidin attached thereto (also referred to as an avidin-modified support). In some embodiments unincorporated sortase-usable nucleophile is removed following the sortagging reaction and prior to contacting the polypeptide comprising a sortagged VHH with the support. This can be accomplished using a variety of different approaches. The approach selected may depend at least in part on the nature and/or size of the particular nucleophile, e.g., the identity of binding pair member $B^1$. In general, any approach that would remove the nucleophile but not the sortagged polypeptide may be used in various embodiments. In some embodiments, the nucleophile is removed by dialysis, e.g., using a cartridge based device, or by spotting aliquots of lysates as individual drops on the surface of a dialysis membrane, or by gel filtration.

Any of a variety of supports, e.g., supports conventionally used in the art for preparation of affinity matrices, can be used. In some embodiments a support comprises particles, e.g., agarose or magnetic particles (e.g., beads). In some embodiments a support comprises at least a portion of the interior of a vessel such as a well (e.g., a well of a multiwell plate), Eppendorf tube, a depression in a substantially planar support such as a slide, etc. In some embodiments immobilization of the sortagged polypeptides facilitates retrieval of target antigen(s) of the VHH, as described further below. In some embodiments a support is modified with a sortase-usable nucleophile, e.g., peptides comprising $(G)_n$ at their N-terminus, and the modified support is used to provide the incoming nucleophile, i.e., the modified support is incubated with sortase and the polypeptide comprising a VHH and a TRS. The sortase-usable nucleophile can be covalently or noncovalently attached to the support using any suitable method. In various embodiments a sortase-usable nucleophile is applied to the support by coating the support with the nucleophile or depositing the nucleophile on the support. The support may be modified over part or all of its surface. The support may comprise one or more functional groups to which the sortase-usable nucleophile can be attached while leaving the $(G)_n$ free for use in a sortase-mediated reaction. In some embodiments, exposure of the surface of the modified support to a crude lysate (or lysate fraction) containing polypeptides comprising the sortaggable VHH in the presence of sortase results in specific immobilization of the polypeptides comprising the VHH, e.g., without requiring an affinity-based purification step.

In some embodiments, a support having polypeptides comprising the VHH attached thereto, e.g., a support generated using any of the approaches described above, is exposed to the crude immunogen used for immunization or a surrogate thereof. The crude immunogen may be, for example, an aliquot of the original preparation that was used for immunization or may be prepared in substantially the same way from the same source or a substantially identical or equivalent source. In various embodiments a surrogate of the immunogen can be any composition that contains the target antigen or may contain the target antigen. One of ordinary skill in the art would be able to select a surrogate that would reasonably be expected to contain the target antigen. For example, if primary cells are used as the immunogen, a surrogate may be an immortalized cell line of the same cell type. After the support has been exposed to the immunogen (or surrogate) for an appropriate period of time to permit binding of at least some target antigen to the VHH attached to the support, unbound material in the immunogen or surrogate is removed, e.g., by washing. A wash buffer and wash conditions that would not be expected to disrupt binding of the VHH to the target antigen may be selected.

In some embodiments a polypeptide comprising the VHH is exposed to the immunogen prior to immobilizing the polypeptide to a support. For example, in some embodiments a method of characterizing a target antigen to which a VHH binds comprises: (a) exposing a polypeptide comprising a VHH and a TRS (e.g., comprising VHH-TRS) to the immunogen or a surrogate thereof under conditions in which the target antigen can bind to the VHH; (b) immobilizing the polypeptide to a support; (c) separating material that binds to the VHH from material that does not bind to the VHH; and (d) subjecting material that binds to the VHH to at least one characterization procedure. In certain embodiments, the polypeptide comprising the VHH is immobilized after allowing material in the immunogen to bind to the VHH in solution for a suitable period of time. Immobilization and separation of unbound material may be performed as described above.

In some embodiments a support is subjected to one or more suitable blocking or washing steps in any of the above procedures in order to, e.g., inhibit nonspecific binding or reaction and/or remove unbound or unreacted material. Exposing a polypeptide comprising a VHH and a TRS to the immunogen or a surrogate thereof under conditions in which the target antigen can bind to the VHH can be performed for varying periods of time. For example in certain nonlimiting embodiments incubation is performed for between 1 and 48 hours, e.g., between 6 and 24 hours. Incubation of a polypeptide comprising a VHH sortagged with a moiety comprising a first member of a binding pair with a moiety comprising a second member of the binding pair can be performed for varying periods of time. For example in certain nonlimiting embodiments incubation is performed for between 1 and 48 hours, e.g., between 6 and 24 hours. Any such step(s) may be performed at a variety of temperatures. For example, in some embodiments a temperature ranging from about 4 degrees C. to about 30 degrees C. is used. In some embodiments room temperature, e.g., about 20-25 degrees C., is used.

In some embodiments material that binds to the VHH is subjected to at least one characterization procedure. "Characterization procedure" refers to any procedure (method, assay, technique, etc.) that provides information regarding the structure and/or other identifying characteristics of a material, e.g., a polypeptide. Exemplary characterization procedures of use include, e.g., mass spectrometry, 2D gel electrophoresis, chemical protein sequencing via Edman degradation, analyzing binding to a protein microarray (e.g., a microarray comprising antibodies whose binding targets are known), spectroscopy, chromatography, etc. In some embodiments structural information comprises an at least partial sequence. For example, in some embodiments structural information comprises the sequence of one or more peptide portions of a protein antigen. In some embodiments an identifying characteristic comprises molecular weight, isoelectric point, retention time on a column of a specified resin composition and/or in a specified solvent (e.g., an ion exchange column, hydrophobic interaction column, etc.), binding (or lack thereof) to an antibody, lectin, metal, etc. In some embodiments sufficient identifying characteristics, e.g., sufficient sequence and/or other information, is obtained to determine the identity of a protein. In some embodiments, determining the identity of a protein comprises determining an accession number or name of the protein or of the gene that encodes the protein, as present in a publicly available database such as any of the databases available at the National Center for Biotechnology Information (NCBI) website (www.ncbi.nih.gov) or available at the Universal Protein Resource website (www.uniprot.org). Exemplary databases include, e.g., RefSeq, Gene, Nucleotide (Genbank), Protein, Genome, UniProtKB/SwissProt, UniProtKB/Trembl, etc. A name can be any name recognized in the art (e.g., in the scientific literature or databases such as the afore-mentioned databases) for a particular protein or gene. In some embodiments a name is an official name recognized or assigned by an art-accepted gene nomenclature committee, such as the HUGO Gene Nomenclature Committee (HGNC) or an art-recognized synonym or alternate name.

In some embodiments, a characterization procedure comprises performing mass spectrometry on material bound to the VHH. In some embodiments a peptide mass fingerprint is obtained. In some embodiments material bound to the VHH is subjected to cleavage in order to generate peptides amenable to mass spectrometric sequence determination. In some embodiments cleavage comprises proteolytic digestion using an enzyme such as trypsin or chymotrypsin or chemical cleavage using a reagent such as cyanogen bromide. In some embodiments the VHH and material bound thereto are removed from the affinity matrix prior to cleavage. In some embodiments VHH and material bound thereto are subjected to cleavage without being removed from the affinity matrix, e.g., the affinity matrix with VHH attached thereto is exposed to the cleavage agent. In some embodiments material bound to the VHH is separated from the VHH.

In some embodiments material bound to the VHH is eluted from the VHH by, e.g., altering ionic strength, altering pH, thermal agitation, and/or the use of organic solvents. In some embodiments proteins bound to VHH are separated from each other or from the VHH based at least in part on their size (e.g., hydrodynamic volume), molecular weight, or isoelectric point via, e.g., size exclusion chromatography or by SDS-PAGE (sodium dodecyl sulfate-polyacrylamide gel electrophoresis) analysis. Proteins can be separated based, e.g., on polarity and/or hydrophobicity via high performance liquid chromatography or reversed-phase chromatography. An isoelectric point can be determined, e.g., by running material through a pH graded gel or an ion exchange column. In some embodiments samples comprising VHH and eluted material are resolved on a gel, e.g., using SDS- PAGE. Bands can be visualized by appropriate staining (e.g., silver staining). Bands that represent material that bound to the VHH are excised and subjected to a characterization procedure such as mass spectrometry. A control can be performed in parallel using a VHH that is specific for an antigen that is not found in the immunogen or surrogate immunogen. The control may help distinguish material that specifically bound to the VHH of interest from nonspecific bands or the VHH itself. Mass spectrometric characterization can be performed using a variety of different approaches known in the art (see, e.g., Griffiths W J, Wang Y Chem Soc Rev. (2009) 38(7):1882-96; Seidler J, et al. Proteomics (2010) 10(4):634-49). In some embodiments peptide sequences are determined by mass spectrometry e.g., by searching the peptide spectra obtained against appropriate sequence databases. Proteins that contain peptides having those sequences are then determined. In some embodiments a characterization procedure comprises assessing the target antigen for presence of a moiety added by co- or post-translational modification, such as phosphorylation or glycosylation. For example, in some embodiments a sample of material is contacted with an enzyme such as a phosphatase or glycosidase that would remove a co- or post-translationally added moiety, and the resulting material is compared with material not contacted with the enzyme. A shift in molecular weight, isoelectric point, or other properties, serves as an indicator that the protein contained a co- or post-translationally added moiety that was removed by the enzyme. Other methods include determining whether the material binds to a lectin, which binding serves as an indicator of the presence of glycosylation.

In some embodiments a target antigen comprises a complex comprising two or more polypeptide chains. For example, certain proteins comprise multiple polypeptide chains, which may be associated by covalent or non-covalent bonds. Some polypeptides are cleaved by endogenous proteases and the cleavage products remain associated via covalent bonds (e.g., disulfide bonds) and/or non-covalent bonds. Some polypeptides are translated as individual chains that become physically associated with each other via covalent and/or non-covalent bonds to form complexes such as homodimers, heterodimers, or multimers comprising three or more chains (which may be identical or different in sequence depending on the particular protein(s) involved). For example, many receptors, channels, enzymes, transcription factors, and other proteins exist as multi-chain complexes when in functional form and/or are regulated at least in part by complex formation/dissociation. In some embodiments a target antigen comprises a complex comprising two or more polypeptide chains. In some embodiments determining the identity of a target antigen to which a VHH binds comprises determining the identity of one or more polypeptide chains that are present in material to which a VHH binds, wherein the one or more polypeptide chains naturally exist in a complex, thereby determining that the complex is a target antigen. In some embodiments determining the identity of a target antigen to which a VHH binds comprises determining the identity of two or more polypeptide chains that are present in material to which a VHH binds, wherein the two or more polypeptide chains naturally exist in a complex, thereby determining that the complex is a target antigen of the VHH. In some embodiments determining the identity of a target antigen to which a VHH binds comprises determining that each of multiple polypeptide chains are present in material to which a VHH binds, wherein the multiple polypeptide chains naturally exist as a complex, thereby determining that the complex is a target antigen of the VHH. In some embodiments the complex is naturally composed of n chains, where n is between 2 and 6, and the method comprises determining that each of the n chains is present in material to which the VHH binds. In some embodiments a method comprises determining to which of multiple chains in a complex the VHH binds or identifying a region of the complex to which the VHH binds.

In some embodiments, a method comprises identifying an epitope to which a VHH binds, e.g., an epitope to which the VHH binds on a target antigen. In some embodiments, a method comprises: (a) determining the identity of a target antigen of a VHH; and (b) identifying an epitope to which a VHH binds. An epitope can be identified using any of various epitope mapping techniques known in the art. Such techniques include, e.g., computational methods of epitope prediction based on the sequence of a protein antigen, X-ray co-crystallography (which allows direct visualization of the interaction between the antigen and antibody), methods that involve monitoring the binding of the antibody to antigen fragments or mutated variants, and competition analysis (e.g., with antigen fragments or, if available, with antibodies for which a target epitope has previously been determined). Examples of epitope identification methods include, e.g., (i) array-based peptide scanning, which uses a library of peptide sequences from overlapping and non-overlapping segments of a target protein and tests for their ability to bind the antibody of interest; (ii) site-directed mutagenesis, in which systematic mutations of amino acids are introduced into a protein sequence followed by measurement of antibody binding in order to identify amino acids that comprise an epitope; (iii) mutagenesis mapping utilizing a comprehensive mutation library, with each clone containing a unique amino acid mutation and the entire library covering every amino acid in the target protein. Amino acids that are required for antibody binding can be identified by a loss of reactivity and mapped onto protein structures to visualize epitopes. Further information on exemplary methods of epitope identification is found in "Epitope Mapping Protocols" Methods in Molecular Biology, 2009, Volume 524. In various embodiments an epitope may be a linear epitope, a discontinuous epitope, a conformational epitope, or an epitope comprising contributions from two or more polypeptides of a protein complex. In some embodiments an epitope comprises a co-translational or post-translational modification.

In some embodiments one or more parameters that characterizes the interaction of a binding agent, e.g., a polypeptide comprising a VHH, with a target entity or target antigen is determined. For example, kinetics (on and/or off rates) and/or binding strength (affinity) between a protein and a target entity or target antigen may be determined. In some embodiments, one or more parameters is determined using surface plasmon resonance (SPR, e.g., using an SPR system such as those available from Biacore, Life Sciences, GE Healthcare), isothermal titration calorimetry, differential scanning calorimetry, or equilibrium dialysis. Other methods that may be used in various embodiments to assess kinetics and/or affinity include, e.g., a quartz crystal microbalance, optical cantilever, microchannel resonator, dual polarisation interferometer, coupled waveguide plasmon resonance, capillary electrophoresis, resonance energy transfer, electrochemiluminescence, fluorescence anisotropy, fluorescence polarization, or fluorescent correlation analysis. In some embodiments SPR is performed on a UTA instrument, e.g., a BIAcore 3000 instrument (BIAcore, Uppsala, Sweden). In some embodiments a target entity or target antigen or polypeptide comprising a VHH is immobilized on an SPR sensor chip, e.g., a BIAcore sensor chip (e.g., BIAcore CM5 sensor chip). Immobilization may be performed using any suitable method. In some embodiments amine coupling or thiol coupling may be used. In some embodiments a polypeptide comprising a target antigen and a TRS is produced, and a sortase-mediated reaction is used to attach the polypeptide to a sensor chip that has a sortase-usable nucleophile attached thereto. Concentration series of the protein can be applied to the chip in an appropriate buffer and at an appropriate flow rate (e.g., a buffer and flow rate recommended by the manufacturer of the SPR apparatus). After each measurement, residual protein is removed. In some embodiments association and/or dissociation rate constants (Ka and Kd) are calculated, e.g., as recommended by the manufacturer and/or using software provided by the manufacturer, or using any appropriate method or software known in the art. KD is calculated by dividing Kd by Ka.

In some embodiments a polypeptide comprising a TRS, e.g., a polypeptide comprising a VHH-TRS is immobilized to a sensor via a sortase-mediated reaction, wherein the sensor has a sortase-usable nucleophile, e.g., a nucleophile comprising $(G)_n$, where n is 1 to 100, attached covalently or noncovalently thereto. In some embodiments a sensor comprising a sortase-usable nucleophile attached covalently or noncovalently thereto is provided. In some embodiments a sensor comprises a surface plasmon resonance (SPR) sensor. In some embodiments a sensor comprises a microcantilever, microbalance, or microchannel.

In some embodiments a binding agent, e.g., an antibody, e.g., a VHH, binds to a target antigen or target entity with a KD of less than about $10^{-6}$M, less than about $10^{-7}$M, less than about $10^{-8}$M less than about $10^{-9}$M, less than about $10^{-10}$M, less than about $10^{-11}$M, or less than about $10^{-12}$M. In certain embodiments a binding agent, e.g., an antibody, e.g., a VHH, binds to a target antigen or target entity with a KD of between about $10^{-6}$M and about $10^{-12}$M, e.g., between about $10^{-6}$M and about $10^{-7}$M, between about $10^{-7}$M and about $10^{-8}$M, between about $10^{-8}$M and about $10^{-9}$M, between about $10^{-9}$M and about $10^{-10}$M, between about $10^{-10}$M and about $10^{-11}$M, or between about $10^{-11}$M and about $10^{-12}$M.

In some embodiments, the invention provides a nucleic acid (e.g., a cDNA or mRNA) that encodes a polypeptide comprising a VHH, e.g., a VHH identified as described herein. In some embodiments the nucleic acid comprises a portion that encodes a TRS, e.g., the nucleic acid encodes a polypeptide comprising a VHH in frame with a TRS. In some embodiments the nucleic acid comprises one or more expression control elements. In some embodiments the open reading frame encoding the VHH is operably linked to an expression control element. In some embodiments the invention provides a vector comprising any of the aforementioned nucleic acid(s). The nucleic acid(s) or vector(s) can be used for any of a variety of purposes. In some embodiments a nucleic acid or vector is introduced into a cell. The nucleic acid(s) or vector(s) may be suitable for introduction into and/or expression in any cells known in the art. In some embodiments the invention provides a cell that expresses a polypeptide comprising a VHH identified or generated as described herein. In some embodiments the cell is genetically modified to express the polypeptide. As used herein, a "genetically modified cell" encompasses an original genetically modified cell and descendants thereof that at least in part retain the genetic modification. In some embodiments expression of a polypeptide comprising a VHH is transient (e.g., achieved via transient transfection). In some embodiments the nucleic acid is stably maintained in the cell. In some embodiments the nucleic acid is in a stable episome or is integrated into the genome of a cell, so that it is inherited by descendants of the cell. In some embodiments the nucleic acid is expressed under control of a regulatable expression control element, e.g., an inducible or repressible promoter. In some embodiments expression is regulated using a recombinase such as Cre (e.g., recombinase-mediated deletion of a region flanked by sites for the cleavage by the recombinase alters expression, e.g., turning expression off by causing deletion of a promoter region or turning expression on by bringing a coding sequence into proximity to a promoter). In some embodiments the nucleic acid is expressed under control of a cell type specific promoter.

Polypeptides comprising VHHs (e.g., polypeptides comprising VHHs for which the identity of the target antigen has been determined or is known or polypeptides comprising VHHs for which the identity of the target antigen is unknown) and/or nucleic acids encoding such polypeptides, can be modified in any of a variety of ways and/or used for any of a variety of purposes. In some embodiments a nucleic acid comprising an open reading frame encoding a fusion protein comprising the VHH and a polypeptide of interest (POI) is produced. In some embodiments VHH is located N-terminal with respect to POI (VHH-POI) In some embodiments VHH is located C-terminal with respect to POT (POI-VHH), For purposes of description, a fusion protein comprising a VHH and an additional polypeptide (POI) may be represented herein as VHH-POI, but it should be understood that embodiments in which VHH and such additional polypeptide are positioned in any order are encompassed. It should also be understood that embodiments in which one or more distinct POIs are present flanking the VHH, e.g., $POI_1$-VHH-$POI_2$ are encompassed. In some embodiments the open reading frame is operably linked to expression control elements appropriate to direct expression in a cell of interest. In some embodiments the nucleic acid is introduced into a cell. In some embodiments the nucleic acid is expressed in the cell, resulting in production of a fusion protein comprising VHH-POI by the cell. In some embodiments the nucleic acid is codon optimized for expression in cell of a species of interest. In some embodiments a polypeptide comprising a VHH is expressed as a fusion with a POI such that the resulting fusion product will be cytoplasmic (e.g., the polypeptide is expressed without a signal sequence (also referred to as a leader sequence or secretion signal sequence) that would otherwise direct secretion). In some embodiments the signal sequence is located at the N-terminus of the polypeptide. In some embodiments the VHH sequence is preceded by a signal sequence appropriate to direct co-translational membrane insertion and translocation in yeast or in other eukaryotes. In some embodiments the VHH-POI is secreted by the cell. In some embodiments the polypeptide comprises a subcellular targeting sequence that directs translocation of the protein into an organelle such as a mitochondrion.

In some embodiments a polypeptide comprising a VHH, e.g., a VHH for which the identity of target antigen has been determined, is fused genetically to any POI. A polypeptide of interest can be a full length polypeptide or a portion thereof (e.g., a portion comprising a protein domain) of interest. In general, a POI can comprise any polypeptide or portion thereof. A protein domain is a distinct functional and/or structural unit of a protein. Protein domains are often recurring (sequence or structure) units, which may exist in various contexts, e.g., in different proteins. In some embodiments a protein domain is listed in a protein domain database such as the NCBI Conserved Domains Database (Marchler- Bauer A, et al., CDD: a Conserved Domain Database for the functional annotation of proteins. Nucleic Acids Res. 2011 January; 39(Database issue): D225-9; available at http://www.ncbi.nlm.nih.gov/cdd). In some embodiments a protein domain comprises a compact structural unit that is found amongst diverse proteins. In some embodiments, a protein domain folds independently within its structural environment. In some embodiments a protein domain comprises a binding domain (e.g., a domain that participates in at least one PPI) or a catalytic domain. In some embodiments a protein domain comprises a DNA binding domain.

In some embodiments a fusion protein comprising VHH-POI is expressed in a cell that comprises a target antigen. The VHH binds to the target antigen, thereby bringing the POI into close proximity to the target antigen. In this manner, the physical juxtaposition of the antigen for which the VHH is specific and the POI fused to the VHH can be achieved. In some embodiments such juxtaposition allows the imposition of protein-protein interactions (PPI) that might not occur naturally, or that might occur only under certain conditions. In some embodiments the fusion protein comprises a secretion signal sequence. In some embodiments the POI comprises a sequence that is naturally encoded or expressed by a cell in which the VHH-POI is to be expressed. In some embodiments the POI comprises a sequence that is not naturally encoded or expressed by the cell in which the VHH-POI is to be expressed. In some embodiments the POI comprises a variant of a protein that is naturally encoded or expressed the cell in which the VHH-POI is to be expressed. In some embodiments the variant comprises a naturally occurring sequence, e.g., a naturally occurring mutant sequence. In some embodiments the variant comprises an artificial sequence.

In some embodiments a POI comprises a reporter protein (RP). In some embodiments a reporter molecule comprises a fluorescent protein (FP). In some embodiments a polypeptide comprising a VHH is expressed as a fusion with a POI such that the resulting fusion product will be cytoplasmic. In some embodiments a nucleic acid construct encoding such a polypeptide is expressed in yeast or other eukaryotic cells (e.g., insect; *C. elegans*; vertebrate). The subcellular distribution of the VHH and its bound target(s) may be determined, e.g., by fluorescence microscopy. In some embodiments the VHH sequence is preceded by a signal sequence appropriate to direct co-translational membrane insertion and translocation in yeast or in other eukaryotes. In this case the polypeptide comprising a VHH-RP fusion should enter the secretory pathway and may report on the distribution of the VHH-bound antigen in the secretory pathway or extracellularly. In some embodiments administration of a VHH-RP to a subject labels cells that express a target antigen, e.g., cells that express a target antigen at their surface.

In some embodiments a polypeptide comprising a VHH comprises one or more amino acids located N-terminal or C-terminal with respect to the VHH and/or located N-terminal or C-terminal with respect to any one or more other elements of the polypeptide. For example, VHH-encompasses embodiments in which VHH is directly fused to RP and embodiments in which VHH and RP are separated by one or more amino acids. Similarly, VHH-POI encompasses embodiments in which VHH is directly fused to POI and embodiments in which VHH and POI are separated by one or more amino acids. In some embodiments one or more amino acids are located N-terminal to VHH and/or one or more amino acids are located C-terminal to RP or POI. For example, in some embodiments the polypeptide comprises $(Xaa)_j$-VHH-$(Xaa)_k$-RP-$(Xaa)_l$, $(Xaa)_j$-VHH-$(Xaa)_k$-POI-$(Xaa)_l$, wherein the Xaa can independently be any amino acid, and j, k, and/or l can each independently be between 0 and 1,000. In some embodiments j, k, and/or l is between 0 and 10, 50, or 100. In some embodiments, $(Xaa)_j$, $(Xaa)_k$, and/or $(Xaa)_l$ comprises a linker, a tag, or both. In some embodiments a polypeptide comprising $(Xaa)_j$-VHH-$(Xaa)_k$-POI-$(Xaa)_l$, or $(Xaa)_j$-VHH-$(Xaa)_k$-POI-$(Xaa)_l$, is in any such use, method, product, or composition described for a polypeptide comprising VHH-RP or VHH-POI, respectively. In some embodiments one or more additional amino acids are located N-terminal or C-terminal to any of VHH, RP, and/or POI, as described for VHH-RP and VHH-POI. In some embodiments a POI comprises at least two distinct polypeptides or portions thereof. For example, in some embodiments a POI comprises at least a portion of each of two naturally occurring polypeptide domains, polypeptides, or variants thereof. In some embodiments at least one of the polypeptides comprises a reporter protein.

In some embodiments, intracellular expression of a polypeptide comprising VHH or comprising VHH-POI is used to assess the effect of inhibiting protein-protein interactions (PPI), or imposing new interactions. In some embodiments, a method of assessing the effect of inhibiting a PPI comprises: (a) inhibiting a PPI of first and second proteins by expressing a polypeptide comprising a VHH in a cell, wherein the VHH binds to the first or second polypeptide; and (b) detecting an alteration in at least one phenotypic characteristic of the cell. In some embodiments, a method of assessing the effect of imposing a PPI comprises: (a) imposing a PPI between a first protein and a POI by expressing a polypeptide comprising a VHH-POI in a cell, wherein the VHH binds to the first polypeptide; and (b) detecting an alteration in at least one phenotype of the cell. The effect of inhibiting or imposing a PPI on any of a wide variety of phenotypic characteristics can be assessed. For example, the effect on cell viability, proliferation, morphology, gene expression, cell surface marker expression, response to extracellular signals, differentiation capacity, or any functional property of interest may be assessed in various embodiments. In some embodiments the cells are diseased cells, e.g., tumor cells, and a disease-associated phenotype is assessed. In some embodiments a PPI or protein is identified as a candidate drug target. For example, in some embodiments if inhibiting a protein has an effect of potential therapeutic benefit, the protein is identified as a candidate drug target. In some embodiments if inhibiting a PPI has an effect of potential therapeutic benefit, the PPI and/or protein is identified as a candidate drug target. In some embodiments a polypeptide comprising a VHH may serve as a candidate drug. In some embodiments a method comprises performing a screen to identify an agent, e.g., a small molecule, that inhibits the PPI or inhibits expression of one of the interacting proteins. In some embodiments a POI has an enzymatic activity. For example, the POI may comprise a kinase, phosphatase, methyltransferase, protease, endonuclease, GTPase, lipase, to name but a few. In some embodiments a VHH-POI comprising a POI that has an enzymatic activity may enzymatically modify a target antigen to which the VHH binds. In some embodiments a VHH binds to a region of a target antigen that is not required for or involved in a known activity of the target antigen. In some embodiments a VHH binds to a region of the target antigen that is required for or involved in a known activity of the target antigen. In some embodiments a POI, if present, comprises a bulky protein that blocks activity of the target antigen or blocks physical interaction of the target antigen with a cellular molecule with which it would otherwise physically interact.

In some embodiments, a nucleic acid (e.g., a cDNA or mRNA) that encodes a target antigen of a VHH of interest is obtained, wherein the VHH of interest is identified as described herein and/or wherein the target antigen has been characterized or its identity has been determined, e.g., as described herein. A nucleic acid that encodes the target antigen can be obtained using a variety of methods. In some embodiments, once the identity or at least partial sequence of a target antigen has been determined, primers can be synthesized and used to clone or amplify a sequence that encodes the target antigen from a cDNA library, which library can be obtained or prepared using standard methods. In some embodiments the VHH is used to screen an expression library, and a cDNA encoding the target antigen is identified. In some embodiments a cDNA encoding a target antigen can be obtained from a commercial or non-commerical source. For example, cDNA clones encoding numerous proteins endogenous to various species can be obtained from, one or more distributors of the I.M.A.G.E. collection (e.g., American Type Culture Collection, Manassas, V; Thermo Fisher Scientific/Open Biosystems, Huntsville, Ala.; Life Technologies/Invitrogen, Carlsbad, Calif. Source BioScience Geneservice™, Cambridge, UK Source BioScience imaGenes GmbH, Berlin Germany, or K.K., DNAFORM (RIKEN cDNA clones) Tsurumi-ku, Yokohama City, Kanagawa, 230-0046, Japan, among others. In some embodiments a vector comprising a nucleic acid encoding an identified target antigen or a portion thereof is generated. The vector can be of any type in various embodiments. In some embodiments the vector is an expression vector, wherein a sequence coding for a target antigen is inserted so that it is operably linked to expression control elements, e.g., a promoter, appropriate to direct transcription in a cell. Expression control elements can be constitutive, regulatable (e.g., inducible or repressible), or tissue specific in various embodiments. In some embodiments a nucleic acid that encodes (i) a target antigen and (ii) a TRS is produced, wherein the TRS is in frame with the sequence encoding the target antigen. Translation of the resulting coding sequence results in a fusion protein comprising the target antigen and the TRS. The fusion protein can then be modified with sortase.

A nucleic acid or vector encoding a polypeptide comprising a target antigen of interest can be used for any of a variety of purposes. In some embodiments the nucleic acid or vector is introduced into a cell. In some embodiments a genetically engineered cell that has a coding sequence comprising a target antigen (e.g., a cDNA encoding the target antigen) integrated into its genome is produced. The cell can be prokaryotic (e.g., bacterial) or eukaryotic (e.g., fungal, insect, mammalian, etc.). In some embodiments the nucleic acid, vector, or cell is used to produce the target antigen using, e.g., recombinant protein expression methods known in the art. In some embodiments a genetically engineered cell that harbors a genetic alteration that at least partly functionally inactivates a gene that encodes a target antigen is produced. In some embodiments a gene is at least partly functionally inactivated by disrupting the gene or by deleting at least a portion of the gene. The genetically engineered cell having an at least partly inactivated gene can be produced using standard methods, such as by insertional mutagenesis using transposons or retroviruses or targeted mutagenesis, e.g., mediated by homologous recombination. Appropriate screening and/or selection can be performed to identify cells harboring a desired genetic alteration. In some embodiments a gene is at least partly functionally inactivated by introducing into a cell or organism an RNAi agent (e.g., a short interfering RNA) or antisense oligonucleotide into a cell or by expressing an RNAi agent (e.g., a short hairpin RNA) or expressing an antisense RNA intracellularly.

In some embodiments a transgenic non-human animal is generated, e.g., a rodent such as a mouse or rat, at least some of whose cells are transgenic for a nucleic acid encoding a target antigen. In some embodiments the transgenic animal, or cells obtained from the transgenic animal, are used, e.g., as a source of the target antigen, to study the role of the target antigen in normal physiology or disease, as animal models for testing candidate agents, etc. In some embodiments a transgenic non-human animal is generated, at least some of whose cells harbor a genetic alteration that at least partly functionally inactivates a gene that encodes a target antigen identified as described herein. In some embodiments the transgenic animal, or cells obtained from the transgenic animal are used, e.g., to study the role of the target antigen in disease, as animal models for testing candidate agents, etc.

In some embodiments the disclosure provides a polypeptide comprising (a) a VHH; and (b) a TRS. In some embodiments the TRS is located at or near the C-terminus of the polypeptide. In some embodiments the VHH may be any VHH. In some embodiments the VHH is identified, isolated, or generated as described herein. In some embodiments a polypeptide comprising (a) a VHH; and (b) a TRS is modified using sortase, using, e.g., any of the following moieties: an amino acid, a peptide, a protein, a polynucleotide, a carbohydrate, a tag, a metal atom, a chelating agent, a contrast agent, a catalyst, a non-polypeptide polymer, a recognition element, a small molecule, a lipid, a label, an epitope, a small molecule, a therapeutic agent, a crosslinker, a toxin, a radioisotope, an antigen, or a click chemistry handle. In some embodiments a moiety comprises two or more of the afore-mentioned moieties. In some embodiments a small molecule is a fluorophore or biotin. In some embodiments a small molecule has one or more useful pharmacological properties. For example, in some embodiments a small molecule is a ligand, e.g., an agonist or antagonist, of a receptor. In some embodiments a small molecule modulates, e.g., activates or inhibits, an enzyme. In some embodiments a small molecule modulates activity or expression of a protein or RNA involved in a biological process of interest.

In some embodiments a moiety prolongs the circulation time of the polypeptide in the blood as compared with the circulation time in the absence of the moiety. In some embodiments the moiety comprises an organic polymer, e.g., a polyalkylene glycol, e.g., PEG. In some embodiments the moiety comprises a peptide that binds to a serum protein that has a relatively long circulation time in the blood, e.g., a circulation time of at least 24, 48, 72 hours, up to about 2-4 weeks, or 4-6 weeks (e.g., on average). In some embodiments the serum protein is albumin (e.g., human serum albumin) or an immunoglobulin or portion thereof. In some embodiments the moiety comprises at least a portion of an immunoglobulin heavy or light chain constant region. In some embodiments the constant region is a human constant region. In some embodiments the moiety comprises a peptide that binds to a serum protein that has a relatively long circulation time in the blood, such as albumin. Exemplary albumin-binding peptides are described, e.g., in PCT/GB2005/001321 (WO/2005/097202) and/or PCT/US2006/

033406 (WO/2007/106120). In some embodiments a moiety comprises a substantially non-immunogenic polypeptide. In some embodiments a bispecific VHH comprises a first VHH that binds to a target antigen of interest and a second VHH that binds to a serum protein that has a relatively long circulation time in the blood. In some embodiments a moiety that prolongs the circulation time of an agent in the blood has a molecular weight of between 5 kD and 200 kD, e.g., about 10 kD, 20 kD, 30 kD, 40 kD, 50 kD, 60 kD, 70 kD, 80 kD, 90 kD, 100 kD, 110 kD, 120 kD, 130 kD, 140 kD, or 150 kD. In some embodiments a preparation of such a moiety has an average molecular weight of between 5 kD and 100 kD, or between 100 kD and 200 kD, e.g., about 10 kD, 20 kD, 30 kD, 40 kD, 50 kD, 60 kD, 70 kD, 80 kd, 90 kD, 100 kD, 110 kD, 120 kD, 130 kD, 140 kD, or 150 kD.

In some embodiments the invention provides a polypeptide comprising a sortase-usable nucleophile comprising a VHH. In some embodiments the VHH binds to any target antigen of interest. In some embodiments the polypeptide comprises one or more glycine residues at its N-terminus. In some embodiments the polypeptide is conjugated using sortase to a moiety that comprises an appropriately positioned TRS thereby producing a conjugate comprising the VHH and the moiety. In some embodiments the moiety is any moiety disclosed herein, wherein the moiety comprises or is modified to comprise a TRS. In some embodiments the VHH is conjugated to a naturally occurring sortase substrate or to a recombinant or synthetically produced polypeptide comprising a TRS.

In some embodiments the invention provides a polypeptide comprising a sortase-usable nucleophile comprising a VHH and a TRS. In some embodiments the VHH binds to any target antigen of interest. In some embodiments the TRS is masked. In some embodiments the polypeptide is conjugated using sortase to a sortase-usable nucleophile and/or to a moiety that comprises an appropriately positioned TRS. In some embodiments the polypeptide is first conjugated using sortase to a sortase-usable nucleophile, the TRS is unmasked, and the polypeptide is then conjugated using sortase to a moiety that comprises an appropriately positioned TRS. In some embodiments the moiety is any moiety disclosed herein, wherein the moiety comprises or is modified to comprise a TRS.

In some embodiments a polypeptide comprising (a) a VHH; and (b) a TRS is modified using sortase by addition of a click chemistry handle as described herein. This approach allows, for example, the creation of precise C-terminal to C-terminal fusions of VHHs to, for example, generate bispecific reagents. In some embodiments the VHH domains in such a bispecific reagent bind to different target entities. In some embodiments the VHH domains in such bispecific VHH domains bind to different target antigens of the same target entity. In some embodiments the VHH domains in such bispecific VHH domains bind to different epitopes of the same target antigen. In some embodiments a polypeptide comprising a target antigen modified by addition of a first click chemistry handle is joined to any moiety that comprises a second click chemistry handle that is compatible with the first click chemistry handle. In some embodiments click chemistry is used to attach a moiety of interest to a VHH that binds to a target antigen of interest. In some embodiments the resulting agent can be used or is used to deliver the moiety to cells that express the target antigen at their cell surface.

In some embodiments one or more click chemistry handles or crosslinkers comprising click chemistry handle at either of both ends is modified with a moiety of interest comprising an amino acid, a peptide, a protein, a polynucleotide, a carbohydrate, a tag, a metal atom, a chelating agent, a contrast agent, a catalyst, a non-polypeptide polymer, a recognition element, a small molecule, a lipid, a label, an epitope, an antigen, a small molecule, a therapeutic agent, a toxin, a radioisotope, a particle, or any other moiety of interest. The moiety of interest can be attached via a covalent bond or linker at any position of the click chemistry handle so long as the resulting modification does not significantly impair the ability of the modified click chemistry handle to participate in a reaction with a partner click chemistry handle. In some embodiments such modification allows the modified click chemistry handles to be used to conjugate moieties together (i.e., moieties comprising first and second partner click chemistry handles, at least one of which is modified) and also equips the resulting conjugate with the moiety of interest. In some embodiments such modification combines the generation of bispecific binding agents, e.g., bispecific VHHs, with moieties that confer properties that allow their detection (e.g., reporters such as fluorescent moieties, isotopes, biotin), isolation (e.g., tags), oligomerization (e.g., moieties such as biotin-streptavidin or other binding pair members), or use to deliver a moiety of interest to a target.

In some embodiments methods of identifying an antigen homologous to a target antigen of interest are provided. For example, in some embodiments a VHH that binds to a target antigen in an immunogen comprising or derived at least in part from cells of a first species is identified. The identity of a target antigen present in the immunogen is determined, e.g., as described herein, and the identity of an antigen having a related structure or sequence, e.g., a homolog (e.g., an ortholog) of the target antigen, endogenous to a different species is then determined. In various embodiments the first and second species may in general be any species. Multiple related, e.g., homologous antigens, endogenous to different species can be determined. For purposes of description any such species may be referred to as a "second species". In some embodiments at least one of the species is a model organism. In some embodiments, at least one species is a multicellular animal. In some embodiments, at least one species is a vertebrate. In some embodiments at least one species is a mammal. In some embodiments the first and second species are mammals. In some embodiments at least one of the species is human. In some embodiments the first species is rodent, e.g., murine, and the second species is human, or vice versa. In some embodiments the first species is human and the second species is rodent, e.g., murine, or vice versa. For example, in some embodiments mouse cells are used as an immunogen, and the identity of a protein that is a target antigen of the VHH is determined. The identity of a homologous human protein is then determined. The identity of one or more homologs can be determined using any of a variety of methods. In some embodiments one or more homologs, e.g., orthologs, of a target protein will already be recognized in the art as a homolog or ortholog and may have been assigned the same name. In some embodiments, if the target antigen is a protein, the sequence is used to search one or more publicly available protein sequence databases for homologous sequences. In some embodiments a related sequence, e.g., a homologous sequence, in a second species comprises a sequence at least 20%, 30%, 40%, 50%, 60%, 70%, 80%, 90%, 95%, 96%, 97%, 98%, 99%, or more identical to the target antigen across at least 20%, 30%, 40%, 50%, 60%, 70%, 80%, 90%, 95%, 96%, 97%, 98%, 99%, or 100% of the target antigen. In some embodiments the VHH that binds to a target antigen endogenous to a first species binds to the homologous antigen endogenous to a second species. For example, the VHH may bind to an epitope that is conserved between the two species. In some embodiments, the VHH can be used to isolate a homologous antigen from a composition comprising or derived at least in part from cells of the second species. The identity of the homologous antigen can be determined using mass spectrometry or other methods, as described above. In some embodiments, the VHH can be used to isolate a homologous antigen from an expression library derived from cells of the second species.

In some embodiments, an antibody, e.g., a VHH, that binds to a homologous target antigen endogenous to a second species is used to identify, label, or isolate cells of the second species that express the homologous target antigen, or to deliver a moiety to the cells of the second species that express the homologous target antigen, or to modulate an activity or a physical interaction of the homologous target antigen. For example, in some embodiments a VHH that binds to mouse cells of a cell type of interest is obtained. The identity of the target antigen is determined, e.g., as described herein. A homologous human antigen is identified, and an antibody, e.g., a VHH, that binds to the human antigen is obtained. In some embodiments the antibody that binds to the human antigen binds to human cells, e.g., human cells that are of the same type as the mouse cells. In some embodiments the antibody is used, e.g., to identify, isolate, or deliver a moiety to such human cells or to modulate an activity or physical interaction of the human antigen.

Once a target antigen of a VHH has been isolated or the identity of a target antigen of a VHH, or the identity of a homologous antigen, has been determined or is known, one or more additional binding agents that bind to such antigen can be obtained, if desired. In some embodiments a method comprises (a) isolating or determining the identity of a target antigen to which a VHH binds; and (b) obtaining one or more additional binding agents that bind to the target antigen. In some embodiments a method comprises (a) isolating or determining the identity of a homolog of a target antigen to which a VHH binds; and (b) obtaining one or more binding agents that bind to the homolog of the target antigen. In some embodiments a binding agent comprises an antibody. In some embodiments a binding agent comprises a VHH, scFv, single domain antibody, conventional monoclonal antibody, adnectin, or aptamer. In general, a binding agent can be generated or identified using any suitable approach known in the art. In some embodiments a conventional monoclonal antibody is obtained by immunizing an animal with an immunogen comprising the target antigen as a purified preparation and using standard hybridoma or display technology or is generated in vitro using one or more display libraries. In some embodiments any of a variety of techniques such as affinity maturation (e.g., starting from synthetic, random, or naturally occurring immunoglobulin sequences), CDR grafting, veneering, combining fragments derived from different immunoglobulin sequences, PCR assembly using overlapping primers, and similar techniques for engineering immunoglobulin sequences is used. In some embodiments multiple distinct monoclonal antibodies that bind to a target antigen or homologous antigen are obtained. The binding agents may be used in any of a variety of different applications, e.g., Western blots, immunoprecipitation, immunohistochemistry, flow cytometry, isolation or detection or neutralization of a target entity, disease diagnosis or therapy, etc. In some embodiments a binding agent, e.g., an antibody, that binds to a target antigen with higher affinity or different kinetics than does an originally identified VHH is obtained. In some embodiments a binding agent, e.g., an antibody, that binds to the same epitope of the target antigen or a homologous antigen as does an originally identified VHH is obtained. In some embodiments a binding agent, e.g., an antibody, that binds to a different epitope of the target antigen or a homologous antigen than does an originally identified VHH is obtained. In some embodiments a binding agent, e.g., an antibody, that binds to a selected epitope of a target antigen or homologous antigen is obtained. In some embodiments an antibody comprising an Fc domain is obtained. In some embodiments an antibody is capable of activating complement or interacting with Fc receptors on immune system cells. In some embodiments a human or fully humanized antibody is obtained. In some embodiments a mouse, rat, rabbit, sheep, goat, chicken, or shark antibody is obtained. In some embodiments an antibody that competes with the VHH for binding to the target antigen or a homologous antigen is obtained. In some embodiments an antibody that binds to the same epitope as the VHH is obtained. Nucleic acids encoding any of the binding agents, e.g., antibodies, can be obtained using standard methods. In some embodiments any of the binding agents is produced recombinantly. In some embodiments any of the binding agents is modified, e.g., by conjugating a moiety to it. In some embodiments any of the binding agents, e.g., antibodies, comprises at least one polypeptide chain comprising a TRS e.g., at or near its C terminus and/or comprises a glycine at its N-terminus. In some embodiments such polypeptide chain is sortagged, e.g., as described herein. Such sortagged or modified antibodies can be used for any application of interest.

In certain embodiments an immunogen comprises or is derived at least in part from a population of cells. In some embodiments cell(s) are obtained from a subject. In some embodiments cells are obtained from any tissue or organ of interest. In some embodiments cells are obtained from a fluid such as blood, sputum, lymph, mucus, saliva, urine, blood, or lymph, from bone marrow, or lymphoid tissue (e.g., lymph node, spleen). In some embodiments cells are obtained from a tumor or site of infection by a pathogen or a site of inflammation or immune-mediated tissue damage. Cell(s) obtained from a subject may be cultured (e.g., expanded in culture) prior to use. In some embodiments, cells are obtained from an individual who is apparently healthy and is not suspected of having a disease, e.g., cancer or an infection, at the time the cells are obtained. In some embodiments a cells are obtained from a subject who has or has had a particular disease. In some embodiments the disease is caused by a pathogen. In some embodiments the disease is cancer. In some embodiments the disease is an auto-immune disease. In some embodiments the subject exhibits resistance to a disease, e.g., a disease caused by a pathogen. In some embodiments the subject is recovering or has recovered from a disease, e.g., a disease caused by a pathogen. In some embodiments cells are obtained from a tissue biopsy such as an excisional biopsy, incisional biopsy, or core biopsy; a fine needle aspiration biopsy; a brushing; or a lavage. In some embodiments cells are obtained from surgical or cellular samples from a subject (e.g., excess or discarded surgical or cellular material). Methods of isolating cells from a sample are well known in the art. In some embodiments cells are obtained from a tissue sample. In some embodiments cells are isolated from a tissue sample, by dissociation, e.g., mechanical or enzymatic dissociation and, if desired, can be further purified by methods such as fluorescence activated cell sorting. Cells used in a method described herein may have been procured directly from a subject or procured indirectly, e.g., by receiving the sample through a chain of one or more persons originating with a person who procured the sample directly from the subject, e.g., by performing a biopsy or other procedure on the subject.

In some embodiments an immunogen comprises or is derived at least in part from a population of cells that exhibit one or more phenotypic characteristic(s) of interest, or are of a selected cell type, or are in a particular cell state. For example, in some embodiments an immunogen comprises or is derived from a population of cells in which at least 10%, 20%, 30%, 40%, 50%, 60%, 70%, 80%, 90%, 95%, 96%, 97%, 98%, 99%, or more of the cells (i) exhibit one or more phenotypic characteristic(s) of interest, or (ii) are of a selected cell type, or (iii) are in a particular cell state. In some embodiments a phenotypic characteristic of interest comprises expression of one or more genes, presence of one or more markers at the cell surface, secretion of one or more substances such as a cytokine or growth factor, a morphological characteristic, a staining pattern, or any other characteristic or property that could be used as a basis to distinguish or separate one or more cells from one or more other cells in a heterogenous population of cells. In some embodiments cells are selected at least in part based on size; nuclear:cytoplasmic ratio; refractility; autofluorescence; ability to exclude or accumulate one or more small molecules (e.g., fluorescent dye); ability to migrate; ability to proliferate or otherwise respond to an extracellular signal; and/or ability to elicit proliferation, activation, or other response in other cells, e.g., cells of a different cell type. In some embodiments a phenotypic characteristic is detectable or measurable using flow cytometry.

In some embodiments, cells used as an immunogen or from which an immunogen is prepared express a marker of interest, e.g., a cell surface marker of interest, or secrete a molecule of interest. Secretion of cytokines or other molecules can be assessed using, e.g., ELISA assays, protein microarrays, etc. In some embodiments a functional assay (e.g., ability to stimulate migration and/or proliferation of other cells) may be used to identify or isolate a population of cells of interest. In some embodiments a cell or population of cells may be considered "positive" or "negative" with respect to expression or secretion. In some embodiments, "positive" refers to readily evident expression or secretion, e.g., robust expression or secretion, while "negative" refers to the absence of expression or secretion (e.g., not significantly different to background levels) or a negligible level of expression or secretion. One of ordinary skill in the art will be able to distinguish cells that are positive or negative for expression of one or more marker(s) of interest and/or secretion of one or more substance(s) of interest. In some embodiments cells may exhibit a range of expression levels. In some embodiments a cell exhibits a particular pattern of cell surface marker expression, e.g., the cell is positive for one or more specified cell surface and/or is negative for one or more specified cell surface markers. In some embodiments cells exhibit a specified level of expression, e.g., cells among the 5%, 10%, 20%, 30%, 40%, or 50% of cells that have the highest expression level among cells that are positive for expression of one or more marker(s), optionally in combination with a lack of expression or low expression of one or more other marker(s). In some embodiments cells that exhibit one or more phenotypic characteristics of interest are separated from cells that do not exhibit the characteristic(s). Separation or isolation of cells can be performed using any of a variety of methods such fluorescence activated cell sorting (FACS), microdissection (e.g., laser capture microdissection, piezo-powered microdissection), binding to affinity matrices bearing one or more affinity reagents (e.g., antibodies, cell surface receptor ligands, or lectins) that bind selectively to markers expressed by desired cells, etc.

In some embodiments cell(s) are exposed to one or more agent(s) prior to use as an immunogen or prior to preparation of an immunogen from the cells. In some embodiments an agent comprises, e.g., a pathogen, a small molecule, a polypeptide, a nucleic acid, or a cell. In some embodiments an agent comprises a growth factor, cytokine, or hormone. In some embodiments cell(s) are exposed to a composition comprising multiple agents or exposed sequentially to two or more agents. In some embodiments cell(s) are exposed to an agent in culture, e.g., the cell is cultured in medium comprising the agent. In some embodiments cells are exposed to a physical condition such as radiation, altered temperature (e.g., heat shock), etc. In some embodiments a subject is exposed to an agent (e.g., an agent is administered to the subject) or physical condition, and cells are subsequently obtained from the subject. The length of exposure and/or the concentration, amount, or intensity of the agent or condition can vary. In some embodiments an exposure period ranges from 1 minute up to about 24 hours. In some embodiments an exposure period ranges from about 24 hours to about 168 hours (7 days). In some embodiments an exposure period ranges from about 7 days to about 30 days. In some embodiments an agent is not an agent that is found in culture medium used for or suitable for use in culturing the cell.

In some aspects, the present disclosure provides methods of use to identify cell surface markers, e.g., markers expressed at the surface of one or more cell types, cell type subsets, or cell states. Cell states encompass various different states that a cell of a given type may assume in response to environmental conditions or stimuli (or lack thereof). For example, a cell may be in an activated or unactivated state depending, e.g., on whether it has encountered particular activating stimuli. Certain aspects of the disclosure provide methods of identifying markers, e.g., cell surface markers, that, in some embodiments, can be used to subdivide a population of cells into multiple distinct subpopulations, which subpopulations may have one or more functional differences. For example, in some embodiments an immunogen comprises or is derived at least in part from a cell population composed of cells that are homogeneous with respect to one or more phenotypes (e.g., morphology, expression of one or more already known markers) or that were isolated from a particular organ, tissue, or subject of interest or are in particular physiological or pathological state or have been (and optionally are still being) exposed to a particular stimulus. VHHs that bind to only a subset of the cells are identified. The identity of the target antigen to which such a VHH binds is determined. Markers thus identified can subsequently be used, e.g., to identify or isolate cells that express the marker. For example, such markers can be used to isolate such cells and obtain a homogenous population thereof, thus allowing more detailed analysis of the cells. VHHs that bind to the markers so identified can be used to isolate cells that express the target antigen or to deliver a moiety of interest to such cells via binding to the target antigen.

In some embodiments an immunogen comprises or is derived at least in part from immune system cells. In some embodiments an immune system cell is a lymphocyte, monocyte, dendritic cell, macrophage, neutrophil, mast cell, eosinophil, basophil, natural killer (NK) cell, or mast cell. In some embodiments a lymphocyte is a cell of the B cell lineage or T cell lineage. In some embodiments a B lymphocyte has rearranged its heavy (H) chain gene. In some embodiments a B lymphocyte expresses a membrane-bound antibody. In some embodiments a T cell is a member of a T cell subset, e.g., a cytotoxic T cell (also called killer T cell) or a helper T cell. Cytotoxic T cells are typically positive for the cell surface marker CD8. Helper T cells are typically positive for the cell surface marker CD4. In some embodiments a cell is a CD4+ T cell. In some embodiments a cell is a CD8+ T cell. In some embodiments a T cell is a regulatory T cell (Treg), e.g., a FoxP3+ regulatory T cell. In some embodiments a T cell is a natural killer T (NKT) cell. In some embodiments a T cell expresses one or more cytokine(s). For example, in some embodiments a T cell has a Th1, Th2, or Th17 cytokine secretion profile. In some embodiments a T cell expresses a αβ T cell receptor (TCR). In some embodiments a T cell expresses a γδ TCR. In some embodiments a monocyte is a precursor of a macrophage or dendritic cell. In some embodiments an immune system cell, e.g., a lymphocyte, is a naïve cell (i.e., a cell that has not encountered an antigen to which its B cell receptor (BCR) or TCR binds and is not descended from a lymphocyte that has encountered an antigen to which its BCR or TCR binds). In some embodiments an immune system cell has encountered, in culture or in vivo, an antigen to which its BCR or TCR binds, or is descended from such a cell. In some embodiments an immune system cell has been activated, in culture or in vivo. In some embodiments an immune system cell is activated by exposure to an antigen presenting cell (APC) that displays an antigen to which the cell's TCR or SCR binds and/or by exposure to one or more cytokines.

In some embodiments a method is of use to identify one or more VHH domains that bind to cell surface marker(s) expressed by one or more functionally distinct leukocyte subsets, e.g., B cell, T cell, or dendritic cell subsets. In some embodiments a method is of use to identify cell surface markers or VHH domains useful for the identification and/or characterization of cells, e.g., leukocytes. In some embodiments a method is of use to identify marker(s) or VHH domains that can be used to divide immune system cells, e.g., lymphocytes, e.g., B cells or T cells, into distinct subpopulations. In some embodiments a method is of use to identify marker(s) or VHH domains that can be used to identify or isolate stem cells from a particular tissue or organ. In some embodiments a method is of use to identify marker(s) or VHH domains that can be used to identify or isolate progenitor cells capable of giving rise to a particular cell lineage.

In some embodiments or more VHH domains, e.g., sortaggable VHH domains, that bind to an immunogen comprising or derived in part from a population of cells (or a surrogate thereof) are obtained as described herein. A VHH domain is labeled, e.g., by sortagging with a detectable label, and contacted with a population of cells having similar or substantially identical characteristics as those from which the immunogen was prepared (e.g., expressing the same marker(s) or secreting the same cytokines as were used to identify or select the cells used to immunize or prepare the immunogen). The ability of the VHH domain to label (stain) the cells is assessed, e.g., using flow cytometry. In various embodiments a VHH domain may stain up to about 0.001%, 0.05%, 0.1%, 0.5%, 1%, 5%, 10%, 20%, 30%, 40%, 50%, 60%, 70%, 80%, 90%, 95%, 96%, 97%, 98%, 99%, or more of the cells. VHH domains that stain less than 100% of the cells (e.g., up to about 0.001%, 0.05%, 0.1%, 0.5%, 1%, 5%, 10%, 20%, 30%, 40%, 50%, 60%, 70%, or 80% of the cells in various embodiments), are candidates for binding to a subset-specific cell surface marker.

In some aspects, the invention provides VHH domains that bind to markers exposed at the surface of immune system cells (e.g., cell surface proteins). In some embodiments immune system cells comprise T cells, B cells, monocytes, macrophages, dendritic cells, NK cells, a precursor of any of these, or a subset of any of these). In some embodiments such VHH domains are obtained as described above, wherein a camelid is immunized with an immunogen comprising or at least in part derived from a population of immune system cells. Nucleic acids encoding VHH domains are obtained from the camelid's lymphocytes, cloned into a display vector, and expressed. VHH domains that bind to the immune system cells are isolated, and nucleic acids encoding them are obtained. In some embodiments such VHH domains are obtained by a method comprising: (a) obtaining nucleic acids encoding VHH domains generated by a camelid that has been immunized with an immunogen comprising or at least in part derived from immune system cells; and (b) isolating one or more VHH domains that bind to immune system cells. In some embodiments the method comprises characterizing a target antigen of at least one of the VHH domains. In some embodiments the method comprises determining the identity of a target antigen of at least one of the VHH domains. In some embodiments the method comprises characterizing and/or determining, for each of multiple VHH domains, the identity of a target antigen of the VHH. In some embodiments the method comprises obtaining a set of at least 5, 10, 15, 20, 25, or more distinct VHH domains that bind to immune system cells, e.g., immune system cells of a selected type. In some embodiments, the invention provides a collection or kit comprising VHH domains that bind to at least 5, 10, 15, 20, 25, or more distinct immune system cell surface proteins. For example, as described in further detail in the Examples, following immunization of a camelid with murine splenocytes, Applicants isolated a set of thirteen VHHs (termed VHH1-VHH13) that bound to B cell surfaces. Polypeptides comprising the individual VHHs fused to a transamidase recognition sequence were produced, labeled with a fluorescent dye using sortase, and evaluated for their ability to stain murine splenocytes. One of the VHHs, VHH7, was found to bind quantitatively to cells that were positive for expression of the B cell marker B220 and negative for the T cell marker TCRβ. Using a sortase-facilitated strategy, Applicants isolated the target antigen of VHH7 and discovered that VHH7 binds to major histocompatibility (MHC) Class II (MHCII) complexes, thereby determining the identity of the target antigen to which VHH7 binds.

In some embodiments a method comprises identifying a VHH that selectively binds to cells of a first cell population, as compared with its binding to cells of a second cell population. Such methods may, for example, be useful if two cell populations can be distinguished morphologically and it is desired to obtain a reagent that could be used to selectively stain cells of one population for purposes of facilitating cell sorting, isolation, etc. In some embodiments the method further comprises characterizing the target antigen of the VHH. In some embodiments the method further comprises determining the identity of the target antigen of the VHH. In various embodiments the first and second cell populations can differ in any way that allows them to be distinguished from each other. In some embodiments the first and second cell populations have been isolated from different sources or using methods that differ in one or more respects. In some embodiments the first and second cell populations have one or more different phenotypic characteristics. A first cell population may be isolated (e.g., at least separated from cells of the second cell population) based on any criteria of interest. Methods of isolating cells are described above. In some embodiments the first and second cell populations are of distinct cell lineages. In some embodiments the first and second cell populations represent different differentiation states within a given cell lineage. In some embodiments cells of the first and/or second populations are exposed to an agent, e.g., a pathogen, a small molecule, or a cell, prior to use as or in preparation of an immunogen. For example, in some embodiments a population of cells is divided into at least two cultures, and one of the cultures is exposed to the agent while the second culture is not exposed to the agent. In some embodiments cells of the first and/or second populations are genetically engineered. In some embodiments cells of one or both populations are not genetically engineered. In some embodiments cells of the first and/or second populations are isolated from a subject. In some embodiments the subject suffers from or has recovered from a disease. In some embodiments the disease is caused by a pathogen. In some embodiments the disease is a cancer. In some embodiments the disease is an auto-immune disease. In some embodiments the subject exhibits resistance to a disease, e.g., a disease caused by a pathogen. In some embodiments an agent has been administered to the subject. In some embodiments the subject has been exposed to a physical condition such as radiation. In some embodiments first and second cell populations are obtained from the same subject at different points in time.

According to certain methods, a camelid is immunized with an immunogen comprising or derived from cells of the first population. Sequences that encode VHH domains are obtained and cloned into a display vector, and VHHs that bind to cells of the first cell population are identified by performing one or more rounds of selection. In some embodiments one or more additional rounds of selection (which may be referred to as counter-selection) are used to deplete the resulting library of phage that bind to cells of the second cell population and thereby enrich for phage that comprise nucleic acids encoding VHH domains that bind selectively to cells of the first cell population. In some embodiments a second cell population (or second cell populations) comprises a diverse set of cell types, e.g., at least 10 different cell types, e.g., between 10-20 or 20-50 different cell types. In some embodiments one or more rounds of depleting a library of phage that bind to cells of a second cell population may be performed prior to, interspersed with, or concurrently with one or more rounds of selecting phage that bind to cells of the first cell population. In some embodiments, following identification of one or more VHH domains that binds to cells (or a cellular antigen) of the first cell population, a target antigen to which one or more such VHH domains binds is characterized, e.g., as described herein. In some embodiments the identity of target antigen to which one or more such VHH domains binds is determined.

In some embodiments cellular antigens, e.g., cell surface antigens, identified as described herein may be used to, e.g., detect, identify, or isolate cells having characteristics of the first cell population, to distinguish between cells having characteristics of the first and second cell populations, and/or to select against cells having characteristics of the second cell population, as targets for the delivery (e.g., selective delivery) of agents to cells having characteristics of the first cell population, as targets for the development of additional binding agents (e.g., additional VHHs or conventional antibodies), or as targets for development of drugs intended to act on cells having characteristics of the first cell population. For example, in some embodiments a sortaggable VHH domain that was used to identify a cell surface antigen (or a different VHH domain that binds to the same cell surface antigen) is sortagged with a moiety comprising an amino acid, a peptide, a protein, a polynucleotide, a carbohydrate, a tag, a metal atom, a chelating agent, a contrast agent, a catalyst, a non-polypeptide polymer, a recognition element, a small molecule, a lipid, a label, an epitope, an antigen, a small molecule, a therapeutic agent, a cross-linker, a toxin, a radioisotope, a particle, a click chemistry handle, or any other moiety whose delivery to a cell having characteristics of the first cell population is desired. In some embodiments the sortagged VHH is contacted with cells in vitro or is administered to a subject, e.g., a subject that comprises or may comprise cells having characteristics of the first cell population. In some embodiments a VHH domain that binds to a cell surface antigen is capable of exerting an effect on such cell by itself and/or independent of any particular moiety attached thereto. For example, a VHH domain may exert an effect at least in part by, e.g., blocking interaction of the cell surface antigen with a ligand. In some embodiments a VHH domain that binds to a cell surface antigen and is sortagged with a detectable label is used to selectively label cells that express the cell surface antigen. In some embodiments a VHH domain that binds to a cell surface antigen and is sortagged with a cytotoxic agent is used to selectively ablate cells that express the cell surface antigen. Such ablation may be useful, e.g., to determine one or more functions of the cells or to treat a disease characterized by excessive proliferation of cells that express the cell surface antigen.

In some embodiments a VHH domain that binds to an antigen that is selectively expressed by tumor cells, e.g., an antigen that is at least partly exposed at the surface of tumor cells, as compared, e.g., with normal cells is identified. For example, a first selection step can be performed to isolate phage expressing VHH domains that bind to tumor cells. A counter-selection step can be used to deplete the resulting library of phage that bind to normal cells. In some embodiments normal cells are of the same cell type or tissue of origin as that from which the tumor arose and/or are normal cell types that are likely to be present in the body at a site where a tumor is found. For example, normal epithelial cells may be used when VHHs that bind to targets antigens on carcinoma cells are desired. In some embodiments a mixture of normal cells of multiple different cell types is used for counter-selection. In some embodiments counter-selection against known tumor antigens is performed, e.g., using cells that express such antigens (e.g., naturally or as a result of genetic modification) or using soluble or surface-bound antigen. In some embodiments the identity of a tumor antigen to which a VHH binds is determined, e.g., as described herein.

Tumor antigens may be used, e.g., detect tumor cells or tumors, as targets for the selective delivery of agents to tumor cells or tumors, and/or as potential targets for anti-tumor drug development. For example, in some embodiments a sortaggable VHH domain that was used to identify the tumor antigen (or a different VHH domain that binds to the same tumor antigen) is sortagged with a moiety comprising an amino acid, a peptide, a protein, a polynucleotide, a carbohydrate, a tag, a metal atom, a chelating agent, a contrast agent, a catalyst, a non-polypeptide polymer, a recognition element, a small molecule, a lipid, a label, an epitope, an antigen, a small molecule, a therapeutic agent, a cross-linker, a toxin, a radioisotope, a particle, a click chemistry handle, or any other moiety whose delivery to a tumor cell or tumor is desired. In some embodiments the sortagged VHH is contacted with tumor cells in vitro or is administered to a subject, e.g., a subject that has been identified as having a tumor or is in need of being evaluated or monitored or is being evaluated or monitored for presence, size, or recurrence of a tumor. In some embodiments a VHH domain that binds to a tumor antigen may exert an anti-tumor effect independent of any particular moiety attached thereto. For example, a VHH domain may exert an anti-tumor effect at least in part by, e.g., blocking interaction of the target tumor antigen with a ligand. In some embodiments identification of a tumor antigen and a VHH domain that binds thereto may be performed using tumor cells (or their descendants) obtained from a particular subject. In some embodiments a VHH domain that binds to the tumor antigen may subsequently be administered to the same subject and/or to different subject(s) in need of treatment for a tumor that expresses the same tumor antigen or a tumor antigen sufficiently similar so as to be recognized by the VHH domain.

In some embodiments, nucleic acids encoding VHH domains are obtained from lymphocytes obtained from one or more camelids that have not been immunized with an immunogen comprising or derived at least in part from a particular target entity of interest. (The camelid may or may not have been immunized with a different immunogen.) In some embodiments a library of VHH domains is obtained or created in vitro by mutagenesis or DNA shuffling. One or more VHH domains can be used as a starting point for such approaches. Such VHH domain(s) may be randomly selected or may have at least some specificity for a particular antigen or epitope. In some embodiments multiple primer pairs are used to amplify portions of a VHH coding sequence (e.g., portions comprising at least one CDR). At least some of the portions are assembled in a display vector to form a sequence encoding a VHH. A library of such display vectors is generated and screened to identify a VHH of interest.

In some embodiments, a non-camelid, non-human animal that is transgenic for a camelid heavy chain IgG locus that gives rise to HCAb in camelids or that is transgenic for a camelized IgG gene (e.g., a camelized human IgG gene) is used as a source of nucleic acid sequences encoding VHH domains or portions thereof, e.g., CDRs. In some embodiments the transgenic animal is a rodent, e.g., a mouse or rat. In some embodiments the transgenic animal is generated using a similar strategy to that used to generate non-human animals transgenic for human IgG loci, for the production of human monoclonal antibodies by such animals. It will be understood that in some embodiments the transgenic animal harbors only a portion of the camelid IgG locus or camelized IgG locus, wherein the portion is sufficient to give rise to antibodies comprising VHH domains of diverse sequence, e.g., sufficient to give rise to at least 10%, 20%, 50%, 75%, 90% or more of the number of VHH domains generated by a camelid. In some embodiments an endogenous Ig locus of the animal is at least in part deleted or replaced by a camelid or camelized heavy chain IgG locus. In some embodiments, a transgenic non-human animal is immunized with an immunogen in order to obtain nucleic acid sequences encoding VHH domains that bind to a target entity of interest. In some embodiments a transgenic animal is used instead of or in addition to a camelid.

In some aspects, products and methods analogous to those described herein pertaining to VHH domain(s) are provided, wherein the products and methods pertain to any single domain antibody format, e.g., from a camelid or from a non-camelid. In some embodiments, for example, the disclosure relates to VH domains obtained or derived from immunoglobulin novel (or new) antigen receptors (IgNAR) found in cartilaginous fish (e.g., sharks, skates and rays)). See, e.g., WO 05/18629; Barelle, C., et al., Adv Exp Med Biol. (2009) 655:49-62, and/or the chapter by Flajnik and Dooley in Antibody Phage Display: Methods and Protocols, Methods in Molecular Biology, 2009 (cited above). In some embodiments, products and methods analogous to those described herein pertaining to VHH domain(s) are provided, wherein an IgNAR VH domain is used in the respective product or method instead of a VHH domain. For example, certain embodiments provide polypeptides comprising an IgNAR VH domain and a transamidase recognition sequence.

In some embodiments a moiety is conjugated covalently or noncovalently to a polypeptide, e.g., a polypeptide comprising a VHH, using any conjugation method and/or cross-linker known in the art. For example, once a VHH that binds to a target entity is identified as described herein, the VHH may be conjugated to any moiety of interest. Sortase-mediated conjugation has a variety of advantages, but other approaches may be used. Many conjugation strategies and crosslinkers are described, for example, in Hermanson, G., *Bioconjugate Techniques, 2$^{nd}$ ed.*, Academic Press, 2008. In some embodiments, conjugation involves coupling to the primary amino group on a lysine residue (epsilon amino group) or on the N terminus (alpha amino group) of a protein, e.g., a polypeptide comprising a VHH. Such amino groups can react with a number of functional groups, such as aldehydes and activated carboxylic acids. In some embodiments a homobifunctional crosslinker is used. Homobifunctional crosslinkers comprise identical reactive functional groups at the ends of a spacer moiety. In some embodiments a heterobifunctional linker is used. Heterobifunctional crosslinkers comprise two distinct reactive functional groups, wherein a first reactive functional group of the linker is capable of reacting to form a covalent bond with a reactive functional group of a first moiety and a second reactive functional group of the crosslinker is capable of reacting to form a covalent bond with a (typically different) reactive functional group of the second moiety, thereby linking the first and second moieties. Exemplary reactive functional groups include, e.g., succinimidyl esters, imidoesters, maleimides, haloacetyl (e.g., bromo- or iodo-), vinyl sulfones, pyridyl disulfide, thiols, amines, aldehydes, carboxyl, and cardodiimides. For example, in some embodiments a heterobifunctional linker comprises an amine-reactive succinimidyl ester (e.g., an NHS ester) at one end and a sulfhydryl-reactive group (e.g., maleimide) on the other end. One of ordinary skill in the art will be aware of appropriate combinations of reactive functional groups and of molecules and crosslinkers that contain them. For example, coupling of NHS esters to amines, coupling of maleimide, haloacetyl, pyridyldisulfinde, or vinyl sulfone to sulfhydryl groups, carbodiimide to carboxyl, may be employed. In some embodiments a molecule is modified so as to provide a desired reactive functional group. For example, a variant polypeptide can be generated that includes a lysine or cysteine residue. In some embodiments a polypeptide sequence is extended at either or both termini to include one or more additional amino acids, wherein the one or more additional amino acids include a lysine or cysteine. Free sulfhydryls can be generated, e.g., by reduction of disulfide bonds or the conversion of amine, aldehyde or carboxylic acid groups to thiol groups. For example, disulfide crosslinks in proteins can be reduced to cysteine residues by dithiothreitol (DTT), tris-(2-carboxyethyl)phosphine (TCEP), or or tris-(2-cyanoethyl)phosphine. Sulfhydryls can be introduced into molecules through reaction with primary amines using sulfhydryl addition or modification reagents, such as 2-iminothiolane (Traut's Reagent), succinimidyl acetylthioacetate (SATA) or succinimidyl 3-(2-pyridyldithio)propionate (SPDP). For example, amines can be indirectly thiolated by reaction with SPDP followed by reduction of the 3-(2-pyridyldithio)propionyl conjugate with DTT or TCEP. Amines can be indirectly thiolated by reaction with SATA followed by removal of the acetyl group with 5hydroxylamine or hydrazine at near-neutral pH. Amines can be directly thiolated by reaction with 2-iminothiolane. Tryptophan residues, e.g., in thiol-free proteins, can be oxidized to mercaptotryptophan residues, which can then be modified by iodoacetamides or maleimides. In some embodiments a crosslinker, e.g., a heterobifunctional linker, comprises a click chemistry handle at one or both ends. In some embodiments the reactive functional groups at the ends of a heterobifunctional linker are selected such that they do not readily react with each other. In some embodiments at least one group is activatable under specified conditions or in response to specified stimuli. For example, in some embodiments a group is photactivatable.

In general, a crosslinker can comprise any of a wide variety of linkers between the reactive ends. In some embodiments a crosslinker comprises an aliphatic, alicyclic, heteroaliphatic, heteroalicyclic, aromatic, or heteroaromatic linker which, in some embodiments, comprises between 1 and 6, 6 and 12, or 12-30 carbon atoms in the main chain connecting the reactive functional groups at each end. In some embodiments a crosslinker or linker comprises a linear saturated hydrocarbon chain, a linear unsaturated hydrocarbon chain, an oligo(ethylene glycol) chain, one or more amino acids (e.g., a peptide), an alicyclic structure, or an aromatic ring. In some embodiments a linker may comprise one or more other functionalities such as ethers, amides, esters, imines, thioethers, etc. In some embodiments a linker comprises moiety such as a sulfate group, which would impart negative charges to the molecule and may increase its water solubility. In some embodiments a crosslinker does not become at least in part incorporated into the product. For example, 1-ethyl-3-(3-dimethylaminopropyl) carbodiimide (EDAC) can react to form "zero-length" crosslinks. Examples of various linkers are mentioned herein for descriptive purposes and are not intended to be limiting. In general, a linker can be selected such that the linked moieties are positioned appropriately relative to one another and such that the resulting structure is stable in the conditions in which it will be used. In some embodiments appropriate positioning of linked moieties comprises placing some distance between them so they will not significantly interfere with each other. In some embodiments a linker is flexible and allows the moieties to assume many different orientations relative to one another.

VHH Domains that Bind to MHCII Complexes and Uses Thereof

In some aspects, the invention provides VHH domains that bind to a mammalian MHCII complex. MHCII complexes are heterodimeric proteins that are expressed on the surface of certain types of antigen presenting cells (APCs) such as B cells, macrophages, and dendritic cells. A primary function of MHCII complexes is to present peptides processed from larger proteins, e.g., internalized extracellular proteins (e.g., proteins derived from foreign antigens), to CD4+ helper T cells. Recognition of peptide-MHCII complexes induces the activation, expansion, and differentiation of naïve CD4+ T cells into effector CD4+ T and memory CD4+ T cells. Effector CD4+ T cells in turn stimulate the immune response by, e.g., providing "help" to other cells of the immune system. For example, effector CD4+ T cells express cell surface molecules that stimulate B cells specific for the peptide and produce cytokines that stimulate a range of immune system cells. MHCII molecules are also expressed on thymic stromal cells, where they regulate the processes of positive and negative selection that occur during T cell maturation and lineage commitment, resulting ordinarily in a repertoire of peripheral CD4+ T cells that are self-tolerant but competent to recognize foreign peptides in the context of self MHCII complexes.

Mature MHC Class II complexes contain two chains, $\alpha$ and $\beta$, each having two domains ($\alpha 1$, $\alpha 2$, $\beta 1$, and $\beta 2$). Portions of $\alpha 1$ and $\beta 1$ form a peptide-binding groove that serves to bind and display the peptide. MHC genes are highly polymorphic, i.e., many different alleles exist in the population. Polymorphic regions are located mainly in the region of peptide contact, thereby permitting presentation of a wide variety of peptides. The human MHCII (human leukocyte antigen, HLA) genomic region, located at chromosome 6p21.3, contains three isotypic loci, DP, DQ, and DR, each of which encode $\alpha$ and $\beta$ subunits that form heterodimeric MHCII complexes. The mouse MHCII genomic region, located on chromosome 17, comprises I-A and I-E loci, each of which likewise encodes an $\alpha$ and $\beta$ chain. MHC Class II complexes assemble in the endoplasmic reticulum (ER), where $\alpha$ and $\beta$ chains form a complex with invariant chain (Ii), which blocks the peptide-binding groove. Immature MHCII complexes are transported into vesicles that contain proteases capable of digesting (processing) proteins taken up by endocytosis or produced in the cell into smaller peptides. These proteases also digest invariant chain to a fragment called CLIP. Release of CLIP from the MHCII complex allows peptide binding to occur. Newly formed peptide-bound complexes are transported to the cell membrane where they are anchored by transmembrane domains of the $\alpha$ and $\beta$ chains.

In some embodiments a VHH domain binds to a primate MHCII complex. In some embodiments a primate MHCII complex is human MHCII complex. In some embodiments a primate MHCII complex is a non-human primate MHCII complex. In some embodiments a VHH domain binds to a rodent MHCII complex, e.g., a mouse MHCII complex. In some embodiments the VHH domain binds to a mature human MHCII complex exposed at the cell surface. In some embodiments the VHH binds to a region of the MHCII complex that is conserved among MHCII complexes encoded by multiple different HLA-DR alleles. In some embodiments the VHH binds to a region of the MHCII complex that is conserved among MHCII complexes encoded by multiple different HLA-DR, HLA-DQ, and HLA-DP alleles. In some embodiments the VHH binds to a human MHCII alpha chain. In some embodiments the VHH binds to a human MHCII beta chain. Table C provides Gene IDs and exemplary mRNA and protein accession numbers of various human MHCII molecules from the NCBI databases. One of ordinary skill in the art will readily be able to obtain sequences of MHCII complex mRNA and proteins of other species.

It will be appreciated that the sequences represented by the accession numbers are exemplary due to the existence of polymorphism. It will be appreciated that the sequences represent precursor polypeptides that comprise a secretion signal sequence, which is cleaved during maturation of the protein.

TABLE C

Human MHCII Genes

| Name | Gene ID | NCBI RefSeq Acc. Nos. for mRNA and protein |
|---|---|---|
| HLA-DPA1 | 3113 | NM_001242524.1 → NP_001229453.1 |
| HLA-DPB1 | 3115 | NM_002121.5 → NP_002112.3 |
| HLA-DQA1 | 3117 | NM_002122.3 → NP_002113.2 |
| HLA-DQA2 | 3118 | NM_020056.4 → NP_064440.1 |
| HLA-DQB1 | 3119 | NM_002123.4 → NP_002114.3 (isoform 1) NM_001243961.1 → NP_001230890.1 (isoform 2) |
| HLA-DQB2 | 3120 | NM_001198858.1 → NP_001185787.1 |
| HLA-DRA | 3122 | NM_019111.4 → NP_061984.2 |
| HLA-DRB1 | 3123 | NM_002124.3 → NP_002115.2 NM_001243965.1 → NP_001230894.1 |
| HLA-DRB3 | 3125 | NM_022555.3 → NP_072049.2 |
| HLA-DRB4 | 3126 | NM_021983.4 → NP_068818.4 |
| HLA-DRB5 | 3127 | NM_002125.3 → NP_002116.2 |

A VHH that binds to an MHCII complex, e.g., a human MHCII complex, can be generated using any suitable method. In some embodiments a VHH that binds to a human MHCII complex is generated by a method comprising immunizing a camelid with an immunogen comprising one or more at least partially purified human MHCII α or β chain proteins or a portion thereof that comprises a sequence of at least 8, 9, 10, 11, 12, 13, 14, 15, 16, 17, 18, 19, 20, or 25 continuous amino acids found in a non-polymorphic region of the protein. In some embodiments a VHH that binds to a human MHCII complex is generated by a method comprising immunizing a camelid with an immunogen comprising one or more at least partially purified human MHCII complexes comprising an α and a β chain. In some embodiments a VHH that binds to a human MHCII complex is generated by a method comprising immunizing a camelid with an immunogen comprising or derived from human cells, e.g., human lymphocytes, that express MHCII complexes. Following immunization, nucleic acids encoding VHH are obtained, and VHH that bind to human MHCII complexes are isolated, e.g., using a display technique such as phage display. Similar methods can be used to obtain VHH that bind to a MHCII complex of a non-human species of interest. For example, as described in the Examples, a VHH that binds to murine MHCII complexes (VHH7) was isolated using phage display, from a phage display library comprising nucleic acids encoding VHH domains from lymphocytes obtained from a camelid that had been immunized with mouse splenocytes.

In some embodiments, a VHH domain has a sequence comprising the sequence of VHH7 (SEQ ID NO: 50) or an antigen-binding fragment thereof. In some embodiments, a VHH domain binds to substantially the same portion of an MHCII complex as does VHH7. In some embodiments a VHH domain competes with VHH7 for binding to an MHCII complex. In some embodiments the disclosure provides a polypeptide comprising a fragment of SEQ ID NO: 50, e.g., a fragment comprising at least 8, 10, 15, 20, or 30 consecutive amino acids of SEQ ID NO: 50. It will be appreciated that the A residue shown at the N-terminus of SEQ ID NO: 50 is not part of FR1 but rather is encoded by nucleotides that are part of a restriction site and an additional nucleotide that preserves reading frame. In some embodiments the N-terminal A of SEQ ID NO: 50 is omitted. In some embodiments the fragment comprises at least one CDR of SEQ ID NO: 50. In some embodiments the disclosure provides a polypeptide comprising a variant of SEQ ID NO: 50, wherein the variant is at least 80%, 85%, 90%, 95%, 96%, 97%, 98%, 99%, or more identical to SEQ ID NO: 50 over at least a portion of SEQ ID NO: 50 that encompasses CDR1, CDR2, and CDR3. In some embodiments a hinge region is at least in part omitted. In some embodiments a VHH7 polypeptide comprises SEQ ID NO: 54 or a variant or fragment thereof. In some embodiments a polypeptide comprises a fragment of SEQ ID NO: 50 comprising CDR1 (SEQ ID NO: 51), CDR2 (SEQ ID NO: 52), and/or CDR3 (SEQ ID NO: 53). In some embodiments the polypeptide comprises at least 2, or all 3 of the CDRs of VHH7 or variants thereof. In some embodiments a variant of a CDR comprises a sequence having no more than 1, 2, or 3 amino acid changes relative to the sequence of the CDR. In some embodiments the polypeptide further comprises at least one framework (FR) region. In some embodiments the at least one FR region is a VHH FR region. For example, in some embodiments one or more CDRs are inserted into a polypeptide scaffold comprising camelid (e.g., VHH) or non-camelid antibody framework regions. For example, in some embodiments a polypeptide comprising FR1-CDR1-FR2-CDR2-FR3-CDR3-FR4 is provided, wherein CDR1, CDR2, and CDR3 comprise SEQ ID NO: 51, SEQ ID NO: 52, and SEQ ID NO: 53, respectively. It will be understood that the precise boundaries of framework regions and/or complementarity determining regions may in certain embodiments be assigned based on alignments with any of a variety of different VHHs, e.g., CDRs are non-conserved or poorly conserved regions while FRs are more highly conserved and may in some embodiments be identical among different VHH sequences. In some embodiments boundaries may be assigned based on alignment of multiple VHH sequences that, in some embodiments, may be from the same or related camelid species or individuals. In some embodiments CDRs of VHH7 comprise SEQ ID NO: 55, SEQ ID NO: 56, and SEQ ID NO: 57, respectively. In some embodiments a fragment or variant of the polypeptide is provided, wherein the fragment or variant comprises at least two CDRs and intervening FR region(s). In some embodiments a polypeptide comprising SEQ ID NO: 50 or a variant or antigen-binding fragment or at least one CDR or variant thereof comprises a TRS. In some embodiments the TRS is located at or near the C-terminus of the polypeptide. In some embodiments a moiety (e.g., any of the moieties disclosed herein) is attached to the polypeptide via the TRS by sortagging. In some embodiments the polypeptide comprises an antigen. In some embodiments the polypeptide comprises a fusion protein comprising (a) SEQ ID NO: 50 or a variant or fragment thereof; and (b) an antigen. In some embodiments the variant or fragment binds to MHCII complexes.

In some embodiments the disclosure provides a nucleic acid that encodes a polypeptide comprising VHH7 or a variant or fragment thereof, e.g., any of the afore-mentioned polypeptides. In some embodiments the disclosure provides a nucleic acid sequence at least 80%, 85%, 90%, 95%, 96%, 97%, 98%, 99%, or 100% identical to a coding region of SEQ ID NO: 49. In some embodiments the nucleic acid is codon optimized for expression in bacteria or yeast.

Figure 26:
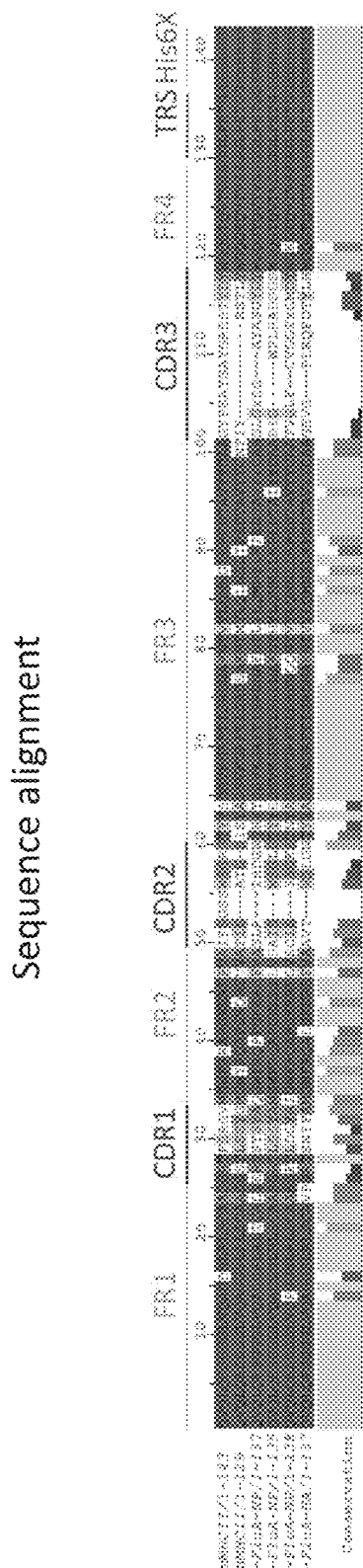
FIG. 26. Alignment of various VHH sequences. Approximate locations of framework regions, CDRs, and sortase recognition motif are indicated. C-terminal amino acid of FR4 (S, at position 130) is followed by a GG linker, sortase recognition motif, G, and 6×-His tag.

As described in Examples 12 and 13, VHHs binding to human MHCII complexes or to proteins of Influenza A virus were isolated. An alignment of polypeptides comprising various representative VHH sequences is shown in FIG. 26. In addition to the VHH sequence itself, these polypeptides comprise a TRS and 6×His tag at the C-terminus, rendering them suitable for sortagging. Approximate positions of CDRs and FR are indicated. It will be understood that the boundaries may be adjusted by up to several amino acids, e.g., 1, 2, 3, 4 amino acids, in either direction in various embodiments.

VHH that bind to human MHCII complexes (VHH4) was isolated from a phage display library comprising nucleic acids encoding VHH domains from lymphocytes obtained from a camelid that had been immunized with purified human MHC Class II proteins. In some embodiments, a VHH domain has a sequence comprising the sequence of VHH4 (SEQ ID NO: 59) or an antigen-binding fragment thereof. In some embodiments, a VHH domain binds to substantially the same portion of an MHCII complex as does VHH4. In some embodiments a VHH domain competes with VHH4 for binding to an MHCII complex. In some embodiments the disclosure provides a polypeptide comprising a fragment of SEQ ID NO: 59, e.g., a fragment comprising at least 8, 10, 15, 20, or 30 consecutive amino acids of SEQ ID NO: 59. In some embodiments the fragment comprises at least one CDR of SEQ ID NO: 59. In some embodiments the disclosure provides a polypeptide comprising a variant of SEQ ID NO: 59, wherein the variant is at least 80%, 85%, 90%, 95%, 96%, 97%, 98%, 99%, or more identical to SEQ ID NO: 59 over at least a portion of SEQ ID NO: 59 that encompasses CDR1, CDR2, and CDR3. In some embodiments a polypeptide comprises a fragment of SEQ ID NO: 59 comprising CDR1 (SEQ ID NO: 60), CDR2 (SEQ ID NO: 61), and/or CDR3 (SEQ ID NO: 62). In some embodiments the polypeptide comprises at least 2, or all 3 of the CDRs of VHH4 or variants thereof. In some embodiments a variant of a CDR comprises a sequence having no more than 1, 2, or 3 amino acid changes relative to the sequence of the CDR. In some embodiments the polypeptide further comprises at least one framework (FR) region. In some embodiments the at least one FR region is a VHH FR region. For example, in some embodiments one or more CDRs are inserted into a polypeptide scaffold comprising camelid (e.g., VHH) or non-camelid antibody framework regions. For example, in some embodiments a polypeptide comprising FR1-CDR1-FR2-CDR2-FR3-CDR3-FR4 is provided, wherein CDR1, CDR2, and CDR3 comprise SEQ ID NO: 60, SEQ ID NO: 61, and SEQ ID NO: 62, respectively. In some embodiments a fragment or variant of the polypeptide is provided, wherein the fragment or variant comprises at least two CDRs and intervening FR region(s). In some embodiments a polypeptide comprising SEQ ID NO: 59 or a variant or antigen-binding fragment or at least one CDR or variant thereof comprises a TRS, which may be located at or near the C-terminus of the polypeptide. For example, the polypeptide may comprise SEQ ID NO: 63. In certain embodiments a polypeptide comprises a variant of SEQ ID NO: 63 in which the TRS of SEQ ID NO: 63 is replaced by a different TRS and/or in which the C-terminal 6×His tag is replaced by a different tag or omitted and/or in which linker(s) between the VHH portion and the TRS and/or between the TRS and the C-terminal tag are omitted, extended, or altered in sequence. In some embodiments a moiety (e.g., any of the moieties disclosed herein) is attached to the polypeptide comprising VHH4 via the TRS using sortase. In some embodiments the polypeptide comprises an antigen. In some embodiments the polypeptide comprises a fusion protein comprising (a) SEQ ID NO: 59 or a variant or fragment thereof; and (b) an antigen. In some embodiments the variant or fragment of SEQ ID NO: 59 binds to MHCII complexes.

In some embodiments the disclosure provides a nucleic acid that encodes a polypeptide comprising VHH4 or a variant or fragment thereof, e.g., any of the afore-mentioned polypeptides. In some embodiments the nucleic acid is codon optimized for expression in bacteria or yeast.

In some embodiments FR regions sequences may comprise any of the FR region sequences depicted in FIG. 26 or variants thereof, though of course other FR region sequences may be used. In some embodiments any VHH may comprise or may lack a hinge region, which may be a long or short hinge region. A representative hinge region may comprise the sequence EPKTPKPQ (SEQ ID NO: 64) and may in some embodiments comprise one or more additional amino acids in a C-terminal direction.

In some embodiments a VHH domain, e.g., a VHH domain that binds to an MHCII complex, is obtained by a method that does not require immunization of a camelid with an immunogen comprising an MHCII polypeptide is used. For example, in some embodiments a library of display vectors encoding VHH domains is obtained or generated based on previously isolated nucleic acid sequences encoding VHH domains, and the library is screened to identify VHH that bind to human MHCII complexes or portions thereof. In some embodiments a VHH that binds to MHCII complexes of multiple different MHC haplotypes is identified. In some embodiments VHHs are screened against a panel of human lymphocytes derived from individuals of different haplotypes to identify one or more VHHs capable of binding to multiple different human MHCII haplotypes. In some embodiments a VHH capable of binding to MHCII complexes of each of at least about 3, 5, 10 or more human MHCII haplotypes is identified. In some embodiments a VHH capable of binding to MHCII complexes of each of at least the 3, 5, 10, or more, most common MHCII haplotypes in the human population or a subpopulation thereof (e.g., a population of a country or region or ethnic group) is identified. Multiple rounds of mutagenesis and screening or other types of in vitro affinity maturation can be performed, e.g., to identify VHH that have a desired affinity. In some embodiments a VHH domain is humanized.

In some aspects, polypeptides comprising a VHH that binds to an MHCII complex are provided. In some embodiments, such polypeptides can be represented as (Xaa)-VHH-(Xaa)$_k$, as described above, wherein VHH binds to an MHCII complex. The VHH, (Xaa), and (Xaa)$_k$ can have any of the properties described herein for VHH, (Xaa)$_j$, and (Xaa)$_k$, respectively, in various embodiments. In some embodiments (Xaa)$_k$ comprises a TRS. Also provided are (i) nucleic acids encoding any of the VHH or polypeptides comprising VHH that bind to an MHCII complex; (ii) vectors (e.g., expression vectors) comprising any of the nucleic acids; and (iii) cells comprising any of the nucleic acids or vectors. In some embodiments the cells produce the VHH or polypeptide comprising the VHH. In some embodiments the cells secrete the VHH or polypeptide comprising the VHH. In some embodiments a method comprises (a) maintaining cells that produce the VHH or polypeptide in culture under conditions in which the VHH or polypeptide is produced; and (b) isolating the VHH from the cells or cell culture medium.

In some embodiments the invention provides an agent comprising: (a) a polypeptide comprising a VHH that binds to MHCII complexes; and (b) a moiety of interest. The moiety of interest can be, e.g., any of the moieties mentioned herein. In some embodiments the moiety comprises or consists of an amino acid, a peptide, a protein, a polynucleotide, a carbohydrate, a tag, a metal atom, a chelating agent, a contrast agent, a catalyst, a polymer, a recognition element, a small molecule, a lipid, a label, an epitope, an antigen, a small molecule, a therapeutic agent, a cross-linker, a toxin, a radioisotope, a particle, or a click chemistry handle. In some embodiments the moiety is conjugated to the polypeptide comprising the VHH. In some embodiments the moiety is conjugated to the polypeptide comprising the VHH via a linker. In some embodiments the moiety comprises a protein, and the agent comprises a fusion protein comprising: (a) a polypeptide comprising VHH that binds to MHCII complexes and (b) the protein. In some embodiments a polypeptide comprises (a) a VHH that binds to MHCII complexes; and (b) a TRS. In some embodiments a moiety of interest is attached to the polypeptide via the TRS using a sortase-mediated reaction. In some embodiments a click chemistry handle is attached to the polypeptide via the TRS using a sortase-mediated reaction. In some embodiments a first click chemistry handle is attached to the polypeptide via the TRS using a sortase-mediated reaction, and a moiety comprising a second click chemistry handle is conjugated to the polypeptide by reaction with the first click chemistry handle. In some embodiments a moiety of interest is linked to a polypeptide comprising a VHH that binds to MHCII complexes, using any conjugation method. In some embodiments a linkage comprises a covalent bond. In some embodiments a linkage comprises a noncovalent bond.

Polypeptides comprising a VHH that binds to MHCII complexes have a variety of uses. In some embodiments a polypeptide comprising a VHH that binds to MHCII complexes is used to detect, label, or isolate cells that express MHCII complexes at their surface. In some embodiments, e.g., as described further below, a polypeptide comprising a VHH that binds to MHCII complexes is used to deliver a moiety to cells that express MHCII complexes at their surface. Thus in some embodiments a VHH that binds to MHCII complexes is used as a targeting moiety to target a moiety to cells that express MHCII complexes at their surface.

VHH that Bind to Influenza Virus Polypeptides and Uses Thereof

In some aspects, provided herein are polypeptides comprising VHH sequences that bind to influenza virus proteins, e.g., influenza A virus proteins. In some embodiments the polypeptides further comprise a sortase recognition motif. The influenza A virus genome is contained on eight single-stranded RNA strands that code for eleven proteins (HA, NA, NP, M1, M2, NS1, NEP, PA, PB1, PB1-F2, PB2). Influenza viruses are typically classified into 17 HA and 9 NA subtypes on the basis of two surface proteins on the virus particle, hemagglutinin (HA) and neuraminidase (NA). In some embodiments polypeptides comprising VHH that bind to influenza A virus nucleoprotein (NP) are provided. In some embodiments VHH bind to intact virus particles. Exemplary VHH that bind to influenza virus NP comprise SEQ ID NO: 65, 66, or 67, or variants or fragments thereof. In some embodiments polypeptides comprising VHH that bind to influenza A virus hemagglutinin (HA) are provided. Exemplary VHH that bind to influenza virus HA comprise SEQ ID NO: 68, or variants or fragments thereof. In some embodiments a variant or fragment comprises 1, 2, or all 3 CDRs of SEQ ID NO: 68. CDRs of exemplary anti-influenza VHH may be inserted a scaffold comprising heterologous framework regions as described above, e.g., to produce a polypeptide comprising FR1-CDR1-FR2-CDR2-FR3-CDR3-FR4, wherein CDR1, CDR2, and CDR3 are SEQ ID NO: 65, 66, 67, 68 or variants thereof. In some embodiments a variant or fragment comprises 1, 2, or all 3 CDRs of SEQ ID NO: 65, 66, 67, or 68. In certain embodiments polypeptides comprising VHH that bind to influenza virus further comprise a transamidase recognition sequence, a tag (e.g., located C-terminal to the TRS), or both. Such sortaggable VHH polypeptides may be conjugated with any moiety of interest using sortase, as described herein. For example, such polypeptides may be conjugated with a detectable label (e.g., a fluorophore), a member of a binding pair, a protein (e.g., an enzyme), a tag, a small molecule, etc. In some embodiments such polypeptides are sortagged with a moiety that facilitates use of the polypeptide, e.g., for detection of influenza virus. In some embodiments two or more such polypeptides are conjugated together using sortase to produce a bifunctional agent, which may be bispecific. In some embodiments click chemistry handles are installed using sortase, allowing N—N or C—C fusions. In some embodiments two or more VHH capable of binding to the same or different influenza virus proteins are produced as a fusion protein or conjugated directly using sortase.

In some embodiments polypeptides comprising VHH that bind to an influenza virus protein may be used to detect influenza virus and/or to detect cells that are infected by influenza virus. In certain embodiments an influenza virus is an influenza A virus. In some embodiments such VHH may be used for diagnosis, e.g., to determine whether a sample or subject harbors influenza virus. In some embodiments a sample may be obtained from a subject, e.g., a sample comprising nasal or nasopharyngeal secretion, saliva, sputum, or other body fluid. A sample may be obtained from a swab, aspirate, or washing from within the respiratory passages, e.g., throat, nasal passages, nasopharynx, etc. The sample may be processed in any of a variety of ways. For example, the sample may be concentrated, contacted with a reagent that disrupts a viral envelope, extracts viral proteins, lyses cells, etc. The sample is contacted with a polypeptide comprising a VHH, which may comprise a moiety that facilitates detection of the polypeptide, such as a detectable label. Binding of the VHH to material in the sample indicates the presence of influenza virus or protein derived therefrom.

A VHH may be used in any of a variety of formats suitable for detection of a target antigen, e.g., any type of immunoassay format, known in the art. Numerous formats are known in which an analyte and an agent capable of binding to the analyte ("binding agent") are contacted under conditions in which binding of the binding agent to the analyte is or can be rendered detectable. In some embodiments a VHH may be attached to a support and used as a capture agent to immobilize an analyte to be detected. In some embodiments a polypeptide comprising a VHH may be used as a detection agent, e.g., as a direct detection antibody or as primary antibody that is detected using a secondary detection agent (e.g., a secondary antibody), which may be labeled. In some embodiments a VHH is used in a sandwich immunoassay. In some embodiments VHH may be adsorbed to the support noncovalently or conjugated to the support using standard methods such as carbodiimide coupling. In some embodiments VHH may be conjugated to the support via a sortase-mediated reaction. The support may be contacted with a sample and maintained for a suitable period of time to permit binding of material in the sample to the VHH to occur. The support may be washed to remove unbound material and contacted with a detection agent capable of binding to the analyte to be detected (e.g., influenza A virus). The detection agent may comprise a VHH, which may be the same VHH as used for capture or a different VHH capable of binding to the analyte. In some embodiments the support may be a substantially planar support. In some embodiments the support may comprise particles such as beads, which may be magnetic. In certain embodiments a bead-based assay utilize color-coded microparticles ("beads") comprising different dyes and/or concentrations thereof (e.g., fluorescent dyes). The different dyes and/or different dye concentrations allow different particles to be distinguished. Each particle type may have a unique spectrial signature based on the frequencies of light absorbed and/or emitted. A particle or particle set can be coated with a reagent specific to a particular bioassay, allowing the capture and detection of specific analytes from a sample. A light source, e.g., in an appropriate analyzer, is used to excite the dyes that identify each particle, and may also be used to excite any reporter dye captured during the assay, thus allowing detection of specific analytes present in a sample. Suitable beads and detectors are available, e.g., through Luminex Corp (Austin, Tex.). Multiplexed assays can be performed, in which any of multiple different analytes present in a sample may be detected in a single assay. VHH that bind to influenza virus may be attached to particles for use in an assay for detection of influenza virus. In some embodiments such particles may be provided or combined with particles capable of detecting other viruses, e.g., other respiratory viruses. In some embodiments a polypeptide VHH is used in a lateral-flow immunoassay (LFA). LFA utilizes a test strip that collects a sample through lateral flow, and detects the presence of a target molecule through a target-specific antibody, which may be labeled with an indicator, e.g., a colorimetric indicator (see, e.g., Posthuma-Trumpie G A, et al., Anal Bioanal Chem. 2009 January; 393(2):569-82.

In some embodiments a kit comprising a polypeptide comprising a VHH capable of binding to influenza virus protein is provided. In some embodiments the polypeptide comprises a TRS, so that the polypeptide is suitable for sortagging. In some embodiments the polypeptide may be sortagged, e.g., with a label, enzyme, or other moiety. In some embodiments a kit may comprise instructions for use. A kit may comprise one or more additional components. The one or more additional components may be selected depending on the uses that may be envisioned for the kit. In some embodiments a kit comprises a sortase and/or a reaction buffer suitable for performing sortagging. In some embodiments a kit comprises a secondary antibody, a sample container or collection device (e.g., a swab), a vessel for performing detection, a dipstick, concentration reagent(s), cell lysis reagent(s), a wash buffer, a positive control (e.g., purified influenza virus protein or inactivated virus), etc.

In some embodiments a VHH capable of binding to influenza virus may be used to characterize and/or screen for compounds that inhibit one or more steps of the influenza virus life cycle, such as viral replication, assembly, or budding. For example, cells susceptible to influenza virus infection (e.g., MDCK cells) may be contacted with influenza A virus in the presence of a candidate agent or may be contacted with a candidate agent after being contacted with influenza A virus. Cells are maintained in culture for a sufficient time period to allow production of influenza virus. A VHH that binds to influenza A virus protein or whole virus may be used to evaluate the ability of the compound to inhibit production or release of virus. In some embodiments compounds capable of inhibiting influenza virus production or release are candidate agents for treatment of influenza virus infection.

Methods of Modulating the Immune Response

In some aspects, methods of modulating the immune system are provided herein. In some aspects, a method of modulating the immune system comprises targeting a moiety to MHCII complexes expressed by immune system cells. In some embodiments the moiety comprises an antigen. In some embodiments the moiety comprises a cytokine. In some aspects, the disclosure provides the recognition that targeting an antigen to MHCII complexes expressed by immune system cells provides an effective means of modulating the immune response to such antigen. Applicants discovered that a VHH that binds to an MHCII complex is capable of modulating response of immune system cells to a moiety attached to the VHH. For example, Applicants discovered that exposure of dendritic cells to a polypeptide comprising a VHH that binds to MHCII complexes, which polypeptide was sortagged with a peptide of interest, markedly stimulated the ability of these DCs to promote proliferation and activation in vitro of CD4+ T cells capable of binding to the same peptide. Administration to mice of the peptide-sortagged VHH and an adjuvant (an anti-CD40 antibody), markedly stimulated the proliferation in vivo of CD4+ T cells capable of binding to the peptide. Thus, targeting an antigen to MHCII complexes can enhance the proliferation and activation of CD4+ T cells specific for the antigen. In some embodiments the antigen is targeted to MHCII complexes on the surface of immune system cells in the presence of an adjuvant or costimulator. In some aspects, CD4+ T cells are capable of providing stimulatory help to a variety of other immune system cells, thereby modulating the immune system, e.g., promoting an effective immune response.

In some embodiments, modulating the immune system comprises modulating one or more biological activities of one or more types of immune system cells. In some embodiments, modulating the immune system comprises modulating an immune response to an antigen. In some embodiments, modulating an immune response to an antigen comprises modulating one or more biological activities of one or more types of immune system cells exposed to the antigen. In some embodiments an immune response comprises migration, proliferation, or activation of one or more types of immune system cells. In some embodiments an immune response comprises development of immature immune system cells into mature, functional cells. In some embodiments an immune response comprises proliferation and/or activation of helper (CD4+) T cells specific for an antigen. In some embodiments an immune response comprises proliferation and/or activation of cytotoxic (CD8+) T lymphocytes (CTLs) specific for an antigen. In some embodiments an immune response to an antigen comprises production of cytokines by, e.g., immune system cells specific for the antigen. In some embodiments an immune response comprises proliferation and/or activation of antibody-producing cells and/or production of antibodies by such cells, wherein the antibodies bind to an antigen. In some embodiments an immune response comprises production of memory T and/or B cells that are capable of providing a rapid immune response to an antigen upon subsequent exposure to the antigen that elicited their production. In some embodiments modulating an immune response comprises modulating any one or more biological activities of immune system cells. In some embodiments modulating an immune response to an antigen comprises modulating any one or more biological activities of immune system cells, wherein the immune system cells are specific for the antigen. In some embodiments modulating an immune response to an antigen modulates an immune response to an entity comprising the antigen. For example, modulating an immune response to a pathogen-derived antigen modulates the immune response to a pathogen comprising the antigen or a cell expressing the antigen or displaying the antigen at its surface. The term "pathogen-derived antigen" encompasses any antigen that is naturally produced by and/or comprises a polypeptide or peptide that is naturally genetically encoded by a pathogen, e.g., any of the various pathogens mentioned herein. In some embodiments a pathogen-derived antigen is a polypeptide, a polysaccharide, a carbohydrate, a lipid, a nucleic acid, or combination thereof that is naturally produced by a pathogen. In some embodiments a pathogen-derived antigen is naturally encoded by a pathogen and is produced by an infected cell as a result of the introduction into the cell of the pathogen's genetic material that encodes the antigen. In some embodiments a pathogen-derived antigen is at least partly exposed at the surface of a cell membrane, cell wall, or capsule. In some embodiments a pathogen-derived antigen is a secreted virulence factor of a pathogen. In some embodiments a pathogen-derived antigen is an antigen that plays a role in entry of the pathogen into a host cell. For example, the antigen may bind to a cell surface molecule of a cell to be infected. In some embodiments a pathogen-derived antigen is a toxin. In some embodiments a pathogen may be an agent that rarely if ever causes disease in healthy, immunocompetent individuals, but that causes disease in at least some individuals who are susceptible, e.g., individuals who immunocompromised for any of a variety of reasons. Such reasons may include, e.g., age (e.g., infants or elderly individuals), pregnancy, genetic immunodeficiency disorders affecting one or more components of the innate and/or adaptive immune system, diseases such as cancer or infections that affect the immune system such as HIV infection, treatment with an immunsuppressive or cytotoxic drug, e.g., for cancer (e.g., cancer chemotherapy) or to prevent or inhibit transplant rejection.

In some aspects, the invention provides a method of modulating an immune response to an antigen, the method comprising targeting the antigen to an MHCII complex. In some embodiments the method comprises targeting the antigen to immune system cells that express an MHCII complex. In some aspects, the invention provides a method of modulating the immunogenicity of an antigen, the method comprising attaching the antigen to a targeting moiety that binds to an MHCII complex. In some aspects, modulation of an immune response according to certain methods disclosed herein that comprise targeting an antigen to MHCII complexes modulates the ability of immune system cells that express MHCII complexes at their surface to respond to the antigen and/or modulates the ability of immune system cells that express MHCII complexes at their surface to modulate one or more biological activities of other immune system cells.

In some embodiments, modulating an immune response comprises stimulating (enhancing, augmenting, eliciting) an immune response. In some embodiments "stimulating" an immune response encompasses causing development of an immune response, enhancing the capacity of a subject to mount an immune response, or increasing an immune response in a subject who is currently mounting an immune response. In some embodiments enhancing the capacity of a subject to mount an immune response results in a faster or more robust immune response. In some embodiments an immune response stimulated by targeting an antigen to MHCII complexes is directed towards foreign entities (e.g., pathogens), infected cells, cancer cells, or other undesirable (e.g., deleterious) cells or substances that comprise the antigen. In some embodiments an antigen is rendered more immunogenic (capable of eliciting a stronger, more robust, more effective, and/or more sustained immune response) by targeting the antigen to an MHCII complex. In some embodiments the antigen is targeted to MHCII complexes on the surface of APCs, e.g., DCs. In some embodiments the APCs are exposed to an adjuvant that induces the APCs to express a molecule that provides costimulation to other immune system cells, e.g., T cells. In some embodiments a costimulator is administered to a subject or provided in vitro. In some embodiments a MHCII complex is a mammalian MHCII complex, e.g., a human MHCII complex. In some embodiments a MHCII complex is expressed by human immune system cells.

In some embodiments an antigen comprises a molecule that is naturally produced by a pathogen or a neoplastic cell (e.g., a cancer cell). In some embodiments an antigen comprises a molecule that is naturally produced by an infected cell as a result of infection by a pathogen. In some embodiments an antigen that is targeted to an MHCII complex comprises a peptide. In some embodiments the peptide is at least 6, 7, 8, 9, 10, 11, 12, 13, 14, or 15 amino acids long. In some embodiments the peptide is between 20 and 50 amino acids long. In some embodiments the peptide is between 15 and 25, between 20 and 30, between 25 and 35, or between 35 and 50 amino acids long. In some embodiments the sequence of the peptide comprises or consists of the sequence of a portion of a longer polypeptide that is naturally encoded by a pathogen or a neoplastic cell. In some embodiments the sequence of the peptide comprises or consists of a portion of a longer polypeptide that is produced by an infected cell as a result of the infection, e.g., that is encoded by genetic material of a pathogen with which the cell is infected. In some embodiments the sequence of an antigen comprises multiple distinct sequences from different distinct polypeptides. For example, sequence of peptides that would be found as portions of distinct antigens in nature may be combined to produce a composite antigen comprising epitopes originating from such distinct antigens. For example, an antigen may comprise a polypeptide represented as X1-X2 . . . -Xn, where X1, X2 . . . Xn represent peptides found in distinct proteins, and in which n may range, e.g., from 2 to 5, 10, 20, or more. It will be understood that X1, X2, etc., may be directly adjacent to each other or joined by intervening linker(s). The resulting composite antigen may be capable of stimulating an immune response to multiple distinct antigens, e.g., each of the distinct antigens. In some embodiments multiple immunodominant epitopes are combined to generate a composite antigen. In some embodiments the sequence of an antigen comprises multiple distinct variants of a polypeptide, wherein such variants are found in different strains, serotypes, or subtypes of a pathogen. For example, an antigen may comprise peptides or polysaccharides obtained from at least 2, 5, 10, 20, or more strains, serotypes, or subtypes (e.g., clades) of a pathogen. In some embodiments the sequence of an antigen comprises multiple distinct variants of a polypeptide, wherein such variants are found in different pathogenic species belonging to a particular genus. In some embodiments at least some of the different polypeptides are naturally encoded by the same pathogen. In some embodiments the different polypeptides are naturally encoded by different pathogens. In some embodiments the different pathogens are viruses. In some embodiments the different pathogens are bacteria. In some embodiments the different pathogens are parasites. In some embodiments the sequence of an antigen comprises multiple distinct sequences from different distinct tumor antigens. In some embodiments an antigen is any antigen known or used in the art as a vaccine or vaccine component. In some embodiments any such antigen is conjugated to a targeting moiety that binds to an MHCII complex or is produced as a fusion protein comprising the antigen and targeting moiety.

In some aspects, disclosed herein are agents comprising (a) a targeting moiety that binds to an MHCII complex; and (b) an antigen. In some embodiments an antigen is targeted to MHCII complexes by contacting cells that express MHCII complexes with an agent comprising: (a) a targeting moiety that binds to the MHCII complex; and (b) the antigen. In general, a targeting moiety capable of binding to an MHCII complex may comprise any of a variety of different moieties, which may be obtained using any suitable method. In some embodiments the targeting moiety comprises an antibody, an antibody chain, an antibody fragment, an scFv, a VHH domain, a single-domain antibody, protein, or an aptamer, wherein the antibody, antibody chain, antibody fragment, scFv, VHH domain, single-domain antibody, protein, or aptamer, binds to an MHCII complex. In some embodiments an aptamer comprises an oligonucleotide that binds specifically and with high affinity to its target, e.g., an MHCII complex. In some embodiments the oligonucleotide is single-stranded (although it may in some embodiments form regions of double-stranded secondary structure through intramolecular complementarity). An aptamer may be identified through a selection process using, e.g., systematic evolution of ligands by exponential enrichment (SELEX), phage display, or various directed evolution techniques. See, e.g., Turek, C. and Gold, L., Science 249: 505-10, 1990; Brody E N and Gold L T, Biotechnol. 3, 74(1):5-13, 2000; L. Cerchia and V. de Franciscis, Trends Biotechnol., 28: 517-525, 2010; Keefe, A. Nat. Rev. Drug Discov. 9: 537-550, 2010. In some embodiments a protein comprises a peptide that binds to a target molecule or complex, e.g., an MHCII complex. In some embodiments the peptide is selected using a display technology, e.g., phage display, or directed evolution. In some embodiments the peptide is selected from a peptide library. In some embodiments a protein may comprise any of a variety of polypeptide scaffolds known in the art including, e.g., those based on or incorporating one or more protein folds or domains from, e.g., protein Z, fibronectin, ankyrin repeat proteins; cysteine-knot miniproteins, Armadillo repeat proteins, lipocalins, or stefin A. In some embodiments a protein comprises an affibody, adnectin, DARPin, knottin, anticalins, or steffin. The protein, e.g., affibody, adnectin, DARPin, knottin, anticalins, or steffin, may be designed or selected to bind to an MHCII complex. In some embodiments a peptide that binds to a target, e.g., an MHCII complex, is inserted into a polypeptide scaffold. See, e.g., Hoffmann, T., et al. Protein Eng Des Sel., 23(5):403-13, 2010, and references therein, for discussion of various proteins and polypeptide scaffolds. In some embodiments any such protein or scaffold is used, e.g., as a targeting moiety. In some aspects, disclosed herein are compositions comprising (i) an agent that comprises (a) a targeting moiety that binds to an MHCII complex; and (b) an antigen; and (ii) an MHCII complex. In some embodiments the targeting moiety is bound to the MHCII complex. In some embodiments the composition is an in vitro composition. In some embodiments the MHCII complex is present at the surface of a cell.

In some embodiments the targeting moiety and the antigen are covalently linked. In some embodiments the targeting moiety and the antigen are linked via a linker. In some embodiments the targeting moiety and the antigen are non-covalently attached to each other or to a third moiety. In some embodiments the antigen comprises a peptide, and the agent comprises a fusion protein comprising the targeting moiety and the peptide. In some embodiments the targeting moiety or antigen comprises or is modified to comprise a TRS. In some embodiments the targeting moiety comprises a polypeptide comprising a VHH. In some embodiments the polypeptide comprises a VHH and a TRS. In some embodiments the antigen is attached to the targeting moiety via a sortase-mediated reaction. In some embodiments the targeting moiety is sortagged with the antigen. In some embodiments the targeting moiety and antigen comprise first and second click chemistry handles, and the agent is prepared by reacting the click chemistry handles with each other. In some embodiments sortagging is used to install click chemistry handles on the targeting moiety and/or the antigen. In some embodiments the targeting moiety and the antigen are conjugated using any conjugation approach or crosslinker known in the art (see discussion above).

In some embodiments the targeting moiety binds to mature MHCII complexes exposed at the cell surface. In some embodiments the targeting moiety binds to a non-polymorphic region of the MHCII complex. In some embodiments the targeting moiety binds to MHCII complexes outside the region to which CD4 binds.

In some aspects, the agent can be represented by formula A-B, wherein A comprises a targeting moiety that binds to an MHCII complex, and B comprises an antigen. In some embodiments A comprises an antibody, an antibody chain, an antibody fragment, an scFv, a VHH domain, a single-domain antibody, a protein, or an aptamer, wherein the antibody, antibody chain, antibody fragment, scFv, VHH domain, single-domain antibody, protein, or aptamer binds to an MHCII complex. In some embodiments A comprises a TRS. In some embodiments A comprises a polypeptide comprising: (a) a VHH domain, VH domain, VL domain, scFv, conventional antibody chain, or protein; and (b) a TRS. In some embodiments the TRS is located at or near the C-terminus of the polypeptide. In some embodiments B comprises or is modified to comprise a sortase-usable nucleophile. For example, in some embodiments B comprises or is modified to comprise one or more free glycine residues. In some embodiments the antigen is attached to the polypeptide via the TRS. In some embodiments, an agent has the following formula:

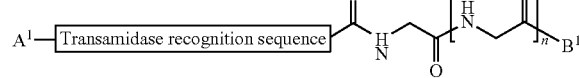

wherein $A^1$ comprises a polypeptide comprising a VHH domain, VH domain, VL domain, scFv, conventional antibody chain, or protein that binds to an MHCII complex, wherein $B^1$ comprises an antigen, and wherein n is between 0 and 100. In general, $B^1$ can comprise or consist of any antigen in various embodiments, e.g., any antigen described herein. For example, in some embodiments $B^1$ comprises a peptide.

In some embodiments modulating the immune response comprises stimulating the immune response. For example, in some embodiments targeting a pathogen-derived antigen to an MHCII complex stimulates an immune response against the antigen. In some embodiments, targeting a pathogen-derived antigen to an MHCII complex stimulates an immune response against a pathogen that produces the antigen. In some embodiments, targeting a pathogen-derived antigen to an MHCII complex stimulates an immune response against infected cells that comprise the antigen as a result of infection by a pathogen. In some embodiments, targeting a tumor antigen to an MHCII complex stimulates an immune response against tumor cells that produce the antigen. In some embodiments a method of enhancing an immune response to a pathogen comprises targeting a pathogen-derived antigen to an MHCII complex. In some embodiments a method of stimulating an immune response to a pathogen-infected cell comprises targeting a pathogen-derived antigen to an MHCII complex. In some embodiments a method of stimulating an immune response to a tumor comprises targeting an antigen expressed by the tumor to an MHCII complex. In some embodiments the antigen is a tumor antigen.

In some embodiments a method of modulating an immune response to an antigen comprises targeting the antigen to dendritic cells (DCs) by targeting the antigen to MHCII complexes present at the surface of such cells. DCs are a class of white blood cells that occur in most tissues of the body, particularly those in contact with the exterior such as the skin (which contains a specialized dendritic cell type termed a Langerhans cell) and mucosal surfaces, as well as in the blood. During certain developmental stages DCs grow membranous projections known as dendrites, from which the cell type gets its name. DCs serve as a link between peripheral tissues and lymphoid organs and play important roles in modulating the activity of other immune system cells. Immature dendritic cells sample the surrounding environment for pathogens such as viruses and bacteria through pattern recognition receptors (PRRs) such as toll-like receptors (TLRs). In response to stimuli such as pathogen components or other danger signals, inflammatory cytokines, and/or antigen-activated T cells, they undergo maturation and migrate to the T cell area of lymph nodes or spleen, where they display fragments of previously phagocytosed and processed antigens at their cell surface using MHCII complexes, as described above. As part of the maturation process, DCs upregulate cell-surface receptors that act as co-receptors in T cell activation, such as CD80 (B7-1), CD86 (B7-2), and/or CD40. DCs activate helper T cells (Th cells) by presenting them with antigens derived from the pathogen in the context of MHCII complexes, together with non-antigen specific costimulators. Binding of CD4+ expressed at the surface of Th cells to a non-polymorphic region of MHCII enhances the physical interaction between DC and Th cells, allowing potent stimulation of helper T cells that express TCR molecules capable of binding the peptide. In addition, DCs have the capacity to directly activate cytotoxic T cells and B-cells through presentation of MHCII-peptide complexes and costimulators and are also able to activate the innate arm of anti-tumor immunity, e.g., NK and NKT effector cells. DC stimulation promotes Th cell proliferation, activation, and differentiation into effector Th cells, memory Th cells, and regulatory Th cells. Effector Th cells provide "help" to cytotoxic T cells, B cells, and macrophages by, e.g., secreting cytokines that exert a variety of stimulatory effects on these cell types. Th help promotes proliferation and activation of cytotoxic T cells, stimulates B-cell proliferation, induces B-cell antibody class switching, and stimulates antibody production. Th stimulation also enhances the killing ability of macrophages. Memory T cells play an important role in promoting the rapid mounting of a specific, strong adaptive immune response upon encountering an antigen to which a subject has previously been exposed. Regulatory Th cells are believed to play an important role in the self-limiting nature of the immune response.

In some embodiments, DCs capable of presenting a particular peptide stimulate both the cell-mediated and humoral branches of the adaptive immune response towards targets containing that peptide as well as enhancing activity of the innate immune system.

In some embodiments, methods disclosed herein of modulating an immune response enhance an adaptive immune response against a pathogen, infected cell, tumor cell, or other undesired cell or substance. In some embodiments, methods disclosed herein of modulating an immune response enhance an innate immune response against a pathogen, infected cell, tumor cell, or other undesired cell or substance. In some embodiments, methods disclosed herein of modulating an immune response enhance both an adaptive immune response and an innate immune response against a pathogen, infected cell, tumor cell, or other unwanted cell or substance. In some embodiments, methods disclosed herein enhance a T cell-mediated immune response, e.g., against a pathogen such as a virus (e.g., HIV), bacterium (e.g., *Mycobacterium*), fungus (e.g., *Aspergillus*) or parasite (e.g., *Plasmodium*), or against a tumor cell or other undesired cell. In some embodiments, methods disclosed herein enhance cell-mediated cytotoxicity towards a pathogen, infected cell, or tumor cell. For example, in some embodiments methods disclosed herein enhance activity of CD8+ cytotoxic T cells against a pathogen, infected cell, or tumor cell.

Dec-205 is a molecule expressed primarily on dendritic cells, but also found on B cells, as well as various other cell types. Targeting antigens to Dec-205 for presentation by dendritic cells has been proposed as an approach to modulate the immune response to such antigens, e.g., to stimulate the immune response for purposes of vaccination against a pathogen or tumor (see, e.g., WO/1996/023882). As described in Example 10, targeting a peptide to MHCII complexes by attaching the peptide to a MHCII-binding VHH using sortase, was significantly more effective in stimulating dendritic cells in vitro than was targeting the same peptide to Dec-205 using a conventional antibody modified to include a TRS at the C-terminus of its heavy chains, which TRS was used to sortag the heavy chains with the peptide. Targeting a peptide to MHCII complexes in vivo using the sortase-modified VHH was effective in stimulating CD4+ T cell activation. Without wishing to be bound by any theory, targeting an antigen to MHCII complexes has the potential to be significantly more effective in stimulating an immune response to the antigen or, if desired, inducing tolerance to the antigen, than targeting an antigen to Dec-205.

In some embodiments an antigen is targeted in vitro to an MHCII complex expressed by immune system cells (e.g., in an in appropriate composition such as in cell culture). In some embodiments a composition comprises (a) immune system cells that express an MHCII complex; and (b) an agent having the formula A-B, wherein A comprises a targeting moiety that binds to an MHCII complex and wherein B comprises an antigen. In some embodiments the composition comprises up to about $10^{14}$ cells, e.g., between about 1, 10, $10^2$, $10^3$, $10^4$, $10^5$, $10^6$, $10^7$, $10^8$, $10^9$, $10^{10}$, $10^{11}$, $10^{12}$, $10^{13}$ or $10^{14}$ cells. In some embodiments the immune system cells comprises a mixed population of immune system cells. In some embodiments immune system cells in a composition comprise monocytes. In some embodiments human monocytes express high levels of CD14 and/or CD16 on their surfaces. In some embodiments. In some embodiments immune system cells in a composition comprise APCs, e.g., professional APCs. In some embodiments professional APCs are dendritic cells. In some embodiments dendritic cells comprise immature dendritic cells, which lack one or more characteristics found in mature dendritic cells present in tissues. For example, immature dendritic cells may lack dendrites and/or lack one or more markers of mature DCs. In some embodiments immature dendritic cells, e.g., immature human dendritic cells, express and/or lack expression of CD83. In some embodiments DCs, e.g., human DCs, comprise myeloid DCs. In some embodiments DCs, e.g., human DCs, comprise plasmacytoid DCs. In some embodiments DCs comprise plasmacytoid CD303+ DCs, myeloid CD1c+ DCs, and/or myeloid CD141+ DCs. In some embodiments professional APCs are macrophages. In some embodiments cells in a composition comprise T cells. In some embodiments cells in a composition T cells comprise naïve T cells. In some embodiments cells in a composition comprise CD4+ T cells. In some embodiments cells in a composition comprise CD8+ T cells. In some embodiments a composition comprises APCs, e.g., dendritic cells, and T cells, e.g., CD4+ T cells and/or CD8+ T cells. In some embodiments a composition is enriched for immune system cells of one or more types. In some embodiments enrichment is performed at least in part based on expression (which may be lack of expression) of one or more cell surface markers using, e.g., FACS or affinity reagents. One can select for or against cells that express particular markers. In some embodiments enrichment is performed at least in part by exposing cells to an agent or combination of agents (e.g., cytokines) that promote differentiation and/or expansion of one or more cell types. In some embodiments a composition comprises at least 10%, 20%, 30%, 40%, 50%, 60%, 70%, 80%, 90%, or more cells of a particular type and/or expressing a particular marker or combination of markers.

In some embodiments a composition comprises an adjuvant or costimulator. In some embodiments an adjuvant induces expression of a costimulator by APCs. In some embodiments a composition comprises at least one cytokine. In some embodiments a cytokine enhances survival, proliferation, maturation, or activation of one or more types of immune system cells. In some embodiments a cytokine is an interleukin. In some embodiments a cytokine is IL-2. In some embodiments a cytokine is IL-12. In some embodiments a cytokine is a colony stimulating factor. In some embodiments a cytokine is an interferon. In some embodiments DCs are treated so as to facilitate DC migration to secondary lymphoid tissues and/or to stimulate expression by the DCs of one or more costimulators and/or cytokines. Such treatment may include, for example, contacting the cells with one or more cytokines and/or genetically modifying the cells. In some embodiments cells are genetically modified to cause them to express one or more costimulators and/or cytokines. Standard methods of genetic modification known in the art can be used. In some embodiments a vector comprising a nucleic acid that encodes a costimulator (e.g., CD40) or cytokine (e.g., IL2, IL-12) is introduced into the cells. In some embodiments a vector comprises nucleic acids encoding multiple costimulators and/or cytokines. In some embodiments a nucleic acid encoding a fusion protein comprising at least a portion of each of two or more cytokines and/or costimulators is used. It will be appreciated that a functional portion or variant of a cytokine or costimulator may be used. In some embodiments multiple vectors are introduced. In some embodiments the nucleic acid(s) are operably linked to expression control elements (e.g., a promoter) appropriate to direct expression in the cells. In some embodiments nucleic acids comprising sequences encoding the costimulators and/or cytokines integrate into the cellular genome. In some embodiments a vector is a virus vector, e.g., a retrovirus (e.g., lentivirus), adenovirus, or adeno-associated virus. In some embodiments a vector is a plasmid. In some embodiments an episomal vector is used. In some embodiments immune system cells may be obtained, processed, and/or expanded in vitro using any approach known in the art, e.g., any approach known in the art for preparation of DC vaccines and/or T cell vaccines, e.g., any protocol for adoptive immunotherapy. In some embodiments a protocol for rapid expansion of T cells is used. In some aspects, any procedure or protocol for cell-based immunotherapy is modified to comprise exposing at least some of the immune system cells to an agent comprising (a) a targeting moiety that binds to MHCII complexes and (b) an antigen.

In some embodiments a composition in which immune system cells are cultured or maintained comprises one or more cytokines, e.g., any of the cytokines mentioned above or a functional variant thereof. In some embodiments the one or more cytokines promotes maturation, survival, proliferation, or activation of at least some of the immune system cells. In some embodiments a cytokine is IL-2. In some embodiments a cytokine is IL-12. In some embodiments a composition in which immune system cells are cultured or maintained comprises one or more adjuvants. In some embodiments the one or more adjuvants induces expression of a costimulator by at least some of the immune system cells. In some embodiments the one or more adjuvants comprises a TLR ligand, PAMP or PAMP mimic, CD40 ligand, or anti-CD40 antibody. In some embodiments a composition in which immune system cells are cultured or maintained comprises one or more costimulators. In some embodiments a costimulator is expressed at the surface of APCs, e.g., DCs. In some embodiments a costimulator is soluble. In some embodiments a costimulator is attached to a surface, e.g., a particle.

In some embodiments a composition in which cells are cultured or maintained is serum-free. For example, in some embodiments a serum-free medium is used to culture the cells. In some embodiments the composition comprises a chemically defined culture medium. In some embodiments a chemically defined culture medium is free or essentially free of biological materials isolated from a human or animal, such as serum, albumin, cell or tissue extracts. In some embodiments cells cultured in the composition satisfy regulatory requirements for administration to a human subject. In some embodiments cells cultured in the composition satisfy regulatory requirements of a government agency such as the US Food and Drug Administration, European Medicines Evaluation Agency, or a similar agency responsible for evaluating the safety of therapeutic agents prior to their administration to humans or being placed on the market for administration to humans.

In some embodiments an immune response comprises maturation, proliferation and/or activation of lymphocytes, e.g., CD4+ helper T cells, that are specific for the antigen, i.e., that express receptors (TCR, BCR) that bind to the antigen, e.g., with high affinity. In some embodiments, cell activation results in increased expression of one or more cytokine genes. In some embodiments, cell activation results in increased secretion of one or more cytokines. In some embodiments, presence or proliferation of T cells with specificity for a particular antigen in vitro or in vivo may be assessed using peptide-MHC tetramers, which can be used to identify or isolate T cells specific for the peptide. Methods for generating peptide-MHC tetramers are known in the art.

See, e.g., Grotenbreg, G., et al., PNAS (2008) 105(10): 3831-3836 and references therein for examples.

In some embodiments, immune system cells that have been generated or modulated in in vitro by exposing them to an agent A-B are administered to a subject. In some embodiments at least some of the cells administered to the subject comprise MHCII complexes that have the agent A-B bound thereto. In some embodiments, such cells stimulate maturation, proliferation and/or activation of endogenous immune system cells (e.g., CD4+ T cells) in the subject. In some embodiments at least some of the cells administered to the subject are APCs (e.g., DCs) that comprise MHCII complexes having the antigen targeted thereto. In some embodiments at least some of the cells administered to the subject were stimulated in vitro by APCs (e.g., DCs) that comprise MHCII complexes having the antigen targeted thereto. In some embodiments, at least some of the cells originated from the subject or from an immunologically compatible donor or are descended from cells that originated from the subject or from an immunologically compatible donor. For example, in some embodiments immune system cells are harvested from the bone marrow, spleen, lymph node, or peripheral blood or lymph of a subject or donor and in some embodiments, contacted in vitro with an agent A-B. In some embodiments immune system cells are obtained from the blood using leukophoresis. In some embodiments immune system cells are generated in vitro from, e.g., hematopoietic stem cells or myeloid lineage progenitor cells. In some embodiments dendritic cells, e.g., immature dendritic cells, are obtained from the blood or generated in vitro from monocytes obtained from the blood. In some embodiments dendritic cells, e.g., immature dendritic cells, are generated in vitro from peripheral blood mononuclear cells (PBMCs). In some embodiments immune system cells are generated in vitro by reprogramming or transdifferentiation of a somatic cell. In some embodiments cells are expanded in culture prior to being contacted with the agent. Immune system cells that have been contacted with agent are introduced into the subject. In some embodiments a culture of immune system cells is maintained. Portions of the culture are contacted with the agent at intervals of days, weeks, months, etc., after which such portions are administered to the subject. In some embodiments different portions are contacted with agents comprising distinct antigens. In some embodiments at least some cells harvested from a subject or expanded in vitro are maintained frozen. Aliquots of frozen cells may be thawed at intervals and used as described herein. Thus in some embodiments, a vaccine comprising an agent having the formula A-B, wherein A comprises a targeting moiety that binds to an MHCII complex and wherein B comprises a pathogen-derived antigen is used in vitro. For example, in some embodiments, immune system cells are obtained, contacted with the vaccine in vitro as described above, and then administered to a subject in need of prophylaxis or in need of treatment of an existing infection or in need of delaying, inhibiting, or preventing recurrence of an infection by the pathogen. In some embodiments, a vaccine comprising an agent having the formula A-B, wherein A comprises a targeting moiety that binds to an MHCII complex and wherein B comprises a tumor antigen is used in vitro. For example, in some embodiments, immune system cells are obtained, contacted with the vaccine in vitro as described above, and then administered to a subject in need of treatment of a tumor or in need of delaying, inhibiting, or preventing recurrence of a tumor.

In some embodiments a composition administered to a subject comprises up to about $10^{14}$ cells, e.g., about $10^3$, $10^4$, $10^5$ $10^6$, $10^7$, $10^8$, $10^9$, $10^{19}$, $10^{11}$, $10^{12}$, $10^{13}$ or $10^{14}$ cells, or any intervening range. In some embodiments between about $10^5$ and about $10^{12}$ cells are administered. In some embodiments between about $10^5$-$10^8$ cells and about $10^{11}$-$10^{13}$ cells are administered. In some embodiments a subject receives a single dose of cells. In some embodiments a subject receives multiple doses of cells, e.g., between 2 and 5, 10, 20, or more doses, over a course of treatment. In some embodiments a course of treatment lasts for about 1-2-months, 2-6 months, 6-12 months, or more, e.g., indefinitely or until the subject is no longer in need of treatment. In some embodiments a subject may be treated about every 2-4 weeks, One of ordinary skill in the art will appreciate that the number of cells and/or doses administered to a subject may be selected based on various factors such as the weight, surface area, and/or blood volume of the subject, the condition being treated, etc.

In some embodiments one or more agents is also administered once or more to the subject in addition to administering cells. In some embodiments an agent is administered to the subject at least once prior to and/or at least once after administration of the cells. In some embodiments an agent comprising a targeting moiety that binds to MHCII complexes and a target antigen is administered to the subject in addition to administering cells. In some embodiments the agent is the same agent as that to which the cells were exposed in vitro. In some embodiments a cytokine is administered to the subject, wherein the cytokine is capable of enhancing survival, proliferation, maturation, or activation of immune system cells. In some embodiments the cytokine is IL-2. In some embodiments the cytokine is IL-12. In some embodiments an adjuvant is administered to the subject. In some embodiments the adjuvant is capable of inducing APCs to express a costimulator. In some embodiments the adjuvant and/or cytokine is administered in the same composition as the cells. In some embodiments the adjuvant, cytokine, and/or cells are administered in different compositions. In some embodiments cells are administered using any suitable route of administration. In some embodiments cells are administered parenterally, e.g., intravenously. In some embodiments cells are administered to or in the vicinity of a tumor or a site that may harbor tumor cells (e.g., a site from which a tumor was removed or rendered undetectable by treatment), site of infection, or site of potential infection (e.g., a break in the skin such as a wound, indwelling device, surgical site, etc.).

In some embodiments, an agent has the formula A-B, wherein A comprises a targeting moiety that binds to an MHCII complex and B comprises a tumor antigen. For example, in some embodiments, immune system cells are obtained (e.g., from the subject or a donor) and contacted with the agent in vitro. At least some of the immune system cells and/or descendants thereof are administered to a subject in need of prophylaxis or in need of treatment of an existing cancer or in need of delaying, inhibiting, or preventing recurrence of cancer. In some embodiments at least some of the introduced cells (or their descendants) mount an immune response against the cancer or against cancer cells remaining in or arising in the body, wherein the cancer or cancer cells comprise the tumor antigen. In some embodiments at least some of the introduced cells (or their descendants) stimulate maturation, proliferation, and/or activation of at least some endogenous immune system cells of the subject, e.g., endogenous T cells, wherein the endogenous immune system cells mount an immune response against the cancer or against cancer cells remaining in or arising in the body, wherein the cancer or cancer cells comprise the tumor antigen. In some embodiments the agent is administered to the subject with or without immune system cells.

In some embodiments a method comprises identifying an antigen expressed by a tumor for which a subject is in need of treatment. The tumor or cells obtained from the tumor can be analyzed for expression of tumor antigens using standard methods such as immunohistochemistry, flow cytometry, etc. In some embodiments, immune system cells are contacted in vitro with an agent comprising a targeting moiety that binds to MHCII complexes and the antigen. The immune system cells and/or descendants thereof are subsequently administered to the subject. In some embodiments, immune system cells are contacted in vivo with an agent comprising a targeting moiety that binds to MHCII complexes and the antigen by administering the agent to the subject in need of treatment for a tumor. In some embodiments immune system cells are obtained from a subject prior to treatment of the subject with chemotherapy or radiation. At least some of the immune system cells may be stored for future use in producing one or more cell preparations to be administered to the subject. In some embodiments one or more of the cell preparations comprise immune system cells that have been contacted in vitro with an agent that targets an antigen derived from the tumor to MHCII complexes. In some embodiments one or more of the cell preparations comprise immune system cells that have been contacted in vitro with an agent that targets a pathogen-derived antigen to MHCII complexes. For example, if the subject subsequently becomes infected by a pathogen, immune system cells that have been contacted in vitro with an agent that targets an antigen derived from the pathogen to MHCII complexes may be administered to the subject.

In some embodiments an antigen is targeted to an MHCII complex expressed by immune system cells in a subject. In some embodiments, a vaccine comprising an agent having the formula A-B, wherein A comprises a targeting moiety that binds to an MHCII complex and wherein B comprises a tumor antigen, is used as an in vivo cancer immunotherapeutic agent, i.e., the vaccine is administered to a subject in need of treatment of an existing cancer or in need of delaying, inhibiting, or preventing recurrence of cancer. In some embodiments, a vaccine comprising an agent having the formula A-B, wherein A comprises a targeting moiety that binds to an MHCII complex and wherein B comprises a pathogen-derived antigen, is administered to a subject in need of prophylaxis of an infection or in need of treatment of an existing infection. In some embodiments, a vaccine comprising an agent having the formula A-B, wherein A comprises a targeting moiety that binds to an MHCII complex and wherein B comprises a tumor antigen, is administered to a subject in need of delaying, inhibiting, or preventing recurrence of cancer. In some embodiments a method comprises providing a subject in need of treatment for a cancer and administering an agent comprising a targeting moiety that binds to an MHCII complex and a tumor antigen to the subject. In some embodiments the tumor expresses the tumor antigen. In some embodiments the method comprises determining that the tumor expresses the tumor antigen.

In some embodiments, a composition comprises first and second agents having the formulas $A\text{-}B_1$ and $A\text{-}B_2$, wherein A comprises a targeting moiety that binds to an MHCII complex, and wherein $B_1$ and $B_2$ comprise distinct antigens, e.g., different peptides. In some embodiments a composition comprises k agents, having the formulas $A\text{-}B_1 \ldots A\text{-}B_k$, wherein A comprises a targeting moiety that binds to an MHCII complex, and wherein $B_1 \ldots B_k$ are different, and wherein k is at least 2. In some embodiments k is between 2 and 5, between 2 and 10, or between 2 and 20. In some embodiments at least some of the $B_1 \ldots B_k$ comprise peptides whose sequences are part of the sequence of a larger naturally occurring antigen. For example, in some embodiments at least some of $B_1 \ldots B_k$ comprise sequences found in a particular protein that is naturally encoded or produced by a pathogen, an infected cell, or a neoplastic cell. In some embodiments at least some of the $B_1 \ldots B_k$ comprise sequences from different larger proteins. For example, in some embodiments at least some of $B_1 \ldots B_k$ comprise sequences found in different proteins that are naturally encoded or produced by a particular pathogen, or sequences found in different proteins produced by an infected cell or a neoplastic cell. In some embodiments at least some of the $B_1 \ldots B_k$ comprise a polysaccharide. In some embodiments at least some of $B_1 \ldots B_k$ comprise antigens derived from different pathogens. For example, in some embodiments at least some of $B_1 \ldots B_k$ comprise sequences found in proteins that are naturally encoded or produced by different pathogens (e.g., different fungal, bacterial, viral, or parasite species). In some embodiments at least some of $B_1 \ldots B_k$ comprise sequences found in different strains, serotypes, subtypes, or variants of a particular pathogen species. In some embodiments at least some of $B_1 \ldots B_k$ comprise peptides derived from a particular protein that differs in sequence among different strains, serotypes, subtypes or variants of a particular pathogen. In some embodiments at least some of $B_1 \ldots B_k$ comprise polysaccharides (e.g., capsular polysaccharides) that differ in structure among different strains, serotypes, subtypes or variants of a particular pathogen. In some embodiments, a composition comprises agents comprising any of multiple different targeting moieties A, which may be conjugated to the same or different antigens. For example, multiple different VHH domains that bind to MHCII complexes may be used as targeting moieties. In some embodiments, moiety "A" in formulas $A\text{-}B_1 \ldots A\text{-}B_k$, may differ among each of the different moieties "B", e.g., $A_1\text{-}B_1, A_2\text{-}B_2, A_3\text{-}B_3 \ldots A_k\text{-}B_k$. In some embodiments, any A moiety may be conjugated to any one or more B moieties, or vice versa. In some embodiments a B moiety may be conjugated to each of multiple different targeting moieties, e.g., $A_1\text{-}B_1, A_2\text{-}B_1, A_3\text{-}B_1$. In some embodiments the number of distinct moieties A in a composition is between 2 and 5, between 2 and 10, or between 2 and 20.

In some embodiments, multiple compositions (e.g., vaccines capable of stimulating the immune response to distinct pathogens) are combined to produce a composition capable of stimulating the immune response to each of the multiple pathogens.

In some embodiments a subject, e.g., a subject to whom a vaccine is administered, is immunocompetent; e.g., the subject has a normally functioning immune system. In some embodiments a subject, e.g., a subject to whom a vaccine is administered, is immunodeficient, e.g., as a result of cancer, treatment with an immunosuppressive agent, infection, inherited immunodeficiency disorder, etc. Immunosuppressive agents include, e.g., cytotoxic or cytostatic drugs, such as a variety of chemotherapeutic drugs used in the treatment of cancer, various drugs administered to reduce the likelihood of transplant rejection or to treat autoimmune diseases. Examples include, e.g., glucocorticoids, immunophilin-interacting agents such as rapamycin or rapamycin analogs, TNF alpha antagonists, etc.). In some embodiments a subject is at increased risk of infection as compared with a normal, average healthy individual, due, e.g., to hospitalization, surgery, chronic disease (e.g., diabetes, cancer, chronic obstructive pulmonary disease, cystic fibrosis), indwelling medical device (e.g., catheter, IV line), implant or prosthesis (e.g., heart valve replacement, cochlear implant), physical trauma, burn, malnourishment, etc. In some embodiments, a vaccine is used to induce or augment an immune response in a subject who has undergone, is undergoing, or will undergo chemotherapy or radiation therapy. In some embodiments a subject is at increased risk of infection because the subject is less than about 1 year of age or is over about 60, 65, 70, 75, or 80 years of age.

In some embodiments, modulating an immune response comprises inhibiting the immune response. As used herein, "inhibiting" an immune response encompasses preventing or delaying development of an immune response to an antigen in a subject not currently exhibiting such response or reducing the intensity of a current or potential future immune response. In some embodiments an immune response is an unwanted immune response, e.g., an immune response that is deleterious to the subject in whom it occurs. In some embodiments, an unwanted immune response is directed against self tissues or cells, transplanted tissue or cells, non-living materials introduced into the body for diagnostic or therapeutic purposes, or an allergen.

In some embodiments an unwanted immune response is an immune response that is excessive or inappropriately prolonged, such that it is deleterious to the subject. For example, an immune response directed against an antigen derived from a pathogen that has infected a subject may initially be beneficial in terms of controlling the pathogen but may be too intense or prolonged, such that it causes tissue damage to the subject (e.g., cell-mediated or antibody-mediated tissue damage) or symptoms due to excessive cytokine release.

In some embodiments, an unwanted immune response is an immune response mounted by a subject against a transplanted tissue or organs or cells, such as blood cells, stem cells, blood vessel, bone marrow, solid organ (e.g., heart, lung, kidney, liver, pancreas), skin, intestine, or cells derived from any of the foregoing. In some embodiments the transplant (also termed a "graft") comprises allogeneic cells or tissues (i.e., the donor and recipient are different individuals from the same species). In some embodiments the transplant comprises xenogeneic cells or tissues (i.e., the donor and recipient are of different species). The immune response may be directed, e.g., against one or more donor antigens, e.g., histocompatibility proteins (e.g., major or minor histocompatibility proteins) of the donor. An immune response directed against a graft may be referred to as "rejection". Rejection may result in damage to the graft, which may reduce its function, may lead to graft failure, and may ultimately require removal of the graft. In some embodiments an unwanted immune response comprises graft-versus-host disease (GVHD). GVHD may occur, for example, after an allogeneic stem cell transplant or bone marrow transplant. Immune cells in the donated marrow or stem cells recognize the recipient (e.g., recipient's cells) as foreign and mount an immune response thereto, e.g., a T cell-mediated immune response.

In some embodiments an unwanted immune response occurs to an autoantigen (also referred to as a self antigen), e.g., in a subject suffering from an autoimmune disease. One of ordinary skill in the art will be aware of various autoantigens involved in particular autoimmune diseases.

In some embodiments an unwanted immune response occurs in response to an allergen. As used herein, an "allergen" is any substance capable of stimulating a type-I hypersensitivity reaction in sensitive (atopic) individuals through immunoglobulin E (IgE) responses. Allergens include, e.g., animal products (e.g., fur, dander, saliva, excretions from, e.g., dog, cat, horse, cockroach, mite, etc), drugs (e.g., penicillins and related drugs, sulfonamides, salicylates); foods (e.g., celery and celeriac, corn or maize, eggs, fruits (e.g., strawberry, peach, pumpkin) legumes (e.g., beans, peas, peanuts, soybeans); dairy products, e.g., milk; seafood (e.g., shellfish such as shrimp, crabs, lobster); sesame; treenuts (e.g., pecans, almonds); wheat; insect venoms (e.g., bee, wasp), mosquito stings; mold (e.g., spores); latex, plant pollens (e.g., grasses such as ryegrass, timothy-grass; weeds such as ragweed, *plantago*, nettle, *artemisia, chenopodium*, sorrel); trees such as birch, alder, hazel, hornbeam, *aesculus*, willow, poplar, *platanus, tilia, olea*, juniper). An "allergenic antigen" is any antigen component of an allergen that is responsible at least in part for the allergenic nature of the allergen. In some embodiments an allergen is a substance that provokes one or more allergic symptoms in a susceptible individual when inhaled. In some embodiments an allergen is a substance that provokes one or more allergic symptoms in a susceptible individual when ingested. In some embodiments an allergen is a substance that provokes one or more allergic symptoms in a susceptible individual when introduced by insect sting, bite, or by injection. In some embodiments an allergen is a substance that provokes one or more allergic symptoms in a susceptible individual when contacted with the skin. Numerous proteins have been identified as allergenic antigens. See, e.g., the AllergenOnline database (http://www.allergenonline.org).

In some embodiments, a method for inducing tolerance comprises generating tolerogenic DCs, e.g., DCs that either delete autoreactive T cells or induce regulatory T (Treg) cells, e.g., CD4+CD25-Foxp3+ regulatory T cells. In some embodiments, a method results in reduction in the number and/or activity of Th17 cells. In some embodiments tolerogenic DCs are generated in vitro and administered to a subject. In some embodiments tolerogenic DCs are generated by a method comprises exposing DCs, e.g., immature DCs, in vitro, to an agent comprising (a) a targeting moiety that binds to MHCII complexes and (b) an antigen, wherein the antigen comprises a self-antigen or allergenic antigen. In some embodiments inhibiting the immune response e.g., induction of tolerance or a tolerogenic state, is achieved by using a suitable concentration or amount of the agent and/or exposing cells or subjects to appropriate cytokines. In some embodiments targeting an antigen to MHCII complexes in the absence of an effective amount of an adjuvant inhibits the immune response to the antigen that would otherwise occur and thereby results in increased tolerance to the antigen. In some embodiments a method of inhibiting an immune response comprises administering to a subject an agent comprising a targeting moiety that binds to an MHCII complex and an antigen, wherein the antigen comprises a self-antigen or allergenic antigen. In some embodiments the antigen is one to which the subject has previously exhibited or continues to exhibit or is at risk of exhibiting an unwanted, e.g., deleterious, immune response. In some embodiments the agent is administered without administering an effective amount of an adjuvant. For example, the agent may be administered in a composition that is substantially free of adjuvants.

In some embodiments inhibiting an unwanted immune response comprises stimulating an immune response against one or more cellular components of the unwanted immune response. For example, in some embodiments an immune response directed against self-reactive immune system cells, e.g., self-reactive T cells, is stimulated. In some embodiments an immune response directed against immune system cells at least in part responsible for an immune-mediated disorder, e.g., allergy, is stimulated. In some embodiments an immune response directed against one or more cellular components of the unwanted immune response at least in part eliminates such cells, resulting in a reduction or inhibition of the unwanted immune response.

In some embodiments a composition, e.g., a composition to be used to induce tolerance in a subject, is substantially free or essentially free of any one or more substances, e.g., any one or more particular adjuvant(s), e.g., any one or more of the adjuvants or classes of adjuvants mentioned above or known in the art. In some embodiments the concentration or amount of adjuvant present, if any, is ineffective to enhance an immune response. In some embodiments the concentration or amount of adjuvant is less than or equal to 1%, 5%, 10%, 15%, 20%, or 25% of the concentration or amount that would be effective to stimulate an immune response, e.g., an amount that would be used by one of ordinary skill in the art seeking to generate or enhance an immune response against an antigen, e.g., in a vaccine. In some embodiments a composition is substantially free or essentially free of any one or more particular adjuvant(s), e.g., any one or more of the adjuvants or classes of adjuvants mentioned above or known in the art. In some embodiments an adjuvant, if present, does not comprise a TLR ligand, PAMP, or CD40 ligand or anti-CD40 antibody.

In certain embodiments a composition is considered "substantially free" of a substance if, e.g., the composition contains 1% or less, e.g., 0.5% or less, e.g., 0.1% or less, e.g., 0.05% or less, e.g., 0.01% or less, 0.005% or less, e.g., 0.001% or less, e.g., 0.0005% or less, e.g., 0.0001% or less, of such substance by weight (e.g., dry weight), volume, or by moles. In some embodiments a composition is considered substantially free of a substance, e.g., an adjuvant, if the substance is not detectable using a standard detection method used in the art for detecting such substance. In some embodiments a composition is prepared without deliberately including a substance, e.g., an adjuvant. In some embodiments a composition is prepared without deliberately including an adjuvant in an amount that would be effective to enhance an immune response when the composition is contacted with cells in vitro or in vivo.

In some embodiments a method comprises identifying an antigen to which a subject is allergic or self-reactive and administering an agent comprising a targeting moiety that binds to an MHCII complex and the antigen to the subject. In some embodiments identifying comprises administering a test dose of one or more antigens to the subject, e.g., performing a skin test. In some embodiments identifying comprises determining the response of the subject to a test dose of one or more allergens or antigens. In some embodiments, if the response to an allergen is abnormally intense, the antigen is identified as one to which the subject is allergic or self-reactive. In some embodiments the subject harbors self-reactive T cells or B cells comprising a TCR or BRC that recognizes the antigen. In some embodiments the subject produces antibodies that bind to the antigen. In some embodiments a method comprises determining whether a subject produces antibodies that bind to an allergenic antigen or self-antigen. In some embodiments a sample comprising cells or serum from a subject is tested against a panel of candidate allergenic antigens or autoantigens in order, e.g., to identify one or more allergenic antigens or self-antigens at least in part responsible for causing an allergy or autoimmune disease.

In some embodiments, an agent comprising (a) a targeting moiety that binds to MHCII complexes and (b) the antigen to which the subject is allergic or self-reactive is produced. In some embodiments, an agent comprising (a) a targeting moiety that binds to MHCII complexes and (b) the antigen to which the subject is allergic or self-reactive is contacted with immune system cells in vitro. In some embodiments at least some of the immune system cells are administered to the subject. In some embodiments, an agent comprising (a) a targeting moiety that binds to MHCII complexes and (b) the antigen to which the subject is allergic or self-reactive is administered to the subject. In some embodiments a method described herein comprises (a) testing or identifying a candidate agent or composition in vitro. In some embodiments a method comprises (a) determining that a candidate agent or composition shows at least one effect suggesting that the candidate agent or composition will be of benefit to a subject in need of treatment for a disease; and (b) testing the candidate agent or composition in an animal model of the disease. In some embodiments the method further comprises identifying the candidate agent or composition as a therapeutic agent or composition or as a candidate therapeutic agent or composition for treating the disease based at least in part on results of step (b). For example, if the animal model exhibits an improvement in, e.g., reduction in severity of, at least one symptom or sign of the disease and/or exhibits increased duration of survival, the candidate agent or composition may be identified as a therapeutic agent or composition or as a candidate therapeutic agent or composition for treating the disease. In some embodiments a benefit, e.g., reduced severity of a symptom or sign, increased duration of survival, etc., is statistically significant. Animal models of various diseases of interest, and methods of assessing benefit, will be apparent to those of ordinary skill in the art.

In some aspects, pharmaceutical compositions comprising one or more of the agents are provided. In some embodiments, one or more of the agents may be administered to a subject in a pharmaceutical composition.

Pharmaceutical Compositions

In some embodiments, the invention provides pharmaceutical compositions comprising any of the modified proteins described herein, for example, a protein that has been modified to carry a click chemistry handle, or a chimeric protein conjugated to a second molecule, for example, another protein, via click chemistry. In some embodiments the protein is conjugated to a polymer, e.g., PEG, via click chemistry. In some embodiments a pharmaceutical composition comprises a VHH, e.g., a VHH identified as described herein. In some embodiments a VHH comprises VHH4, VHH7, or an antigen-binding fragment or variant thereof. In some embodiments a pharmaceutical composition comprises a VHH that binds to MHC Class II. In some embodiments a pharmaceutical composition comprises a VHH that binds to an influenza virus protein, e.g. VHH52, VHH54, VHH62, VHH68, or an antigen-binding fragment or variant thereof.

A pharmaceutical composition may comprise a variety of pharmaceutically acceptable carriers. Pharmaceutically acceptable carriers are well known in the art and include, for example, aqueous solutions such as water, 5% dextrose, or physiologically buffered saline or other solvents or vehicles such as glycols, glycerol, oils such as olive oil, or injectable organic esters that are suitable for administration to a human or non-human subject. See, e.g., Remington: *The Science and Practice of Pharmacy*, 21$^{st}$ edition; Lippincott Williams & Wilkins, 2005. In some embodiments, a pharmaceutically acceptable carrier or composition is sterile. A pharmaceutical composition can comprise, in addition to the active agent, physiologically acceptable compounds that act, for example, as bulking agents, fillers, solubilizers, stabilizers, osmotic agents, uptake enhancers, etc. Physiologically acceptable compounds include, for example, carbohydrates, such as glucose, sucrose, lactose; dextrans; polyols such as mannitol; antioxidants, such as ascorbic acid or glutathione; preservatives; chelating agents; buffers; or other stabilizers or excipients. The choice of a pharmaceutically acceptable carrier(s) and/or physiologically acceptable compound(s) can depend for example, on the nature of the active agent, e.g., solubility, compatibility (meaning that the substances can be present together in the composition without interacting in a manner that would substantially reduce the pharmaceutical efficacy of the pharmaceutical composition under ordinary use situations) and/or route of administration of the composition. The pharmaceutical composition could be in the form of a liquid, gel, lotion, tablet, capsule, ointment, cream, transdermal patch, etc. A pharmaceutical composition can be administered to a subject by various routes including, for example, parenteral administration. Exemplary routes of administration include intravenous administration; respiratory administration (e.g., by inhalation), intramuscular administration, nasal administration, intraperitoneal administration, oral administration, subcutaneous administration and topical administration. For oral administration, the compounds can be formulated with pharmaceutically acceptable carriers as tablets, pills, dragees, capsules, liquids, gels, syrups, slurries, suspensions, etc. In some embodiments a compound may be administered directly to a target tissue. Direct administration could be accomplished, e.g., by injection or by implanting a sustained release implant within the tissue. Of course a sustained release implant could be implanted at any suitable site. In some embodiments, a sustained release implant may be particularly suitable for prophylactic treatment of subjects at risk of developing a recurrent cancer. In some embodiments, a sustained release implant delivers therapeutic levels of the active agent for at least 30 days, e.g., at least 60 days, e.g., up to 3 months, 6 months, or more. One skilled in the art would select an effective dose and administration regimen taking into consideration factors such as the patient's weight and general health, the particular condition being treated, etc, Exemplary doses may be selected using in vitro studies, tested in animal models, and/or in human clinical trials as standard in the art.

A pharmaceutical composition comprising a modified protein according to aspects of this invention may be delivered in an effective amount, by which is meant an amount sufficient to achieve a biological response of interest, e.g., reducing one or more symptoms or manifestations of a disease or condition. The exact amount required will vary from subject to subject, depending on factors such as the species, age, weight, sex, and general condition of the subject, the severity of the disease or disorder, the particular compound and its activity, its mode of administration, concurrent therapies, and the like. In some embodiments, a compound, e.g., a protein, is formulated in unit dosage unit form for ease of administration and uniformity of dosage, which term as used herein refers to a physically discrete unit of agent appropriate for the patient to be treated. It will be understood, however, that the total daily dosage will be decided by the attending physician within the scope of sound medical judgment. In some embodiments, e.g., when administering a PEG-conjugated protein, information available regarding a suitable dose of the unPEGylated version, optionally in conjunction with in vitro activity data, can be used as a guideline in selecting an appropriate dose for preclinical testing and/or for clinical use.

The pharmaceutical compositions can be used to treat a wide variety of different diseases and disorders. In some embodiments, a pharmaceutical composition is used, e.g., to treat any disease or condition for which the unmodified protein is of use. Thus the invention provides methods of treatment comprising administering an inventive protein to a subject in need thereof. The subject is typically a mammalian subject, e.g., a human. In some embodiments the subject is a non-human animal that serves as a model for a disease or disorder that affects humans. The animal model may be used, e.g., in preclinical studies, e.g., to assess efficacy and/or determine a suitable dose.

In some embodiments, an inventive protein is administered prophylactically, e.g., to a subject who does not exhibit signs or symptoms of the disease or disorder (but may be at increased risk of developing the disorder or is expected to develop the disease or disorder). In some embodiments an inventive protein is administered to a subject who has developed one or more signs or symptoms of the disease or disorder, e.g., the subject has been diagnose as having the disease or disorder. Optionally, the method comprises diagnosing the subject as having a disease or disorder for which the protein is an appropriate treatment. For example, interferons have a variety of uses, e.g., in the treatment of autoimmune diseases (e.g., multiple sclerosis) and infectious diseases (e.g., viral infections such as those caused by viruses belonging to the Flaviviridae family, e.g., HBV, HCV; bacterial infections, fungal infections, parasites). Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus; viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus.

Interferon therapy is used (often in combination with chemotherapy and radiation) as a treatment for many cancers, which term is used herein to encompass solid tumors (carcinomas, sarcomas), and leukemias. In some embodiments the tumor is an adenocarcinoma. In some embodiments the tumor is a sarcoma. In some embodiments the tumor affects an organ or organ system selected from breast, lymph node, prostate, kidney, bladder, lung, liver, gastrointestinal tract, colon, testis, stomach, pancreas, thyroid, skin, ovary, uterus, cervix, skin, nerve, bone, and nervous system (e.g., brain). In some embodiments, an interferon is used for treating a hematological malignancy, e.g., a leukemia or a lymphoma, e.g., hairy cell leukemia, chronic myeloid leukemia, nodular lymphoma, cutaneous T-cell lymphoma. In some embodiments an IFN, e.g., IFN-α1b, is used to treat a melanoma.

Erythropoiesis stimulating agents such as EPO are of use to treat anemia, which may result from a variety of causes. For example, the anemia may be an anemia of chronic disease, anemia associated with medications (e.g., cancer chemotherapy), radiation, renal disease (e.g., diabetes), infectious diseases, or blood loss. Colony stimulating factors such as G-CSF, GM-CSF, and/or M-CSF may be used to treat leukopenia, e.g., neutropenia and/or lymphopenia, which may result, e.g., from medications (e.g., cancer chemotherapy), radiation, infectious disease, or blood loss.

Neurotrophic factor proteins may be used, e.g., to treat neurodegenerative diseases (e.g., amyotrophic lateral sclerosis, Huntington disease, Alzheimer disease, Parkinson disease), central or peripheral nervous system injury.

Growth hormone may be used, e.g., to treat children's growth disorders and adult growth hormone deficiency.

Interleukins are of use to modulate the immune response for a wide variety of purposes, e.g., to stimulate an immune response against an infectious agent or cancer. In some embodiments, an interleukin stimulates immune system cells and/or increases the intensity and/or duration of innate and/or adaptive immune responses. As known in the art, certain interleukins help to limit the intensity and/or duration of innate and/or adaptive immune responses. Administration of such interleukins may be of use in treatment of autoimmune diseases, sepsis, or other conditions in which an aberrant or overactivated immune response can be deleterious.

Autoimmune disorders include acute disseminated encephalomyelitis, alopecia areata, antiphospholipid syndrome, autoimmune hepatitis, autoimmune myocarditis, autoimmune pancreatitis, autoimmune polyendocrine syndromes, autoimmune uveitis, inflammatory bowel disease (Crohn's disease, ulcerative colitis), type diabetes (e.g., juvenile onset diabetes), multiple sclerosis, scleroderma, ankylosing spondylitis, sarcoid, pemphigus vulgaris, myasthenia gravis, systemic lupus erythemotasus, sarcoid, rheumatoid arthritis, juvenile arthritis, Behcet's syndrome, Reiter's disease, Berger's disease, polymyositis, dermatomyositis, antineutrophil cytoplasmic antibody-associated vasculitides, such as Wegener's granulomatosis, autoimmune myocarditis, anti-glomerular basement membrane disease (including Goodpasture's syndrome), dilated cardiomyopathy, thyroiditis (e.g., Hashimoto's thyroiditis, Graves' disease), transverse myelitis, and Guillane-Barre syndrome.

Diseases caused by gram-positive or gram-negative bacteria, mycobacteria, fungi such as *Candida* or *Aspergillus*, *helminths*, etc., are of interest in certain embodiments. Exemplary bacteria and fungi include those falling within the following groups Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, Dermatocycoses, Enterobacteriaceae (*Klebsiella, Salmonella, Serratia, Yersinia*), *Erysipelothrix, Helicobacter, Legionella, Leptospires Listeria*, Mycoplasmatales, Neisseriaceae (e.g., *Acinetobacter, Menigococci*), Pasteurellacea (e.g., *Actinobacillus, Heamophilus, Pasteurella*), *Pseudomonas*, Rickettsiaceae, Chlamydiaceae, *Treponema*, and Staphylococci.

In some embodiments a modified, e.g., PEGylated protein exhibits increased efficacy relative to an unmodified form and/or requires a lower dose or less frequent administration (greater dosing interval) to achieve equivalent efficacy and/or exhibits reduced toxicity (reduced side effects, greater tolerability, greater safety) and/or can be administered by a more convenient or preferable route of administration.

It should be noted that the invention is not limited to the foregoing, exemplary click chemistry handles, and additional click chemistry handles, reactive click chemistry handle pairs, and reaction conditions for such click chemistry handle pairs will be apparent to those of skill in the art.

The following working examples are intended to describe exemplary reductions to practice of the methods, reagents, and compositions provided herein and do not limit the scope of the invention.

EXAMPLES

Example 1: Production of N-to-N and C-to-C Protein Fusions Created by Combining Click Chemistry with a Sortase-Catalyzed Transacylation Protein fusions are useful tools in biochemistry. Using genetic constructs, a large variety of proteins fused to GFP have been expressed. One major disadvantage of protein fusion technology is, however, that only C-to-N linked protein fusions can be achieved, in which the C-terminus of one protein is fused to the N-terminus of another protein. This limits the scope of such protein fusions to those that do not require an unoccupied, or unfused N- or C-terminus. For example, the N-terminus of antibodies is required for antigen recognition and therefore bispecific antibodies cannot be produced using conventional recombinant technologies, including protein fusion techniques. Other proteins, such as ubiquitin, require an unmodified C-terminus for normal activity.

Some aspects of this invention provide methods and reagents for the preparation of N-to-N and C-to-C protein fusions using a combination of the sortase reaction and click chemistry. The sortase-catalyzed transacylation allows the facile installation of all manner of substituents at the C-terminus of a suitably modified protein. The sole requirement for a successful transacylation reaction is the presence of a suitably exposed LPXTG (SEQ ID NO: 81) motif in the target protein. The design of nucleophiles that can be used in a sortase catalyzed reaction is likewise straight-forward: a short run of glycine residues, or even an alkylamine suffices to allow the reaction to proceed. For an exemplary scheme for the generation of C—C and N—N conjugated proteins via sortase-mediated installation of click chemistry handles and subsequent click chemistry reaction, see FIG. 1. The click handles azide and cyclooctyne are represented by N3 and an octagon, respectively.

Figure 2:
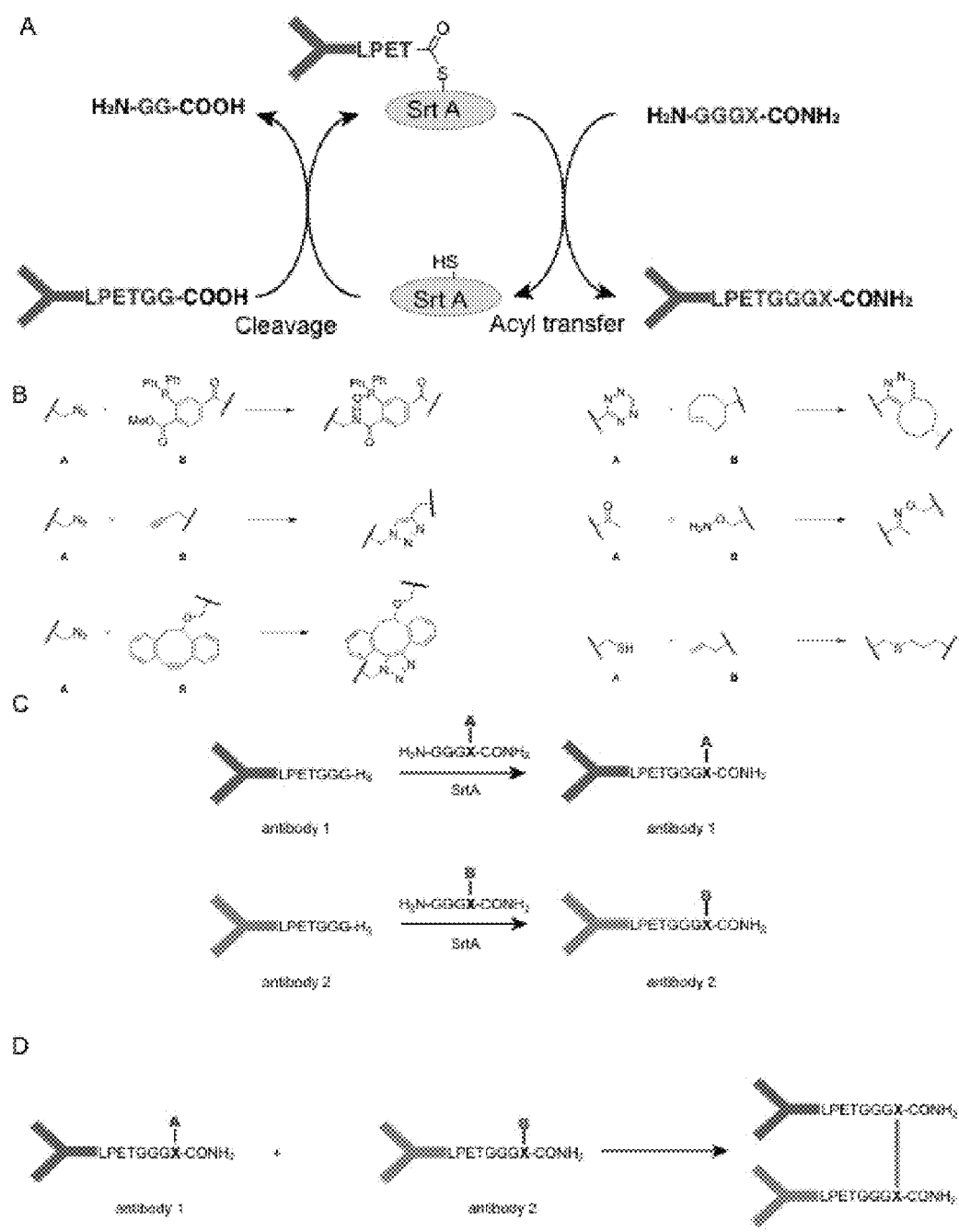
FIG. 2. A) Schematic representation of the sortase-catalyzed transacylation reaction. B) Exemplary click chemistry handles and reactions suitable for the generation of conjugated proteins. C) Installation of C-terminal click handles A and B on Antibodies 1 and 2. D) Dimerization of Antibodies 1 and 2.

The key advantages of the installation of click chemistry handles on proteins via a sortase reaction are ease of synthesis of the required nucleophile for the sortase reaction, and execution of the reaction on native proteins under physiological conditions (FIG. 2A). The nucleophiles that have previously been used in the sortase reaction contained any of the following modifications: biotin, fluorophores, fatty acids, nucleic acids, lipids, radioisotopes, carbohydrates or even proteins with a suitably exposed N-terminal stretch of glycine residues (e.g., 1-10 G residues).

Some aspects of this invention provide an extended range of protein modifications through the synthesis of nucleophiles that provide the handles for click-reaction. This allows for the creation of proteins fused at their C-termini. Any type of bioorthogonal click-reaction can be used for this purpose and some examples that can be applied, but not limited to, are the copper-catalyzed click reaction, the (traceless) Staudinger ligation, the strain-promoted click reaction, thioene reaction, (inverse-electron demand) Diels-Alder reaction, oxime ligation and the native chemical ligation (see Table I and FIG. 2B). In some embodiments, these functionalities are introduced on the side-chain of natural amino acids or by incorporation of non-natural amino acids.

Some aspects of this invention provide methods and reagents for the generation of bi-specific, chimeric antibodies. In some embodiments, two antibodies are conjugated via click chemistry at their C termini to form a chimeric antibody. C—C terminal conjugation allows the antigen-binding N-termini of the conjugated antibodies to retain their antigen-binding properties. If two antibodies so conjugated bind different antigens, the resulting chimeric antibody is bi-specific.

Some aspects of this invention provide a strategy for the preparation of bispecific antibodies according to some embodiments of this invention. In some embodiments, antibodies are provided that contain a C-terminal sortase recognition sequence, for example, a C-terminal LPXTGG (SEQ ID NO: 82) sequence. In some embodiments, the antibodies further comprise a C-terminal tag, for example, a hexahistidine (His6) tag. Such antibodies can be obtained via recombinant methods and using reagents that are well known to those of skill in the art.

In some embodiments, the nucleophile for the sortase reaction, for example, a GGG-peptide, comprising a click chemistry handle, is synthesized employing standard solid phase peptide synthesis.

In some embodiments, a first antibody comprising a C-terminal sortase recognition motif is modified by a sortase catalyzed reaction in the presence of a nucleophile comprising a first click chemistry handle (e.g., handle A, see FIG. 2B). A second antibody comprising a sortase recognition motif, for example, an antibody binding a different antigen than the first antibody, is modified by a sortase catalyzed reaction in the presence of a nucleophile comprising a second click chemistry handle (e.g., handle B, see FIG. 2B). The two click chemistry handles (e.g., handle A and B) are typically click "partners," meaning that they can react in a click chemistry reaction to form a covalent bond. Some exemplary click reactions and partner click handles are described in Table 1 and FIG. 2B. As result of the sortase reaction, antibodies on which a C-terminal click chemistry handle is installed, are obtained (FIG. 2C).

In some embodiments, the sortase-modified antibodies are isolated or purified, for example, using His-tag purification, size exclusion chromatography and/or ion exchange chromatography. In some embodiments, the first and the second sortase-modified antibody are mixed under physiological conditions suitable for the respective click reaction to take place. For example, if the click reaction requires a catalyst, such as copper, to take place under physiological conditions, conditions suitable for the reaction to take place would include the provision of a copper catalyst in an amount effective to catalyze the click reaction. In some embodiments, the click reaction is followed using LC/MS and gel chromatography, for example, to determine completion of the reaction. In some embodiments, when the reaction is complete, the C-to-C-fused proteins are isolated or purified, for example, with the above-mentioned methods (FIG. 2D)

Example 2: Installation of Non-Click Functionalities Via Sortase Reaction

The functionalities that can be incorporated in the nucleophiles for the sortase reaction are not limited to click chemistry handles. Sortase nucleophiles may be equipped with any of the functionalities that previously have been used in the sortase reaction (FIG. 3A). For example, in some embodiments, biotin is incorporated, which allows for visualization, purification and tetramerization of the modified protein, e.g., the sortase-modified antibody, using streptavidin. In some embodiments, a fluorophore is incorporated, for example, a fluorescent protein, or a fluorescent moiety, which allows for visualization of protein dimers. Especially for bispecific antibodies, this is a useful feature allowing them to be used in FACS and microscopy experiments. Moreover, combinations of compatible click handles may be used for the synthesis of even more complex structures, such as protein trimers, and PEGylated protein dimers (FIG. 3B).

Taking into account the flexibility afforded by solid phase synthesis, the inclusion of yet other functionalities at the site of suture can be used to further expand the range of properties imparted on such chimeric protein. For example, sortase-mediated installation of a synthetic polymer, for example, a PEG moiety, can extend the half-life of peptides and proteins, for example, such a modification extends the circulatory half-life of cytokines. Incorporation of detectable labels, such as fluorophores, fluorescent proteins, dyes, bioluminescent enzymes and probes, or radioisotopes enables access to all commonly used imaging modalities.

Example 3: Generation of Bi-Specific, Chimeric Antibodies

An exemplary strategy of sortase-mediated installation of click chemistry handles was applied to generate bispecific antibody fragments based on the use of the VHH domains typical of camelid antibodies. Unlike other mammalian species, camelids possess an additional class of antibodies whose binding site is constructed from a VH domain only. These domains can be expressed in bacteria as so-called nanobodies. Their small size and ease of manipulation make them attractive targets for the construction of therapeutics. Especially the ability to combine two distinct recognition specificities in a single reagent holds promise for the construction of so called bi-specific antibodies.

VHH fragments were expressed in E. coli as nanobodies. The VHH fragments were based on an antibody raised in vicuna against GFP and an antibody raised in llama against 2-microglobulin. Both nanobodies were equipped with an LPXTG motif to prepare them for a sortagging reaction. The design of the nucleophiles involved the installation of a strained cyclooctyne on one nanobody, and of an azide on the other nanobody, respectively, to allow a copper-free click reaction to proceed.

Figure 4:
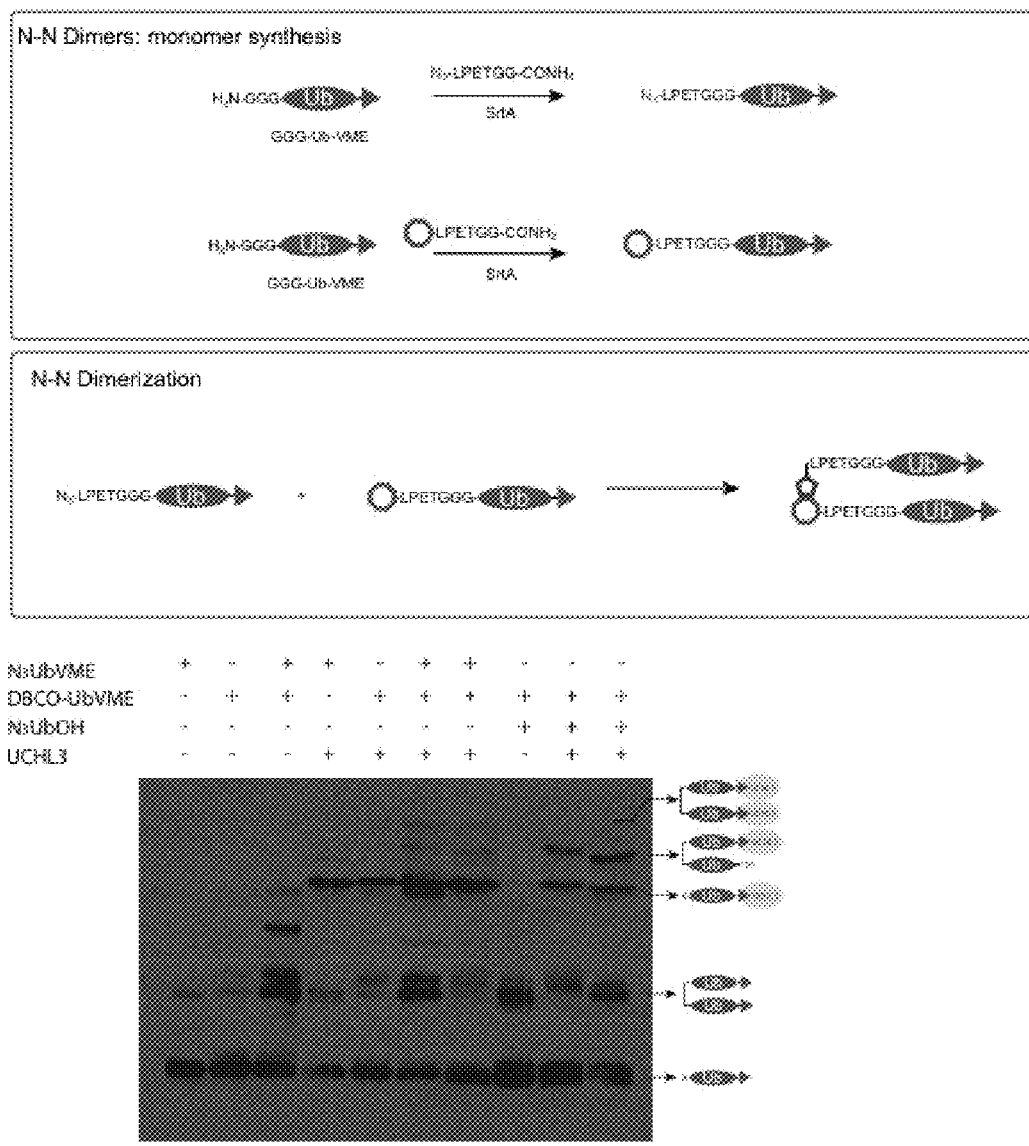
FIG. 4. Optimization of the click chemistry using N-terminally labeled ubiquitin analogues. A) Labeling of $G_3$Ub-VME with the click-handles. B) Determination of the activity the formed constructs. UbVME monomers and dimmers were incubated with UCHL3. Labeling of the DUB results in a shift of molecular weight.

Optimal conditions for the click reaction were established using an N-terminal labeling reaction executed on suitably modified ubiquitin (Ub, FIG. 4, scheme), ubiquitin vinyl methyl ester (UbVME), an electrophilic Ub derivative that covalently modifies ubiquitin-specific proteases. For this reaction a $(Gly)_3$ extended version of UbVME was chosen. Execution of the click reaction yielded a UbVME dimer, the functionality of which was assessed by modification of the ubiquitin C-terminal hydrolase, UCHL3 (FIG. 4, gel image). An important aspect of the chemistry employed is the avoidance of harsh conditions that might inflict damage on the proteins that are the substrates in this reaction. All transformations are performed in an aqueous environment at neutral pH.

It was observed that the N- and C-terminal sortagging reactions proceed with comparable efficiency (FIG. 5), and so the scheme employed here not only allows C-to-C but also N-to-N fusions, both of which are impossible to accomplish by conventional recombinant technologies. In some embodiments, where the reactants of the sortase reaction (e.g., input nanobodies) as well as the sortase used in the reaction are equipped with a tag, for example, a His6 tag, adsorption onto an appropriate binding agent, e.g., NiNTA agarose, effectively depletes these reactants, allowing for a one-step purification of the desired, "sortagged" product.

Figure 6:
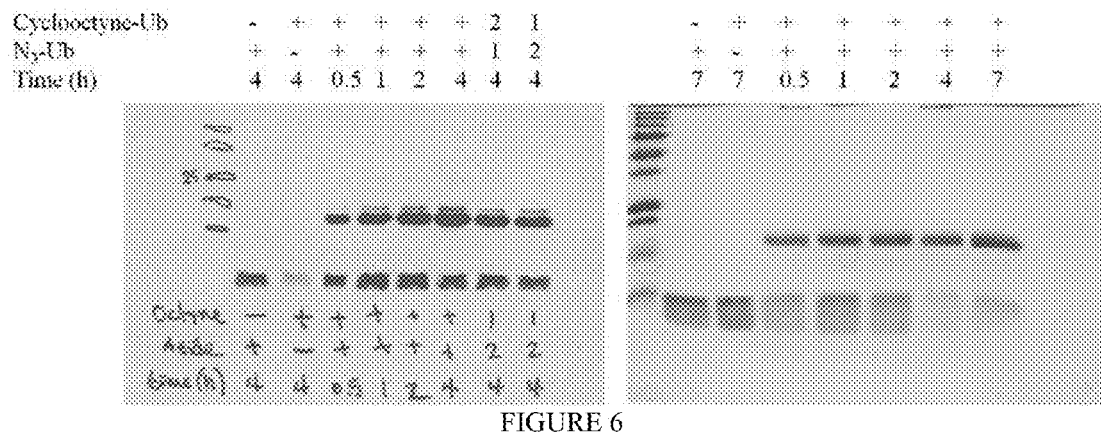
FIG. 6. Kinetics of the click chemistry N—N dimerization of azide-Ub and cyclooctyne-Ub.

The kinetics of the dimerization reaction of azide-modified Ub and cyclooctyne-modified Ub was investigated (FIG. 6). Dimerization was not observed in samples comprising only either N3-Ub or cyclooctyne-Ub. When incubated together, however, dimerization was detectable after 30 minutes of incubation, and reached a plateau at 1 hr of incubation time. The reaction was efficient at different mixing ratios of N3- and cyclooctyne-Ub.

Figure 7:
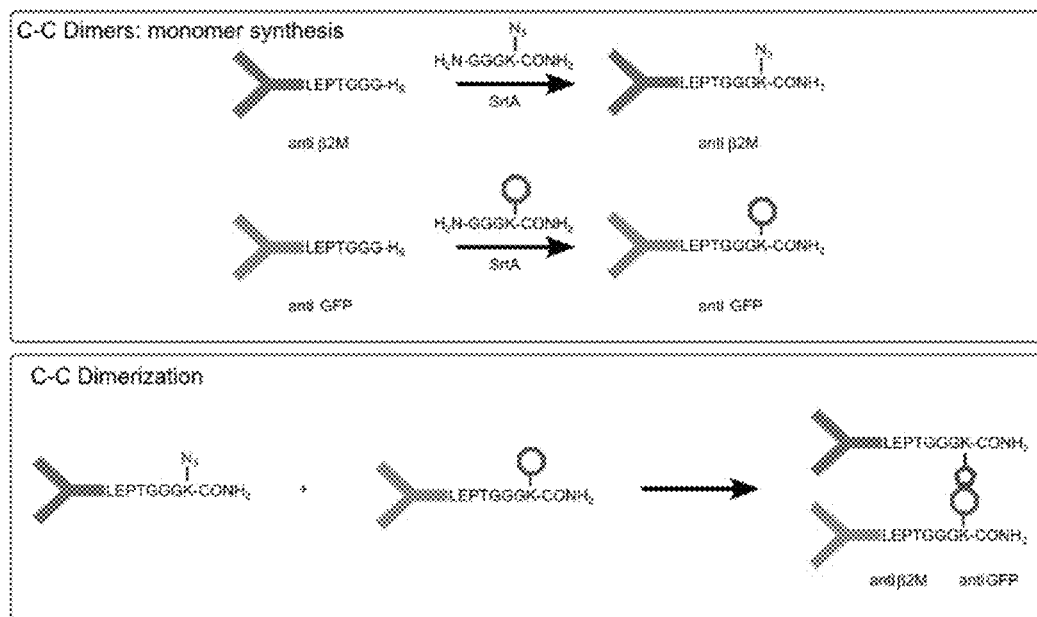
FIG. 7. Schematic of C—C dimerization of anti-β2M and anti-GFP antibodies.
Figure 8:
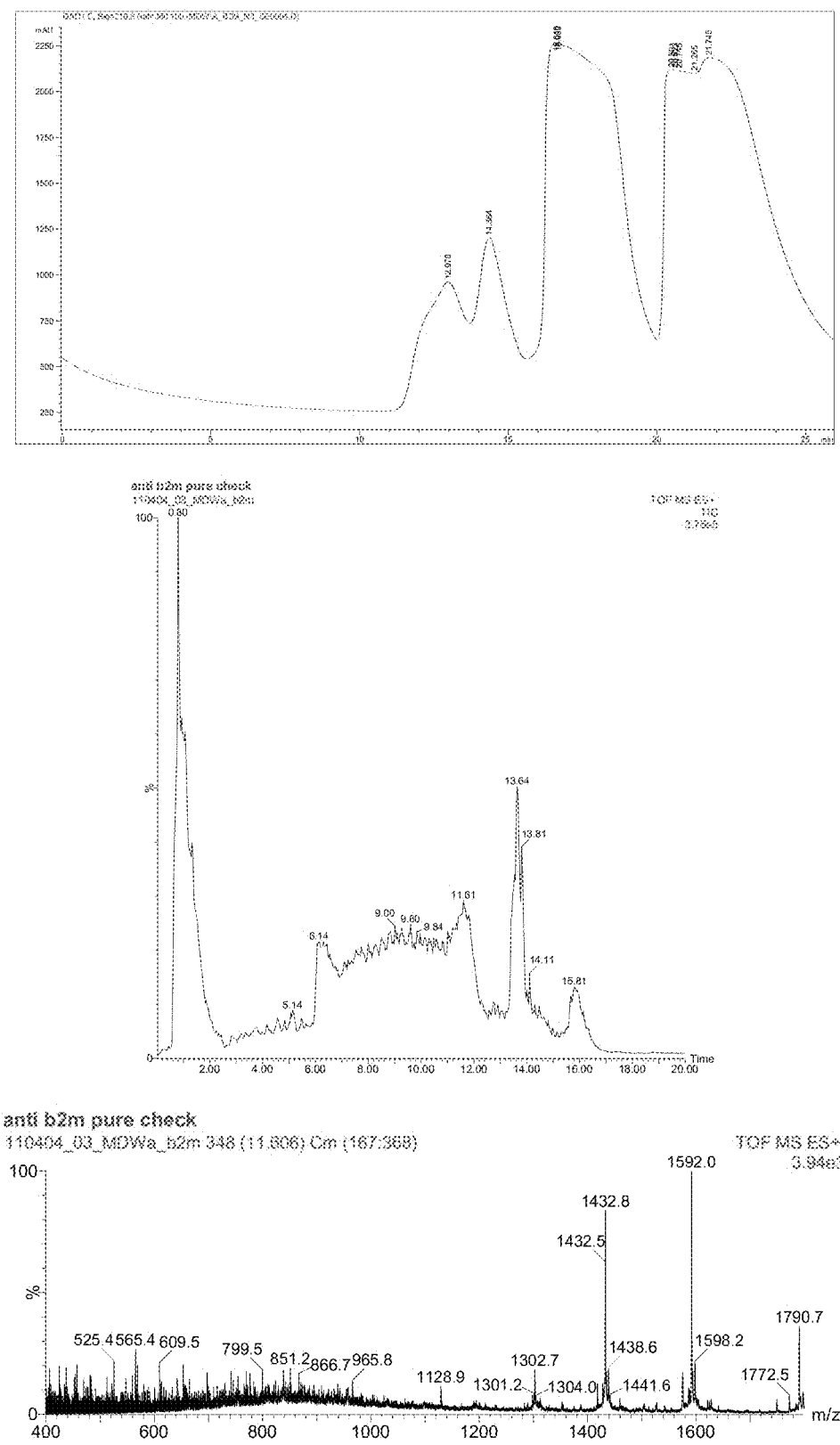
FIG. 8. Purification by size exclusion chromatography.
Figure 9:
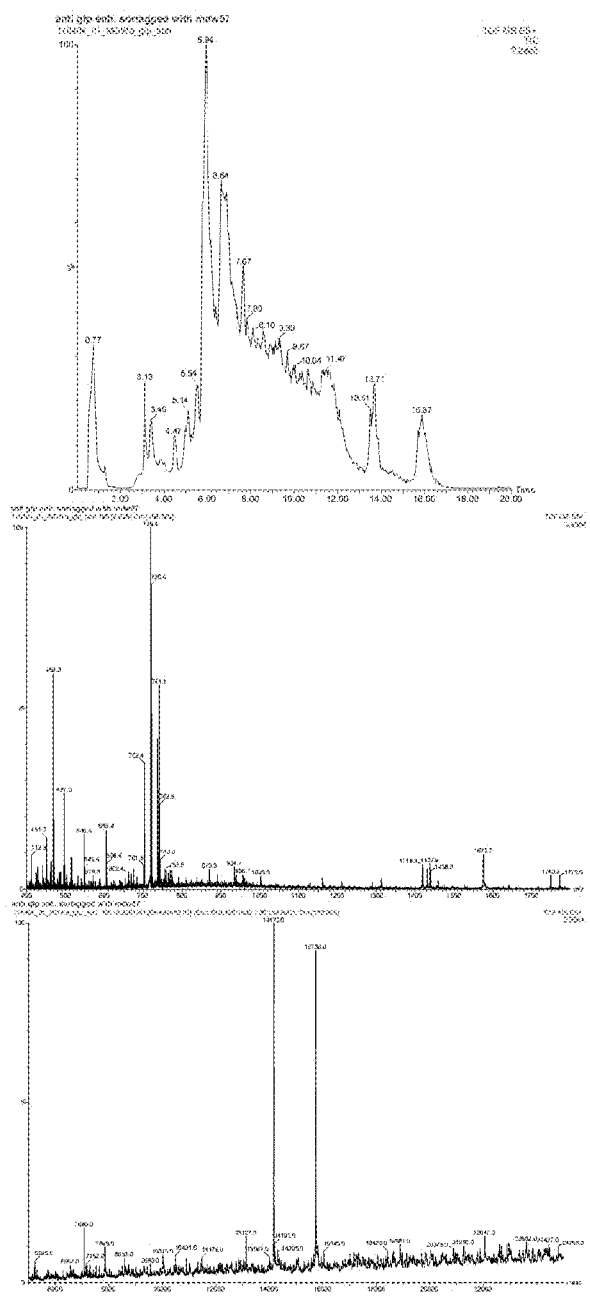
FIG. 9. Sortagging of an anti-GFP nanobody.
Figure 10:
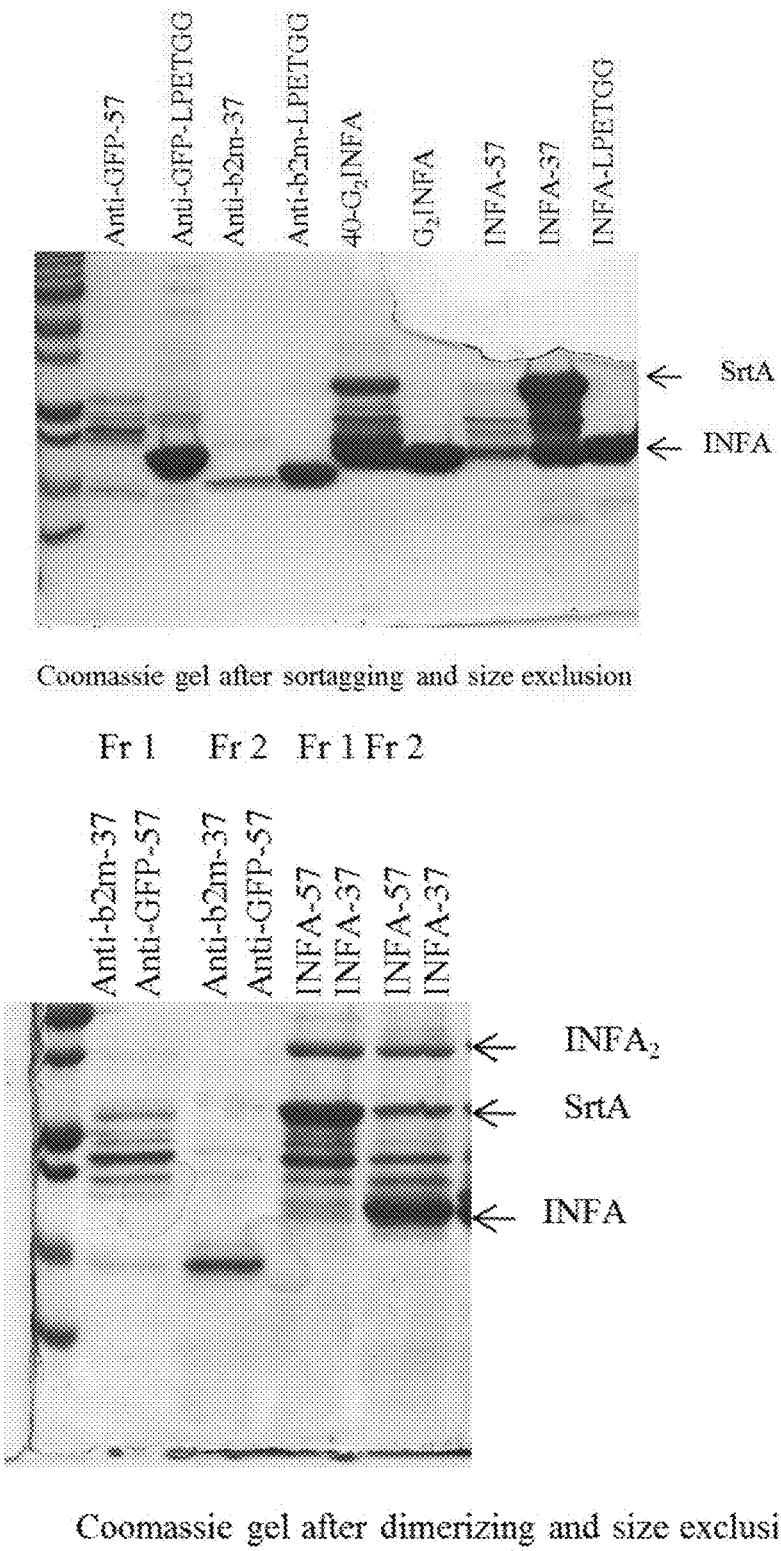
FIG. 10. Sortagging of interferon alpha and anti-GFP (anti-eGFP) nanobody. 37: C-terminal azide; 57: C-terminal cyclooctyne; 40: N-terminal cyclooctyne; 41: N-terminal azide.
Figure 11:
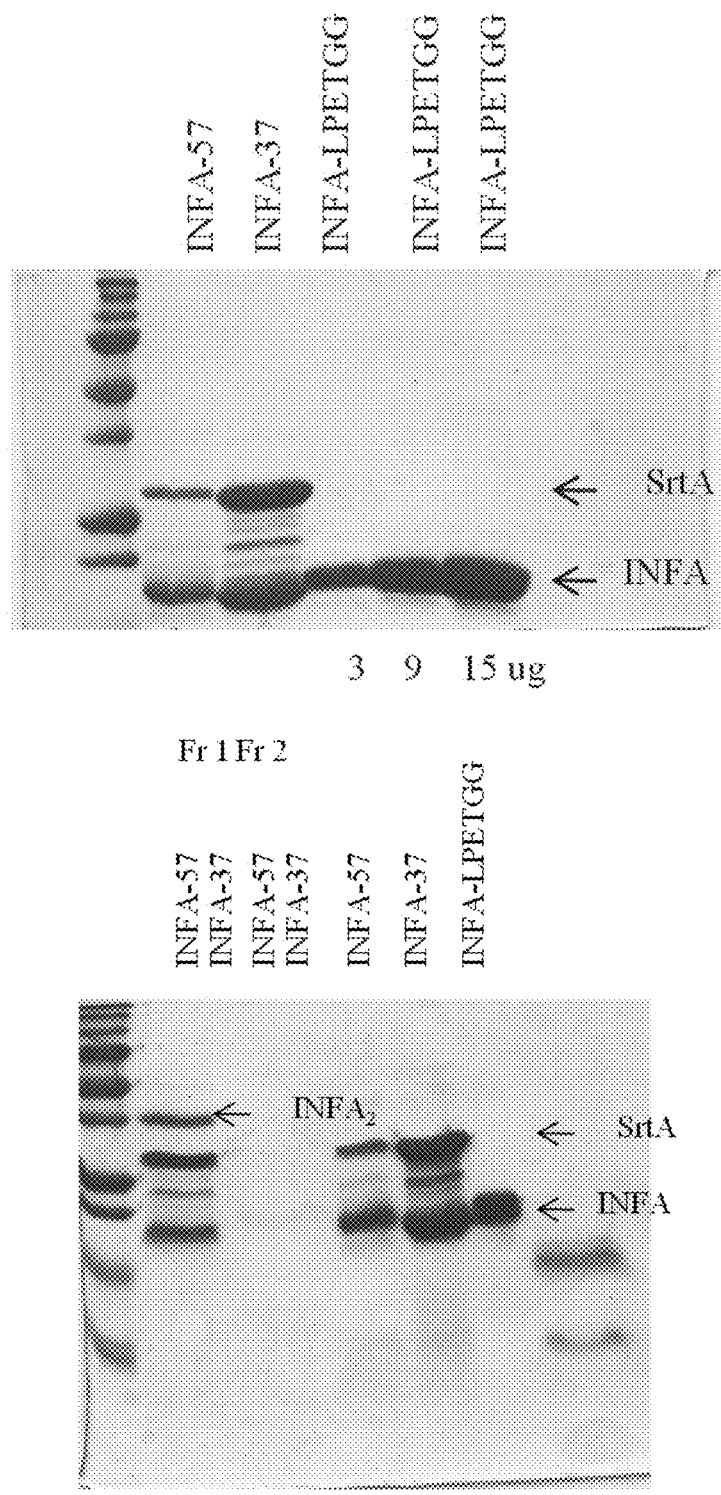
FIG. 11. Sortagging of INFA and anti-GFP.

The two nanobodies were subjected to a sortase-mediated installation of a click chemistry handle, an azide, and a cyclooctyne, respectively under the optimized reaction conditions determined for Ub (see Example 4 for reaction conditions, FIG. 7). The resulting nanobodies comprising a suitable click handle each, were purified by size exclusion chromatography to remove any unincorporated sortase reaction nucleophile (FIG. 8). The purified nanobodies can be conjugated via a click chemistry reaction analogous to the dimerization of ubiquitin. The conjugation products can be purified by size exclusion chromatography on an S75 column, and the desired product characterized by SDS-PAGE and MS/MS to confirm the identity of the C-to-C nanobody fusion product.

A crude reaction mixture can be prepared and incubated with saturating amounts of the target antigens, beta-2-microglobulin and eGFP, both expressed in *E. coli*, Size exclusion chromatography followed by SDS-PAGE and silver staining of individual fractions allows for the identification of unbound antigen at their expected Stokes' radii, as well as that of the separate nanobodies, each complexed with their cognate antigen. The examples of N-to-N and of C-to-C protein conjugation demonstrate that chimeric proteins, inaccessible by standard genetic methods, may be obtained in good yields using the methods and reagents provided herein.

Example 4: Materials and Methods

Solid Phase Peptide Synthesis of the Sortase Reaction Peptides

Rink-amide resin was solvated in NMP and after removal of the Fmoc-group by treating the resin with 20% piperidine in NMP, the resin was loaded and elongated using the consecutive steps. (I) The resin was washed with NMP (3×), $CH_2Cl_2$ (3×) and NMP. (II) Fmoc-protected amino acid (either commercially available or home-made) were condensed under the agency of HOBt (3 equiv.), PyBOP (3 equiv.) and DiPEA (6 equiv.). (III) The resin was washed again using the same conditions as in step (I). (IV) The coupling was monitored using Kaiser test and if complete, (V) the Fmoc-protective group was removed using 20% piperidine in NMP.

Finally, the peptides were cleaved off resin by agitating the resin in the presence 95% TFA, 2.5% TIS, 2.5% $H_2O$ for 3 h. Ice-cold $Et_2O$ was added to the cleavage solution and the formed precipitate was pelleted by centrifugation of the solution for 30 min at 4° C. The crude peptides were purified by reverse phase HPLC purification (buffers used: A: $H_2O$, B: ACN, C: 10% TFA in $H_2O$).

C-Terminal Peptides $H_2N$-GGGK(Azidohexanoic acid)-$CONH_2$

Rink amide resin (100 mg, 50 µmol) was loaded with Fmoc-Lys(Mtt)-OH and elongated with Fmoc-GGG-OH as described in the general method. After washing the resin with $CH_2Cl_2$, the Mtt protective group was removed by treating the resin twice with 1% TFA, 1% TIS in $CH_2Cl_2$ for 30 min (or until the yellow color completely disappeared). The resin was washed with $CH_2Cl_2$ (5×), NMP (5×) and NMP containing 5 equivalents of DiPEA. Azidohexanoic acid (31 mg, 200 µmol) was condensed using PyBOP (104 mg, 200 µmol) and DiPEA (70 µL, 400 µmol). After 2 hours shaking, the Kaiser test showed complete conversion. The N-terminal Fmoc group was removed and the peptide was cleaved off resin as described in the general method. Reverse phase HPLC purification (15-24% B in 12 min (3 CV), Rt=8 min) gave the title compound (15.4 mg, 33 µmol, 67%) as an off-white solid.

$H_2N$-GGGC(DBCO)-$CONH2$

Rink amide resin (167 mg, 100 µmol) was loaded with Fmoc-Cys(Trt)-OH and elongated with Fmoc-GGG-OH, and cleaved off the resin as described in the general method affording crude $H_2N$-GGGC—$CONH_2$ in quantitative yield. This peptide (38 mg, 83 µmol) was dissolved in PBS (0.25 mL) and to this was added DBCO-maleimide (17 mg, 40 µmol) in DMF (0.25 mL). The reaction was stirred overnight, acidified with TFA and purified by RP-HPLC (20-35% B in 20 min (5 CV)) gave the title compound (15.3 mg, 22 µmol, 27%) as a white solid.

N-Terminal Peptides

Azidohexanoic acid-LPETGG-$CONH_2$

Rink amide resin (60 µmol) was loaded with Fmoc-Glyc-OH, elongated with the appropriately protected amino acids and cleaved off the resin as described in the general method. For the final coupling azidohexanoic acid was used. RP-HPLC (26-35% B in 12 min (3 CV)) gave the title compound (9.5 mg, 13 µmol, 13%) as a white solid.

DBCO-LPETGG-$CONH2$

Rink amide resin was loaded with Fmoc-Glyc-OH, elongated with the appropriately protected amino acids and cleaved off the resin as described in the general method. Precipitation from $Et_2O$ afforded crude $H_2N$-LPETGG-$CONH_2$ (SEQ ID NO: 83) (17.9 mg, 31.3 .mu.mol), which was dissolved in DMF (0.5 mL). DBCO-OSu (14 mg, 20 µmol) was added and the reaction was stirred overnight. The solution was diluted before being purified by RP-HPLC (25-34% B in 12 min (3 CV)) gave the title as an off-white solid.

Sortagging of Ubiquitin

Sortase (7.2 µL, 700 µM) and probe (10 µL, 5 mM) were added to ubiquitin (58 µM) in 100 µL sortase buffer (50 mM Tris, pH 7.4, 150 mM NaCl, 10 mM $CaCl_2$). The resulting mixture was incubated at 37° C. for 2 h. Next, the solution was acidified and purified by reverse phase HPLC. The resulting purified protein was concentrated in vacuo, redissolved in $H_2O$ and quantified by gel-electrophoresis.

Sortagging of Nanobodies

Sortase (7.2 µL, 700 µM) and probe (10 µL, 5 mM) were added to the nanobody (15 µM) in 100 µL sortase buffer (50 mM Tris, pH 7.4, 150 mM NaCl, 10 mM $CaCl_2$). The resulting mixture was incubated at 37° C. overnight. Next, the solution was diluted with $Et_3N$ HOAc (pH 5) and purified by size exclusion HPLC. The resulting purified protein was concentrated in vacuo, redissolved in $H_2O$ and quantified by gel-electrophoresis.

Dimerization of Ubiquitin

Azido-modified ubiquitin and DBCO-modified ubiquitin were mixed in a one to one ratio and incubated for 0.5-7 h at 37° C. The conversion to the dimerized product was analyzed using gel electrophoresis.

Activity-Assay

Azido-modified UbVME and DBCO-modified UbVME were mixed in a one to one ratio and were incubated overnight at 37° C. After dimerization, the samples were diluted with Tris buffer (7 μL) and UCHL3 (2 μL, 5 fold excess to UbVME) was added. The resulting mixture was incubated for 2 h, denatured with sample buffer (4×) and loaded on 15% gel. The proteins were transferred to a PVDF-membrane. The membrane was blocked with 4% milk in PBS/Tween (0.1%). Rabbit polyclonal anti-ubiquitin (1:100) was added and the membrane was agitated for 30 min at room temperature. The membrane was four times washed with 0.1% Tween in PBS before the secondary antibody (HRP-goat anti rabbit, 1:25000) was added. After 30 min shaking at room temperature, the membrane was washed with 0.1% Tween in PBS (4×) and the proteins were visualized using ECL plus.

Figure 12:
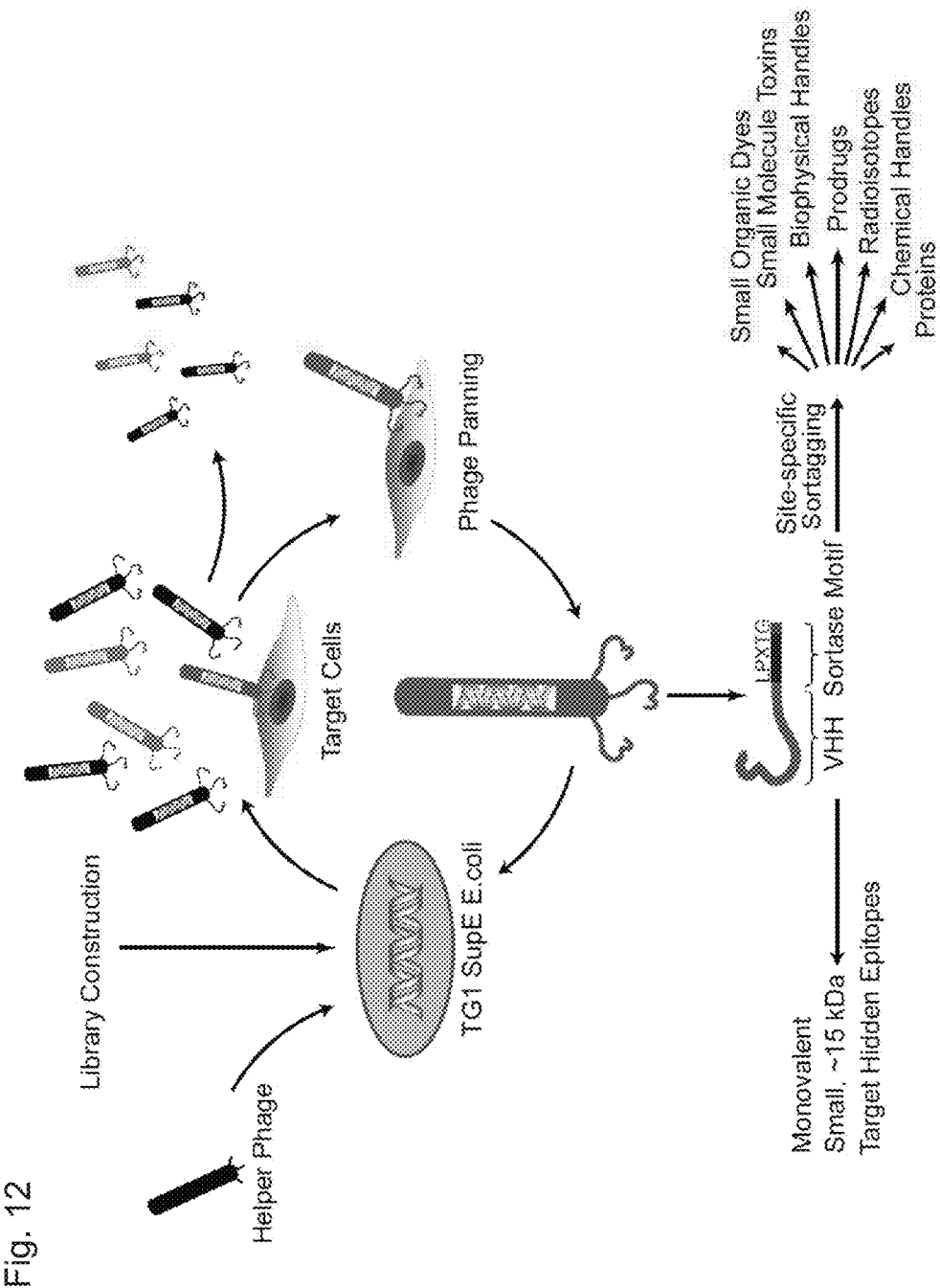
FIG. 12. Schematic of phage display process to identify cell surface specific VHHs FIG. 13. Structure of pIII phage display vector with VHH sequence inserts FIG. 14. Random VHH purified by osmotic shock is labeled by sortase FIG. 15. Twelve VHH's identified by panning on hybridoma cells are labeled by sortase with a G3K(biotin)C(ATTO647N) multifunctional probe FIG. 16. VHH7 Monomer staining of splenocytes with bifunctional G3K(biotin)C(ATTO647N) probe FIG. 17. VHH7 Tetramer staining with Strep-Alexa488

Example 5: Isolation of Cell Surface Specific VHH and their Expression as Fusion Proteins Containing a Sortase Recognition Sequence This Example describes isolation of VHH domains that bind to B cell surfaces. A schematic diagram of the process is shown in FIG. 12. Peripheral blood lymphocytes (PBLs) harvested from alpacas that had been immunized with murine splenocytes were used as a source of RNA, from which cDNA was made using standard procedures. (Animals were injected with one spleen equivalent of murine splenocytes, seven times over the span of 4 months, and PBL's were harvested 2 days after the final injection.) The VHH repertoire was cloned into the multi-cloning site of a phage display vector using degenerate primers:

```
Forward primer,

A1VHH-F1:
CTTGCGGCCGCTCAGKTGCAGCTCGTGGAGWCNGGNGG
(SEQ ID NO: 84) and

Reverse primers:

A1VHH-short hinge R1:
GATCGGCGCGCCGAGGGGTCTTCGCTGTGGTGCG
(SEQ ID NO: 85),

A1VHH-long hinge R1:
GATCGGCGCGCCGGTTGTGGTTTTGGTGTCTTGGG
(SEQ ID NO: 86)
```

The phage display vector was designed such that it contained a sequence encoding a sortase recognition sequence (LPETG) (SEQ ID NO: 87), followed by a hexahistidine (6×His) tag, downstream of the multi-cloning site. The resulting phage display vector contained a pELB leader sequence followed by the VHH, the sortase LPETG tag, a hexahistidine tag, an amber suppressor codon, and the pIII coat protein of phage M13. TG1 supE *E. coli* reads through the amber stop codon creating a fusion between the VHH and pIII, and the pELB leader directs the VHH/pIII fusion to the periplasm, where M13 is assembled. Infection of transformed TG1 by helper M13 phage (to provide the necessary structural proteins) produced phage with roughly three copies of the VHH displayed on the surface of the particle, with the phagemid encoding the VHH packaged within. Phage were first depleted several times on plastic and irrelevant cells (EL4 cells), followed by incubation with target cells (anti-Alexa 647 hybridoma cells, which served as surrogate B cells). Unbound phage were washed away and bound phage were eluted with low pH followed by detergent lysis of target cells to recover tightly bound phage. (Low pH elution was performed with 0.2M glycine, pH 2.2 for 10 minutes after which eluates were immediately neurtralized with 1M Tris, pH 9.0. Cells were then lysed with 1% Triton X-100, 50 mM Tris-HCL, 150 mM NaCl, pH 8.0.) The eluted phage were used to reinfect TG1 cells and the panning process was repeated. DNA encoding VHHs that bound to target cells were subcloned into a pET based expression vector containing a multi-cloning site, followed by the LPETG tag and a hexahistidine tag, for bacterial expression.

Figure 13:
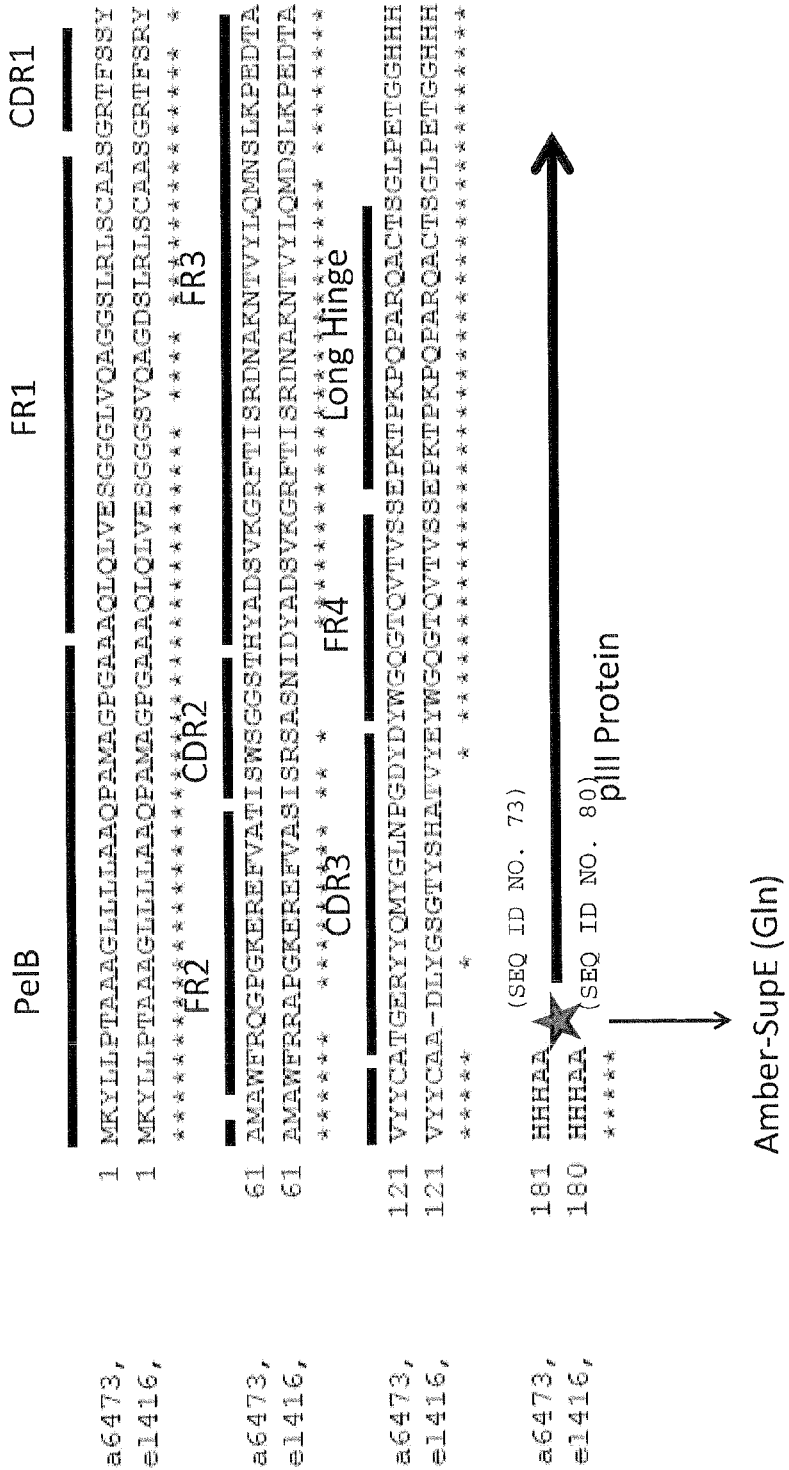

DNA encoding two randomly picked VHHs was sequenced. The structure of these VHHs cloned into the phage display vector is shown in FIG. 13. The PelB leader directs the VHH/pIII fusion to the periplasm, where M13 is assembled. The VHH contains four framework regions of nearly invariant sequence, with three hypervariable CDR regions interspersed. VHHs contain either a long hinge or a short hinge region (amplified separately in the PCR step and cloned at equal ratios into the phage display library). The phage display vector contains the LPETG sortase tag followed by a hexahistidine tag and the amber suppressor codon. This is followed by the M13 pIII protein.

Example 6: Labeling of Bacterially Expressed VHHs Using Sortase

Figure 3:
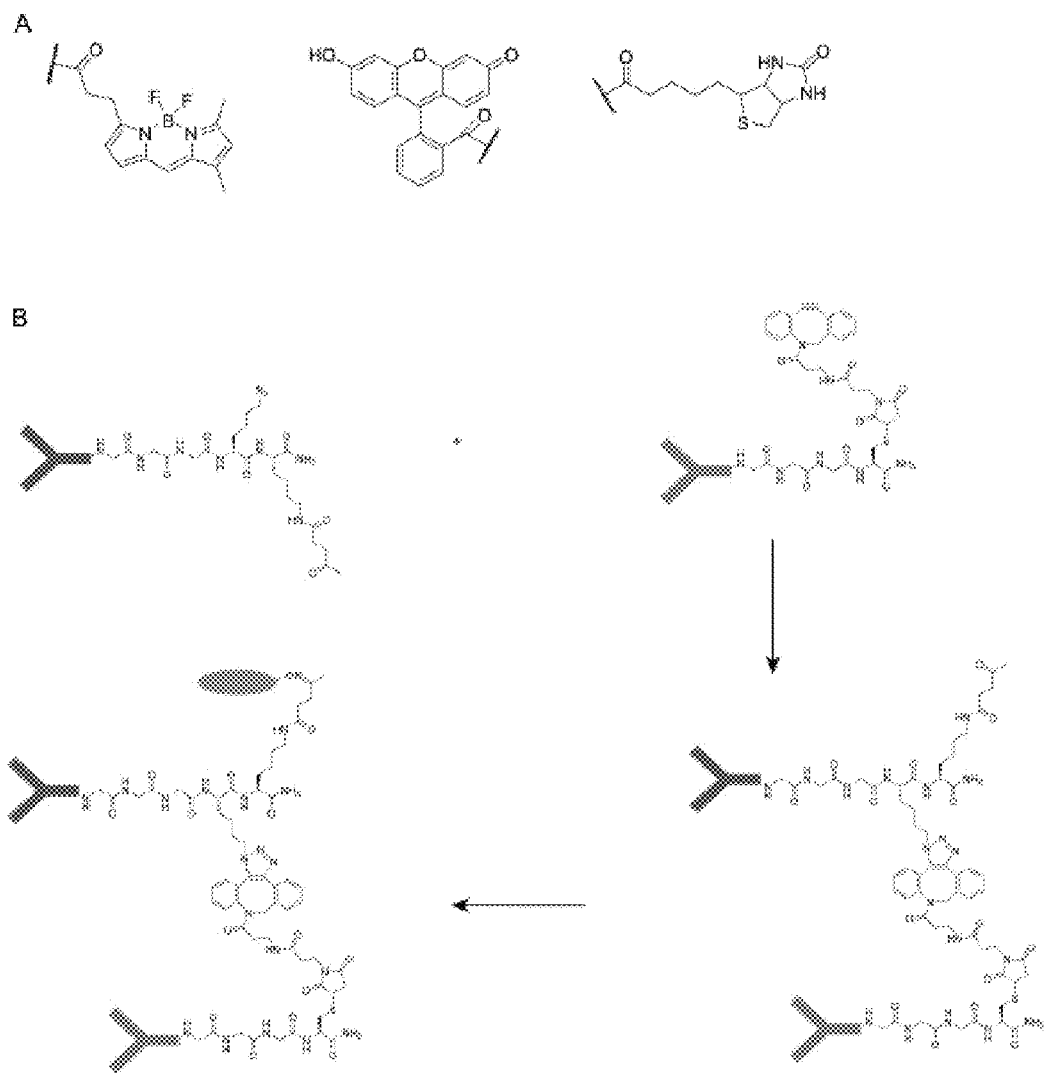
FIG. 3. A) Exemplary additional functionalities that may be incorporated onto proteins using click chemistry. B) Synthesis of PEGylated bispecific antibodies and protein trimers.
Figure 14:
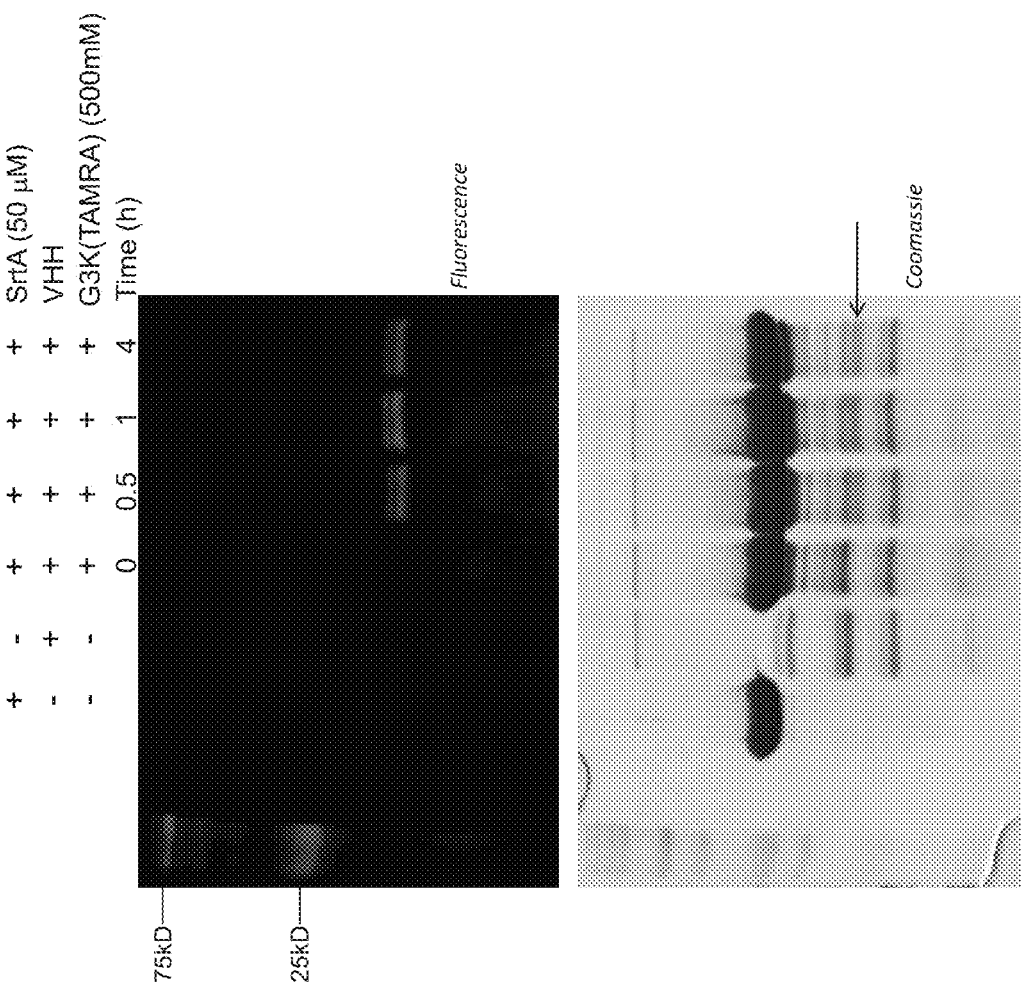

A random VHH cloned into the phage display vector and transformed into TG1 cells was picked. Expression was induced with IPTG to overwhelm the SupE system and produce VHH protein terminated after the hexahistidine tag. Protein was partially purified from osmotic shock supernatants and a randomly picked VHH was labeled with a G3K(TAMRA) probe using sortase. Aliquots were run on an SDS-PAGE gel. FIG. 14 (upper panel) shows the fluorescently labeled VHH. The amounts of sortase and G3K (TAMRA) probe used are indicated. FIG. 3 (lower panel) shows the Coomassie stained gel. The doublet is likely due to incomplete cleavage of the PelB leader.

VHH libraries were panned on either EL4 (surrogate T-cell line) or anti-Alexa 647 hybridoma cells (surrogate B-cells) as described in Example 5. Thirteen VHHs (VHH1-VHH13) were subcloned into a pET expression vector and expressed in BL-21 codon plus cells. The GFP-enhancer (ENH) camelid antibody was expressed as a control VHH. 384 ul of each partially purified VHH eluate was labeled with 280 uM G3K(biotin)C(Atto647N) probe using 58 uM SrtA in 10 mM CaCl2, 150 uM Tris pH8, and 250 mM NaCl in a volume of 500 uL. (The G3K(biotin)C(Atto647N) probe was synthesized manually using standard Fmoc chemistry. The G3K(biotin)C scaffold was first made on rink amide resin, cleaved with 94% trifluoroacetic acid/3%2-mercaptoethanol/2% triisopropylsilane, precipitated with ice-cold ether, and purified by RP-HPLC using a C18 column. Coupling of the dye to the scaffold was achieved by mixing purified peptide (2 equivalents) with Atto647N maleimide (Jena biosciences, structure proprietary) in PBS, for 3 hours at room temperature. The reaction was precipitated with ice-cold ether and the dye-peptide conjugate was again purified by RP-HPLC using a C18 column.) Reactions were incubated overnight at room temperature, followed by supplementation with 40 uM imidazole. SrtA and uncleaved VHH were depleted with Ni-NTA for 30 minutes at 4 degrees C. The Ni-NTA flow through was desalted on a NAP-5 column to remove free probe. This material was resolved by SDS-PAGE (FIG. 15) and used for subsequent experiments.

Figure 5:
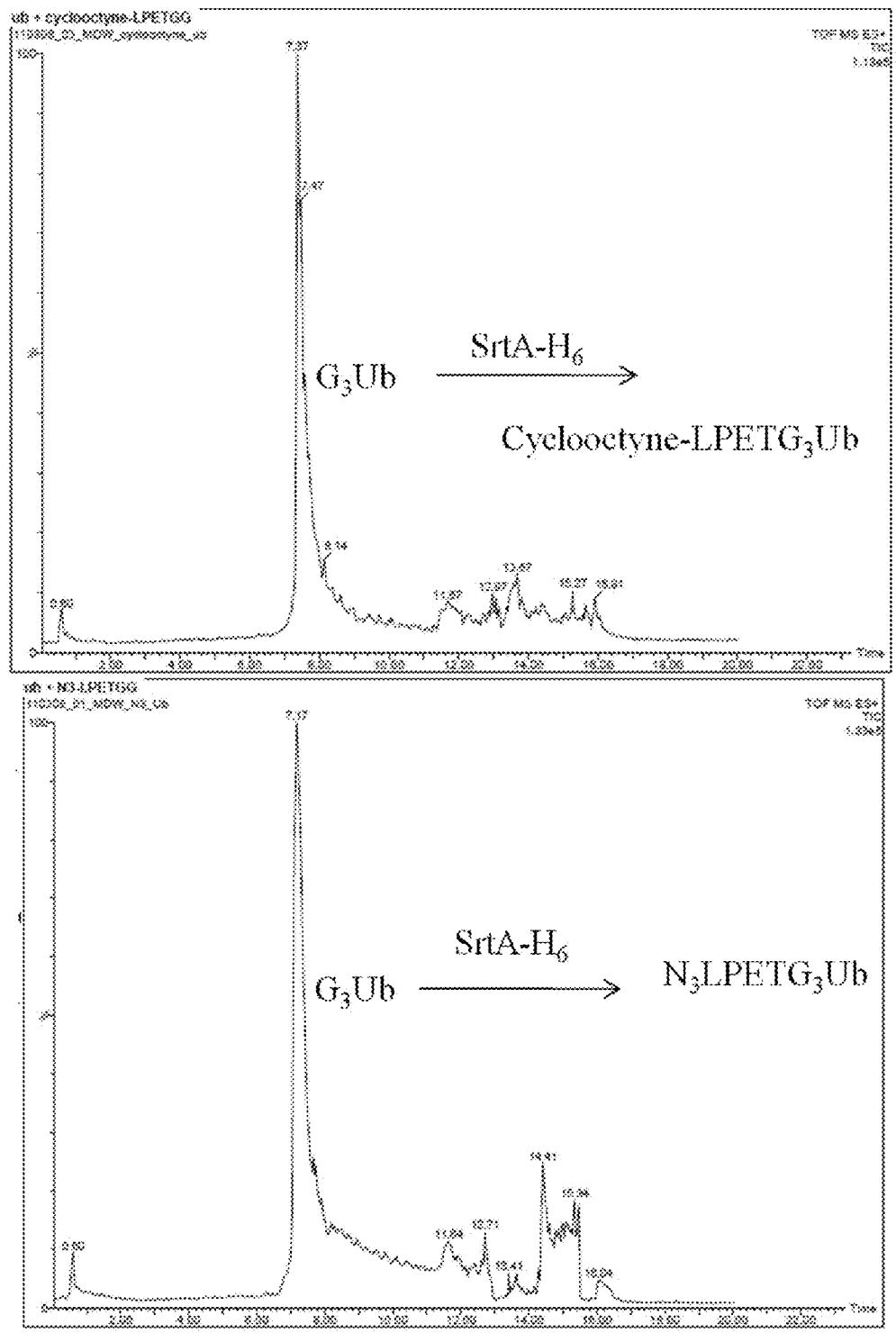
FIG. 5. N-terminal sortagging using ubiquitin as a model protein.
Figure 16:
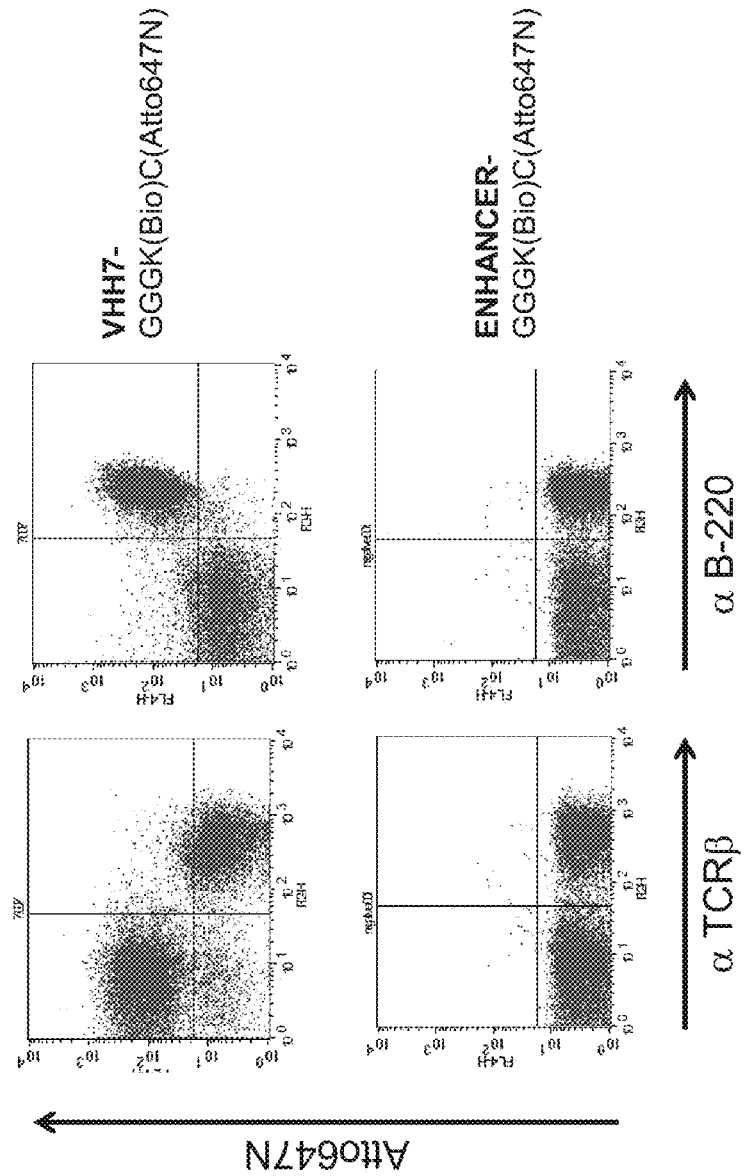
Figure 17:
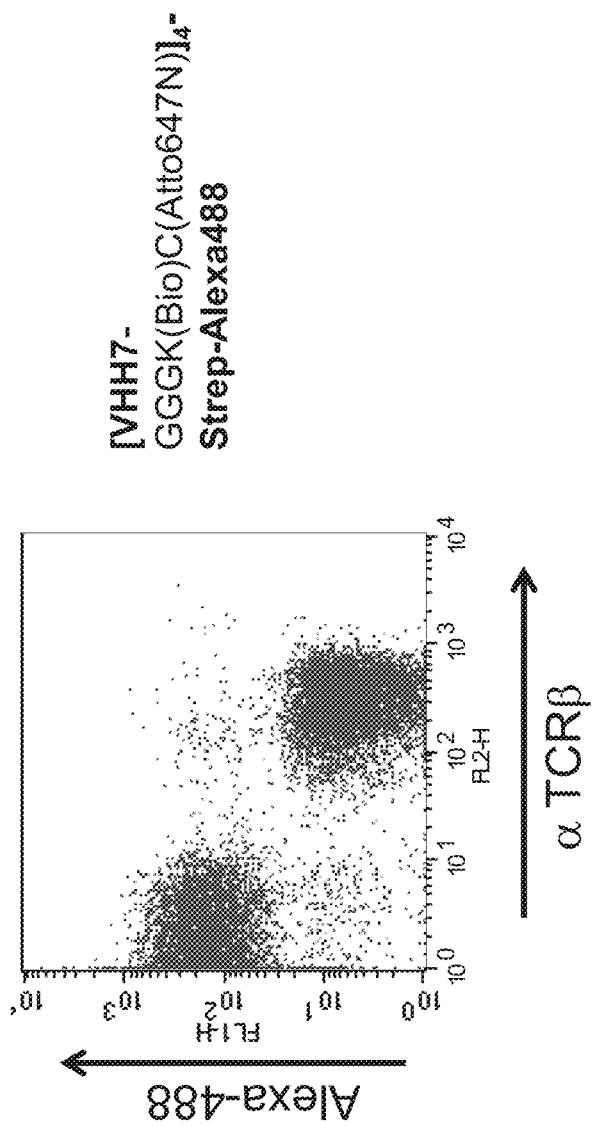

Example 7: Identification of a VHH (VHH7) that Quantitatively Stains Murine Splenocytes Murine splenocytes were stained with anti-TCRb, anti-B220, and each of the 13 expressed VHHs prepared as described in Example 6. Stained preparations were interrogated by flow cytometry. Labeled Enhancer VHH was used as a negative control (FIG. 5, lower left and right panels). Of the thirteen VHHs tested, VHH7 was found to quantitatively stain cells that stain with anti-B220 (FIG. 16, upper right panel). The stained population is also TCRb low (FIG. 16, upper left panel). VHH7 labeled with G3K(biotin)C (Atto647N) probe was prepared as described in Example 6 and was tetramerized by incubation with strepavidin-488 and used to stain splenocytes. Tetramers stain the TCRb low population, as expected (FIG. 17). Other tested VHHs showed staining patterns that were distinct from that of VHH7. These VHHs may identify novel splenocyte surface markers, which may be of use, e.g., to identify functionally distinct cell populations.

The sequence encoding VHH7 was obtained using standard methods. The nucleotide sequence and the encoded VHH7 amino acid sequence, followed by a C-terminal sortase recognition sequence (LPETG) and hexahistidine (6×His) tag, are shown in FIG. 22.

Example 8: Labeling and Purification of VHH7 with a Cleavable Linker Probe

Figure 15:
Figure 18:
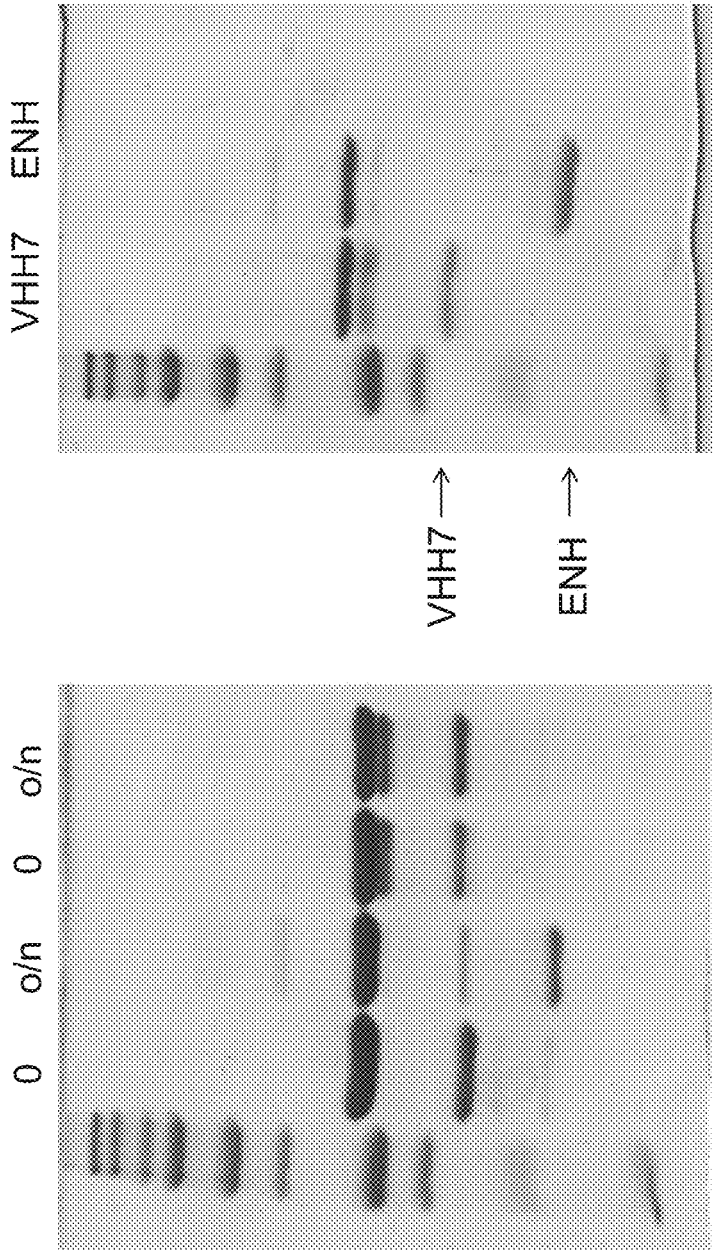
FIG. 18. VHH7 Monomer labeling with a G3C(bis-aryl hydrazone)biotin probe

VHH7 and GFP enhancer was labeled overnight at 25 degrees C. with 1 mM G3K(bisaryl hydrazone)-biotin probe (shown below) using 50 uM SrtA. Aliquots were run on an SDS-PAGE gel. The Coomassie-stained gel is shown in FIG. 18 (left). After an additional 24 h at room temperature, this material was purified and desalted as described in Example 6 (FIG. 15). Aliquots were run on an SDS-PAGE gel. The Coomassie-stained gel is shown in FIG. 18 (right).

Example 9: Immunoprecipitation of VHH7 Antigen from Digitonin Solubilized Murine Splenocytes and Identification of its Target Splenocytes from 11 mice were solubilized in 30 ml of 2% digitonin buffer (2% digitonin/PBS/protease inhibitor) for 2 hours at 4 degrees C. Nuclei were pelleted at 10000×g for 30 minutes and the lysate was divided into two portions. The VHH7 preparation from Example 8 (FIG. 8) was added to one portion and 75% of the GFP enhancer preparation was added to the other portion. Samples were incubated overnight at 4 degrees C. Washed Neutravidin-agarose beads were added and incubated for 2 hours. Beads were then washed with 50 ml each of 2% digitonin, 0.5% digitonin, 0.1% digitonin. Beads were eluted with 100 mM phosphate pH 6.0/100 mM aniline/100 mM hydroxylamine, followed by incubation with SDS sample buffer. Eluates were concentrated by SpeedVac and resolved by SDS-PAGE, The PAGE gel was silver-stained and the indicated bands were excised for MS/MS identification.

Figure 20:
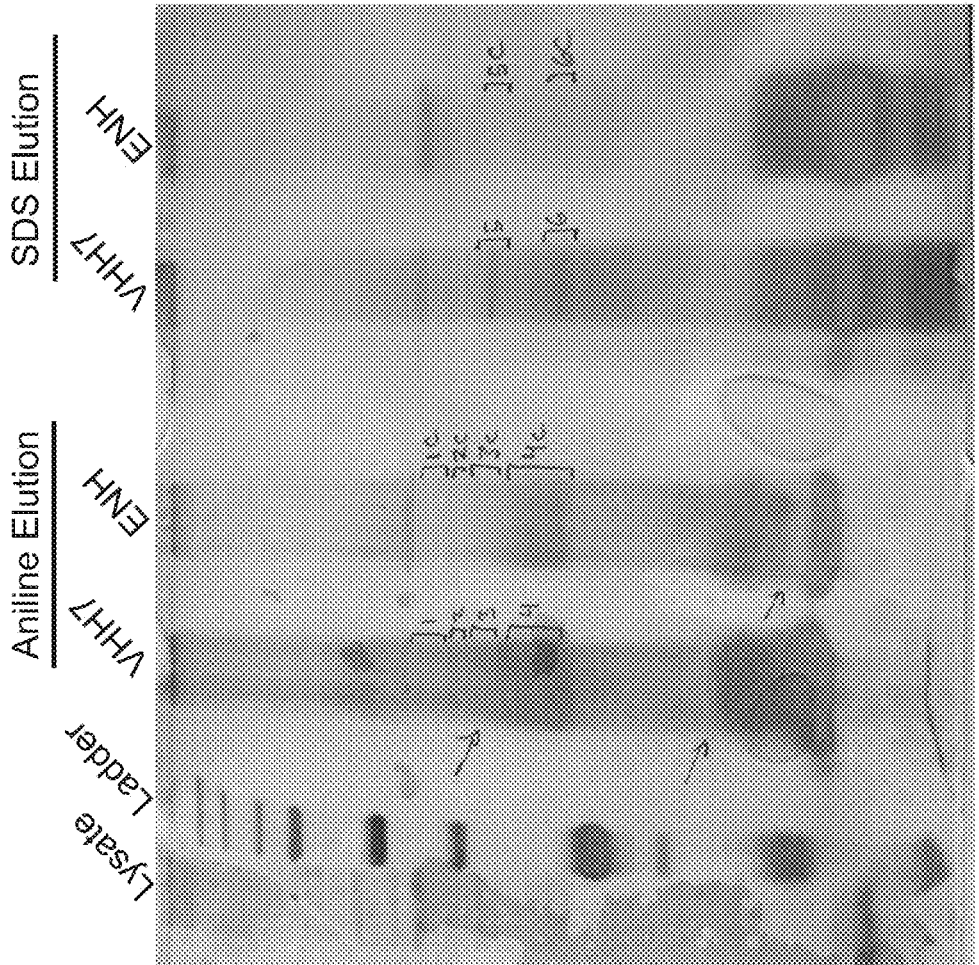
Figure 21:
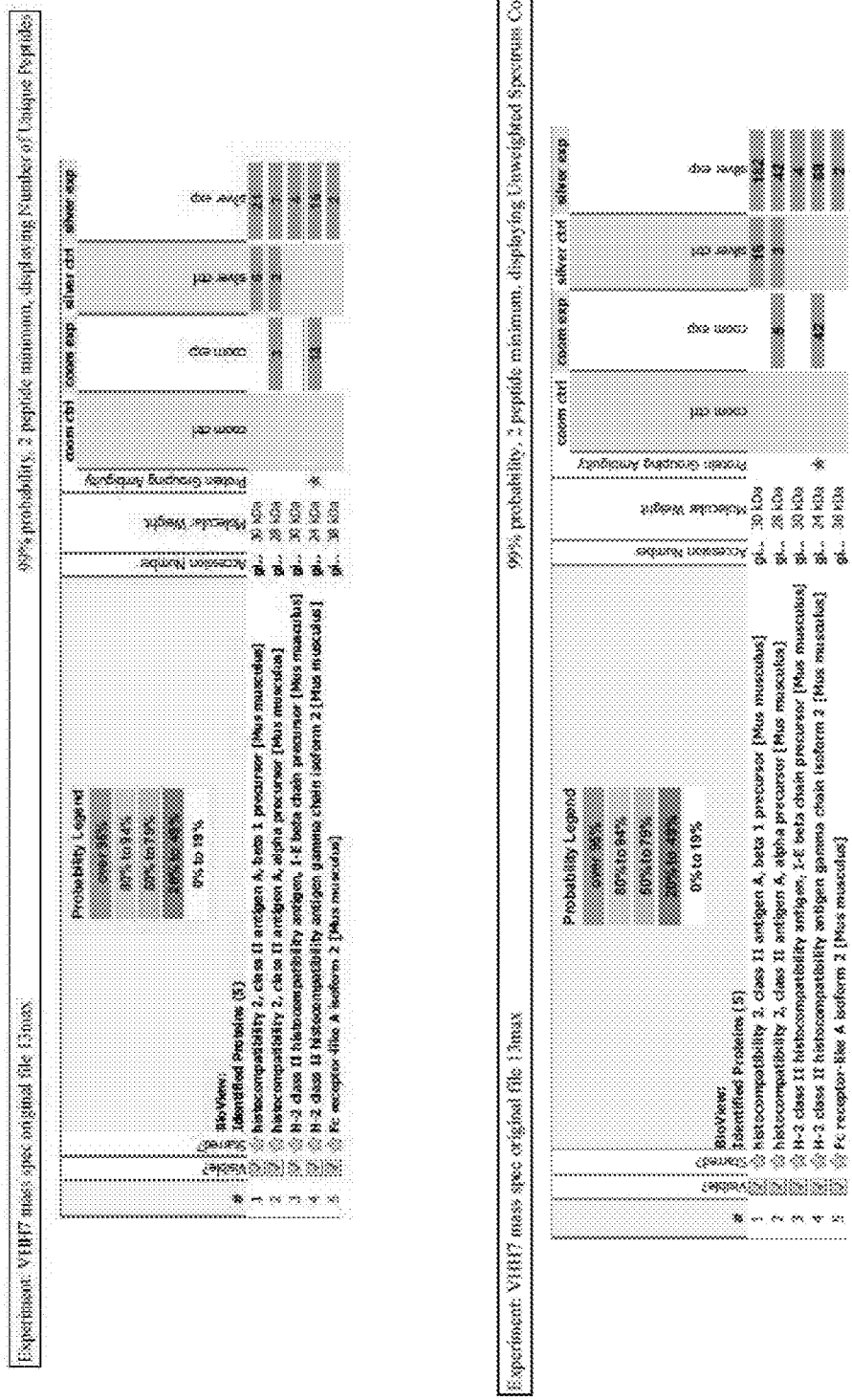

Bands excised from silver-stained gel (FIG. 20) were subjected to trypsinolysis followed by MS/MS analysis. Components of the MHCII complex (beta, alpha, and gamma chains) were identified and are displayed in FIG. 21 and listed in the table below along with their NCBI Gene ID and RefSeq accession numbers of mRNA and protein sequences. Number of unique peptides found for each protein is displayed (FIG. 21, top) as well as the spectral counts for each protein (FIG. 21, bottom). Coom ctrl and Coom exp are from an SDS-PAGE gel loaded with the same eluates as in FIG. 20, but stained with colloidal Coomassie.

Figure 23:
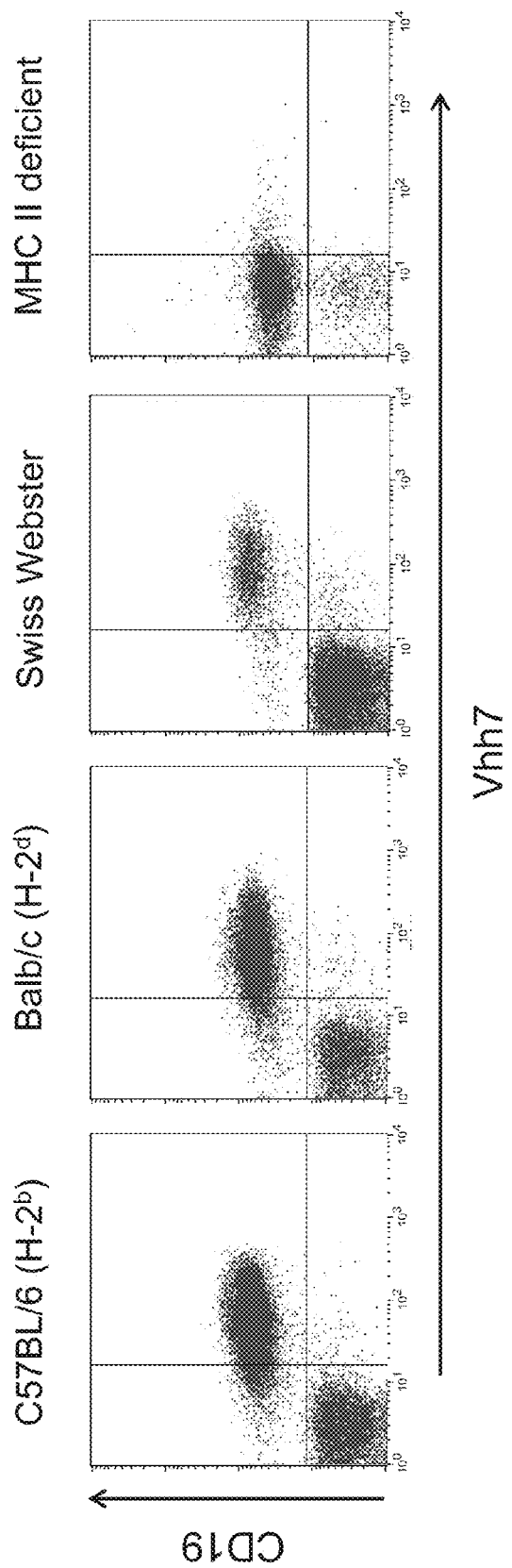
FIG. 23. Staining of murine B lymphocytes of various haplotypes with VHH7 sortagged with Alexa 647 nucleophile.

In order to confirm that the target of VHH7 is the MHCII complex, splenocytes obtained from normal mice of three strains having different MHC haplotypes (C57BL/6 (H-2b); Balb/c (H-2d); Swiss Webster) or from MHCII deficient mice (MHCII−/− mice) were stained with VHH7 sortagged with Alexa 647 nucleophile. As shown in FIG. 23, VHH7

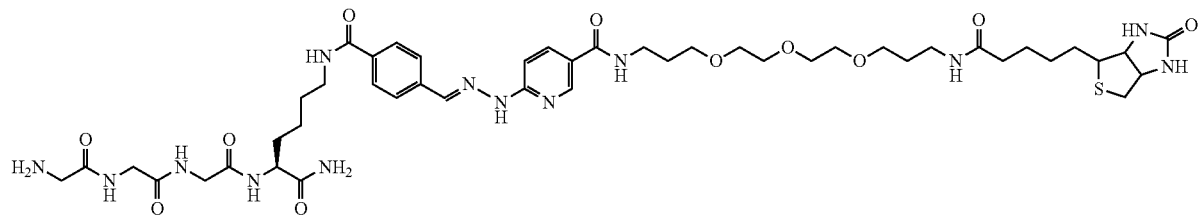 [SMILES: NCC(=O)NCC(=O)NCC(=O)N[C@@H](CCCCNC(=O)c1ccc(/C=N/Nc2ccc(C(=O)NCCCOCCOCCOCCCNC(=O)CCCCC3SCC4NC(=O)NC43)cn2)cc1)C(N)=O]

Figure 19:
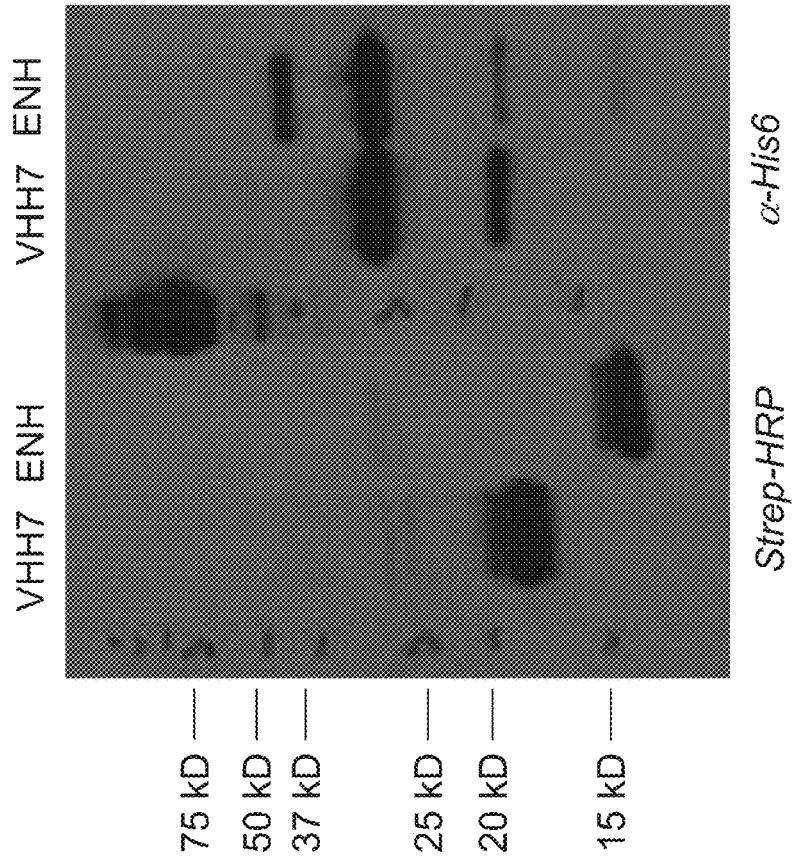
FIG. 19. Final preparations of VHH7 monomer labeling with a G3C(bis-aryl hydrazone)biotin probe FIG. 20. Immunoprecipitation of VHH7 antigen from murine splenocytes FIG. 21. Identification of VHH7 antigen from murine splenocytes FIG. 22. (A) Nucleotide sequence encoding VHH7 fusion protein. The start codon (ATG) is underlined and in bold. The first underlined sequence (closest to the 5' terminus) originates from the pET vector and a restriction site. The second underlined sequence (closest to the 3' terminus) encodes the following elements in an N- to C-terminal direction: (1) a spacer consisting of a single glycine residue (2) a sortase recognition sequence; (3) a spacer consisting of two glycine residues and (4) a 6×His tag. The stop codon is in bold. (B) VHH7 fusion protein sequence. The first (N-terminal) underlined sequence originates from the pET vector and a restriction site. The second (C-terminal) underlined sequence contains the following elements in an N- to C-terminal direction: (1) a spacer consisting of a single glycine residue; (2) a sortase recognition sequence; (3) a spacer consisting of two glycine residues and a serine residue and; (4) a 6×His tag. (C) Nucleotide sequence encoding VHH7. (D) VHH7 protein sequence. CDR regions are shown in bold and are also listed below the complete protein sequence. (E) VHH7 CDR1, CDR2, and CDR3 sequences. (F) Sequence of sortaggable VHH7 protein without hinge region. The C-terminal underlined sequence contains the following elements in an N- to C-terminal direction: (1) a spacer consisting of two glycine residues; (2) a sortase recognition sequence; (3) a spacer consisting of one glycine residue and (4) a 6×His tag. CDR regions are shown in bold and are also listed below the complete protein sequence. (G) VHH7 CDR1, CDR2, and CDR3 sequences.

Streptavidin-HRP and anti-hexahistidine-HRP were used to generate immunoblots of the gel from FIG. 18 using standard methods. The resulting streptavidin (left) and anti-hexahistidine immunoblots (right) are shown in FIG. 19 and demonstrate that the VHH7 and ENH VHH are labeled with the G3K(bisaryl hydrazone)-biotin probe. Both VHH's have the biotin moiety incorporated (used for IP/Mass spectrometry identification of antigen, see Example 9) and show massive loss of the hexahistidine tag (downstream from the LPXTG cleavage site). These preparations were used as input preparations in Example 9. Small amounts of sortase remain (compare to FIG. 18, right) but do not affect the strongly stains CD19+ splenocytes from normal mice stain but fails to stain CD19+ MHCII-deficient splenocytes, thus confirming MHCII as the target of VHH7.

| Name | Gene ID | NCBI RefSeq Acc. No. (mRNA) | NCBI RefSeq Acc. No. (protein) |
|---|---|---|---|
| H2-Aa histocompatibility 2, class II antigen A, alpha precursor | 14960 | NM_010378.2 | NP_034508.2 |
| H2-Ab1 histocompatibility 2, class II antigen A, beta 1 precursor | 14961 | NM_207105.3 | NP_996988.2 |

-continued

| Name | Gene ID | NCBI RefSeq Acc. No. (mRNA) | NCBI RefSeq Acc. No. (protein) |
|---|---|---|---|
| H-2 class II histocompatibility antigen, I-E beta chain precursor | 14969 | NM_010382.2 | NP_034512.2 |
| H-2 class II histocompatibility antigen gamma chain isoform 2 | 16149 | NM_010545.3 | NP_034675.1 |

Example 10: Exposure of Dendritic Cells to VHH7-OVA$_{323-339}$ In Vitro Stimulates their Ability to Promote Activation of CD4+ T Cells VHH7, αGFP-VHH, and αDec-205 heavy chain were each sortagged at their C-termini with (Gly)$_3$-OVA$_{323-339}$ in standard sortagging reactions, and the products were purified from the reaction mixture using size exclusion chromatography. OVA$_{323-339}$ is a peptide consisting of aa 323-339 of ovalbumin. αGFP-VHH is a VHH that binds to GFP and is used as a control. αDec-205 is a conventional antibody that binds to murine Dec-205. Dec-205 is a molecule expressed on dendritic cells. VHH7 sortagged with (Gly)$_3$-OVA$_{323-339}$ is sometimes referred to as VHH7-OVA$_{323-339}$, and αDec-205 with heavy chains sortagged with (Gly)$_3$-OVA$_{323-339}$, is sometimes referred to as αDec-205-OVA$_{323-339}$. In experiments comparing VHH7-OVA$_{323-339}$ and αDec-205-OVA$_{323-339}$, the αDec-205-OVA$_{323-339}$ was used at a 5-fold greater concentration on a weight basis than VHH7-OVA$_{323-339}$ in order to compensate for the greater weight of αDec-205-OVA$_{323-339}$ taking into consideration the fact that αDec-205-OVA$_{323-339}$ bears an OVA$_{323-339}$ on each of its two heavy chains.

Figure 24:
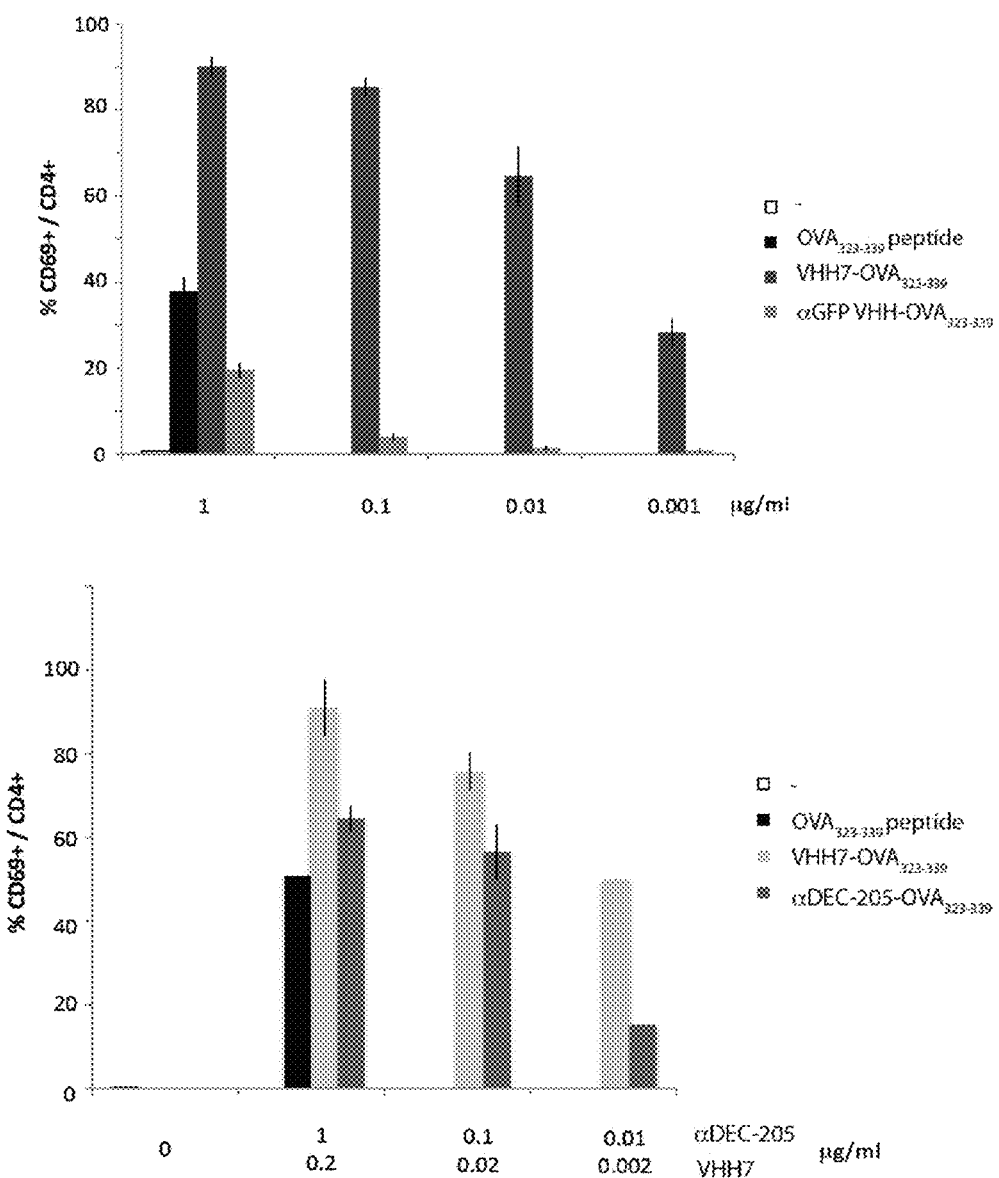
FIG. 24. Activation of CD4+ T cells, as assessed by monitoring CD69 expression by flow cytometry, after co-culture with dendritic cells that had been exposed to indicated concentrations of OVA323-339 peptide, αGFP VHH sortagged with (Gly)3-OVA$_{323-339}$, VHH7 sortagged with (Gly)3-OVA$_{323-339}$, or αDec205 sortagged with (Gly)3-OVA323-339.

The ability of VHH7-OVA$_{323-339}$ to stimulate the ability of dendritic cells to promote activation of CD4+ T cells was assessed as follows: Bone marrow derived murine dendritic cells were incubated with OVA$_{323-339}$ peptide, VHH7 sortagged with (Gly)3-OVA$_{323-339}$ (VHH7-OVA$_{323-339}$) or αGFP-VHH sortagged with (Gly)3-OVA$_{323-339}$ (αGFP-VHH-OVA$_{323-339}$) at various concentrations indicated in FIG. 24 (upper panel). Cells were then washed and co-cultured with OVA$_{323-339}$-specific CD4+ T cells from OT II transgenic mice (which carry a transgenic T cell receptor (TCR) from CD4+ T cells specific for the MHC class II-restricted OVA peptide aa 323-339). T cell activation was monitored 24 hours after co-culture by measuring CD69 expression on CD4 T cells by flow cytometry. Histograms in FIG. 24 (upper panel) show average of 3 independent measures+/−standard deviation. Exposure to VHH7-OVA$_{323-339}$ at each concentration tested markedly stimulated the ability of dendritic cells to promote activation of CD4+ T cells.

Figure 25:
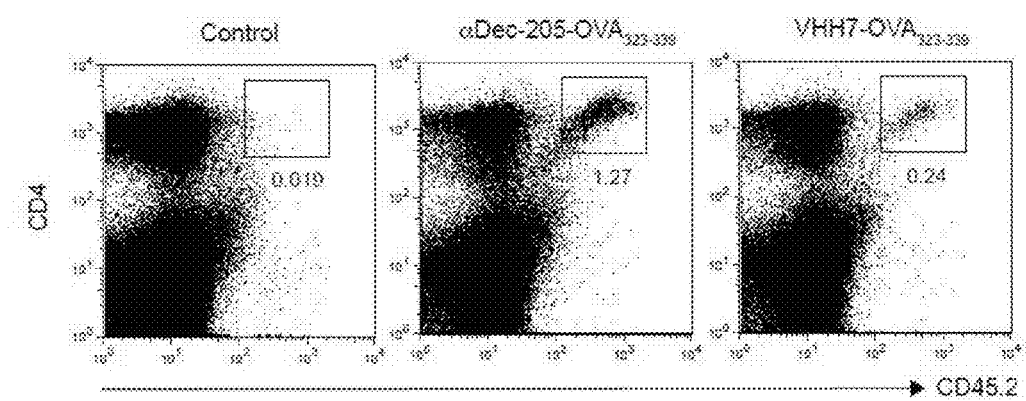
FIG. 25. Expansion of OVA$_{323-339}$-specific CD4+ T cells following transfer into C57BL/6 congenic mice subsequently immunized intraperitoneally with αDec-205 sortagged with (Gly)3-OVA323-339 or VHH7 sortagged with (Gly)3-OVA$_{323-339}$, in each case together with αCD40 and Poly I:C. Dot plots show the percentage of donor OVA323-339-specific cells in the spleen of control (left), mice or mice immunized with αDec-205-OVA323-339 or VHH7-OVA323-339 respectively, as monitored by flow cytometry.

The ability of VHH7-(Gly)3-OVA$_{323-339}$ to stimulate the ability of dendritic cells to promote activation of CD4+ T cells was compared with that of αDec-205-OVA$_{323-339}$ as follows: Bone marrow derived dendritic cells were incubated with OVA$_{323-339}$ peptide, VHH7-OVA$_{323-339}$ or αDec-205-OVA$_{323-339}$ at various concentrations indicated in FIG. 24 (lower panel). Cells were then washed and co-cultured with OVA$_{323-339}$-specific CD4 T cells from OT II transgenic mice. T cell activation was monitored 24 hours after co-culture by measuring CD69 expression on CD4 T cells by flow cytometry. Histograms in FIG. 24 (lower panel) show average of 3 independent measures+/−standard deviation. Exposure to VHH7-OVA$_{323-339}$ at each concentration tested markedly stimulated the ability of dendritic cells to promote activation of CD4+ T cells. As in the previous experiment, exposure to VHH7-OVA$_{323-339}$ at each concentration tested markedly stimulated the ability of dendritic cells to promote activation of CD4+ T cells. The stimulation exceeded that resulting from exposure to αDec-205-OVA$_{323-339}$ Example 11: Immunization of Mice with VHH7-OVA$_{323-339}$ Protein Stimulates Expansion of CD4+ T Cells OVA$_{323-339}$-specific CD4 T cells from OTII transgenic mice were transferred intravenously into C57BL/6 congenic mice. 24 hours after T cells transfer, mice were immunized intraperitoneally with 1 µg of αDec-205 sortagged with (Gly)$_3$-OVA$_{323-339}$ or 0.2 µg of VHH7 sortagged with (Gly)$_3$-OVA$_{323-339}$, in each case together with 25 µg of αCD40 and 50 µg of Poly I:C. Control mice were immunized with phosphate buffered saline (PBS). Seven days after immunization, expansion of transferred cells was monitored by flow cytometry. Dot plots in FIG. 25 show the percentage of donor OVA$_{323-339}$-specific cells in the spleen of control mice (left) or mice immunized with αDec-205-OVA$_{323-339}$ (middle) or VHH7-OVA$_{323-339}$ (right) respectively. Antibody to CD45.2 specifically recognizes donor cells and their descendants. As shown in FIG. 25, immunization with VHH7-OVA$_{323-339}$ markedly stimulated proliferation of transferred cells.

Example 12: Further Characterization of VHH7

A sortaggable VHH7 polypeptide lacking a hinge region was produced in E. coli. The camelid-derived portion of the sequence (i.e., without sortase recognition motif, linkers, and C-terminal 6xHis tag) is presented below.

(SEQ ID NO: 54)
QVQLQESGGGLVQAGGSLRLSCAASGSTLSSYGMGWYRQAPGKQREV

VATISATGSISYADSVKGRFTISRDSAKNTMYLQLNSLTPEDTAVYY

CNTIYRSTLYWGQGTQVTVSS

Approximate CDR sequences of SEQ ID NO: 54 are:

CDR1:
(SEQ ID NO: 55)
GRTFSRGV,

CDR2:
(SEQ ID NO: 56)
IFSGSSWSGRS,
and

CDR3:
(SEQ ID NO: 57)
GYPEAYSAYGRESTYDY.

A sortaggable version of the sequence, including a sortase recognition motif and a 6xHis tag, is as follows:

(SEQ ID NO: 58)
QVQLQESGGGLVQAGGSLRLSCAASGSTLSSYGMGWYRQAPGKQREV

VATISATGSISYADSVKGRFTISRDSAKNTMYLQLNSLTPEDTAVYY

CNTIYRSTLYWGQGTQVTVSSGGLPETGGHHHHHH

Figure 27:
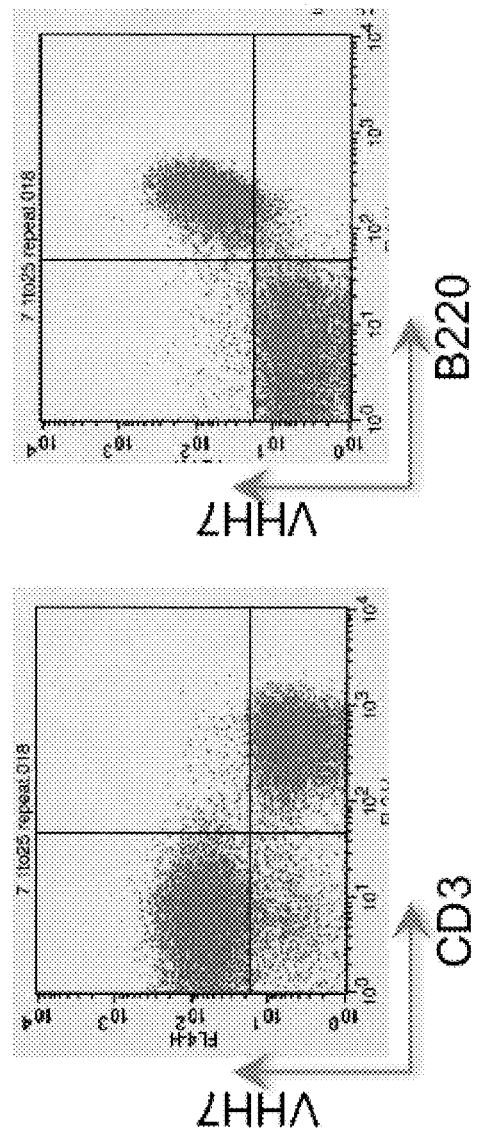
FIG. 27. Flow cytometry of murine splenocytes costained with VHH7 and anti-CD3 (T cell marker) antibody (left panel) or with VHH7 and anti-B220 (B cell marker) antibody (right panel).

As shown in FIG. 27, flow cytometry of murine splenocytes costained with fluorophore-sortagged VHH7 and anti- CD3 (T cell marker) antibody (left panel) or with VHH7 and anti-B220 (B cell marker) antibody (right panel), confirmed that VHH7 stains B cells, consistent with its binding to MHC Class II.

Example 13: Identification and Characterization of a VHH that Binds to Human MHC Class II An alpaca was immunized with recombinant purified human MHC Class II protein (HLA-DR1, HLA-DR2 and HLA-DR4). Peripheral lymphocytes were harvested and used as a source of RNA, from which cDNA was made using standard procedures. Nucleic acids encoding a VHH repertoire were cloned into the multi-cloning site of a phage display vector similarly as described in Example 5 to produce a library of VHH potentially capable of binding to any one or more of the three MHC Class II proteins used for immunization. Phage were produced and two rounds of panning of increasing stringency were performed using purified recombinant biotinylated HLA-DR1, HLA-DR2 and HLA-DR4 in separate tubes, followed by streptavidin magnetic bead immunoprecipitation to recover binders. The DNA insert of phage encoding binders was sequenced using standard methods. A clone encoding a VHH termed VHH4 was the dominant clone recover from each of them (HLA-DR1, HLA-DR2 and HLA-DR4) after the selection process. The amino acid sequence of VHH4 is as follows:

(SEQ ID NO: 59)
QVQLQESGGGLVQAGGSLRLSCAASGSTLSSYGMGWYRQAPGKQREV

VATISATGSISYADSVKGRFTISRDSAKNTMYLQLNSLTPEDTAVYY

CNTIYRSTLYWGQGTQVTVSS

VHH4 CDR sequences were defined approximately as follows based on alignment of multiple VHH sequences:

```
CDR1:
                            (SEQ ID NO: 60)
GSTLSSYGM

CDR2:
                            (SEQ ID NO: 61)
ISATGS

CDR3:
                            (SEQ ID NO: 62)
NTIYRSTLY
```

The amino acid sequence of VHH4, followed by a GG linker, sortase recognition sequence (LPETG), G linker, and hexahistidine (6×His) tag (GGLPETGGHHHHHH; SEQ ID NO: 63) is as follows:

(SEQ ID NO: 64)
QVQLQESGGGLVQAGGSLRLSCAASGSTLSSYGMGWYRQAPGKQREV

VATISATGSISYADSVKGRFTISRDSAKNTMYLQLNSLTPEDTAVYY

CNTIYRSTLYWGQGTQVTVSSGGLPETGGHHHHHH.

Figure 28:
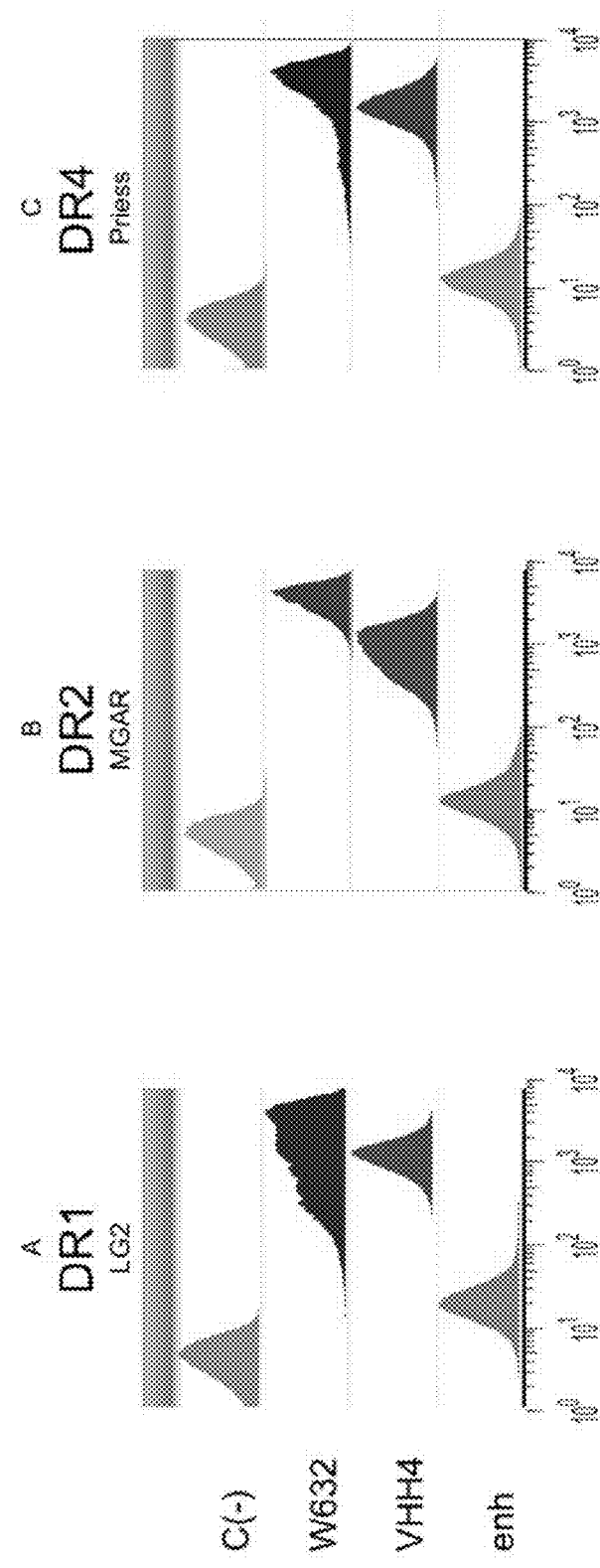
FIG. 28. VHH4 recognizes human MHC class II molecules. Flow cytometry of human B cell lines expressing HLA-DR1, HLA-DR2, or HLA-DR4 stained with: no antibody (C(−)), anti-MHC Class I antibody W632, VHH4, or an anti-GFP VHH (enh) as indicated.

The polypeptide was expressed in *E. coli* cells, purified and conjugated to fluorophores using Sortase A from *S. aureus* or adsorbed on agarose beads for biochemical studies. Sortase A was used to conjugate the VHH4 polypeptide with a GGGK(Alexa 647) probe (in which the fluorescent dye Alexa 647 is attached to the side chain of the lysine residue). To confirm the ability of VHH4 to bind to human MHC Class II, human B cell lines expressing HLA-DR1 (LG2 cells), HLA-DR2 (MGAR cells), or HLA-DR4 (Priess cells) were stained with either: no antibody, Alexa 647-conjugated anti MHC Class I antibody W632 (a mouse monoclonal antibody that binds to human MHC Class I), Alexa 647-conjugated VHH4, or Alexa-conjugated anti-GFP antibody (as a negative control). Anti GFP is a VHH that binds to GFP (Kirchofer, A, et al., Nat Struct Mol Biol. (2010) 17(1):133-8, termed "enhancer" therein). Anti-GFP VHH was modified to contain a sortase recognition motif and was coupled with Alexa 647 using sortase to obtain the conjugate. The stained B cells were subjected to flow cytometry. As shown in FIG. 28, VHH4 stains all three human B cell lines comparably to W632. The lack of staining by anti-GFP VHH confirms that the ability of VHH to bind to and stain human B cells is specific to particular VHH.

Example 14: Identification and Characterization of VHH that Bind to Influenza a Virus Proteins This example describes identification and characterization of VHH that bind to influenza A virus. An alpaca was immunized with inactivated Influenza A virus strain PR8. Peripheral lymphocytes were harvested and used as a source of RNA, from which cDNA was made using standard procedures. Nucleic acids encoding a VHH repertoire were cloned into the multi-cloning site of a phage display vector similarly to the way described in Example 5 to produce a library of sortaggable VHH polypeptides potentially capable of binding to any of various influenza proteins. The polypeptides contained a sortase recognition motif and 6×His epitope tag at the C-terminal end. Phage were produced and incubated with intact Influenza A virus for the selection followed by streptavidin magnetic bead immunoprecipitation to recover binders. Two rounds of panning of increasing stringency were performed. The specificity for particular influenza A virus antigens (hemagglutinin (HA) and nucleoprotein (NP)) was then determined using purified proteins. A panel of phage encoding different VHH sequences (anti-FluA VHH panel) was obtained. The DNA inserts of phage encoding VHH that bound to NP or HA were sequenced using standard methods and conceptually translated. The amino acid sequence of three VHH that bound to NP protein (termed VHH52, VHH54, and VHH62) and one VHH that bound to HA protein (termed VHH68) are presented below.

VHH52 (binds to FluA-NP)
(SEQ ID NO: 65)
QVQLQESGGGLVQAGGSLRLTCALSERTSTSYAQGWFRQPPGKEREF
VASLRTHDGNTHYTDSVKGRFTISRDNAENTLYLQMNSLKTEDTAVY
YCAASLGYSGAYASGYDYWGQGTQVTVSS VHH54 (binds to FluA-NP)
(SEQ ID NO: 66)
QVQLQESGGGLVQAGGSLRLSCAASGRTLSSYAMGWFRQAPGKEREL
VSAISWSGLSTYYEDSVKGRFTISRDNAKNTMYLQMNSLKPEDTAIY
YCAADIGWPLRADSGSWGQGTQVTVSS VHH62 (binds to FluA-NP)
(SEQ ID NO: 67)
QVQLQESGGGLVQPGGSLRLSCAASGFTLDGYAIGWFRQAPGKEREG
VSCISSSGKSTNYADSVKGRFTISRDNQQNTVYLQMNSLKPEDTAVY
YCAATVGLFCVGGTYGMDYWGKGTQVTVSS VHH68 (binds to FluA-HA)
(SEQ ID NO: 68)
QVQLQESGGGLVQAGGSLRLSCAVPGRTSNIFAMGWFRQALGKEREF
VAAVTWSLGNTYYADSVKGRFTISRDNAKNTVYLQMNSLKPEDTAVY
YCAAGEVGPLRQPDTYLHWGQGTQVTVSS In the following sortaggable VHH polypeptides, the camelid-derived portion of the VHH is followed by a GG linker, sortase recognition sequence, G linker, and hexahistidine (6×His) tag (i.e., SEQ ID NO: 63):

```
VHH52 (binds to FluA-NP)
                                        (SEQ ID NO: 69)
QVQLQESGGGLVQAGGSLRLTCALSERTSTSYAQGWFRQPPGKEREF
VASLRTHDGNTHYTDSVKGRFTISRDNAENTLYLQMNSLKTEDTAVY
YCAASLGYSGAYASGYDYWGQGTQVTVSSGGLPETGGHHHHHH VHH54 (binds to FluA-NP)
                                        (SEQ ID NO: 70)
QVQLQESGGGLVQAGGSLRLSCAASGRTLSSYAMGWFRQAPGKEREL
VSAISWSGLSTYYEDSVKGRFTISRDNAKNTMYLQMNSLKPEDTAIY
YCAADIGWPLRADSGSWGQGTQVTVSSGGLPETGGHHHHHH VHH62 (binds to FluA-NP)
                                        (SEQ ID NO: 71)
QVQLQESGGGLVQPGGSLRLSCAASGFTLDGYAIGWFRQAPGKEREG
VSCISSSGKSTNYADSVKGRFTISRDNQQNTVYLQMNSLKPEDTAVY
YCAATVGLFCVGGTYGMDYWGKGTQVTVSSGGLPETGGHHHHHH VHH68 (binds to FluA-HA)
                                        (SEQ ID NO: 72)
QVQLQESGGGLVQAGGSLRLSCAVPGRTSNIFAMGWFRQALGKEREF
VAAVTWSLGNTYYADSVKGRFTISRDNAKNTVYLQMNSLKPEDTAVY
YCAAGEVGPLRQPDTYLHWGQGTQVTVSSGGLPETGGHHHHHH
```

MDCK cells were radiolabelled with $^{35}$S using standard methods and infected with influenza A strain PR8. Proteins were immunoprecipitated from MDCK cell lysate using different members of the sortaggable anti-FluA VHH panel, subjected to polyacrylamide gel electrophoresis, and visualized using autoradiography. The resulting autoradiograph is presented in FIG. 29. As shown, VHH52, VHH54, and VHH62 specifically immunoprecipitated a band running at slightly more than 50 kD, while VHH68 specifically immunoprecipitated a band running at around 60 kD, consistent with the predicted molecular weight of the NP and HA proteins.

Figure 30:
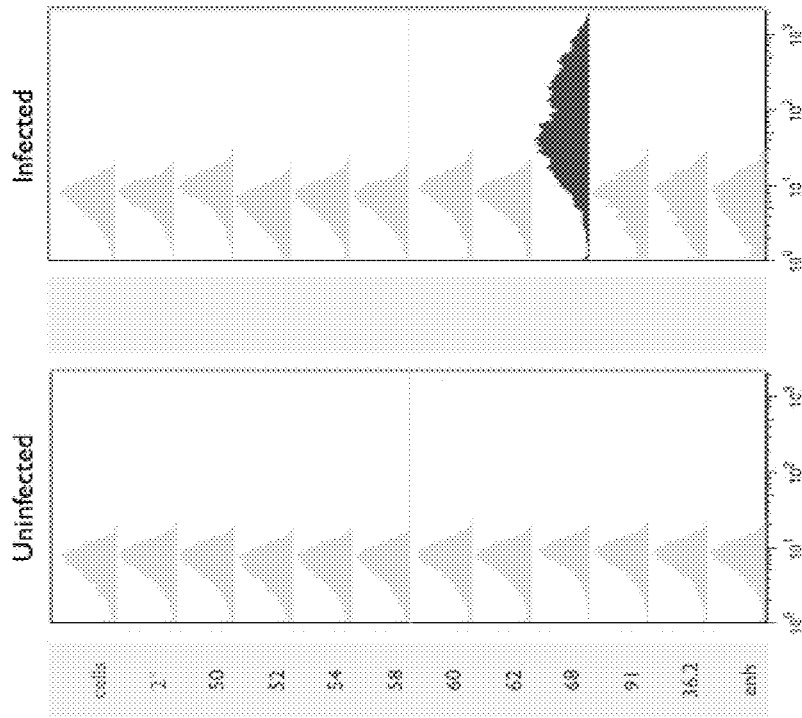
FIG. 30. VHH68 recognizes the hemagglutinin protein from Influenza A virus. Flow cytometry of MDCK cells either infected (right) or uninfected (left) with influenza A virus.

MDCK cells were infected with PR8 virus. Samples were stained with different members of the anti-FluA VHH panel, followed by staining with secondary antibody labeled with phycoerythrin. As shown in FIG. 30, VHH68 labels cells infected with influenza A virus.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments described herein, which fall within the scope of the claims. The scope of the present invention is not to be limited by or to embodiments or examples described above.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided.

Articles such as "a", "an", "the" and the like, may mean one or more than one unless indicated to the contrary or otherwise evident from the context.

The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process. Any one or more claims may be amended to explicitly exclude any embodiment, aspect, feature, element, or characteristic, or any combination thereof. Any one or more claims may be amended to exclude any agent, composition, amount, dose, administration route, cell type, target, cellular marker, antigen, targeting moiety, or combination thereof.

Embodiments in which any one or more limitations, elements, clauses, descriptive terms, etc., of any claim (or relevant description from elsewhere in the specification) is introduced into another claim are provided. For example, a claim that is dependent on another claim may be modified to include one or more elements or limitations found in any other claim that is dependent on the same base claim. It is expressly contemplated that any amendment to a genus or generic claim may be applied to any species of the genus or any species claim that incorporates or depends on the generic claim.

Where a claim recites a composition, methods of using the composition as disclosed herein are provided, and methods of making the composition according to any of the methods of making disclosed herein are provided. Where a claim recites a method, a composition for performing the method is provided. Where elements are presented as lists or groups, each subgroup is also disclosed. It should also be understood that, in general, where embodiments or aspects is/are referred to herein as comprising particular element(s), feature(s), agent(s), substance(s), step(s), etc., (or combinations thereof), certain embodiments or aspects may consist of, or consist essentially of, such element(s), feature(s), agent(s), substance(s), step(s), etc. (or combinations thereof). It should also be understood that, unless clearly indicated to the contrary, in any methods claimed herein that include more than one step or act, the order of the steps or acts of the method is not necessarily limited to the order in which the steps or acts of the method are recited. Any method of treatment may comprise a step of providing a subject in need of such treatment. Any method of treatment may comprise a step of providing a subject having a disease for which such treatment is warranted. Any method of treatment may comprise a step of diagnosing a subject as being in need of such treatment. Any method of treatment may comprise a step of diagnosing a subject as having a disease for which such treatment is warranted.

Where ranges are given herein, embodiments in which the endpoints are included, embodiments in which both endpoints are excluded, and embodiments in which one endpoint is included and the other is excluded, are provided. It should be assumed that both endpoints are included unless indicated otherwise. Unless otherwise indicated or otherwise evident from the context and understanding of one of ordinary skill in the art, values that are expressed as ranges can assume any specific value or subrange within the stated ranges in various embodiments, to the tenth of the unit of the lower limit of the range, unless the context clearly dictates otherwise. "About" in reference to a numerical value generally refers to a range of values that fall within ±10%, in some embodiments ±5%, in some embodiments ±1%, in some embodiments ±0.5% of the value unless otherwise stated or otherwise evident from the context. In any embodiment in which a numerical value is prefaced by "about", an embodiment in which the exact value is recited is provided. Where an embodiment in which a numerical value is not prefaced by "about" is provided, an embodiment in which the value is prefaced by "about" is also provided. Where a range is preceded by "about", embodiments are provided in which "about" applies to the lower limit and to the upper limit of the range or to either the lower or the upper limit, unless the context clearly dictates otherwise. Where a phrase such as "at least", "up to", "no more than", or similar phrases, precedes a series of numbers, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated.

What is claimed is:

1. A method of modulating the immune response of a subject to an antigen, the method comprising administering an agent comprising (a) a targeting moiety A comprising a VHH that binds to MHCII complexes HLA-DR1, HLA-DR2 and HLA-DR4, wherein the VHH comprises SEQ ID NO: 59 or competes for binding to MHCII complexes HLA-DR1, HLA-DR2 and HLA-DR4 with a VHH comprising SEQ ID NO: 59; and (b) an antigen B that comprises a polypeptide, polysaccharide, or lipid that is from a pathogen or tumor cell, wherein the targeting moiety A and antigen B are physically associated with each other, or a composition comprising the agent and an adjuvant to the subject.

2. The method of claim 1, wherein the targeting moiety A further comprises that binds to MHCII complex an antibody, an antibody chain, an antibody fragment, an scFv, a VHH domain, a single-domain antibody, an adnectin, or an aptamer, that binds to an MHCII complex.

3. The method of claim 1, wherein the targeting moiety A comprises a VHH domain.

4. The method of claim 1, wherein the antigen obtained from a pathogen.

5. The method of claim 1, wherein the antigen comprises a tumor antigenan.

6. The method of claim 1, wherein the antigen comprises a peptide.

7. The method of claim 1, wherein the subject is human.

8. The method of claim 1, wherein modulating the immune response comprises stimulating an immune response to the antigen.

9. The method of claim 1, wherein the targeting moiety and the antigen are covalently linked.

10. The method of claim 1, wherein the antigen is a viral antigen.

11. The method of claim 1, wherein the antigen is a bacterial antigen.

12. The method of claim 1, wherein the antigen is an envelope protein, capsid protein, secreted protein, structural protein, cell wall protein, cell wall polysaccharide, capsule protein, capsule polysaccharide, enzyme, or toxin.

13. The method of claim 1, wherein the antigen comprises a fragment at least 15 amino acids long of a viral, bacterial, fungal, or parasite polypeptide.

14. The method of claim 1, wherein the antigen comprises a recombinantly produced polypeptide.

15. The method of claim 1, wherein the polypeptide, polysaccharide, or lipid is isolated from a source from which it originates.

\* \* \* \* \*

UNITED STATES PATENT AND TRADEMARK OFFICE
CERTIFICATE OF CORRECTION

PATENT NO. : 9,751,945 B2  
APPLICATION NO. : 14/394046  
DATED : September 5, 2017  
INVENTOR(S) : Hidde Ploegh, Maximilian Popp and Juanjo Cragnolini Page 1 of 1

It is certified that error appears in the above-identified patent and that said Letters Patent is hereby corrected as shown below:

In the Claims

Column 254, Claim 4, Lines 44-45, delete "the antigen obtained" and insert --the antigen is obtained--.

Column 254, Claim 5, Line 57, delete "a tumor antigenan" and insert --a tumor antigen--.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*